(12) United States Patent
Reed et al.

(10) Patent No.: US 6,638,517 B2
(45) Date of Patent: Oct. 28, 2003

(54) LEISHMANIA ANTIGENS FOR USE IN THE THERAPY AND DIAGNOSIS OF LEISHMANIASIS

(75) Inventors: Steven G. Reed, Bellevue, WA (US); Antonio Campos-Neto, Bainbridge Island, WA (US); John R. Webb, Manotick, CA (US); Davin C. Dillon, Issaquah, WA (US); Yasir A. W. Skeiky, Bellevue, WA (US); Ajay Bhatia, Seattle, WA (US); Rhea N. Coler, Seattle, WA (US); Peter Probst, Seattle, WA (US); Mark Brannon, Seattle, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/874,923

(22) Filed: Jun. 4, 2001

(65) Prior Publication Data

US 2002/0081320 A1 Jun. 27, 2002

Related U.S. Application Data

(63) Continuation-in-part of application No. 09/639,206, filed on Aug. 14, 2000, which is a continuation-in-part of application No. 09/565,501, filed on May 5, 2000, which is a continuation-in-part of application No. 09/551,974, filed on Apr. 14, 2000, which is a continuation-in-part of application No. 09/183,861, filed on Oct. 30, 1998, now Pat. No. 6,365,165, which is a continuation-in-part of application No. 09/022,765, filed on Feb. 12, 1998, now Pat. No. 6,395,955, which is a continuation-in-part of application No. 08/920,609, filed on Aug. 27, 1997, which is a continuation-in-part of application No. 08/798,841, filed on Feb. 12, 1997, which is a continuation-in-part of application No. 08/533,669, filed on Sep. 22, 1995, now Pat. No. 5,834,592.

(51) Int. Cl.$^7$ .............. A61K 39/008; A61K 39/00; A61K 39/002; A61K 38/00; A61K 45/00

(52) U.S. Cl. .............. 424/269.1; 424/184.1; 424/191.1; 424/192.1; 424/265.1; 424/85.2; 424/450; 514/12; 514/44; 514/2; 530/300; 530/350; 536/23.1; 536/23.4; 435/69.7

(58) Field of Search .............. 435/69.7; 424/191.1, 424/192.1, 186.1, 265.1, 269.1; 530/300, 350; 536/23.1, 23.4

(56) References Cited

U.S. PATENT DOCUMENTS

| 4,870,006 A | 9/1989 | Dragon et al. |
|---|---|---|
| 5,411,865 A | 5/1995 | Reed |
| 5,571,515 A | 11/1996 | Scott et al. .............. 424/208.1 |
| 5,719,263 A | 2/1998 | Reed |
| 5,834,592 A | 11/1998 | Reed et al. |
| 5,846,748 A | 12/1998 | Mandal et al. |
| 5,876,735 A | 3/1999 | Reed |
| 5,876,966 A | 3/1999 | Reed |
| 5,879,687 A | 3/1999 | Reed |
| 5,910,306 A | 6/1999 | Alving et al. |
| 5,912,166 A | 6/1999 | Reed et al. |
| 5,961,970 A | 10/1999 | Lowell et al. |
| 5,965,142 A | 10/1999 | Dillon et al. |
| 5,980,898 A | 11/1999 | Glenn et al. |
| 5,985,284 A | 11/1999 | Lowell |
| 6,013,268 A | 1/2000 | Reed |

FOREIGN PATENT DOCUMENTS

| WO | WO 95/29239 | 11/1995 |
|---|---|---|
| WO | WO 96/39524 | 12/1996 |
| WO | WO 97/11180 | 3/1997 |
| WO | WO 98/35045 | 8/1998 |

OTHER PUBLICATIONS

Ulrich and Myers 1995, Pharmacol.Biotechnol, 6:495–524.*

Afonso et al., "The adjuvant effect of interleukin–12 in a vaccine against *Leishmania major*," *Science* 263:235–237, Jan. 14, 1994.

Bixler et al., *Synthetic Vaccines Volume 1*, CRC Press Inc., Boca Raton, Florida, 1987, Chapter 4, "B cell recognition of protein antigens—perspectives form the submolecular level," pp. 40–71.

Bowie et al., "Deciphering the message in protein sequences: Tolerance to amino acid substitution," *Science* 247:1306–1310, 1990.

Bunn–Moreno et al., "Lectin(s) extracted from seeds of *Artocarpus integrifolia* (jackfruit): potent and selective stimulator(s) of distinct human T and B cell functions," *The Journal of Immunology* 127(2):427–429, Aug. 1981.

Burns et al., "Molecular characterization of a kinesin–related antigen of *Leishmania chagasi* that detects specific antibody in African and American visceral leishmaniasis," *Proc. Natl. Acad. Sci. USA* 90:775–779, Jan. 1993.

Campos–Neto et al., "Cloning and expression of *Leishmania donovani* gene instructed by a peptide isolated from major histocompatability complex class II molecules of infected macrophages," *Journal of Experimental Medicine* 182(5):1423–1433, 1995.

Champsi and McMahon–Pratt, "Membrane glycoprotein M–2 protects against *Leishmania amazonesis* infection," *Infection and Immunity* 52(12):3272–3279, Dec. 1988.

(List continued on next page.)

*Primary Examiner*—Mark Navarro
*Assistant Examiner*—Padmavathi v Baskar
(74) *Attorney, Agent, or Firm*—Seed Intellectual Property Law Group PLLC

(57) ABSTRACT

Compositions and methods for preventing, treating and detecting leishmaniasis and stimulating immune responses in patients are disclosed. The compounds provided include polypeptides that contain at least an immunogenic portion of one or more Leishmania antigens, or a variant thereof. Vaccines and pharmaceutical compositions comprising such polypeptides, or polynucleotides encoding such polypeptides, are also provided and may be used, for example, for the prevention and therapy of leishmaniasis, as well as for the detection of Leishmania infection.

3 Claims, 33 Drawing Sheets

OTHER PUBLICATIONS

Chatelain et al., "IL–4 induces a Th2 response in Leishmania major–infected mice," *The Journal of Immunology* 148(4):1182–1187, Feb. 15, 1992.

Cornelissen et al., "Vaccines against protozoal diseases of veterinary importance," *FEMS Immunology and Medical Microbiology* 15(2–3):61–72, Sep. 1996.

Coulsen et al., "Differential expression of *Leishmania major* beta–tubulin genes during the acquisition of promastigote infectivity," *Mol Biochem Parasitol* 82(2):227–236, Nov. 1996.

Curry et al., "A sensitive immunochemical assay for biologically active MuIFN–γ," *Journal of Immunological Methods* 104:137–142, 1987.

De Andrade et al., "Recombinant Leishmania Hs90 and Hsp70 are recognized by sera from visceral leishmaniasis patients but not Chagas' disease patients," *Journal of Clinical Microbiology* 30(2):330–335, 1992.

Dillon et al., "Characterization of a Leishmania tropica antigen that detects immune responses in desert storm viscerotropic leishmaniasis patients," *Proc. Natl. Acad. Sci USA* 92:7981–7985, 1995.

Flinn et al., "Expression of a hydrophilic surface protein in infective stages of *Leishmania major*," *Molecular and Biochemical Parasitology* 65:259–270, 1994.

Fong and Lee, "Beta tubulin gene of the parasitic protozoan *Leishmania mexicana*," *Mol Biochem Parasitol* 31(1):97–106, Oct. 1988.

Frommel et al., "Vaccine–induced immunity against cutaneous Leishmaniasis in BALB/c mice," *Infection and Immunity* 56(4):843–848, 1988.

GenBank Accession No. AC003679, "*Leishmania major* chromosome 1, complete sequence," Mar. 24, 1999.

GenBank Accession No. U73845, "*Leishmania major* protein antigen LmSTI1 mRNA," Dec. 3, 1996.

GenBank Accession No. X86551, "*L. donovani* mRNA for 23 kDa cell surface protein," Apr. 26, 1995.

Houghten, "Relative importance of position and individual amino acid residues in peptide antigen–antibody interactions: Implications in the mechanism of antigenic drift and antigenic shift," *Vaccines* 86:21–25, 1986.

Mosmann and Fong, "Specific assay for cytokine production by T cells," *Journal of Immunological Methods* 116:151–158, 1989.

Mougneau et al., "Expression cloning of a protective Leishmania antigen," *Science* 268:563–566, 1995.

Nascimento et al., "Vaccination of humans against cutaneous leishmaniasis: cellular and humoral immune responses," *Infection and Immunity* 58(7):2198–2203, Jul. 1990.

Osland et al., "Isolation and characterization of recombinant antigens form *Leishmania aethiopica* that react with human antibodies," *Infection and Immunity* 60(4):1368–1374.

Pan et al., "Developmental life cycle of Leishmania—cultivation and characterization of cultured extracellular amastigotes," *The Journal of Eukaryotic Microbiology* 40(2):213–223, Mar.–Apr. 1993.

Pir2 Database Accession No. S54162, "*Leishmania donovani*," Jul. 8, 1995.

Reiner and Locksley, "The regulation of immunity to *Leishmania major*," *Annu. Rev. Immunol.* 13:151–177, 1995.

Rodrigues et al., "Selective inability of spleen antigen presenting cells from *Leishmania donovani* infected hamsters to mediate specific T cell proliferation to parasite antigens," *Parasite Immunology* 14(1):49–58, Jan. 1992.

Shapira and Pedraza, "Sequence analysis and transcriptional inactivation of heat shock protein 83 of *Leishmania mexicanca amazonesis*," *Molecular and Biochemical Pathology* 42(2):247–255, 1990.

Skeiky et al., "A recombinant Leishmania antigen that stimulates human peripheral blood mononuclear cells to express a Th1–type cytokine profile and to produce interleukin 12," *Journal of Experimental Medicine* 181(4):1527–1537, 1995.

Skeiky et al., "Proliferative and cytokine responses of human PBMC to cloned *Leishmania braziliensis* heat shock and ribosomal antigens," *Journal of Immunology* 158(8 pt. 2):93A, Abstract #517, 1993.

Skeiky et al., "Antigens shared by Leishmania species and *Trypanosoma cruzi*: immunological comparison of the acidic ribosomal P0 proteins," *Infection and Immunity* 62(5):1643–1651, May 1994.

Skeiky et al., "Cloning and expression of *Trypanosoma cruzi* ribosomal protein PO and epitope analysis of Anti–PO autoantibodies in Chagas' disease patients," *J. Exp. Med.* 176(1):201–211, Jul. 1, 1992.

Webb et al., "Human and murine immune responses to a novel *Leishmania major* recombinant protein encoded by members of a multicopy gene family," *Infection and Immunity* 66(7):3279–3289, Jul. 1998.

Yang et al., "Identification and characterization of host–protective T cell epitopes of a major surface glycoprotein (gp63) from *Leishmania major*," *Immunology* 72(1):3–9, Jan. 1991.

Levinson et al., Medical Microbiology & Immunology, 1994, pg. 293.

Webb, J.R. et al., "Molecular Cloning of a Novel Protein Antigen of *Leishmania major* That Elicits a Potent Immune Response in Experimental Murine Leishmaniasis." Journal of Immunology 157: 5034–5041, 1996.

Genbank Database, Accession No. U19888, Apr. 21, 1995.

Singh, S. et al., "Diagnostic and prognostic value of K39 recombinant antigen in Indian leishmaniasis," *Journal of Parasitology* 81(6): 1000–1003, Dec. 1995.

\* cited by examiner

```
                     ------------------------------------------------SLTDPAVLGEETHLRVRVVPDKANKTLTVEDNGIGMTK   85
         MTETFAFQAEINQLMSLIINTFYSNKEIFLRDVISNASDACDKIRYQ.........DA.R.C.......E..............    85
.........................................EL..............NQ....D.S...I................T......   85
MPEETQTQDQPMEEEEV..........A.............EL...S...L.....E.....SK.DSGKE.HINLI.N.QDRA..IV.T......  100

P                                       P
ADLVNNLGTIARSGTKAFMEALEAGGDMSMIGQFGVGFYSAYLVADRVTVVSKNNSDEAY-WESSAGGTFTITSVQESDMKRGTSTTLHLKEDQQEYLEE  184
...................A......................T.....V.V..........AP.....LPARI........L....A  185
.E...................................................D....T.....V.PTPDC.L....RIV...........  185
...I......K......Q..A.I..........EK...IT.H.D..Q.A.......S..VRTDTGEP.G...KVI.......T......  200

RRVKELIKKHSEFIGYDIELMVEKTAEKEVTDE----DEEEDESKKKSCGDEGEPKVEEVTEGG-ED-KKKKTKKVKEVKKT-YEVK---NKHKPLWTRD  274
..L...................T........----.....---A..ADE.GE..........-E..-.........T.E-...Q---..........  272
..L.D..........AT........----...D.--AAATKNEEGE.......KDDAE.GE..........TQE-FV.Q---..........  275
..I..IV....Q.....P.T.F...ERD....S.DEAEEK.DKE.E.E.EEKESEDKPEI.DVGSDE..E..DGD..K.KKI.EK.ID.EEL..T..I...N  300

┌── Lbhsp83b
TKDVTKEEYAAFYKAISNDWEDTAATKHFSVEGQLEFRAIAFVPKRAPFDMFEPNKKRNNIKLYVRRVFIMDNCEDLCPDWLGFVKGVVDSEDLPLNISR  374
P.......................PP.............M..........L...........................  372
P...............EPLS............L..........S...............E..A..R...........  375
PD.I.N...GE...SLT.....HL.V.......LL...R.....L..NR..K..........E.I.EY.N.IR.......  400

ENLQQNKILKVIRKNIVKKCLELFEEIAENKEDYKQFYEQFGKNIKLGIHEDTANRKKLMELLRFYSTESGEEMTTLKDYVTRMKPEQKSIYYITGDSKK  474
................M..V..............................................V.........A..N........  472
............A........K......V......S.........H.S...D........EG..C..V......  475
.M...S........L........T.L..D..N..K.....S.........SQ.....S....Y.TSA..D..VS....C....EN..H.....ET.D  500

KLESSPFIEKARRCGLEVLFMTEPIDEYVMQQVKDFEDKKFACLTKEGVHFEESEEEKKQREEKKAACEKLCKTMKEVLGDKVEKVTVSERLLTSPCILV  574
..........Q.K.R.F........Y................E..T................S......  572
...T.....Q..R.F......I............T......E.T.Y.R...A..D........V.....A.......  575
QVAN.A.V.RL.KH....IY.I......CV..L.E..G.TLVSV....LELP.D.....KQ....TKF.N...I..DI.EK.....V..N..V....C..  600

P
TSEFGWSAHMEQIMRNQALRDSSMAQYMVSKKTMEVNPDHPIIKELRRRVEADENDKAVKDLVFLLFDTSLLTSGFQLDDPTGYAERINRMIKLGLSLDE  674
............M...............M.....L..K............................E..-.......  671
............SA..M......I..A...V..K.........Y.....A.....T.....S....H..........D  675
..TY..T.N..R..KA.....N.TMG..AA..HL.I...S..ET..QKA...K...S.....I..YE.A..S...S.E..QTH.N..Y.......GI..  700

EE--EEVA-EAPPAEAAPAEVTAGTSSMEQVD   703   Lbhsp83
..E--.E.V..AV..T............L..   701   Lahsp83
.D---NGNE..E..A.V...PV.........   704   Tchsp83
DDPTADDTSA.VTE.MP.L.GDDD..R..E..  734   Huhsp89
```

Fig. 19

```
GAATTCGGCACGAGGTTTCTGTACTTTATTGCTTCCAGCCTTTATTCACTCTTCGATTTCCTCTAACACCATGTCCTCCGAGCGCACCTTTATTGCCGTC
|5'-Adaptor|Splicad-leader|        5'-UT                                                              |  100
                                                                                M  S  S  E  R  T  F  I  A  V
AAGCCGGACGGCGTGCAGCGCGGCCTCGTTGGCGAGATCATCGCCCGCTTCGAGCGCAAGGGCTACAAGCTCGTCGCCTTGAAGATACTGCAGCCGACGA  200

K  P  D  G  V  Q  R  G  L  V  G  E  I  I  A  R  F  E  R  K  G  Y  K  L  V  A  L  K  I  L  Q  P  T
CGGAGCAGGCCCAGGGTCACTATAAGGACCTTTGCTCCAAGCCGTTTTTCCCGGCCCTTGTGAAGTACTTCTCCTCTGGCCCGATCGTGTGTATGGTGTG  300

T  E  Q  A  Q  G  H  Y  K  D  L  C  S  K  P  F  F  P  A  L  V  K  Y  F  S  S  G  P  I  V  C  M  V  W
GGAGGGTAAGAACGTGGTGAAGAGCGGCCGCGTGCTGCTCGGCGCGACGAACCCGGCCGACTCACAGCCCGGCACGATCCGTGGCGACTTTGCCGTGGAT  400

E  G  K  N  V  V  K  S  G  R  V  L  L  G  A  T  N  P  A  D  S  Q  P  G  T  I  R  G  D  F  A  V  D
GTGGGCCGCAACGTGTGCCACGGGTCCGACTCTGTGGAGAGCGCGGAGCGCGAGATCGCCTTTTGGTTCAAGGCGGATGAGATCGCGAGCTGGACGTCGC  500

V  G  R  N  V  C  H  G  S  D  S  V  E  S  A  E  R  E  I  A  F  W  F  K  A  D  E  I  A  S  W  T  S
ACTCCGTGTCCCAGATCTATGAGTAACGGTGATTGCGGACACGCTTTGAGGACGTAGCTGTACCCCCAATGAATTCTTCTCTGAAAACCACATCATAAGC  600
                                    →|               3'-UT                                         |
 H  S  V  S  Q  I  Y  E
CTCTTAAGAGGTTATTTTTCTTGATCGATGCCCGGTGGTGACCAGCACCATTCCTTTATCGGATTCACTCACACTCCTAGCGAATCATGTAGTGCGGTGA  700
                                            3'-UT

GAGTGGGCTCTGGAGGAGACTGTTGTGTAGCCATGGCTTCAGGAGAGAAAACAAAATACAAGGAAAGGCAATATGTAACTATGGGGTTCCCTTTTTTACT  800
                                            3'-UT

ATGCAAAGTTTTTATAACTCCTGATCGGCAAAAACAACAACAACCGCCATACACCAAGAGCAAATGCTTTCTTCTGCGGACTGTGCTTCTGTTTTTTTT  900
                                            3'-UT

ATGAAGGAGTGACTCGCGCGATGAAAAGTGTGTGCGTGGGAGATGTATTTCCTTTTTTTTGTTCATAGTGGCGACAGCTCACTGTTGACGATGACAAAAAA 1000
                                            3'-UT

AAAAAAAAAAAAAACTCGAG  1019
|Poly A tail/ Xhoi >
```

Fig. 21

SEQUENCE LISTING

<160> NUMBER OF SEQ ID NOS: 122

<210> SEQ ID NO 1
<211> LENGTH: 3134
<212> TYPE: DNA
<213> ORGANISM: Leishmania major
<220> FEATURE:
<221> NAME/KEY: misc_feature
<222> LOCATION: (1)...(3134)
<223> OTHER INFORMATION: n = A,T,C or G

<400> SEQUENCE: 1

| | | | | | |
|---|---|---|---|---|---|
| caagtgtcga | aggacagtgt | tcnccgtgtg | agatcgccgg | ctgtgcgtgt | gaaggcggtg | 60 |
| ccatcggana | aacaacaccg | gtggnnccgc | aggaaaccat | ctttctccgc | aggtctcttt | 120 |
| ttgttgtcga | ttgagagtgc | nccaaaccct | gctggtgccc | ttctcacata | tcatgttttt | 180 |
| cgttgtgcgc | tcgctttgcc | tttcctctcc | tttccctctc | ttccgtggtg | ccgtgtatac | 240 |
| ttctggcacc | cgctacgtca | cttcgctggt | ttgaacagaa | ccactgtgaa | cacccacggg | 300 |
| cgatcgcaca | catacacatc | cctcactcac | acacacagct | acatctatcc | tacataaagc | 360 |
| tgaaaaaaaa | gtctacgaac | aattttgttt | ttacagtgcg | ttgccgcaca | tttctccgta | 420 |
| atggacgcaa | ctgagctgaa | gaacaagggg | aacgaagagt | tctccgccgg | ccgctatgtg | 480 |
| gaggcggtga | actacttctc | aaaggcgatc | cagttggatg | agcagaacag | tgtcctctac | 540 |
| agcaaccgct | ccgcctgttt | tgcagccatg | cagaaataca | aggacgcgct | ggacgacgcc | 600 |
| gacaagtgca | tctcgatcaa | gccgaattgg | gccaagggct | acgtgcgccg | aggagcagct | 660 |
| ctccatggca | tgcgccgcta | cgacgatgcc | attgccgcgt | atgaaaaggg | gctcaaggtg | 720 |
| gacccttcca | acagcggctg | cgcgcagggc | gtgaaggacg | tgcaggtagc | caaggcccgc | 780 |
| gaagcacgtg | accccatcgc | tcgcgtcttc | accccggagg | cgttccgcaa | gatccaagag | 840 |
| aatcccaagc | tgtctctact | tatgctgcag | ccggactacg | tgaagatggt | agacaccgtc | 900 |
| atccgcgacc | cttcgcaggg | ccggctgtac | atggaagacc | agcgctttgc | cctgacgctc | 960 |
| atgtacctga | gcggaatgaa | gattcccaac | gatggtgatg | gcgaggagga | ggaacgtccg | 1020 |
| tctgcgaagg | cggcagagac | agcgaagcca | aagaggagaa | agcctctcac | cgacaacgag | 1080 |
| aaggaggccc | tggcgctcaa | ggaggagggc | aacaagctgt | acctctcgaa | gaagtttgag | 1140 |
| gaggcgctga | ccaagtacca | agaggcgcag | gtgaaagacc | ccaacaacac | tttatacatt | 1200 |
| ctgaacgtgt | cggccgtgta | cttcgagcag | ggtgactacg | acaagtgcat | cgccgagtgc | 1260 |
| gagcacggta | tcgagcacgg | tcgcgagaac | cactgcgact | acacaatcat | tgcgaagctc | 1320 |
| atgacccgga | acgccttgtg | cctccagagg | cagaggaagt | acgaggctgc | tatcgacctt | 1380 |
| tacaagcgcg | cccttgtcga | gtggcgtaac | cctgacaccc | tcaagaagct | gacggagtgc | 1440 |
| gagaaggagc | accaaaaggc | ggtggaggaa | gcctacatcg | atcctgagat | cgcgaagcag | 1500 |
| aagaaagacg | aagtaacca | gtacttcaag | gaggataagt | tccccgaggc | cgtggcagcg | 1560 |
| tacacggagg | ccatcaagcg | caaccctgcc | gagcacacct | cctacagcaa | tcgcgcggcc | 1620 |
| gcgtacatca | agcttggagc | cttcaacgac | gccctcaagg | acgcggagaa | gtgcattgag | 1680 |
| ctgaagcccg | actttgttaa | gggctacgcg | cgcaagggtc | atgcttactt | ttggaccaag | 1740 |
| cagtacaacc | gcgcgctgca | ggcgtacgat | gagggcctca | aggtggaccc | gagcaatgcg | 1800 |
| gactgcaagg | atgggcggta | tcgcacaatc | atgaagattc | aggagatggc | atctggccaa | 1860 |
| tccgcggatg | gcgacgaggc | ggcgcgccgg | gccatggacg | atcctgaaat | cgcggcaatc | 1920 |

-continued

```
atgcaagata gctacatgca actagtgttg aaggagatgc agaacgatcc cacgcgcatt   1980
caggagtaca tgaaggactc cgggatctca tcgaagatca caagctgat ttcagctggc    2040 atcattcgtt ttggtcagta gacttctacg ctgcctcatc ttttccgtgt ctttgcgtcg   2100
gcgggtatcg taaagcacaa taaagcagcg attcacatgc acgagtaaag tgctgcgcct   2160
ctcaaacacg acgtcgaggc tgtggtgcag atgcgcgtcc tgcatgaagg tagtgaagag   2220
gaaagtaagg gatgttgttt gtgggccttc gtggctgcgc acacacctct tatctccttc   2280
gcttggtacc ttctcccttt ttcgtcttca ccccccttc tcttctcacg ctctccctgg    2340
cgcggtggtg caacgatttc gttttattta cgtctgtgta gctcctctat caacggtgc    2400 gatgacgcta acgaagctgg cctgtattcg gctaaggcga aggcaaaaga ctaggagggg   2460 gggggaagg agacggcgtg accatcactg cgaagaaaca agccgaagaa aaggccccga    2520
acgcctgcat ttccgcgcgc cctcgcccgc cttccttcct tccttcgctc tctctctctc   2580
tctctctcgc tatcttctca acggagacat gaaaggcgtt tgttaggaaa agagggggg    2640 gggaagagtg ggacgacgcg ctgcgtcttt tgggcactgg tcacgtgcgt caccctcttt   2700
ttttatctct attggcactg tcttgtttct tttccctttc ctatcatacg cgtctcgcaa   2760
acgactccgc gctgagcagc catgtgctgc ggcgtggagg aagtacacag acatcacgga   2820
tgcatatgtg cgcgtccgtg tacgcgcttg tatggggctt ctaacagcgc ctgtgtgtgt   2880
ttgtgtgtgt gtgtgtgtgt gtgtctgtgt atttcgagcg tctgtatgct attctattaa   2940
gcaccgaaga agagacacac acgacagcga aggagatggt gtcggctttt cggctaatca   3000
ctcccttcca tagcttctct gaaggaggct ctcttccaga ggaatagact gcagatgggg   3060
tccacgttta tctgaggagt caacggaaaa aaaaaaaaa aaaaaaaaa aaaaaaaa     3120 aaaaaaaact cgag                                                    3134
```

<210> SEQ ID NO 2
<211> LENGTH: 546
<212> TYPE: PRT
<213> ORGANISM: Leishmania major

<400> SEQUENCE: 2

```
Met Asp Ala Thr Glu Leu Lys Asn Lys Gly Asn Glu Glu Phe Ser Ala
 1               5                  10                  15

Gly Arg Tyr Val Glu Ala Val Asn Tyr Phe Ser Lys Ala Ile Gln Leu
            20                  25                  30

Asp Glu Gln Asn Ser Val Leu Tyr Ser Asn Arg Ser Ala Cys Phe Ala
        35                  40                  45

Ala Met Gln Lys Tyr Lys Asp Ala Leu Asp Asp Ala Asp Lys Cys Ile
    50                  55                  60

Ser Ile Lys Pro Asn Trp Ala Lys Gly Tyr Val Arg Arg Gly Ala Ala
65                  70                  75                  80

Leu His Gly Met Arg Arg Tyr Asp Asp Ala Ile Ala Ala Tyr Glu Lys
                85                  90                  95

Gly Leu Lys Val Asp Pro Ser Asn Ser Gly Cys Ala Gln Gly Val Lys
            100                 105                 110

Asp Val Gln Val Ala Lys Ala Arg Glu Ala Arg Asp Pro Ile Ala Arg
        115                 120                 125

Val Phe Thr Pro Glu Ala Phe Arg Lys Ile Gln Glu Asn Pro Lys Leu
    130                 135                 140

Ser Leu Leu Met Leu Gln Pro Asp Tyr Val Lys Met Val Asp Thr Val
```

-continued

```
            145                 150                 155                 160
    Ile Arg Asp Pro Ser Gln Gly Arg Leu Tyr Met Glu Asp Gln Arg Phe
                    165                 170                 175

Ala Leu Thr Leu Met Tyr Leu Ser Gly Met Lys Ile Pro Asn Asp Gly
                180                 185                 190

Asp Gly Glu Glu Glu Arg Pro Ser Ala Lys Ala Ala Glu Thr Ala
                195                 200                 205

Lys Pro Lys Glu Glu Lys Pro Leu Thr Asp Asn Glu Lys Glu Ala Leu
                210                 215                 220

Ala Leu Lys Glu Glu Gly Asn Lys Leu Tyr Leu Ser Lys Lys Phe Glu
    225                 230                 235                 240

Glu Ala Leu Thr Lys Tyr Gln Glu Ala Gln Val Lys Asp Pro Asn Asn
                    245                 250                 255

Thr Leu Tyr Ile Leu Asn Val Ser Ala Val Tyr Phe Glu Gln Gly Asp
                260                 265                 270

Tyr Asp Lys Cys Ile Ala Glu Cys Glu His Gly Ile Glu His Gly Arg
                275                 280                 285

Glu Asn His Cys Asp Tyr Thr Ile Ile Ala Lys Leu Met Thr Arg Asn
    290                 295                 300

Ala Leu Cys Leu Gln Arg Gln Arg Lys Tyr Glu Ala Ala Ile Asp Leu
    305                 310                 315                 320

Tyr Lys Arg Ala Leu Val Glu Trp Arg Asn Pro Asp Thr Leu Lys Lys
                    325                 330                 335

Leu Thr Glu Cys Glu Lys Glu His Gln Lys Ala Val Glu Glu Ala Tyr
                340                 345                 350

Ile Asp Pro Glu Ile Ala Lys Gln Lys Lys Asp Glu Gly Asn Gln Tyr
                355                 360                 365

Phe Lys Glu Asp Lys Phe Pro Glu Ala Val Ala Ala Tyr Thr Glu Ala
                370                 375                 380

Ile Lys Arg Asn Pro Ala Glu His Thr Ser Tyr Ser Asn Arg Ala Ala
    385                 390                 395                 400

Ala Tyr Ile Lys Leu Gly Ala Phe Asn Asp Ala Leu Lys Asp Ala Glu
                    405                 410                 415

Lys Cys Ile Glu Leu Lys Pro Asp Phe Val Lys Gly Tyr Ala Arg Lys
                420                 425                 430

Gly His Ala Tyr Phe Trp Thr Lys Gln Tyr Asn Arg Ala Leu Gln Ala
                435                 440                 445

Tyr Asp Glu Gly Leu Lys Val Asp Pro Ser Asn Ala Asp Cys Lys Asp
                450                 455                 460

Gly Arg Tyr Arg Thr Ile Met Lys Ile Gln Glu Met Ala Ser Gly Gln
    465                 470                 475                 480

Ser Ala Asp Gly Asp Glu Ala Ala Arg Arg Ala Met Asp Asp Pro Glu
                    485                 490                 495

Ile Ala Ala Ile Met Gln Asp Ser Tyr Met Gln Leu Val Leu Lys Glu
                500                 505                 510

Met Gln Asn Asp Pro Thr Arg Ile Gln Glu Tyr Met Lys Asp Ser Gly
                515                 520                 525

Ile Ser Ser Lys Ile Asn Lys Leu Ile Ser Ala Gly Ile Ile Arg Phe
                530                 535                 540

Gly Gln
    545

<210> SEQ ID NO 3
```

<211> LENGTH: 676
<212> TYPE: DNA
<213> ORGANISM: Leishmania donovani

<400> SEQUENCE: 3

```
aattcggcac gaggcattgt gcataatggt caagtcccac tacatctgcg cgggccgcct      60
ggtgcgcatc ctgcgtggcc cccgccagga ccgcgttggt gtgatcgtcg acattgtcga     120
cgcgaaccgc gtgctggtgg agaacccgga ggacgcgaag atgtggcgcc acgtgcagaa     180
cctgaagaac gtggagccgc tgaagtactg cgtgagcgtc agccgcaact gcagcgcgaa     240
ggcgctgaag gatgcgctgg cctcgtcgaa ggcgctggag aagtacgcga agacgcgcac     300
tgctgcgcgc gtgaggcga agaaggcgtg cgccgcgtcg acggacttcg agcgctacca     360
gctgcgcgtt gcgcgccgtt ctcgcgcgca ctgggcgcgc aaggtgttcg acgagaagga     420
cgcgaagacg cccgtgtcgt ggcacaaggt tgcgctgaag aagatgcaga gaaggccgc      480
aaagatggac tcgaccgagg gcgctaagag gcgcatgcag aaggcgatcg ctgcccgcaa     540
ggcgaaaaag taaggccata ccctcacttc gcttgtttcg tgattttcg tgggagtcgg      600
tggccctacc agcggtcttt cattggctta tttctatccg gtctgaaaga ggtacaaaaa     660
aaaaaaaaaa aaaaaa                                                    676
```

<210> SEQ ID NO 4
<211> LENGTH: 175
<212> TYPE: PRT
<213> ORGANISM: Leishmania donovani

<400> SEQUENCE: 4

```
Met Val Lys Ser His Tyr Ile Cys Ala Gly Arg Leu Val Arg Ile Leu
  1               5                  10                  15

Arg Gly Pro Arg Gln Asp Arg Val Gly Val Ile Val Asp Ile Val Asp
             20                  25                  30

Ala Asn Arg Val Leu Val Glu Asn Pro Glu Asp Ala Lys Met Trp Arg
         35                  40                  45

His Val Gln Asn Leu Lys Asn Val Glu Pro Leu Lys Tyr Cys Val Ser
     50                  55                  60

Val Ser Arg Asn Cys Ser Ala Lys Ala Leu Lys Asp Ala Leu Ala Ser
 65                  70                  75                  80

Ser Lys Ala Leu Glu Lys Tyr Ala Lys Thr Arg Thr Ala Ala Arg Val
                 85                  90                  95

Glu Ala Lys Lys Ala Cys Ala Ala Ser Thr Asp Phe Glu Arg Tyr Gln
            100                 105                 110

Leu Arg Val Ala Arg Arg Ser Arg Ala His Trp Ala Arg Lys Val Phe
        115                 120                 125

Asp Glu Lys Asp Ala Lys Thr Pro Val Ser Trp His Lys Val Ala Leu
    130                 135                 140

Lys Lys Met Gln Lys Lys Ala Ala Lys Met Asp Ser Thr Glu Gly Ala
145                 150                 155                 160

Lys Arg Arg Met Gln Lys Ala Ile Ala Ala Arg Lys Ala Lys Lys
                165                 170                 175
```

<210> SEQ ID NO 5
<211> LENGTH: 2040
<212> TYPE: DNA
<213> ORGANISM: Leishmania braziliensis

<400> SEQUENCE: 5

-continued

```
cgcggtggcg gccgctctag aactagtgga tcccccgggc tgcaggaatt cggcacgaga      60
gagcctgacg gacccggcgg tgctgggcga ggagactcac ctgcgcgtcc gcgtggtgcc     120
ggacaaggcg aacaagacgc tgacggtgga ggataacggc atcggcatga ccaaggcgga    180
cctcgtgaac aatctgggca cgatcgcgcg ctccggcacg aaggctttca tggaggcact    240
ggaggccggc ggcgacatga gcatgatcgg ccagttcggt gtcggcttct actccgcgta    300
ccttgtggcg gaccgcgtga cggtggtgtc gaagaacaac tcggacgagg cgtactggga    360
atcgtctgcg gggggcacgt tcaccatcac gagcgtgcag gagtcggaca tgaagcgcgg    420
cacgagtaca acgctgcacc taaaggagga ccagcaggag tacctggagg agcgccgggt    480
gaaggagctg atcaagaagc actccgagtt catcggctac gacatcgagc tgatggtgga    540
gaagacggcg gagaaggagg tgacggacga ggacgaggag gaggacgagt cgaagaagaa    600
gtcctgcggg gacgagggcg agccgaaggt ggaggaggtg acggagggcg gcgaggacaa    660
gaagaagaag acgaagaagg tgaaggaggt gaagaagacg tacgaggtca gaacaagca    720
caagccgctc tggacgcgcg cacgaaggca cgtgacgaag gaggagtacg cggccttcta    780
caaggccatc tccaacgact gggaggacac ggcggcgacg aagcacttct cggtggaggg    840
ccagctggag ttccgcgcga tcgcgttcgt gccgaagcgc gcgccgttcg acatgttcga    900
gccgaacaag aagcgcaaca acatcaagct gtacgtgcgc gcgtgttca tcatggacaa    960
ctgcgaggac ctgtgcccgg actggctcgg cttcgtgaag gcgtcgtgg acagcgagga   1020
cctgccgctg aacatctcgc gcgagaacct gcagcagaac aagatcctga aggtgatccg   1080
caagaacatc gtgaagaagt gcctggagct gttcgaagag atagcggaga caaggagga   1140
ctacaagcag ttctacgagc agttcggcaa gaacatcaag ctgggcatcc acgaggacac   1200
ggcgaaccgc aagaagctga tggagttgct gcgcttctac agcaccgagt cggggggagga   1260
gatgacgaca ctgaaggact acgtgacgcg catgaagccg gagcagaagt cgatctacta   1320
catcactggc gacagcaaga agaagctgga gtcgtcgccg ttcatcgaga aggcgagacg   1380
ctgcgggctc gaggtgctgt tcatgacgga gccgatcgac gagtacgtga tgcagcaggt   1440
gaaggacttc gaggacaaga gttcgcgtg cctgacgaag gaaggcgtgc acttcgagga   1500
gtccgaggag gagaagaagc agcgcgagga gaagaaggcg gcgtgcgaga agctgtgcaa   1560
gacgatgaag gaggtgctgg gcgacaaggt ggagaaggtg accgtgtcgg agcgcctgtt   1620
gacgtcgccg tgcatcctgg tgacgtcgga gtttgggtgg tcggcgcaca tggaacagat   1680
catgcgcaac caggcgctgc gcgactccag catggcgcag tacatggtgt ccaagaagac   1740
gatggaggtg aaccccgacc accccatcat caaggagctg cgccgccgcg tggaggcgga   1800
cgagaacgac aaggccgtga aggacctcgt cttcctgctc ttcgacacgt cgctgctcac   1860
gtccggcttc cagctggatg acccccaccgg ctacgccgag cgcatcaacc gcatgatcaa   1920
gctcggcctg tcgctcgacg aggaggagga ggaggtcgcc gaggcgccgc cggccgaggc   1980
agcccccgcg gaggtcaccg ccggcacctc cagcatggag caggtggact gagccggtaa   2040
```

<210> SEQ ID NO 6
<211> LENGTH: 656
<212> TYPE: PRT
<213> ORGANISM: Leshmania brailiensis

<400> SEQUENCE: 6

```
Ser Leu Thr Asp Pro Ala Val Leu Gly Glu Glu Thr His Leu Arg Val
 1               5                  10                  15
```

-continued

```
Arg Val Val Pro Asp Lys Ala Asn Lys Thr Leu Thr Val Glu Asp Asn
            20                  25                  30
Gly Ile Gly Met Thr Lys Ala Asp Leu Val Asn Asn Leu Gly Thr Ile
        35                  40                  45
Ala Arg Ser Gly Thr Lys Ala Phe Met Glu Ala Leu Glu Ala Gly Gly
    50                  55                  60
Asp Met Ser Met Ile Gly Gln Phe Gly Val Gly Phe Tyr Ser Ala Tyr
65                  70                  75                  80
Leu Val Ala Asp Arg Val Thr Val Val Ser Lys Asn Asn Ser Asp Glu
                85                  90                  95
Ala Tyr Trp Glu Ser Ser Ala Gly Gly Thr Phe Thr Ile Thr Ser Val
            100                 105                 110
Gln Glu Ser Asp Met Lys Arg Gly Thr Ser Thr Thr Leu His Leu Lys
        115                 120                 125
Glu Asp Gln Gln Glu Tyr Leu Glu Glu Arg Arg Val Lys Glu Leu Ile
    130                 135                 140
Lys Lys His Ser Glu Phe Ile Gly Tyr Asp Ile Glu Leu Met Val Glu
145                 150                 155                 160
Lys Thr Ala Glu Lys Glu Val Thr Asp Glu Asp Glu Glu Glu Asp Glu
                165                 170                 175
Ser Lys Lys Lys Ser Cys Gly Asp Glu Gly Pro Lys Val Glu Glu
            180                 185                 190
Val Thr Glu Gly Gly Glu Asp Lys Lys Lys Thr Lys Lys Val Lys
        195                 200                 205
Glu Val Lys Lys Thr Tyr Glu Val Lys Asn Lys His Lys Pro Leu Trp
    210                 215                 220
Thr Arg Asp Thr Lys Asp Val Thr Lys Glu Glu Tyr Ala Ala Phe Tyr
225                 230                 235                 240
Lys Ala Ile Ser Asn Asp Trp Glu Asp Thr Ala Ala Thr Lys His Phe
                245                 250                 255
Ser Val Glu Gly Gln Leu Glu Phe Arg Ala Ile Ala Phe Val Pro Lys
            260                 265                 270
Arg Ala Pro Phe Asp Met Phe Glu Pro Asn Lys Lys Arg Asn Asn Ile
        275                 280                 285
Lys Leu Tyr Val Arg Arg Val Phe Ile Met Asp Asn Cys Glu Asp Leu
    290                 295                 300
Cys Pro Asp Trp Leu Gly Phe Val Lys Gly Val Val Asp Ser Glu Asp
305                 310                 315                 320
Leu Pro Leu Asn Ile Ser Arg Glu Asn Leu Gln Gln Asn Lys Ile Leu
                325                 330                 335
Lys Val Ile Arg Lys Asn Ile Val Lys Lys Cys Leu Glu Leu Phe Glu
            340                 345                 350
Glu Ile Ala Glu Asn Lys Glu Asp Tyr Lys Gln Phe Tyr Glu Gln Phe
        355                 360                 365
Gly Lys Asn Ile Lys Leu Gly Ile His Glu Asp Thr Ala Asn Arg Lys
    370                 375                 380
Lys Leu Met Glu Leu Leu Arg Phe Tyr Ser Thr Glu Ser Gly Glu Glu
385                 390                 395                 400
Met Thr Thr Leu Lys Asp Tyr Val Thr Arg Met Lys Pro Glu Gln Lys
                405                 410                 415
Ser Ile Tyr Tyr Ile Thr Gly Asp Ser Lys Lys Leu Glu Ser Ser
            420                 425                 430
Pro Phe Ile Glu Lys Ala Arg Arg Cys Gly Leu Glu Val Leu Phe Met
```

-continued

```
                435                 440                 445

Thr Glu Pro Ile Asp Glu Tyr Val Met Gln Gln Val Lys Asp Phe Glu
            450                 455                 460
Asp Lys Lys Phe Ala Cys Leu Thr Lys Glu Gly Val His Phe Glu Glu
465                 470                 475                 480
Ser Glu Glu Glu Lys Lys Gln Arg Glu Lys Lys Ala Ala Cys Glu
                485                 490                 495
Lys Leu Cys Lys Thr Met Lys Glu Val Leu Gly Asp Lys Val Glu Lys
                500                 505                 510
Val Thr Val Ser Glu Arg Leu Leu Thr Ser Pro Cys Ile Leu Val Thr
            515                 520                 525
Ser Glu Phe Gly Trp Ser Ala His Met Glu Gln Ile Met Arg Asn Gln
530                 535                 540
Ala Leu Arg Asp Ser Ser Met Ala Gln Tyr Met Val Ser Lys Lys Thr
545                 550                 555                 560
Met Glu Val Asn Pro Asp His Pro Ile Ile Lys Glu Leu Arg Arg Arg
                565                 570                 575
Val Glu Ala Asp Glu Asn Asp Lys Ala Val Lys Asp Leu Val Phe Leu
            580                 585                 590
Leu Phe Asp Thr Ser Leu Leu Thr Ser Gly Phe Gln Leu Asp Asp Pro
            595                 600                 605
Thr Gly Tyr Ala Glu Arg Ile Asn Arg Met Ile Lys Leu Gly Leu Ser
        610                 615                 620
Leu Asp Glu Glu Glu Glu Val Ala Glu Ala Pro Pro Ala Glu Ala
625                 630                 635                 640
Ala Pro Ala Glu Val Thr Ala Gly Thr Ser Ser Met Glu Gln Val Asp
                645                 650                 655

<210> SEQ ID NO 7
<211> LENGTH: 1771
<212> TYPE: DNA
<213> ORGANISM: Leishmania tropica

<400> SEQUENCE: 7
caggcccgcg tccaggccct cgaggaggca gcgcgtctcc gcgcggagct ggaggcggcc      60
gaggaggcgg cccgcctgga tgtcatgcat gcggccgagc aggcccgtgt ccaggccctc     120
gaggaggcag cgcgtctccg cgcggagctg gaggaggccg aggaggcggc ccgcctggat     180
gtcatgcatg cggccgagca ggcccgcgtc caggccctcg aggaggcagc gcgtctccgc     240
gcggagctgg aggctgccga ggaggcggcc cgcctggagg ccatgcacga ggccgagcag     300
gcccgctccc aggccctcga ggaggcagcg cgtctccgcg cggagctgga ggaagccgag     360
gaggcggccc gcctggatgt catgcatgcg ccgagcagg cccgcgtcca ggccctcgag     420
gaggcagcgc gtctccgcgc ggagctggag gaggccgagg aggcggcccg cctggaggcc     480
atgcacgagg ccgagcaggc ccgctcccag gccctcgagg aggcagcgcg tctccgcgcg     540
gagctggagc cggccgagga ggcggcccgc ctggatgtca tgcacgaggc cgagcaggcc     600
cgtgtccagg ccctcgagga ggcggcgcgc ctggatgtca tgcacgaggc cgagcaggcc     660
cgcgtccagg ccctcgagga ggcagcgcgt tccgcgcgg agctggaggc ggccgaggag     720
gcggcccgcc tggatgtcat gcacgaggcc gagcaggccc gcgtccaggc cctcgaggag     780
gcagcgcgtc tccgcgcgga gctggaggcg gccgaggagg cggcccgcct ggatgtcatg     840
cacgagggcg agcaggcccg tgtccaggcc ctcgaggagg cggcccgcct ggaggccatg     900
```

-continued

| | |
|---|---|
| cacgaggccg agcaggcccg ctcccaggcc ctcgaggagg cagcgcgtct ctgcgcggag | 960 |
| ctggaggctg aggaggagga aaaagatgag cggccggcga cgtcgagcta cagcgaggag | 1020 |
| tgcaaagggc gactgctatc gagggcgcgg ccggatccgc ggaggccgct gccgcggccg | 1080 |
| ttcattggga tgtcactgtt ggaggatgtg agaagagta ttctcattgt ggacgggctc | 1140 |
| tacagggatg ggccggcgta ccagacgggc atccgcctcg gggatgtcct cttgcgtatc | 1200 |
| gcggggtttt acgtggattc aatagcgaag gcgaggcagg tggtcgatgc gcgttgccgc | 1260 |
| tgcggctgcg tcgttcccgt gacgctggcg acgaagatga accagcagta cagcgtggct | 1320 |
| ctgtatatca tgacggtgga tccgcagcac aacgacaagc ccttttttt tgatgtgcac | 1380 |
| atccaccacc gcatcgagag ctcgcacatg gggaagaagg cgcagtggat ggaagttctt | 1440 |
| gagagcccat ccgtatcttc ggctgccacc acccctctcg tgccgctctt gcgtgagccg | 1500 |
| acgccgcgta ggggctcaga gctgcagtca agtgctcgtt ccgccttcgt tgccacgtct | 1560 |
| tacttctcga gcgcgcgcag gtcggtcagc tcagaaagtg agcgaccgcg cgggtcctct | 1620 |
| agcgtggcta tggcggagga ggcgatcgcg ctggcgccgc aagggtatac cccacccaac | 1680 |
| caagtgcgcg gccgtagttg acgtctctgt gtgagtgtgt gtcgctccgt ctccttcctt | 1740 |
| tttcgtcatg tgttttattc atttcttttt c | 1771 |

<210> SEQ ID NO 8
<211> LENGTH: 566
<212> TYPE: PRT
<213> ORGANISM: Leishmania tropica

<400> SEQUENCE: 8

```
Gln Ala Arg Val Gln Ala Leu Glu Glu Ala Ala Arg Leu Arg Ala Glu
 1               5                  10                  15
Leu Glu Ala Ala Glu Glu Ala Ala Arg Leu Asp Val Met His Ala Ala
            20                  25                  30
Glu Gln Ala Arg Val Gln Ala Leu Glu Glu Ala Ala Arg Leu Arg Ala
        35                  40                  45
Glu Leu Glu Glu Ala Glu Glu Ala Ala Arg Leu Asp Val Met His Ala
    50                  55                  60
Ala Glu Gln Ala Arg Val Gln Ala Leu Glu Glu Ala Ala Arg Leu Arg
65                  70                  75                  80
Ala Glu Leu Glu Ala Ala Glu Glu Ala Ala Arg Leu Glu Ala Met His
                85                  90                  95
Glu Ala Glu Gln Ala Arg Ser Gln Ala Leu Glu Glu Ala Ala Arg Leu
            100                 105                 110
Arg Ala Glu Leu Glu Glu Ala Glu Glu Ala Ala Arg Leu Asp Val Met
        115                 120                 125
His Ala Ala Glu Gln Ala Arg Val Gln Ala Leu Glu Glu Ala Ala Arg
    130                 135                 140
Leu Arg Ala Glu Leu Glu Glu Ala Glu Glu Ala Ala Arg Leu Glu Ala
145                 150                 155                 160
Met His Glu Ala Glu Gln Ala Arg Ser Gln Ala Leu Glu Glu Ala Ala
                165                 170                 175
Arg Leu Arg Ala Glu Leu Glu Ala Ala Glu Glu Ala Ala Arg Leu Asp
            180                 185                 190
Val Met His Glu Ala Glu Gln Ala Arg Val Gln Ala Leu Glu Glu Ala
        195                 200                 205
Ala Arg Leu Asp Val Met His Glu Ala Glu Gln Ala Arg Val Gln Ala
    210                 215                 220
```

Leu Glu Glu Ala Ala Arg Leu Arg Ala Glu Leu Ala Glu Glu
225                 230                 235                 240

Ala Ala Arg Leu Asp Val Met His Glu Ala Glu Gln Ala Arg Val Gln
            245                 250                 255

Ala Leu Glu Glu Ala Ala Arg Leu Arg Ala Glu Leu Glu Ala Ala Glu
        260                 265                 270

Glu Ala Ala Arg Leu Asp Val Met His Glu Gly Glu Gln Ala Arg Val
            275                 280                 285

Gln Ala Leu Glu Glu Ala Ala Arg Leu Glu Ala Met His Glu Ala Glu
        290                 295                 300

Gln Ala Arg Ser Gln Ala Leu Glu Glu Ala Ala Arg Leu Cys Ala Glu
305                 310                 315                 320

Leu Glu Ala Glu Glu Glu Lys Asp Glu Arg Pro Ala Thr Ser Ser
                325                 330                 335

Tyr Ser Glu Glu Cys Lys Gly Arg Leu Leu Ser Arg Ala Arg Pro Asp
            340                 345                 350

Pro Arg Arg Pro Leu Pro Arg Pro Phe Ile Gly Met Ser Leu Leu Glu
355                 360                 365

Asp Val Glu Lys Ser Ile Leu Ile Val Asp Gly Leu Tyr Arg Asp Gly
370                 375                 380

Pro Ala Tyr Gln Thr Gly Ile Arg Leu Gly Asp Val Leu Leu Arg Ile
385                 390                 395                 400

Ala Gly Val Tyr Val Asp Ser Ile Ala Lys Ala Arg Gln Val Val Asp
                405                 410                 415

Ala Arg Cys Arg Cys Gly Cys Val Val Pro Val Thr Leu Ala Thr Lys
            420                 425                 430

Met Asn Gln Gln Tyr Ser Val Ala Leu Tyr Ile Met Thr Val Asp Pro
            435                 440                 445

Gln His Asn Asp Lys Pro Phe Phe Asp Val His Ile His His Arg
    450                 455                 460

Ile Glu Ser Ser His Met Gly Lys Lys Ala Gln Trp Met Glu Val Leu
465                 470                 475                 480

Glu Ser Pro Ser Val Ser Ser Ala Ala Thr Thr Pro Leu Val Pro Leu
            485                 490                 495

Leu Arg Glu Pro Thr Pro Arg Arg Gly Ser Glu Leu Gln Ser Ser Ala
                500                 505                 510

Arg Ser Ala Phe Val Ala Thr Ser Tyr Phe Ser Ser Ala Arg Arg Ser
        515                 520                 525

Val Ser Ser Glu Ser Glu Arg Pro Arg Gly Ser Ser Val Ala Met
530                 535                 540

Ala Glu Glu Ala Ile Ala Leu Ala Pro Gln Gly Tyr Thr Pro Pro Asn
545                 550                 555                 560

Gln Val Arg Gly Arg Ser
            565

<210> SEQ ID NO 9
<211> LENGTH: 1618
<212> TYPE: DNA
<213> ORGANISM: Leishmania braziliensis

<400> SEQUENCE: 9
ccactctctc ggtcgtctgt ctcccacgcg cgcacgcagt tgatttccgc cttcttaaac    60
gctctctttt ttttattttt tcacctgacc aaccgcacca cgtcggcctc catcatgtcg   120

-continued

```
cagcaagacc gagttgcccc acaggaccag gactcgttcc tcgacgacca gcccggcgtc    180
cgcccgatcc cgtccttcga tgacatgccg ttgcaccaga accttctgcg cggcatctac    240
tcgtacggct tcgagaaacc gtccagcatc cagcagcgcg ccatcgcccc cttcacgcgc    300
ggcggcgaca tcatcgcgca ggcgcagtcc ggtaccggca agacgggcgc cttctccatc    360
ggcctgctgc agcgcctgga cttccgccac aacctgatcc agggcctcgt gctctccccg    420
acccgcgagc tggccctgca gacggcggag gtgatcagcc gcatcggcga gttcctgtcg    480
aacagcgcga agttctgtga gacctttgtg ggtggcacgc gcgtgcagga tgacctgcgc    540
aagctgcagg ctggcgtcgt cgtcgccgtg gggacgccgg gccgcgtgtc cgacgtgatc    600
aagcgcggcg cgctgcgcac cgagtccctg cgcgtgctgg tgctcgacga ggctgatgag    660
atgctgtctc agggcttcgc ggatcagatt tacgagatct tccgcttcct gccgaaggac    720
atccaggtcg cgctcttctc cgccacgatg ccggaggagg tgctggagct gacaaagaag    780
ttcatgcgcg accccgtacg cattctcgtg aagcgcgaga gcctgacgct ggagggcatc    840
aagcagttct tcatcgccgt cgaggaggag cacaagctgg acacgctgat ggacctgtac    900
gagaccgtgt ccatcgcgca gtccgtcatc ttcgccaaca cccgccgcaa ggtggactgg    960
atcgccgaga agctgaatca gagcaaccac accgtcagca gcatgcacgc cgagatgccc   1020
aagagcgacc gcgagcgcgt catgaacacc ttccgcagcg gcagctcccg cgtgctcgta   1080
acgaccgacc tcgtggcccg cggcatcgac gtgcaccacg tgaacatcgt catcaacttc   1140
gacctgccga cgaacaagga gaactacctg caccgcattg ccgcggcgg ccgctacggc   1200 gtaaagggtg ttgccatcaa cttcgtgacg gagaaagacg tggagctgct gcacgagatc   1260
gaggggcact accacacgca gatcgatgag ctcccggtgg actttgccgc ctacctcggc   1320
gagtgagcgg gcccctgccc cccttccctg ccccctctc gcgacgagag aacgcacatc   1380
gtaacacagc cacgcgaacg atagtaaggg cgtgcggcgg cgttccctc ctcctgccag   1440 cggccccccct ccgcagcgct tctcttttga gagggggca ggggaggcg ctgcgcctgg   1500 ctggatgtgt gcttgagctt gcattccgtc aagcaagtgc tttgttttaa ttatgcgcgc   1560
cgttttgttg ctcgtcccctt tcgttggtgt tttttcggcc gaaacggcgt ttaaagca    1618
```

210> SEQ ID NO 10
<211> LENGTH: 403
<212> TYPE: PRT
<213> ORGANISM: Leishmania braziliensis

<400> SEQUENCE: 10

Met Ser Gln Gln Asp Arg Val Ala Pro Gln Asp Gln Asp Ser Phe Leu
1               5                   10                  15

Asp Asp Gln Pro Gly Val Arg Pro Ile Pro Ser Phe Asp Asp Met Pro
            20                  25                  30

Leu His Gln Asn Leu Leu Arg Gly Ile Tyr Ser Tyr Gly Phe Glu Lys
        35                  40                  45

Pro Ser Ser Ile Gln Gln Arg Ala Ile Ala Pro Phe Thr Arg Gly Gly
    50                  55                  60

Asp Ile Ile Ala Gln Ala Gln Ser Gly Thr Gly Lys Thr Gly Ala Phe
65                  70                  75                  80

Ser Ile Gly Leu Leu Gln Arg Leu Asp Phe Arg His Asn Leu Ile Gln
                85                  90                  95

Gly Leu Val Leu Ser Pro Thr Arg Glu Leu Ala Leu Gln Thr Ala Glu
            100                 105                 110

```
Val Ile Ser Arg Ile Gly Glu Phe Leu Ser Asn Ser Ala Lys Phe Cys
        115                 120                 125

Glu Thr Phe Val Gly Gly Thr Arg Val Gln Asp Asp Leu Arg Lys Leu
    130                 135                 140

Gln Ala Gly Val Val Val Ala Val Gly Thr Pro Gly Arg Val Ser Asp
145                 150                 155                 160

Val Ile Lys Arg Gly Ala Leu Arg Thr Glu Ser Leu Arg Val Leu Val
                165                 170                 175

Leu Asp Glu Ala Asp Glu Met Leu Ser Gln Gly Phe Ala Asp Gln Ile
            180                 185                 190

Tyr Glu Ile Phe Arg Phe Leu Pro Lys Asp Ile Gln Val Ala Leu Phe
        195                 200                 205

Ser Ala Thr Met Pro Glu Glu Val Leu Glu Leu Thr Lys Lys Phe Met
    210                 215                 220

Arg Asp Pro Val Arg Ile Leu Val Lys Arg Glu Ser Leu Thr Leu Glu
225                 230                 235                 240

Gly Ile Lys Gln Phe Phe Ile Ala Val Glu Glu His Lys Leu Asp
                245                 250                 255

Thr Leu Met Asp Leu Tyr Glu Thr Val Ser Ile Ala Gln Ser Val Ile
            260                 265                 270

Phe Ala Asn Thr Arg Arg Lys Val Asp Trp Ile Ala Glu Lys Leu Asn
        275                 280                 285

Gln Ser Asn His Thr Val Ser Ser Met His Ala Glu Met Pro Lys Ser
    290                 295                 300

Asp Arg Glu Arg Val Met Asn Thr Phe Arg Ser Gly Ser Ser Arg Val
305                 310                 315                 320

Leu Val Thr Thr Asp Leu Val Ala Arg Gly Ile Asp Val His His Val
                325                 330                 335

Asn Ile Val Ile Asn Phe Asp Leu Pro Thr Asn Lys Glu Asn Tyr Leu
            340                 345                 350

His Arg Ile Gly Arg Gly Gly Arg Tyr Gly Val Lys Gly Val Ala Ile
        355                 360                 365

Asn Phe Val Thr Glu Lys Asp Val Glu Leu Leu His Glu Ile Glu Gly
    370                 375                 380

His Tyr His Thr Gln Ile Asp Glu Leu Pro Val Asp Phe Ala Ala Tyr
385                 390                 395                 400

Leu Gly Glu

<210> SEQ ID NO 11
<211> LENGTH: 12
<212> TYPE: PRT
<213> ORGANISM: Leishmania donovani
<220> FEATURE:
<221> NAME/KEY: VARIANT
<222> LOCATION: (1)...(5)
<223> OTHER INFORMATION: Xaa = any amino acid
<221> NAME/KEY: VARIANT
<222> LOCATION: (6)...(6)
<223> OTHER INFORMATION: Xaa = Leu or Lys
<221> NAME/KEY: VARIANT
<222> LOCATION: (7)...(12)
<223> OTHER INFORMATION: Xaa = any amino acid

<400> SEQUENCE: 11

Xaa Gln Xaa Pro Gln Xaa Val Phe Asp Glu Xaa Xaa
 1               5                  10

<210> SEQ ID NO 12
```

```
<211> LENGTH: 26
<212> TYPE: DNA
<213> ORGANISM: Artificial Sequence
<220> FEATURE:
<223> OTHER INFORMATION: Sense PCR primer
<221> NAME/KEY: modified_base
<222> LOCATION: (1)...(26)
<223> OTHER INFORMATION: I
<221> NAME/KEY: misc_feature
<222> LOCATION: (1)...(26)
<223> OTHER INFORMATION: n = A,T,C or G

<400> SEQUENCE: 12
ggaattcccc ncagctngtn ttcgac                                       26

<210> SEQ ID NO 13
<211> LENGTH: 5
<212> TYPE: PRT
<213> ORGANISM: Leishmania donovani

<400> SEQUENCE: 13

Lys Val Phe Asp Glu
 1               5

<210> SEQ ID NO 14
<211> LENGTH: 30
<212> TYPE: DNA
<213> ORGANISM: Artificial Sequence
<220> FEATURE:
<223> OTHER INFORMATION: PCR primer

<400> SEQUENCE: 14
ggatccatgg tcaagtccca ctacatctgc                                   30

<210> SEQ ID NO 15
<211> LENGTH: 33
<212> TYPE: DNA
<213> ORGANISM: Artificial Sequence
<220> FEATURE:
<223> OTHER INFORMATION: PCR primer

<400> SEQUENCE: 15
gaattcagac cggatagaaa taagccaatg aaa                                33

<210> SEQ ID NO 16
<211> LENGTH: 701
<212> TYPE: PRT
<213> ORGANISM: Leishmania amozonensis

<400> SEQUENCE: 16

Met Thr Glu Thr Phe Ala Phe Gln Ala Glu Ile Asn Gln Leu Met Ser
 1               5                  10                  15

Leu Ile Ile Asn Thr Phe Tyr Ser Asn Lys Glu Ile Phe Leu Arg Asp
                20                  25                  30

Val Ile Ser Asn Ala Ser Asp Ala Cys Asp Lys Ile Arg Tyr Gln Ser
            35                  40                  45

Leu Thr Asp Pro Ala Val Leu Gly Asp Ala Thr Arg Leu Cys Val Arg
        50                  55                  60

Val Val Pro Asp Lys Glu Asn Lys Thr Leu Thr Val Glu Asp Asn Gly
 65                  70                  75                  80

Ile Gly Met Thr Lys Ala Asp Leu Val Asn Asn Leu Gly Thr Ile Ala
                85                  90                  95

Arg Ser Gly Thr Lys Ala Phe Met Glu Ala Leu Glu Ala Gly Ala Asp
            100                 105                 110
```

```
Met Ser Met Ile Gly Gln Phe Gly Val Gly Phe Tyr Ser Ala Tyr Leu
            115                 120                 125
Val Ala Asp Arg Val Thr Val Thr Ser Lys Asn Asn Ser Asp Glu Val
            130                 135                 140
Tyr Val Trp Glu Ser Ser Ala Gly Gly Thr Phe Thr Ile Thr Ser Ala
145                 150                 155                 160
Pro Glu Ser Asp Met Lys Leu Pro Ala Arg Ile Thr Leu His Leu Lys
                165                 170                 175
Glu Asp Gln Leu Glu Tyr Leu Glu Ala Arg Arg Leu Lys Glu Leu Ile
            180                 185                 190
Lys Lys His Ser Glu Phe Ile Gly Tyr Asp Ile Glu Leu Met Val Glu
            195                 200                 205
Lys Thr Thr Glu Lys Glu Val Thr Asp Glu Asp Glu Glu Ala Lys
210                 215                 220
Lys Ala Asp Glu Asp Gly Glu Glu Pro Lys Val Glu Glu Val Thr Glu
225                 230                 235                 240
Gly Glu Glu Asp Lys Lys Lys Thr Lys Lys Val Lys Glu Val Thr
                245                 250                 255
Lys Glu Tyr Glu Val Gln Asn Lys His Lys Pro Leu Trp Thr Arg Asp
            260                 265                 270
Pro Lys Asp Val Thr Lys Glu Glu Tyr Ala Ala Phe Tyr Lys Ala Ile
            275                 280                 285
Ser Asn Asp Trp Glu Asp Pro Pro Ala Thr Lys His Phe Ser Val Glu
            290                 295                 300
Gly Gln Leu Glu Phe Arg Ala Ile Met Phe Val Pro Lys Arg Ala Pro
305                 310                 315                 320
Phe Asp Met Leu Glu Pro Asn Lys Lys Arg Asn Asn Ile Lys Leu Tyr
                325                 330                 335
Val Arg Arg Val Phe Ile Met Asp Asn Cys Glu Asp Leu Cys Pro Asp
                340                 345                 350
Trp Leu Gly Phe Val Lys Gly Val Val Asp Ser Glu Asp Leu Pro Leu
            355                 360                 365
Asn Ile Ser Arg Glu Asn Leu Gln Gln Asn Lys Ile Leu Lys Val Ile
370                 375                 380
Arg Lys Asn Ile Val Lys Lys Cys Leu Glu Met Phe Glu Glu Val Ala
385                 390                 395                 400
Glu Asn Lys Glu Asp Tyr Lys Gln Phe Tyr Glu Gln Phe Gly Lys Asn
                405                 410                 415
Ile Lys Leu Gly Ile His Glu Asp Thr Ala Asn Arg Lys Lys Leu Met
            420                 425                 430
Glu Leu Leu Arg Phe Tyr Ser Thr Glu Ser Gly Glu Val Met Thr Thr
            435                 440                 445
Leu Lys Asp Tyr Val Thr Arg Met Lys Ala Glu Gln Asn Ser Ile Tyr
            450                 455                 460
Tyr Ile Thr Gly Asp Ser Lys Lys Leu Glu Ser Ser Pro Phe Ile
465                 470                 475                 480
Glu Gln Ala Lys Arg Arg Gly Phe Glu Val Leu Phe Met Thr Glu Pro
                485                 490                 495
Tyr Asp Glu Tyr Val Met Gln Gln Val Lys Asp Phe Glu Asp Lys Lys
                500                 505                 510
Phe Ala Cys Leu Thr Lys Glu Gly Val His Phe Glu Glu Ser Glu Glu
            515                 520                 525
```

```
Glu Lys Lys Gln Arg Glu Glu Lys Ala Thr Cys Glu Lys Leu Cys
    530                 535                 540

Lys Thr Met Lys Glu Val Leu Gly Asp Lys Val Glu Lys Val Thr Val
545                 550                 555                 560

Ser Glu Arg Leu Ser Thr Ser Pro Cys Ile Leu Val Thr Ser Glu Phe
                565                 570                 575

Gly Trp Ser Ala His Met Glu Gln Met Met Arg Asn Gln Ala Leu Arg
                580                 585                 590

Asp Ser Ser Met Ala Gln Tyr Met Met Ser Lys Lys Thr Met Glu Leu
                595                 600                 605

Asn Pro Lys His Pro Ile Ile Lys Glu Leu Arg Arg Val Glu Ala
        610                 615                 620

Asp Glu Asn Asp Lys Ala Val Lys Asp Leu Val Phe Leu Leu Phe Asp
625                 630                 635                 640

Thr Ser Leu Leu Thr Ser Gly Phe Gln Leu Glu Asp Pro Thr Tyr Ala
                645                 650                 655

Glu Arg Ile Asn Arg Met Ile Lys Leu Gly Leu Ser Leu Asp Glu Glu
                660                 665                 670

Glu Glu Glu Glu Ala Val Glu Ala Ala Val Ala Glu Thr Ala Pro Ala
            675                 680                 685

Glu Val Thr Ala Gly Thr Ser Ser Met Glu Leu Val Asp
            690                 695                 700

<210> SEQ ID NO 17
<211> LENGTH: 704
<212> TYPE: PRT
<213> ORGANISM: T. Cruzi

<400> SEQUENCE: 17

Met Thr Glu Thr Phe Ala Phe Gln Ala Glu Ile Asn Gln Leu Met Ser
  1               5                  10                  15

Leu Ile Ile Asn Thr Phe Tyr Ser Asn Lys Glu Ile Phe Leu Arg Glu
                20                  25                  30

Leu Ile Ser Asn Ala Ser Asp Ala Cys Asp Lys Ile Arg Tyr Gln Ser
            35                  40                  45

Leu Thr Asn Gln Ala Val Leu Gly Asp Glu Ser His Leu Arg Ile Arg
        50                  55                  60

Val Val Pro Asp Lys Ala Asn Lys Thr Leu Thr Val Glu Asp Thr Gly
65                  70                  75                  80

Ile Gly Met Thr Lys Ala Glu Leu Val Asn Asn Leu Gly Thr Ile Ala
                85                  90                  95

Arg Ser Gly Thr Lys Ala Phe Met Glu Ala Leu Glu Ala Gly Gly Asp
            100                 105                 110

Met Ser Met Ile Gly Gln Phe Gly Val Gly Phe Tyr Ser Ala Tyr Leu
        115                 120                 125

Val Ala Asp Arg Val Thr Val Val Ser Lys Asn Asn Asp Asp Glu Ala
    130                 135                 140

Tyr Thr Trp Glu Ser Ser Ala Gly Gly Thr Phe Thr Val Thr Pro Thr
145                 150                 155                 160

Pro Asp Cys Asp Leu Lys Arg Gly Thr Arg Ile Val Leu His Leu Lys
                165                 170                 175

Glu Asp Gln Gln Glu Tyr Leu Glu Glu Arg Arg Leu Lys Asp Leu Ile
            180                 185                 190

Lys Lys His Ser Glu Phe Ile Gly Tyr Asp Ile Glu Leu Met Val Glu
        195                 200                 205
```

-continued

```
Lys Ala Thr Glu Lys Glu Val Thr Asp Glu Asp Glu Ala Ala
    210                 215                 220
Ala Thr Lys Asn Glu Glu Gly Glu Glu Pro Lys Val Glu Glu Val Lys
225                 230                 235                 240
Asp Asp Ala Glu Glu Gly Glu Lys Lys Lys Thr Lys Lys Val Lys
                245                 250                 255
Glu Val Thr Gln Glu Phe Val Val Gln Asn Lys His Lys Pro Leu Trp
                260                 265                 270
Thr Arg Asp Pro Lys Asp Val Thr Lys Glu Glu Tyr Ala Ala Phe Tyr
                275                 280                 285
Lys Ala Ile Ser Asn Asp Trp Glu Glu Pro Leu Ser Thr Lys His Phe
    290                 295                 300
Ser Val Glu Gly Gln Leu Glu Phe Arg Ala Ile Leu Phe Val Pro Lys
305                 310                 315                 320
Arg Ala Pro Phe Asp Met Phe Glu Pro Ser Lys Lys Arg Asn Asn Ile
                325                 330                 335
Lys Leu Tyr Val Arg Arg Val Phe Ile Met Asp Asn Cys Glu Asp Leu
                340                 345                 350
Cys Pro Glu Trp Leu Ala Phe Val Arg Gly Val Val Asp Ser Glu Asp
                355                 360                 365
Leu Pro Leu Asn Ile Ser Arg Glu Asn Leu Gln Gln Asn Lys Ile Leu
    370                 375                 380
Lys Val Ile Arg Lys Asn Ile Val Lys Lys Ala Leu Glu Leu Phe Glu
385                 390                 395                 400
Glu Ile Ala Glu Asn Lys Glu Asp Tyr Lys Lys Phe Tyr Glu Gln Phe
                405                 410                 415
Gly Lys Asn Val Lys Leu Gly Ile His Glu Asp Ser Ala Asn Arg Lys
                420                 425                 430
Lys Leu Met Glu Leu Leu Arg Phe His Ser Ser Glu Ser Gly Glu Asp
                435                 440                 445
Met Thr Thr Leu Lys Asp Tyr Val Thr Arg Met Lys Glu Gly Gln Lys
    450                 455                 460
Cys Ile Tyr Tyr Val Thr Gly Asp Ser Lys Lys Lys Leu Glu Thr Ser
465                 470                 475                 480
Pro Phe Ile Glu Gln Ala Arg Arg Gly Phe Glu Val Leu Phe Met
                485                 490                 495
Thr Glu Pro Ile Asp Glu Tyr Val Met Gln Gln Val Lys Asp Phe Glu
                500                 505                 510
Asp Lys Lys Phe Ala Cys Leu Thr Lys Glu Gly Val His Phe Glu Glu
                515                 520                 525
Thr Glu Glu Glu Lys Lys Gln Arg Glu Glu Lys Thr Ala Tyr Glu
                530                 535                 540
Arg Leu Cys Lys Ala Met Lys Asp Val Leu Gly Asp Lys Val Glu Lys
545                 550                 555                 560
Val Val Val Ser Glu Arg Leu Ala Thr Ser Pro Cys Ile Leu Val Thr
                565                 570                 575
Ser Glu Phe Gly Trp Ser Ala His Met Glu Gln Ile Met Arg Asn Gln
                580                 585                 590
Ala Leu Arg Asp Ser Ser Met Ser Ala Tyr Met Met Ser Lys Lys Thr
                595                 600                 605
Met Glu Ile Asn Pro Ala His Pro Ile Val Lys Glu Leu Lys Arg Arg
    610                 615                 620
```

-continued

```
Val Glu Ala Asp Glu Asn Asp Lys Ala Val Lys Asp Leu Val Tyr Leu
625                 630                 635                 640

Leu Phe Asp Thr Ala Leu Leu Thr Ser Gly Phe Thr Leu Asp Asp Pro
                645                 650                 655

Thr Ser Tyr Ala Glu Arg Ile His Arg Met Ile Lys Leu Gly Leu Ser
            660                 665                 670

Leu Asp Asp Glu Asp Asn Gly Asn Glu Glu Ala Glu Pro Ala Ala Ala
        675                 680                 685

Val Pro Ala Glu Pro Val Ala Gly Thr Ser Ser Met Glu Gln Val Asp
    690                 695                 700
```

<210> SEQ ID NO 18
<211> LENGTH: 732
<212> TYPE: PRT
<213> ORGANISM: Homo sapien

<400> SEQUENCE: 18

```
Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Ser Leu
        50                  55                  60

Thr Asp Pro Ser Lys Leu Asp Ser Gly Lys Glu Leu His Ile Asn Leu
65                  70                  75                  80

Ile Pro Asn Lys Gln Asp Arg Ala Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Asp Glu Lys Lys Asp Gly
            260                 265                 270

Asp Lys Lys Lys Lys Lys Ile Lys Glu Lys Tyr Ile Asp Lys Glu
        275                 280                 285

Glu Leu Asn Lys Thr Lys Pro Ile Trp Thr Arg Asn Pro Asp Asp Ile
    290                 295                 300
```

-continued

```
Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
            325                 330                 335

Phe Arg Ala Leu Leu Phe Val Pro Arg Arg Ala Pro Phe Asp Leu Phe
            340                 345                 350

Glu Asn Arg Lys Lys Lys Asn Ile Lys Leu Tyr Val Arg Arg Val
            355                 360                 365

Phe Ile Met Asp Asn Cys Glu Glu Leu Ile Pro Glu Tyr Leu Asn Phe
370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
            405                 410                 415

Val Lys Lys Cys Leu Glu Leu Phe Thr Glu Leu Ala Glu Asp Lys Glu
            420                 425                 430

Asn Tyr Lys Lys Phe Tyr Glu Gln Phe Ser Lys Asn Ile Lys Leu Gly
            435                 440                 445

Ile His Glu Asp Ser Gln Asn Arg Lys Lys Leu Ser Glu Leu Leu Arg
450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
            485                 490                 495

Glu Thr Lys Asp Gln Val Ala Asn Ser Ala Phe Val Glu Arg Leu Arg
            500                 505                 510

Lys His Gly Leu Glu Val Ile Tyr Met Ile Glu Pro Ile Asp Glu Tyr
            515                 520                 525

Cys Val Gln Gln Leu Lys Glu Phe Glu Gly Lys Thr Leu Val Ser Val
            530                 535                 540

Thr Lys Glu Gly Leu Glu Leu Pro Glu Asp Glu Glu Glu Lys Lys Lys
545                 550                 555                 560

Gln Glu Glu Lys Lys Thr Lys Phe Glu Asn Leu Cys Lys Ile Met Lys
            565                 570                 575

Asp Ile Leu Glu Lys Lys Val Glu Lys Val Val Val Ser Asn Arg Leu
            580                 585                 590

Val Thr Ser Pro Cys Cys Leu Val Thr Ser Thr Tyr Gly Trp Thr Ala
            595                 600                 605

Asn Met Glu Arg Ile Met Lys Ala Gln Ala Leu Arg Asp Asn Ser Thr
610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
            645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
            675                 680                 685

Tyr Arg Met Ile Lys Leu Gly Leu Gly Ile Asp Glu Asp Pro Thr
            690                 695                 700

Ala Asp Asp Thr Ser Ala Ala Val Thr Glu Glu Met Pro Pro Leu Glu
705                 710                 715                 720
```

Gly Asp Asp Asp Thr Ser Arg Met Glu Glu Val Asp
                725                      730

<210> SEQ ID NO 19
<211> LENGTH: 1019
<212> TYPE: DNA
<213> ORGANISM: Leishmania major

<400> SEQUENCE: 19

```
gaattcggca cgaggtttct gtactttatt gcttccagcc tttattcact cttcgatttc     60
ctctaacacc atgtcctccg agcgcacctt tattgccgtc aagccggacg gcgtgcagcg    120
cggcctcgtt ggcgagatca tcgcccgctt cgagcgcaag ggctacaagc tcgtcgcctt    180
gaagatactg cagccgacga cggagcaggc ccagggtcac tataaggacc tttgctccaa    240
gccgttttc ccggcccttg tgaagtactt ctcctctggc ccgatcgtgt gtatggtgtg     300
ggagggtaag aacgtggtga agagcggccg cgtgctgctc ggcgcgacga acccggccga    360
ctcacagccc ggcacgatcc gtggcgactt gccgtggat gtgggccgca acgtgtgcca     420
cgggtccgac tctgtggaga gcgcggagcg cgagatcgcc ttttggttca aggcggatga    480
gatcgcgagc tggacgtcgc actccgtgtc ccagatctat gagtaacggt gattgcggac    540
acgctttgag gacgtagctg taccccaat gaattcttct ctgaaaacca catcataagc     600
ctcttaagag gttattttc ttgatcgatg cccggtggtg accagcacca ttcctttatc     660
ggattcactc acactcctag cgaatcatgt agtgcggtga gagtgggctc tggaggagac    720
tgttgtgtag ccatggcttc aggagagaaa acaaaataca aggaaaggca atatgtaact    780
atggggttcc ctttttact atgcaaagtt tttataactc ctgatcggca aaaacaacaa     840
caaccgccat acaccaagag caaatgcttt cttctgcgga ctgtgcttct gtttttttt     900
atgaaggagt gactcgcgcg atgaaaagtg tgtgcgtggg agatgtattt cctttttttg    960
ttcatagtgg cgacagctca ctgttgacga tgacaaaaaa aaaaaaaaaa aaactcgag   1019
```

<210> SEQ ID NO 20
<211> LENGTH: 151
<212> TYPE: PRT
<213> ORGANISM: Leishmania major

<400> SEQUENCE: 20

Met Ser Ser Glu Arg Thr Phe Ile Ala Val Lys Pro Asp Gly Val Gln
1               5                   10                  15

Arg Gly Leu Val Gly Glu Ile Ile Ala Arg Phe Glu Arg Lys Gly Tyr
            20                  25                  30

Lys Leu Val Ala Leu Lys Ile Leu Gln Pro Thr Thr Glu Gln Ala Gln
        35                  40                  45

Gly His Tyr Lys Asp Leu Cys Ser Lys Pro Phe Pro Ala Leu Val
    50                  55                  60

Lys Tyr Phe Ser Ser Gly Pro Ile Val Cys Met Val Trp Glu Gly Lys
65                  70                  75                  80

Asn Val Val Lys Ser Gly Arg Val Leu Leu Gly Ala Thr Asn Pro Ala
                85                  90                  95

Asp Ser Gln Pro Gly Thr Ile Arg Gly Asp Phe Ala Val Asp Val Gly
            100                 105                 110

Arg Asn Val Cys His Gly Ser Asp Ser Val Glu Ser Ala Glu Arg Glu
        115                 120                 125

Ile Ala Phe Trp Phe Lys Ala Asp Glu Ile Ala Ser Trp Thr Ser His
    130                 135                 140

Ser Val Ser Gln Ile Tyr Glu
145                 150

<210> SEQ ID NO 21
<211> LENGTH: 1523
<212> TYPE: DNA
<213> ORGANISM: Leishmania major

<400> SEQUENCE: 21

```
gaattcggca cgagtgctgc ccgacatgac atgctcgctg accggacttc agtgcacaga        60
cccgaactgc aagacctgca caacttacgg tcagtgcaca gactgcaacg acggctacgg       120
tctcacctcc tccagcgttt gcgtgcgctg cagtgtagcg ggctgcaaga gctgccccgt       180
cgacgctaac gtctgcaaag tgtgtctcgg cggcagcgag ccgatcaaca atatgtgccc       240
ctgcaccgac cccaactgcg ccagctgccc cagcgacgct ggcacgtgca ctcagtgcgc       300
gaacggctac ggtctcgtgg acggcgcctg tgtgagatgc aggagcccca actgcttcag       360
ctgcgacagc gacgcgaata gtgcacaca atgtgcgccg aactactacc tcaccccgct        420
cttgacctgc tccccggtgg cctgcaacat cgagcactgc atgcagtgcg acccacagac       480
gccgtcgcgc tgccaggagt gcgtgtcccc ctacgtggtt gacagctacg acggcctctg       540
caggctctcc gatgcctgct ccgtgcccaa ctgcaagaag tgcgagaccg gtacctccag       600
gctctgcgcc gagtgcgaca ccggctacag tctctccgcc gacgcgacga gctgcagcag       660
tccaaccacg cagccgtgcg aggtggagca ctgcaacaca tgtgtgaacg gcgatagcac       720
ccgctgtgcc tactgcaaca ccggctacta cgtctccgat ggcaagtgca aggccatgca       780
gggctgctac gtgtcgaact gcgcgcagtg catgctgctt gacagcacca gtgctccac       840
gtgcgtgaaa gggtacctgc tcacgtcgtc ctacagttgc gtctcgcaga agtcatcaa       900
cagtgcggcc gcgccctact ctctgtgggt ggccgccgcc gtgctcctca cctcttttgc       960
catgcacctg gcatagtgcg cagcggcatg cgaacaaccc cactctcatt ctccaacatg      1020
tgcatacaca cacacacaga cagcggggca gcaccccctc cccacacaca cacacgcact      1080
tcccccttgt cttgttcttc tttcctcgtt cgcatttctt tctctcgtgc gctggcgccg      1140
gcctcctgca cgtcgctccc ctcccccctaa cctctattct ctctctctct ctctctcgcc      1200
ggcatcattg cttcttaccc ttttctgatc cttgctcgcg tgggcggaca ctgccacagt      1260
cccacagcgc agacacacgt gtttaaacgg cgcaggcatc cctccctatc acttcatttc      1320
tcctaaagcc actcaccaag tcgcacaccg ccctccccca tcggccgccc ttccgggcgc      1380
agctgtgcgg aatgggtgtg tgctcgacct cgttcctggc agctcactcg catgtgtaca      1440
gccactccaa ccacgaaagc tctcttctgc gcacataaaa aaaaaaaaa aaaaaaaact      1500
cgagggggg cccggtaccc aaa                                              1523
```

<210> SEQ ID NO 22
<211> LENGTH: 320
<212> TYPE: PRT
<213> ORGANISM: Leishmania major

<400> SEQUENCE: 22

Val Leu Pro Asp Met Thr Cys Ser Leu Thr Gly Leu Gln Cys Thr Asp
 1               5                  10                  15

Pro Asn Cys Lys Thr Cys Thr Thr Tyr Gly Gln Cys Thr Asp Cys Asn
             20                  25                  30

```
Asp Gly Tyr Gly Leu Thr Ser Ser Val Cys Val Arg Cys Ser Val
            35                  40                  45
Ala Gly Cys Lys Ser Cys Pro Val Asp Ala Asn Val Cys Lys Val Cys
 50                  55                  60
Leu Gly Gly Ser Glu Pro Ile Asn Asn Met Cys Pro Cys Thr Asp Pro
 65                  70                  75                  80
Asn Cys Ala Ser Cys Pro Ser Asp Ala Gly Thr Cys Thr Gln Cys Ala
                 85                  90                  95
Asn Gly Tyr Gly Leu Val Asp Gly Ala Cys Val Arg Cys Gln Glu Pro
            100                 105                 110
Asn Cys Phe Ser Cys Asp Ser Asp Ala Asn Lys Cys Thr Gln Cys Ala
            115                 120                 125
Pro Asn Tyr Tyr Leu Thr Pro Leu Leu Thr Cys Ser Pro Val Ala Cys
            130                 135                 140
Asn Ile Glu His Cys Met Gln Cys Asp Pro Gln Thr Pro Ser Arg Cys
145                 150                 155                 160
Gln Glu Cys Val Ser Pro Tyr Val Val Asp Ser Tyr Asp Gly Leu Cys
                165                 170                 175
Arg Leu Ser Asp Ala Cys Ser Val Pro Asn Cys Lys Lys Cys Glu Thr
            180                 185                 190
Gly Thr Ser Arg Leu Cys Ala Glu Cys Asp Thr Gly Tyr Ser Leu Ser
            195                 200                 205
Ala Asp Ala Thr Ser Cys Ser Ser Pro Thr Thr Gln Pro Cys Glu Val
210                 215                 220
Glu His Cys Asn Thr Cys Val Asn Gly Asp Ser Thr Arg Cys Ala Tyr
225                 230                 235                 240
Cys Asn Thr Gly Tyr Tyr Val Ser Asp Gly Lys Cys Lys Ala Met Gln
                245                 250                 255
Gly Cys Tyr Val Ser Asn Cys Ala Gln Cys Met Leu Leu Asp Ser Thr
            260                 265                 270
Lys Cys Ser Thr Cys Val Lys Gly Tyr Leu Leu Thr Ser Ser Tyr Ser
            275                 280                 285
Cys Val Ser Gln Lys Val Ile Asn Ser Ala Ala Pro Tyr Ser Leu
            290                 295                 300
Trp Val Ala Ala Val Leu Leu Thr Ser Phe Ala Met His Leu Ala
305                 310                 315                 320

<210> SEQ ID NO 23
<211> LENGTH: 797
<212> TYPE: DNA
<213> ORGANISM: Leishmania major

<400> SEQUENCE: 23
ctgtacttta ttgccaccag ccagccatgt cctgcggtaa cgccaagatc aactctcccg      60
cgccgtcctt cgaggaggtg gcgctcatgc ccaacggcag cttcaagaag atcagcctct     120
cctcctacaa gggcaagtgg gtcgtgctct tcttctaccc gctcgacttt agcttcgtgt     180
gcccgacaga ggtcatcgcg ttctccgaca gcgtgagtcg cttcaacgag ctcaactgcg     240
aggtcctcgc gtgctcgata gacagcgagt acgcgcacct gcagtggacg ctgcaggacc     300
gcaagaaggg cggcctcggg accatggcga tcccaatgct agccgacaag accaagagca     360
tcgctcgttc ctacggcgtg ctggaggaga gccagggcgt ggcctaccgc ggtctcttca     420
tcatcgaccc ccatggcatg ctgcgtcaga tcaccgtcaa tgacatgccg gtgggccgca     480
gcgtggagga ggttctacgc ctgctggagg cttttcagtt cgtggagaag cacggcgagg     540
```

```
tgtgccccgc gaactggaag aagggcgccc ccacgatgaa gccggaaccg aatgcgtctg    600
tcgagggata cttcagcaag cagtaaacct gtgagcgtcg caggagtcag tgtgacctca    660
cccgcctctg ccagtgggtg cgagagggcg tgagggattg tgggaaggct gttggatatg    720
atgcagacag cgatgaatgc aactcccaca cactggccct cctcagccct ctccacacag    780
acacacgcac gcatgtg                                                   797
```

<210> SEQ ID NO 24
<211> LENGTH: 199
<212> TYPE: PRT
<213> ORGANISM: Leishmania major

<400> SEQUENCE: 24

```
Met Ser Cys Gly Asn Ala Lys Ile Asn Ser Pro Ala Pro Ser Phe Glu
 1               5                  10                  15

Glu Val Ala Leu Met Pro Asn Gly Ser Phe Lys Lys Ile Ser Leu Ser
            20                  25                  30

Ser Tyr Lys Gly Lys Trp Val Val Leu Phe Phe Tyr Pro Leu Asp Phe
        35                  40                  45

Ser Phe Val Cys Pro Thr Glu Val Ile Ala Phe Ser Asp Ser Val Ser
    50                  55                  60

Arg Phe Asn Glu Leu Asn Cys Glu Val Leu Ala Cys Ser Ile Asp Ser
65                  70                  75                  80

Glu Tyr Ala His Leu Gln Trp Thr Leu Gln Asp Arg Lys Lys Gly Gly
                85                  90                  95

Leu Gly Thr Met Ala Ile Pro Met Leu Ala Asp Lys Thr Lys Ser Ile
            100                 105                 110

Ala Arg Ser Tyr Gly Val Leu Glu Glu Ser Gln Gly Val Ala Tyr Arg
        115                 120                 125

Gly Leu Phe Ile Ile Asp Pro His Gly Met Leu Arg Gln Ile Thr Val
    130                 135                 140

Asn Asp Met Pro Val Gly Arg Ser Val Glu Glu Val Leu Arg Leu Leu
145                 150                 155                 160

Glu Ala Phe Gln Phe Val Glu Lys His Gly Glu Val Cys Pro Ala Asn
                165                 170                 175

Trp Lys Lys Gly Ala Pro Thr Met Lys Pro Glu Pro Asn Ala Ser Val
            180                 185                 190

Glu Gly Tyr Phe Ser Lys Gln
        195
```

<210> SEQ ID NO 25
<211> LENGTH: 637
<212> TYPE: DNA
<213> ORGANISM: Leishmania tropica

<400> SEQUENCE: 25

```
ttacatatgc atcaccacca ccaccacatg tcctgcggta acgccaagat caactctccc     60
gcgccgccct tcgaggagat ggcgctcatg cccaacggca gcttcaagaa gatcagcctc    120
tccgcctaca agggcaagtg gtcgtgctc ttcttctacc cgctcgactt caccttcgtg    180
tgcccgacag agatcatcgc gttctccgac aacgtgagtc gcttcaacga gctcaactgc    240
gaggtcctcg cgtgctcgat ggacagcgag tacgcgcacc tgcagtggac gctgcaggac    300
cgcaagaagg gcggcctcgg ggccatggcg atcccaatgc tggccgacaa gactaagagc    360
atcgctcgtt cctacggcgt gctggaggag agccagggcg tggcctaccg cggtctcttc    420
```

```
atcatcgacc cccgtggcat ggtgcgtcag atcaccgtca acgacatgcc ggtgggccgc    480
aacgtggagg aggctctgcg cctgctggag gctttgcagt tcgtggagaa gcacggcgag    540
gtgtgccccg cgaactggaa gaagggcgcc cccacgatga agccggaacc gaaggcgtct    600
gtcgagggat acttcagcaa gcagtaagaa ttccatg                             637
```

<210> SEQ ID NO 26
<211> LENGTH: 206
<212> TYPE: PRT
<213> ORGANISM: Leishmania tropica

<400> SEQUENCE: 26

```
Met His His His His His Met Ser Cys Gly Asn Ala Lys Ile Asn
 1               5                  10                  15

Ser Pro Ala Pro Pro Phe Glu Glu Met Ala Leu Met Pro Asn Gly Ser
                20                  25                  30

Phe Lys Lys Ile Ser Leu Ser Ala Tyr Lys Gly Lys Trp Val Val Leu
            35                  40                  45

Phe Phe Tyr Pro Leu Asp Phe Thr Phe Val Cys Pro Thr Glu Ile Ile
        50                  55                  60

Ala Phe Ser Asp Asn Val Ser Arg Phe Asn Glu Leu Asn Cys Glu Val
65                  70                  75                  80

Leu Ala Cys Ser Met Asp Ser Glu Tyr Ala His Leu Gln Trp Thr Leu
                85                  90                  95

Gln Asp Arg Lys Lys Gly Gly Leu Gly Ala Met Ala Ile Pro Met Leu
            100                 105                 110

Ala Asp Lys Thr Lys Ser Ile Ala Arg Ser Tyr Gly Val Leu Glu Glu
        115                 120                 125

Ser Gln Gly Val Ala Tyr Arg Gly Leu Phe Ile Ile Asp Pro Arg Gly
    130                 135                 140

Met Val Arg Gln Ile Thr Val Asn Asp Met Pro Val Gly Arg Asn Val
145                 150                 155                 160

Glu Glu Ala Leu Arg Leu Leu Glu Ala Leu Gln Phe Val Glu Lys His
                165                 170                 175

Gly Glu Val Cys Pro Ala Asn Trp Lys Lys Gly Ala Pro Thr Met Lys
            180                 185                 190

Pro Glu Pro Lys Ala Ser Val Glu Gly Tyr Phe Ser Lys Gln
        195                 200                 205
```

<210> SEQ ID NO 27
<211> LENGTH: 51
<212> TYPE: DNA
<213> ORGANISM: Artificial Sequence
<220> FEATURE:
<223> OTHER INFORMATION: PCR primer

<400> SEQUENCE: 27

```
caattacata tgcatcacca tcaccatcac atgtcctgcg gtaacgccaa g              51
```

<210> SEQ ID NO 28
<211> LENGTH: 31
<212> TYPE: DNA
<213> ORGANISM: Artificial Sequence
<220> FEATURE:
<223> OTHER INFORMATION: PCR primer

<400> SEQUENCE: 28

```
catggaattc ttactgcttg ctgaagtatc c                                    31
```

<210> SEQ ID NO 29
<211> LENGTH: 520
<212> TYPE: DNA
<213> ORGANISM: Leishmania major
<220> FEATURE:
<221> NAME/KEY: misc_feature
<222> LOCATION: (1)...(520)
<223> OTHER INFORMATION: n = A, T, C or G

<400> SEQUENCE: 29

| | | | | | |
|---|---|---|---|---|---|
| ggcacgagcc | cttgcctaca | tttgctcgcc | gatattcgcg | gggagttctt | caatttgcgt | 60 |
| cgcgtagaac | tgctcaatgt | cgcgcaacaa | gcgcagctcg | tcgtggcgca | cgaaggtgat | 120 |
| ggccagtcca | gtgcggccca | tgcggccagt | gcggccgatg | cggtgaatgt | actgctcacg | 180 |
| cgcgagcggc | aaatcgtagc | tgaggacgag | cgagacgcgc | tccacatcaa | tgccacgcgc | 240 |
| ccacaggtcc | gttgtaatga | ncacgcggct | gtgtccatta | cggaatgccg | cataatctcg | 300 |
| tcgcgctccg | cctggggcat | gtcgccgtgc | atggcggaca | cagcgaaatt | ctcgcgcgtc | 360 |
| atcttcttgg | caagctgctc | cacctttttg | cgggtgttgc | anaaaaccac | ngcgtgggcg | 420 |
| atcgttaagc | tgtcgtacaa | actccatcaa | gaaatcgaat | ttgttttct | cttcgtcnac | 480 |
| nganacaaan | tactgtttaa | cgctntccac | ggtgatctca | | | 520 |

<210> SEQ ID NO 30
<211> LENGTH: 600
<212> TYPE: DNA
<213> ORGANISM: Leishmania major
<220> FEATURE:
<221> NAME/KEY: misc_feature
<222> LOCATION: (1)...(600)
<223> OTHER INFORMATION: n = A, T, C or G

<400> SEQUENCE: 30

| | | | | | |
|---|---|---|---|---|---|
| ggcacaaggt | tttcgggtta | tcttcacgca | tggtggagcg | cagatgggtg | aagtaaatac | 60 |
| gcggaccgaa | ctgcttgatc | atatcaacca | gatcgttgtc | agcacgcacg | ccgtangaac | 120 |
| cggtgcacat | ggtaaaaccg | tntgccatgc | tgtttacggt | atcaaccatc | cactgcatat | 180 |
| cttcaatggt | ggaaacaatg | cgcggcaggc | cgaggatccg | cgcgcggctca | tcatnnagnt | 240 |
| natnaaccan | tcgcacgtct | anttctgcac | taaactacaa | natcggtna | catatnataa | 300 |
| ggccnatttt | cggtccagga | ntatgtnctn | tcaaaatgcc | ncgttannca | ctcttaaatg | 360 |
| tctcangngn | aaantngttc | taaagggtgt | ccaaaanntn | nttaccnttc | cccncttact | 420 |
| tcaananctc | ctcnaattcc | cnggcccttn | gacnannatt | tnctattaaa | anatanaann | 480 |
| ttcaaattna | ttcccnacct | nccntnncca | aanntancna | ataatcannc | ccctntcann | 540 |
| anntcccanc | ttaccctccn | ntngnngggn | nnccnattn | ccccaancc | ncnctaaata | 600 |

210> SEQ ID NO 31
<211> LENGTH: 600
<212> TYPE: DNA
<213> ORGANISM: Leishmania major
<220> FEATURE:
<221> NAME/KEY: misc_feature
<222> LOCATION: (1)...(600)
<223> OTHER INFORMATION: n = A, T, C or G

<400> SEQUENCE: 31

| | | | | | |
|---|---|---|---|---|---|
| ggcacgagcc | tcagtggagc | tcaatgaaga | tattgcagta | tcttactctg | gatggcactc | 60 |
| aggtctccgg | cacgctgccg | ccccagtgga | gcgcgatggc | atcggtgcga | attcttaacc | 120 |

```
tgnagggtac tgaggtctct ggtacgctgc cgcctgagtg gatatcnatg ancaggctgc      180
aaactctgaa tctgcggcgc acgaaantat ccggcactct gccgcccgaa tgganttcta      240
tgaacagcct ggagtacttt cacctttatc ttactcaggt ctccggcacg ctgccgcccg      300
agtggagtgg gatgtcnaag gccgcatact tctggctgga atactgcgac ctgtccggca      360
ntctgccgcc cnagtggtcg tcnatgccaa agctgcgcgg tatctcactg ancggcaaca      420
aattcttgcg ngtgtntncc ngactcntgg gattcagaaa ggtggtcctt gttgttgggc      480
atcnaaggan caaaccccaa ngggcccncn aattgcttgg gcntgcttaa ggganttgcac      540 naaccaacnc cnccaaaaac cccccccacc ncnaaannac nanccccac ttaanncccn        600

<210> SEQ ID NO 32
<211> LENGTH: 600
<212> TYPE: DNA
<213> ORGANISM: Leishmania major
<220> FEATURE:
<221> NAME/KEY: misc_feature
<222> LOCATION: (1)...(600)
<223> OTHER INFORMATION: n = A,T,C or G

<400> SEQUENCE: 32
ngcacgagaa gcgcaactgg cgcatcgcat ctgtgactat ctgcctgaac agggggcaatn     60 gtttgttggt aacagcctgg tggtacgtct gattgatncg cttncgcaan ttccggcagg      120
ttacccggtg tacancaacc gtggggccan cggtatcnac nggctgcttt cgaccgccgc      180
cggngttcan cgggcaacg gcaaaccgac gctggcgatt gtgggcgatc tctccgcact       240
ttacgatctc aacgcnctgg cgttattgcg tcaggtttct gcgccgctgg tattaattgt       300
ggtgaacaac aacggcnggg caaaattttc tcgctgttgc caacgccccc aaagcnagcg     360
tgaagcgttt ctatctgatg ccgcaaaacg tccattttga aacacgccgc cncccatgtt     420
tcganctgaa aatatcatcg tccgcaaaac tggcangaaa cttngaaaac cgcattttgc     480 cgacncccctg gcncacgccc aacccaccca ccggttgatt gaaaatggtg ggttaacgaa    540
nccnnatggg tgccccaaan cncnnccanc caaatttctg ggcccaggtt aaanccctttt   600

<210> SEQ ID NO 33
<211> LENGTH: 600
<212> TYPE: DNA
<213> ORGANISM: Leishmania major
<220> FEATURE:
<221> NAME/KEY: misc_feature
<222> LOCATION: (1)...(600)
<223> OTHER INFORMATION: n = A,T,C or G

<400> SEQUENCE: 33
acgatgacca tgccccgaag gaggatggcc atgcgccgaa gaacgatgac catgccccga      60
aggaggatgg ccatgcgccg aagaacgatg accatgcccc gaaggaggat ggccatgcgc      120
cgaagaacga cggggatgtg cagaanaaga gcgaagatgg agacaacgtg ggagagggag     180
gcaagggcaa tgaggatggt aacgatgatc agccgaagga gcacgctgcc ggcaactagt      240
gggctgcgtc cgggcttgtg tgcganccgt gctctgcacc ccgccgctcg tgcatcctcg      300
catgtggact gcgtgtgtct ctcccgcttt gtctctctcc cccacacagt ggctgatgcc      360 tgcacgggt tgctgtggct gcacctcctg accactgcca gctttcttgg cttgcctccc      420
ctctgcgcct ccgtcgtgc cgtcgtgcc gaattcgata tcaagcttat cgataccgtc        480
nacctcgaag gggggcccgg ttaccattc gccctatant gagtcntatt acaattcctg     540
gcgtcgtttt acacgtcgtg actgggaaaa accctggcgt tccccactta tcgccttgca    600
```

<210> SEQ ID NO 34
<211> LENGTH: 516
<212> TYPE: DNA
<213> ORGANISM: Leishmania major

<400> SEQUENCE: 34

| | | | | | |
|---|---|---|---|---|---|
| agctgcagca | gcgcctagac | accgccacgc | agcagcgcgc | cgagctggag | gcacgggtgg | 60 |
| cacggctggc | cgcggaccgc | gacgaggcgc | gccagcagct | ggccgcgaac | gccgaggagc | 120 |
| tgcagcagcg | cctagacacc | gccacgcagc | agcgcgccga | gctggaggca | cgggtggcac | 180 |
| ggctggccgc | ggacggcgac | gaggcccgcc | agcagctggc | cgcgaacgcc | gaggagctgc | 240 |
| agcagcgcct | agacaccgcc | acgcagcagc | gcgccgagct | ggaggcacag | gtggcacggc | 300 |
| tggccgcgaa | cgccgaggag | ctgcagcagc | gcctagacac | cgccacgcag | cagcgcgccg | 360 |
| agctggaggc | acgggtggca | cggctggccg | cggaccgcga | cgaggcgcgc | cagcagctgg | 420 |
| ccgcgaacgc | cgaggagctg | cagcagcgcc | tagacaccgc | cacgcagcag | cgcgccgagc | 480 |
| tggargcaca | ggtggcacgg | ctggccgcga | amgccg | | | 516 |

<210> SEQ ID NO 35
<211> LENGTH: 822
<212> TYPE: DNA
<213> ORGANISM: Leishmania major
<220> FEATURE:
<221> NAME/KEY: misc_feature
<222> LOCATION: (1)...(822)
<223> OTHER INFORMATION: n = A,T,C or G

<400> SEQUENCE: 35

| | | | | | |
|---|---|---|---|---|---|
| ggcacganag | atcttcgtga | agacgctgac | cggcaanacg | atcgcgctgg | aggtggagcc | 60 |
| gagcgacacg | atcgagaacg | tgaaggccaa | gatccaggac | aaggagggca | tcccgccgga | 120 |
| ccagcagcgc | ctgatcttcg | ccggcaagca | gctggaggan | ggccgcacgc | tctcggacta | 180 |
| caacatccag | aaggagtcca | cgctgcacct | ggtgctgcgc | ctgcgcggcg | gcatgcanat | 240 |
| cttcgtgaaa | acgctnaccg | gcaanacaat | cgcgctgaa | gtggagccga | acgaccnatc | 300 |
| gaaaacgtga | aggccnanat | ccangacaag | gaaggcntcc | cgccgganca | gcacgcctga | 360 |
| tcttccnccg | gcaaccactt | gangaagggc | ncacgctctc | ngactacnac | atccanaaag | 420 |
| gattccnccc | tgcaccttgt | tgcttgcncc | ttgctcgggg | ggcatgccna | atcttccttn | 480 |
| aaaacctcaa | ccggcaanaa | caatcccccn | cngaagttgg | aacccaacca | ncccattcna | 540 |
| aaactttaaa | ggccnnnatt | ccngaacaan | gaagggcttc | cccccggac | cnncaancnc | 600 |
| cctgattntt | ccccggnnn | ncantttgga | angaagggcc | ccncctccn | ccgaattncn | 660 |
| acntcccnaa | anggattccc | ccctnccct | tgnttttgc | gccnnnnnc | ggcnncntnc | 720 |
| cnaaattccg | nccnaaggnc | cccantanan | cnactttccc | nttccccccc | nnnnttttgc | 780 |
| ntaaantttt | tncccccnna | aanntcccnt | ttncnanttn | an | | 822 |

<210> SEQ ID NO 36
<211> LENGTH: 146
<212> TYPE: PRT
<213> ORGANISM: Leishmania major
<220> FEATURE:
<221> NAME/KEY: VARIANT
<222> LOCATION: (1)...(146)
<223> OTHER INFORMATION: Xaa = Any Amino Acid

<400> SEQUENCE: 36

```
Gly Thr Ser Pro Cys Leu His Leu Leu Ala Asp Ile Arg Gly Glu Phe
1               5                   10                  15

Phe Asn Leu Arg Arg Val Glu Leu Leu Asn Val Ala Gln Gln Ala Gln
                20                  25                  30

Leu Val Val Ala His Glu Gly Asp Gly Gln Ser Ser Ala Ala His Ala
            35                  40                  45

Ala Ser Ala Ala Asp Ala Val Asn Val Leu Leu Thr Arg Glu Arg Gln
50                      55                  60

Ile Val Ala Glu Asp Glu Arg Asp Ala Leu His Ile Asn Ala Thr Arg
65                  70                  75                      80

Pro Gln Val Arg Cys Asn Xaa His Ala Ala Val Ser Ile Thr Glu Cys
                85                  90                  95

Arg Ile Ile Ser Ser Arg Ser Ala Trp Gly Met Ser Pro Cys Met Ala
                100                 105                 110

Asp Thr Ala Lys Phe Ser Arg Val Ile Phe Leu Ala Ser Cys Ser Thr
            115                 120                 125

Phe Leu Arg Val Leu Xaa Lys Thr Thr Ala Trp Ala Ile Val Lys Leu
        130                 135                 140

Ser Tyr
145

<210> SEQ ID NO 37
<211> LENGTH: 77
<212> TYPE: PRT
<213> ORGANISM: Leishmania major
<220> FEATURE:
<221> NAME/KEY: VARIANT
<222> LOCATION: (1)...(77)
<223> OTHER INFORMATION: Xaa = Any Amino Acid

<400> SEQUENCE: 37

Ala Gln Gly Phe Arg Val Ile Phe Thr His Gly Gly Ala Gln Met Gly
1               5                   10                  15

Glu Val Asn Thr Arg Thr Glu Leu Leu Asp His Ile Asn Gln Ile Val
                20                  25                  30

Val Ser Thr His Ala Val Xaa Thr Gly Ala His Gly Lys Thr Val Cys
            35                  40                  45

His Ala Val Tyr Gly Ile Asn His Pro Leu His Ile Phe Asn Gly Gly
        50                  55                  60

Asn Asn Ala Arg Gln Ala Glu Asp Pro Ala Arg Leu Ile
65                  70                  75

<210> SEQ ID NO 38
<211> LENGTH: 68
<212> TYPE: PRT
<213> ORGANISM: Leishmania major
<220> FEATURE:
<221> NAME/KEY: VARIANT
<222> LOCATION: (1)...(68)
<223> OTHER INFORMATION: Xaa = Any Amino Acid

<400> SEQUENCE: 38

His Glu Pro Gln Trp Ser Ser Met Lys Ile Leu Gln Tyr Leu Thr Leu
1               5                   10                  15

Asp Gly Thr Gln Val Ser Gly Thr Leu Pro Pro Gln Trp Ser Ala Met
                20                  25                  30

Ala Ser Val Arg Ile Leu Asn Leu Xaa Gly Thr Glu Val Ser Gly Thr
            35                  40                  45

Leu Pro Pro Glu Trp Ile Ser Met Xaa Arg Leu Gln Thr Leu Asn Leu
```

```
        50                  55                  60

Arg Arg Thr Lys
 65

<210> SEQ ID NO 39
<211> LENGTH: 65
<212> TYPE: PRT
<213> ORGANISM: Leishmania major
<220> FEATURE:
<221> NAME/KEY: VARIANT
<222> LOCATION: (1)...(65)
<223> OTHER INFORMATION: Xaa = Any Amino Acid

<400> SEQUENCE: 39

Ala Arg Glu Ala Gln Leu Ala His Arg Ile Cys Asp Tyr Leu Pro Glu
 1               5                  10                  15

Gln Gly Gln Xaa Phe Val Gly Asn Ser Leu Val Val Arg Leu Ile Asp
                20                  25                  30

Xaa Leu Xaa Gln Xaa Pro Ala Gly Tyr Pro Val Tyr Xaa Asn Arg Gly
        35                  40                  45

Ala Xaa Gly Ile Xaa Xaa Leu Leu Ser Thr Ala Ala Gly Val Xaa Arg
    50                  55                  60

Ala
 65

<210> SEQ ID NO 40
<211> LENGTH: 78
<212> TYPE: PRT
<213> ORGANISM: Leishmania major
<220> FEATURE:
<221> NAME/KEY: VARIANT
<222> LOCATION: (1)...(78)
<223> OTHER INFORMATION: Xaa = Any Amino Acid

<400> SEQUENCE: 40

Asp Asp His Ala Pro Lys Glu Asp Gly His Ala Pro Lys Asn Asp Asp
 1               5                  10                  15

His Ala Pro Lys Glu Asp Gly His Ala Pro Lys Asn Asp Asp His Ala
                20                  25                  30

Pro Lys Glu Asp Gly His Ala Pro Lys Asn Asp Gly Asp Val Gln Xaa
        35                  40                  45

Lys Ser Glu Asp Gly Asp Asn Val Gly Glu Gly Lys Gly Asn Glu
    50                  55                  60

Asp Gly Asn Asp Asp Gln Pro Lys Glu His Ala Ala Gly Asn
 65                  70                  75

<210> SEQ ID NO 41
<211> LENGTH: 169
<212> TYPE: PRT
<213> ORGANISM: Leishmania major

<400> SEQUENCE: 41

Leu Gln Gln Arg Leu Asp Thr Ala Thr Gln Gln Arg Ala Glu Leu Glu
 1               5                  10                  15

Ala Arg Val Ala Arg Leu Ala Ala Asp Arg Asp Glu Ala Arg Gln Gln
                20                  25                  30

Leu Ala Ala Asn Ala Glu Glu Leu Gln Gln Arg Leu Asp Thr Ala Thr
        35                  40                  45

Gln Gln Arg Ala Glu Leu Glu Ala Arg Val Ala Arg Leu Ala Ala Asp
    50                  55                  60
```

```
Gly Asp Glu Ala Arg Gln Gln Leu Ala Ala Asn Ala Glu Glu Leu Gln
 65                  70                  75                  80

Gln Arg Leu Asp Thr Ala Thr Gln Gln Arg Ala Glu Leu Glu Ala Gln
                 85                  90                  95

Val Ala Arg Leu Ala Ala Asn Ala Glu Glu Leu Gln Gln Arg Leu Asp
                100                 105                 110

Thr Ala Thr Gln Gln Arg Ala Glu Leu Glu Ala Arg Val Ala Arg Leu
            115                 120                 125

Ala Ala Asp Arg Asp Glu Ala Arg Gln Gln Leu Ala Ala Asn Ala Glu
            130                 135                 140

Glu Leu Gln Gln Arg Leu Asp Thr Ala Thr Gln Gln Arg Ala Glu Leu
145                 150                 155                 160

Glu Ala Gln Val Ala Arg Leu Ala Ala
                165
```

```
<210> SEQ ID NO 42
<211> LENGTH: 98
<212> TYPE: PRT
<213> ORGANISM: Leishmania major
<220> FEATURE:
<221> NAME/KEY: VARIANT
<222> LOCATION: (1)...(98)
<223> OTHER INFORMATION: Xaa = Any Amino Acid

<400> SEQUENCE: 42
```

```
Ala Arg Xaa Ile Phe Val Lys Thr Leu Thr Gly Xaa Thr Ile Ala Leu
  1               5                  10                  15

Glu Val Glu Pro Ser Asp Thr Ile Glu Asn Val Lys Ala Lys Ile Gln
                 20                  25                  30

Asp Lys Glu Gly Ile Pro Pro Asp Gln Gln Arg Leu Ile Phe Ala Gly
             35                  40                  45

Lys Gln Leu Glu Xaa Gly Arg Thr Leu Ser Asp Tyr Asn Ile Gln Lys
 50                  55                  60

Glu Ser Thr Leu His Leu Val Leu Arg Leu Arg Gly Gly Met Xaa Ile
 65                  70                  75                  80

Phe Val Lys Thr Leu Thr Gly Xaa Thr Ile Ala Leu Glu Val Glu Pro
                 85                  90                  95

Asn Asp
```

```
<210> SEQ ID NO 43
<211> LENGTH: 39
<212> TYPE: PRT
<213> ORGANISM: Leishmania major

<400> SEQUENCE: 43
```

```
Leu Gln Gln Arg Leu Asp Thr Ala Thr Gln Gln Arg Ala Glu Leu Glu
  1               5                  10                  15

Ala Arg Val Ala Arg Leu Ala Ala Asp Arg Asp Glu Ala Arg Gln Gln
                 20                  25                  30

Leu Ala Ala Asn Ala Glu Glu
            35
```

```
<210> SEQ ID NO 44
<211> LENGTH: 600
<212> TYPE: DNA
<213> ORGANISM: Leishmania chagasi
<220> FEATURE:
<221> NAME/KEY: misc_feature
<222> LOCATION: (1)...(600)
<223> OTHER INFORMATION: n = A,T,C or G
```

<400> SEQUENCE: 44

```
cggccgcctc agcgaggagg agatcgagcg catggtgcgc gaggctgccg agttcgagga      60
tgaggaccgc aaggtgcgcg aacgtgtcga agcgaagaac tcgctagaga gcatcgcgta     120
ctcgcttcgc aaccagatca acgacaagga caagcttggt gacaagctcg ccgcggacga     180
caagaaggcg atcgaggagg ctgtgaagga tgccctcgac tttgtccacg agaaccccaa     240
tgcagaccgt gaggagttcg aggctgctcg cacgaagctg cagagtgtga cgaaccccat     300
cattcaaaag gtgtaccagg gcgccgccgg ctctggtgca agagaggcgg acgcgatgga     360
tgacttgtta gtcggccgcg tgaaaagaaa acagggaaa gcgggaacat nccacaanaa     420
ccnaagaaga aagggggtng cgacaccgct cgaacaccga cggcncacat ncntcatggg     480
catgctcagc tttcctctcc ccaacaaacc agaaggtttt ctccaaacnc cgtctcngcn     540
cccaaaatac ggaaangtta ancgaaaaan ccccttccac caattgnngt tcttttgttt     600
```

<210> SEQ ID NO 45
<211> LENGTH: 1748
<212> TYPE: DNA
<213> ORGANISM: Leishmania chagasi

<400> SEQUENCE: 45

```
ctagtggatc ccccgggctg caggaattca cggaatacgt acctcctccc ccttcttggt      60
agaagaacaa caacaacgtt caagacgacg ccgcgccttc ttgtaccgca tttgcttctg     120
agcacgttca atccgtgcct tgcaaacatg gaggcgtaca agaagctgga aacgatcttt     180
acgaaggtct accgcctgga ccacttcctc ggtctgggca actgggacat gaacacaaac     240
atgcccccca agggcgagga atcacgcggt gaggcgatgg cgatgctctc ggagctccgc     300
tttggcttca tcacggcacc ggaggtgaaa agcctgattg agagtgccac caagggcagc     360
gaggagctga atgcggtgca gcgcgctaac ttgcgggaga tgaggcgtgc gtggaagagc     420
gccaccgcct tgccggctga gtttgtgggc cgcaagatgc gcctcacgac acacgcgcac     480
agcgtgtggc gcgacagccg caaagcaaat gacttcgcca agttcctacc ggtgctcagg     540
gacctggtgg cgctcgcccg tgaggagggc tcatacctcg ccgccggcac ctcccctctcc     600
ccgtatgagg cgctcatgaa cgagtacgag ccaggaatca cgacacaaaa gctggatgag     660
gtgtacgcaa atgtaaagtc gtggctgccg cagctgctaa aggacattgt gcagaagcag     720
tccggcgagt cggtgattgc gttctcgcat aagttcccgc aggacaagca ggaagcactg     780
tgcaaggaat tcatgaagat ctggcacttc gacaccgatg ccggtcgcct cgacgtcagc     840
ccccaccctt tcacgggaat gacgaaggag gactgccgac tcacaacaaa ctacatcgaa     900
gacacgtttg ttcagagctt gtatggcgtc atccacgaga gtgggcatgg caagtacgag     960
cagaactgtg gccacgcgga gcacatcacg cagccggtgt gcaacgcccg ctctcttggc    1020
ctgcatgaga gccagagcct ctttgcggag tttcagatcg ccacgcgac gcccttcatc    1080
gactacctca caactcgcct tcctgagttc ttcgaggcgc agccagcgtt ctcgcaggac    1140
aacatgcgca agtcgctgca gcaggtgaag ccgggctaca ttcgcgtcga tgccgatgag    1200
gtgtgctacc ctctgcacgt gatcctgcgc tacgagatcg agcgcgactt gatggagggc    1260
aaaatggagg tggaagacgt gccgcgcgcg tggaacgcaa agatgcagga gtacttgggt    1320
ctctcaacgg agggccgtga cgacgttggg tgcctgcagg acgtgcattg gtccatggtg    1380
cgctcggcta ctctccgacg tactcgctcg gcgccatgta tgcggcgcag atcatggcga    1440
```

| gcatccgaaa ggagctggga gacgacaagg tggatgagtg cctgcgcacc ggtgagctcg | 1500 |
| gcccctcct ggaaaagcag caggagaaga tctgggatca tgggtgcctg tacgagacgg | 1560 |
| acgacctcat gacgcgtgcg acgggcgaga cgctgaaccc cgagtacctg cgccgccacc | 1620 |
| tggaggcgcg ctacataaac gcctgagtcg cgagcggttg acacacgcgc tcgctagcac | 1680 |
| atgacgcgtc tttattattc tttgttgtgc attcggaatt ccgcggaatt cgatatcaag | 1740 |
| cttatcga | 1748 |

<210> SEQ ID NO 46
<211> LENGTH: 560
<212> TYPE: DNA
<213> ORGANISM: Leishmania chagasi
<220> FEATURE:
<221> NAME/KEY: misc_feature
<222> LOCATION: (1)...(560)
<223> OTHER INFORMATION: n = A,T,C or G

<400> SEQUENCE: 46

| cggaaggagg atggccatac acagaaaaat gacggcgatg ccctaagga ggacggccgt | 60 |
| acacagaaaa acgacgacgg tggccctaag gaggacggcc atacacagaa aaatgacggc | 120 |
| gatggcccta aggaggacgg ccgtacacag aaaaataacg gcgatggccc tnaggaggac | 180 |
| ggccatacac agaaaaatga cggcgatgcc cctnaggagg acggccgtac acanaaaaat | 240 |
| gacggcnatg gccctnagga ggacggccgt acacagaaaa atgacngcca tggcccttag | 300 |
| gangacgccg tacacagaaa aatgacgcna tggccctnag gaggacggc catacccana | 360 |
| aaaattgacg gcnatngccc ttaggangac ggccgtnccc anaaanantg acngcggtng | 420 |
| cccttaagga agatgaaaat ctgccaccaa aacnattggg aatgcncagg aaaanaacna | 480 |
| anatngaccc cacgtggggg atggacttaa cngcnattaa nattgttacc attatcnacc | 540 |
| naaggacnng ttgccgncaa | 560 |

<210> SEQ ID NO 47
<211> LENGTH: 600
<212> TYPE: DNA
<213> ORGANISM: Leishmania chagasi
<220> FEATURE:
<221> NAME/KEY: misc_feature
<222> LOCATION: (1)...(600)
<223> OTHER INFORMATION: n = A,T,C or G

<400> SEQUENCE: 47

| cgtccgagaa acccgtacat gtatgctgct ggtagaaggc gcagagctgg tccctctgat | 60 |
| gcacaagcat gaggtcgtac attgcctggt tcgtcatttt ccagagcaca acgagcagcg | 120 |
| tcatcataca gcatccaata gccgccagag tgaatgcgat gcgcacacca agtcgaaagt | 180 |
| ggtcgaccag tagggaatg tgaccctggc tgcgtgcaa catgatcgcc acgccagcgg | 240 |
| tgggccacac cacaacagag gcgacgaaag agaacatgaa cttgctcacg aagctnacaa | 300 |
| taagggcgtc gctngtgatg ctaagaacca cgccnaggta gacggcgaag ancaaactaa | 360 |
| acacaagcgt gacgatcccg aaaagaagga tctctgcgga attttcgtga gatagnaaat | 420 |
| gcccgtactg gaaaaanaag ccggcaggcg cgcgataacg ctgcaacttg ccgctcctcg | 480 |
| cgggcgcgtt ttcgctcctt ctccgacttg atggcgcngt cngncttgac aaaacggtta | 540 |
| agctcctcat gccccagccg attcccagct cacggtccac ttccggccat gcccacggac | 600 |

<210> SEQ ID NO 48
<211> LENGTH: 1053

```
<212> TYPE: DNA
<213> ORGANISM: Leishmania chagasi
<220> FEATURE:
<221> NAME/KEY: misc_feature
<222> LOCATION: (1)...(1053)
<223> OTHER INFORMATION: n = A,T,C or G

<400> SEQUENCE: 48
gggaaaaaag tggagctcca ccgcggtggc ggccgctcta gaactagtgg atccccgggg      60
ctgcaggaat tcgcggaat tccgcggaat tccgcggaat tccgtccgac gcggcacccg     120 cacagggtc gacagtgacg caacctcctc caccactgcg gcctacgacg cgccggctc      180 cgcgccagtg atggttgacg ccaatgtgag ccaccctccg tacgcgggc atgaccaagt     240 gtacatgcac gtcggcaagc ccatcgtggg caacaccctc gacggataca acgggtgcgt     300
gttcgcctac gggcanacgg gcagcggcaa aaccttcacg atgctcggnt acgcgccgag     360
cacgancgac atccgcgctc gcaaaggtc cgtcccctgc ggggccagca gcatggagaa     420
cagcactcct cttgacagcg ctgtggagcc gtttgagagc gatgacggcg acgacgtggt     480
ggacaagacg gggctggatc cgaacgagct gcaaggcatc atcccgcgcg cgtgcacgga     540
cctgttcgat ggtctccgtg cgaagcgcgc caaggactcc gacttcacgt accgcgtgga     600
ggtgtcttac tacgagatct acaacagaaa ggtgttcgat ctcatccggc cgcagcgcaa     660
cacggacctg aggatacgta actcgcccaa ctccggtcca tttatcgaag gcctgacgtg     720
gaagatggtg tccaaggagg aagacgtcgc ccgcgtgatt cgcaagggca tgcaggagcg     780
ccacacggct gcgaccaagt tcaacgaccg cagcagccgc agccacgcca tcctcacctt     840
caacattgtg cagctgtcga tggacgactc cgacaacgcg ttccagatgc gcagcaagct     900
gaacctggtg gaccttgctg gtcggagcg cactggtgcg gccggagccg agggcaatga     960
gttccacgac ggtgtgaaga tcaaccactc gctgacggtg ctggggcgcg tgatcgaccg    1020
tctggcggac ctctcgcaga acaagggagg ggg                                 1053

<210> SEQ ID NO 49
<211> LENGTH: 136
<212> TYPE: PRT
<213> ORGANISM: Leishmania chagasi

<400> SEQUENCE: 49

Gly Arg Leu Ser Glu Glu Glu Ile Glu Arg Met Val Arg Glu Ala Ala
 1               5                  10                  15

Glu Phe Glu Asp Glu Asp Arg Lys Val Arg Glu Arg Val Glu Ala Lys
                20                  25                  30

Asn Ser Leu Glu Ser Ile Ala Tyr Ser Leu Arg Asn Gln Ile Asn Asp
            35                  40                  45

Lys Asp Lys Leu Gly Asp Lys Leu Ala Ala Asp Lys Lys Ala Ile
        50                  55                  60

Glu Glu Ala Val Lys Asp Ala Leu Asp Phe Val His Glu Asn Pro Asn
 65                  70                  75                  80

Ala Asp Arg Glu Glu Phe Glu Ala Ala Arg Thr Lys Leu Gln Ser Val
                85                  90                  95

Thr Asn Pro Ile Ile Gln Lys Val Tyr Gln Gly Ala Ala Gly Ser Gly
               100                 105                 110

Ala Glu Glu Ala Asp Ala Met Asp Asp Leu Leu Val Gly Arg Val Lys
           115                 120                 125

Arg Lys Thr Gly Lys Ala Gly Thr
       130                 135
```

<210> SEQ ID NO 50
<211> LENGTH: 510
<212> TYPE: PRT
<213> ORGANISM: Leishmania chagasi

<400> SEQUENCE: 50

| Tyr | Leu | Leu | Pro | Leu | Gly | Arg | Arg | Thr | Thr | Thr | Phe | Lys | Thr |
|-----|-----|-----|-----|-----|-----|-----|-----|-----|-----|-----|-----|-----|-----|
| 1 | | | | 5 | | | | | 10 | | | | 15 |

| Thr | Pro | Arg | Leu | Leu | Val | Pro | His | Leu | Leu | Ser | Thr | Phe | Asn | Pro |
| | | | 20 | | | | | 25 | | | | | 30 | |

Cys Leu Ala Asn Met Glu Ala Tyr Lys Lys Leu Glu Thr Ile Phe Thr
          35                  40                  45

Lys Val Tyr Arg Leu Asp His Phe Leu Gly Leu Gly Asn Trp Asp Met
 50                      55                  60

Asn Thr Asn Met Pro Pro Lys Gly Glu Glu Ser Arg Gly Glu Ala Met
 65                  70                  75                  80

Ala Met Leu Ser Glu Leu Arg Phe Gly Phe Ile Thr Ala Pro Glu Val
             85                  90                  95

Lys Ser Leu Ile Glu Ser Ala Thr Lys Gly Ser Glu Glu Leu Asn Ala
             100                 105                 110

Val Gln Arg Ala Asn Leu Arg Glu Met Arg Arg Ala Trp Lys Ser Ala
             115                 120                 125

Thr Ala Leu Pro Ala Glu Phe Val Gly Arg Lys Met Arg Leu Thr Thr
 130                     135                 140

His Ala His Ser Val Trp Arg Asp Ser Arg Lys Ala Asn Asp Phe Ala
 145                     150                 155                 160

Lys Phe Leu Pro Val Leu Arg Asp Leu Val Ala Leu Ala Arg Glu Glu
                 165                 170                 175

Gly Ser Tyr Leu Ala Ala Gly Thr Ser Leu Ser Pro Tyr Glu Ala Leu
             180                 185                 190

Met Asn Glu Tyr Glu Pro Gly Ile Thr Thr Gln Lys Leu Asp Glu Val
             195                 200                 205

Tyr Ala Asn Val Lys Ser Trp Leu Pro Gln Leu Leu Lys Asp Ile Val
 210                     215                 220

Gln Lys Gln Ser Gly Glu Ser Val Ile Ala Phe Ser His Lys Phe Pro
225                     230                 235                 240

Gln Asp Lys Gln Glu Ala Leu Cys Lys Glu Phe Met Lys Ile Trp His
                 245                 250                 255

Phe Asp Thr Asp Ala Gly Arg Leu Asp Val Ser Pro His Pro Phe Thr
                 260                 265                 270

Gly Met Thr Lys Glu Asp Cys Arg Leu Thr Thr Asn Tyr Ile Glu Asp
             275                 280                 285

Thr Phe Val Gln Ser Leu Tyr Gly Val Ile His Glu Ser Gly His Gly
 290                     295                 300

Lys Tyr Glu Gln Asn Cys Gly Pro Arg Glu His Ile Thr Gln Pro Val
305                     310                 315                 320

Cys Asn Ala Arg Ser Leu Gly Leu His Glu Ser Gln Ser Leu Phe Ala
                 325                 330                 335

Glu Phe Gln Ile Gly His Ala Thr Pro Phe Ile Asp Tyr Leu Thr Thr
             340                 345                 350

Arg Leu Pro Glu Phe Phe Glu Ala Gln Pro Ala Phe Ser Gln Asp Asn
 355                     360                 365

Met Arg Lys Ser Leu Gln Gln Val Lys Pro Gly Tyr Ile Arg Val Asp

```
                370                 375                 380
Ala Asp Glu Val Cys Tyr Pro Leu His Val Ile Leu Arg Tyr Glu Ile
385                 390                 395                 400

Glu Arg Asp Leu Met Glu Gly Lys Met Glu Val Glu Asp Val Pro Arg
                405                 410                 415

Ala Trp Asn Ala Lys Met Gln Glu Tyr Leu Gly Leu Ser Thr Glu Gly
                420                 425                 430

Arg Asp Asp Val Gly Cys Leu Gln Asp Val His Trp Ser Met Val Arg
                435                 440                 445

Ser Ala Thr Leu Arg Arg Thr Arg Ser Ala Pro Cys Met Arg Arg Arg
                450                 455                 460

Ser Trp Arg Ala Ser Glu Arg Ser Trp Glu Thr Thr Arg Trp Met Ser
465                 470                 475                 480

Ala Cys Ala Pro Val Ser Ser Ala Pro Ser Trp Lys Ser Ser Arg Arg
                485                 490                 495

Arg Ser Gly Ile Met Gly Ala Cys Thr Arg Arg Thr Thr Ser
                500                 505                 510

<210> SEQ ID NO 51
<211> LENGTH: 107
<212> TYPE: PRT
<213> ORGANISM: Leishmania chagasi
<220> FEATURE:
<221> NAME/KEY: VARIANT
<222> LOCATION: (1)...(107)
<223> OTHER INFORMATION: Xaa = Any Amino Acid

<400> SEQUENCE: 51

Gly Arg Arg Met Ala Ile His Arg Lys Met Thr Ala Met Ala Leu Arg
1               5                   10                  15

Arg Thr Ala Val His Arg Lys Thr Thr Thr Val Ala Leu Arg Arg Thr
                20                  25                  30

Ala Ile His Arg Lys Met Thr Ala Met Ala Leu Arg Arg Thr Ala Val
                35                  40                  45

His Arg Lys Ile Thr Ala Met Ala Leu Arg Arg Thr Ala Ile His Arg
            50                  55                  60

Lys Met Thr Ala Met Pro Leu Arg Arg Thr Ala Val His Xaa Lys Met
65                  70                  75                  80

Thr Ala Met Ala Leu Arg Arg Thr Ala Val His Arg Lys Met Thr Ala
                85                  90                  95

Met Ala Leu Arg Xaa Thr Pro Tyr Thr Glu Lys
                100                 105

<210> SEQ ID NO 52
<211> LENGTH: 63
<212> TYPE: PRT
<213> ORGANISM: Leishmania chagasi

<400> SEQUENCE: 52

Val Arg Glu Thr Arg Thr Cys Met Leu Leu Val Glu Gly Ala Glu Leu
1               5                   10                  15

Val Pro Leu Met His Lys His Glu Val Val His Cys Leu Val Arg His
                20                  25                  30

Phe Pro Glu His Asn Glu Gln Arg His His Thr Ala Ser Asn Ser Arg
            35                  40                  45

Gln Ser Glu Cys Asp Ala His Thr Lys Ser Lys Val Val Asp Gln
            50                  55                  60
```

```
<210> SEQ ID NO 53
<211> LENGTH: 324
<212> TYPE: PRT
<213> ORGANISM: Leishmania chagasi
<220> FEATURE:
<221> NAME/KEY: VARIANT
<222> LOCATION: (1)...(324)
<223> OTHER INFORMATION: Xaa = Any Amino Acid

<400> SEQUENCE: 53

Phe Arg Gly Ile Pro Arg Asn Ser Val Arg Gly Thr Arg Thr Gly
 1               5                  10                  15

Val Asp Ser Asp Ala Thr Ser Ser Thr Thr Ala Ala Tyr Asp Gly Ala
                20                  25                  30

Gly Ser Ala Pro Val Met Val Asp Ala Asn Val Ser His Pro Pro Tyr
            35                  40                  45

Ala Gly His Asp Gln Val Tyr Met His Val Gly Lys Pro Ile Val Gly
        50                  55                  60

Asn Thr Leu Asp Gly Tyr Asn Gly Cys Val Phe Ala Tyr Gly Xaa Thr
65                  70                  75                  80

Gly Ser Gly Lys Thr Phe Thr Met Leu Gly Tyr Ala Pro Ser Thr Xaa
                85                  90                  95

Asp Ile Arg Ala Arg Lys Gly Ser Val Pro Cys Gly Ala Ser Ser Met
            100                 105                 110

Glu Asn Ser Thr Pro Leu Asp Ser Ala Val Glu Pro Phe Glu Ser Asp
        115                 120                 125

Asp Gly Asp Asp Val Val Asp Lys Thr Gly Leu Asp Pro Asn Glu Leu
    130                 135                 140

Gln Gly Ile Ile Pro Arg Ala Cys Thr Asp Leu Phe Asp Gly Leu Arg
145                 150                 155                 160

Ala Lys Arg Ala Lys Asp Ser Asp Phe Thr Tyr Arg Val Glu Val Ser
                165                 170                 175

Tyr Tyr Glu Ile Tyr Asn Glu Lys Val Phe Asp Leu Ile Arg Pro Gln
            180                 185                 190

Arg Asn Thr Asp Leu Arg Ile Arg Asn Ser Pro Asn Ser Gly Pro Phe
        195                 200                 205

Ile Glu Gly Leu Thr Trp Lys Met Val Ser Lys Glu Glu Asp Val Ala
    210                 215                 220

Arg Val Ile Arg Lys Gly Met Gln Glu Arg His Thr Ala Ala Thr Lys
225                 230                 235                 240

Phe Asn Asp Arg Ser Ser Arg Ser His Ala Ile Leu Thr Phe Asn Ile
                245                 250                 255

Val Gln Leu Ser Met Asp Asp Ser Asp Asn Ala Phe Gln Met Arg Ser
            260                 265                 270

Lys Leu Asn Leu Val Asp Leu Ala Gly Ser Glu Arg Thr Gly Ala Ala
        275                 280                 285

Gly Ala Glu Gly Asn Glu Phe His Asp Gly Val Lys Ile Asn His Ser
    290                 295                 300

Leu Thr Val Leu Gly Arg Val Ile Asp Arg Leu Ala Asp Leu Ser Gln
305                 310                 315                 320

Asn Lys Gly Gly

<210> SEQ ID NO 54
<211> LENGTH: 1585
<212> TYPE: DNA
<213> ORGANISM: Leishmania major
```

```
<220> FEATURE:
<221> NAME/KEY: misc_feature
<222> LOCATION: (1)...(1585)
<223> OTHER INFORMATION: n = A,T,C or G

<400> SEQUENCE: 54
aaagctggag ctccaccgcg gtggcggccg ctctagaact agtggatccc ccgggctgca      60
ggaattcggc acgagtgctg cccgacatga catgctcgct gaccggactt cagtgcacag     120
acccgaactg caagacctgc acaacttacg gtcagtgcac agactgcaac gacggctacg     180
gtctcacctc ctccagcgtt tgcgtgcgct gcagtgtagc gggctgcaag agctgccccg     240
tcgacgctaa cgtctgcaaa gtgtgtctcg gcggcagcga gccgatcaac aatatgtgcc     300
cctgcaccga ccccaactgc gccagctgcc ccagcgacgc tggcacgtgc actcagtgcg     360
cgaacggcta cggtctcgtg gacggcgcct gtgtgagatg ccaggagccc aactgcttca     420
gctgcgacag cgacgcgaat aagtgcacac aatgtgcgcc gaactactac ctcaccccgc     480
tcttgacctg ctccccggtg gcctgcaaca tcgagcactg catgcagtgc gacccacaga     540
cgccgtcgcg ctgccaggag tgcgtgtccc cctacgtggt tgacagctac gacggcctct     600
gcaggctctc cgatgcctgc tccgtgccca actgcaagaa gtgcgagacc ggtacctcca     660
ggctctgcgc cgagtgcgac accggctaca gtctctccgc cgacgcgacg agctgcagca     720
gtccaaccac gcagccgtgc gaggtggagc actgcaacac atgtgtgaac ggcgatagca     780
cccgctgtgc ctactgcaac accggctact acgtctccga tggcaagtgc aaggccatgc     840
agggctgcta cgtgtcgaac tgcgcgcagt gcatgctgct tgacagcacc aagtgctcca     900
cgtgcgtgaa agggtacctg ctcacgtcgt cctacagttg cgtctcgcag aaagtcatca     960
acagtgcggc cgcgccctac tctctgtggg tggccgccgc cgtgctcctc acctcttttg    1020
ccatgcacct agcatagtgc gcagcggcat gcgaacaacc ccactctcat tctccaacat    1080
gtgcatacac acacacacag acagcggggc agcaccccct cccacacac acacacgcac    1140
ttccccttg tcttgttctt ctttcctcgn ttcgcatttc tttctctcgt gcgctggcgc     1200
cggcctcctg cacgtcgctc ccctcccct aacctctatt ctctctctct ctctctctcg    1260
ccggcatcat tgcttcttac ccttttctga tccttgctcg cgtgggcgga cactgccaca    1320
gtcccacagc gcagacacac gtgtttaaac ggcgcaggca tccctcccta tcacttcatt    1380
tctcctaaag ccactcacca agtcgcacac cgccctcccc catcgccgcc ccttccgggc    1440
gcagctgtgc ggaatgggtg tgtgctcgac ctcgttcctg gcagctcact cgcatgtgta    1500
cagccactcc aaccacgaaa gctctcttct gcgcacataa aaaaaaaaa aaaaaaaaa    1560
ctcgaggggg ggcccggtac ccaaa                                          1585
```

```
<210> SEQ ID NO 55
<211> LENGTH: 320
<212> TYPE: PRT
<213> ORGANISM: Leishmania major

<400> SEQUENCE: 55

Val Leu Pro Asp Met Thr Cys Ser Leu Thr Gly Leu Gln Cys Thr Asp
 1               5                  10                  15

Pro Asn Cys Lys Thr Cys Thr Thr Tyr Gly Gln Cys Thr Asp Cys Asn
             20                  25                  30

Asp Gly Tyr Gly Leu Thr Ser Ser Ser Val Cys Val Arg Cys Ser Val
         35                  40                  45

Ala Gly Cys Lys Ser Cys Pro Val Asp Ala Asn Val Cys Lys Val Cys
```

-continued

```
            50                  55                  60
Leu Gly Gly Ser Glu Pro Ile Asn Asn Met Cys Pro Cys Thr Asp Pro
 65                  70                  75                  80

Asn Cys Ala Ser Cys Pro Ser Asp Ala Gly Thr Cys Thr Gln Cys Ala
                 85                  90                  95

Asn Gly Tyr Gly Leu Val Asp Gly Ala Cys Val Arg Cys Gln Glu Pro
            100                 105                 110

Asn Cys Phe Ser Cys Asp Ser Asp Ala Asn Lys Cys Thr Gln Cys Ala
            115                 120                 125

Pro Asn Tyr Tyr Leu Thr Pro Leu Leu Thr Cys Ser Pro Val Ala Cys
            130                 135                 140

Asn Ile Glu His Cys Met Gln Cys Asp Pro Gln Thr Pro Ser Arg Cys
145                 150                 155                 160

Gln Glu Cys Val Ser Pro Tyr Val Val Asp Ser Tyr Asp Gly Leu Cys
                165                 170                 175

Arg Leu Ser Asp Ala Cys Ser Val Pro Asn Cys Lys Lys Cys Glu Thr
            180                 185                 190

Gly Thr Ser Arg Leu Cys Ala Glu Cys Asp Thr Gly Tyr Ser Leu Ser
            195                 200                 205

Ala Asp Ala Thr Ser Cys Ser Ser Pro Thr Thr Gln Pro Cys Glu Val
210                 215                 220

Glu His Cys Asn Thr Cys Val Asn Gly Asp Ser Thr Arg Cys Ala Tyr
225                 230                 235                 240

Cys Asn Thr Gly Tyr Tyr Val Ser Asp Gly Lys Cys Lys Ala Met Gln
                245                 250                 255

Gly Cys Tyr Val Ser Asn Cys Ala Gln Cys Met Leu Leu Asp Ser Thr
            260                 265                 270

Lys Cys Ser Thr Cys Val Lys Gly Tyr Leu Leu Thr Ser Ser Tyr Ser
            275                 280                 285

Cys Val Ser Gln Lys Val Ile Asn Ser Ala Ala Pro Tyr Ser Leu
            290                 295                 300

Trp Val Ala Ala Ala Val Leu Leu Thr Ser Phe Ala Met His Leu Ala
305                 310                 315                 320

<210> SEQ ID NO 56
<211> LENGTH: 14
<212> TYPE: PRT
<213> ORGANISM: Leishmania major

<400> SEQUENCE: 56

Pro Lys Glu Asp Gly His Ala Pro Lys Asn Asp Asp His Ala
  1               5                  10

<210> SEQ ID NO 57
<211> LENGTH: 7
<212> TYPE: PRT
<213> ORGANISM: Leishmania major

<400> SEQUENCE: 57

Pro Lys Glu Asp Gly His Ala
  1               5

<210> SEQ ID NO 58
<211> LENGTH: 7
<212> TYPE: PRT
<213> ORGANISM: Leishmania major

<400> SEQUENCE: 58
```

```
Pro Lys Asn Asp Asp His Ala
 1               5
```

<210> SEQ ID NO 59
<211> LENGTH: 264
<212> TYPE: DNA
<213> ORGANISM: Leishmania chagasi

<400> SEQUENCE: 59

| | | | | | |
|---|---|---|---|---|---|
| atgcaccatc | atcaccatca | catgggaagc | tcctgcacga | aggactccgc | aaaggagccc | 60 |
| cagaagcgtg | ctgataacat | cgatacgacc | actcgaagcg | atgagaagga | cggcatccat | 120 |
| gtccaggaga | gcgccggtcc | tgtgcaggag | aacttcgggg | atgcgcagga | gaagaacgaa | 180 |
| gatggacaca | acgtggggga | tggagctaac | gacaatgagg | atggtaacga | tgatcagccg | 240 |
| aaggagcagg | ttgccggcaa | ctag | | | | 264 |

<210> SEQ ID NO 60
<211> LENGTH: 744
<212> TYPE: DNA
<213> ORGANISM: Leishmania chagasi

<400> SEQUENCE: 60

| | | | | | |
|---|---|---|---|---|---|
| atgggagcct | actgcacgaa | ggactccgca | aaggagcccc | agaagcgtgc | tgataacatc | 60 |
| cataaaacca | ctgaggccaa | tcacagaggc | gccgccggtg | tgcccccgaa | gcacgccggc | 120 |
| ggtgcgatga | cgactctgc | cccgaaggag | gatggccata | cacagaaaaa | tgacggcgat | 180 |
| ggccctaagg | aggacggccg | tacacagaaa | aacgacgacg | gtgggcctaa | ggaggacggc | 240 |
| catacacaga | aaaatgacgg | cgatggccct | aaggaggacg | gccgtacaca | gaaaaataac | 300 |
| ggcgatggcc | ctaaggagga | cggccataca | gaaaaatg | acggcgatgc | cctaaggag | 360 |
| gacggccgta | cacagaaaaa | tgacggcgat | ggccctaagg | aggacggccg | tacacagaaa | 420 |
| aatgacggcg | atggccctaa | ggaggacggc | cgtacacaga | aaaatgacgg | cgatggccct | 480 |
| aaggaggacg | gccgtacaca | gaaaaatgac | ggcgatggcc | ctaaggagga | cggccataca | 540 |
| cagaaaaatg | acggcgatgg | ccctaaggag | gacggccgta | cacagaaaaa | tgacggcggt | 600 |
| ggccctaagg | aggatgagaa | tctgcagcaa | acgatggga | atgcgcagga | gaagaacgaa | 660 |
| gatggacaca | acgtggggga | tggagctaac | ggcaatgagg | atggtaacga | tgatcagccg | 720 |
| aaggagcagg | ttgccggcaa | ctag | | | | 744 |

<210> SEQ ID NO 61
<211> LENGTH: 80
<212> TYPE: PRT
<213> ORGANISM: Leishmania chagasi

<400> SEQUENCE: 61

```
Met Gly Ser Ser Cys Thr Lys Asp Ser Ala Lys Glu Pro Gln Lys Arg
 1               5                  10                  15

Ala Asp Asn Ile Asp Thr Thr Thr Arg Ser Asp Glu Lys Asp Gly Ile
            20                  25                  30

His Val Gln Glu Ser Ala Gly Pro Val Gln Glu Asn Phe Gly Asp Ala
        35                  40                  45

Gln Glu Lys Asn Glu Asp Gly His Asn Val Gly Asp Gly Ala Asn Asp
    50                  55                  60

Asn Glu Asp Gly Asn Asp Asp Gln Pro Lys Glu Gln Val Ala Gly Asn
65                  70                  75                  80
```

-continued

```
<210> SEQ ID NO 62
<211> LENGTH: 247
<212> TYPE: PRT
<213> ORGANISM: Leishmania chagasi

<400> SEQUENCE: 62
```

Met Gly Ala Tyr Cys Thr Lys Asp Ser Ala Lys Glu Pro Gln Lys Arg
 1               5                  10                  15

Ala Asp Asn Ile His Lys Thr Thr Glu Ala Asn His Arg Gly Ala Ala
                20                  25                  30

Gly Val Pro Pro Lys His Ala Gly Gly Ala Met Asn Asp Ser Ala Pro
            35                  40                  45

Lys Glu Asp Gly His Thr Gln Lys Asn Asp Gly Asp Gly Pro Lys Glu
    50                  55                  60

Asp Gly Arg Thr Gln Lys Asn Asp Asp Gly Gly Pro Lys Glu Asp Gly
65                  70                  75                  80

His Thr Gln Lys Asn Asp Gly Asp Gly Pro Lys Glu Asp Gly Arg Thr
                85                  90                  95

Gln Lys Asn Asn Gly Asp Gly Pro Lys Glu Asp Gly His Thr Gln Lys
            100                 105                 110

Asn Asp Gly Asp Ala Pro Lys Glu Asp Gly Arg Thr Gln Lys Asn Asp
        115                 120                 125

Gly Asp Gly Pro Lys Glu Asp Gly Arg Thr Gln Lys Asn Asp Gly Asp
    130                 135                 140

Gly Pro Lys Glu Asp Gly Arg Thr Gln Lys Asn Asp Gly Asp Gly Pro
145                 150                 155                 160

Lys Glu Asp Gly Arg Thr Gln Lys Asn Asp Gly Asp Gly Pro Lys Glu
                165                 170                 175

Asp Gly His Thr Gln Lys Asn Asp Gly Asp Gly Pro Lys Glu Asp Gly
            180                 185                 190

Arg Thr Gln Lys Asn Asp Gly Gly Pro Lys Glu Asp Glu Asn Leu
        195                 200                 205

Gln Gln Asn Asp Gly Asn Ala Gln Glu Lys Asn Glu Asp Gly His Asn
    210                 215                 220

Val Gly Asp Gly Ala Asn Gly Asn Glu Asp Gly Asn Asp Asp Gln Pro
225                 230                 235                 240

Lys Glu Gln Val Ala Gly Asn
                245

```
<210> SEQ ID NO 63
<211> LENGTH: 14
<212> TYPE: PRT
<213> ORGANISM: Leishmania chagasi
<220> FEATURE:
<221> NAME/KEY: VARIANT
<222> LOCATION: (6)...(6)
<223> OTHER INFORMATION: Xaa = His or Arg
<221> NAME/KEY: VARIANT
<222> LOCATION: (12)...(12)
<223> OTHER INFORMATION: Xaa = Gly or Asp
<221> NAME/KEY: VARIANT
<222> LOCATION: (13)...(13)
<223> OTHER INFORMATION: Xaa = Asp or Gly

<400> SEQUENCE: 63
```

Pro Lys Glu Asp Gly Xaa Thr Gln Lys Asn Asp Xaa Xaa Gly
 1               5                  10

```
<210> SEQ ID NO 64
<211> LENGTH: 7
```

```
<212> TYPE: PRT
<213> ORGANISM: Leishmania chagasi
<220> FEATURE:
<221> NAME/KEY: VARIANT
<222> LOCATION: (6)...(6)
<223> OTHER INFORMATION: Xaa = His or Arg

<400> SEQUENCE: 64

Pro Lys Glu Asp Gly Xaa Thr
 1               5

<210> SEQ ID NO 65
<211> LENGTH: 7
<212> TYPE: PRT
<213> ORGANISM: Leishmania chagasi
<220> FEATURE:
<221> NAME/KEY: VARIANT
<222> LOCATION: (5)...(5)
<223> OTHER INFORMATION: Xaa = Gly or Asp
<221> NAME/KEY: VARIANT
<222> LOCATION: (6)...(6)
<223> OTHER INFORMATION: Xaa = Asp or Gly

<400> SEQUENCE: 65

Gln Lys Asn Asp Xaa Xaa Gly
 1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 66

Gly Cys Gly Pro Lys Glu Asp Gly Arg Thr Gln Lys Asn Asp Gly Asp
 1               5                  10                  15

Gly

<210> SEQ ID NO 67
<211> LENGTH: 31
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 67

Gly Cys Gly Pro Lys Glu Asp Gly Arg Thr Gln Lys Asn Asp Gly Asp
 1               5                  10                  15

Gly Pro Lys Glu Asp Gly Arg Thr Gln Lys Asn Asp Gly Asp Gly
             20                  25                  30

<210> SEQ ID NO 68
<211> LENGTH: 45
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 68

Gly Cys Gly Pro Lys Glu Asp Gly Arg Thr Gln Lys Asn Asp Gly Asp
 1               5                  10                  15

Gly Pro Lys Glu Asp Gly Arg Thr Gln Lys Asn Asp Gly Asp Gly Pro
             20                  25                  30
```

Lys Glu Asp Gly Arg Thr Gln Lys Asn Asp Gly Asp Gly
          35                  40                  45

<210> SEQ ID NO 69
<211> LENGTH: 17
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 69

Gly Cys Gly Pro Lys Glu Asp Gly His Thr Gln Lys Asn Asp Gly Asp
1               5                   10                  15

Gly

<210> SEQ ID NO 70
<211> LENGTH: 31
<212> TYPE: PRT
<213> ORGANISM: Artificial Sequence
<220> FEATURE:
<223> OTHER INFORMATION: Synthetic peptide to asses diagnostic potential
      of repeat in Lc Gene B

<400> SEQUENCE: 70

Gly Cys Gly Pro Lys Glu Asp Gly His Thr Gln Lys Asn Asp Gly Asp
1               5                   10                  15

Gly Pro Lys Glu Asp Gly His Thr Gln Lys Asn Asp Gly Asp Gly
            20                  25                  30

<210> SEQ ID NO 71
<211> LENGTH: 45
<212> TYPE: PRT
<213> ORGANISM: Gly Cys Gly Pro Lys Glu Asp Gly His Thr Gln
<220> FEATURE:
<223> OTHER INFORMATION: Synthetic peptide to asses diagnostic potential
      of repeat in Lc Gene B

<400> SEQUENCE: 71

Gly Cys Gly Pro Lys Glu Asp Gly His Thr Gln Lys Asn Asp Gly Asp
1               5                   10                  15

Gly Pro Lys Glu Asp Gly His Thr Gln Lys Asn Asp Gly Asp Gly Pro
            20                  25                  30

Lys Glu Asp Gly His Thr Gln Lys Asn Asp Gly Asp Gly
          35                  40                  45

<210> SEQ ID NO 72
<211> LENGTH: 664
<212> TYPE: DNA
<213> ORGANISM: Leishmania major
<220> FEATURE:
<221> NAME/KEY: misc_feature
<222> LOCATION: (1)...(664)
<223> OTHER INFORMATION: n = A,T,C or G

<400> SEQUENCE: 72
gctgcaggaa ttcggcacga gattgcttcc cagcccacct tcgctatcca gccactctcg      60
ctcttctaca tctcccaccc cctcacaccg ccatggcttc ttcccgcaag gcttccaacc     120
cgcacaagtc gcaccgcaag ccgaagcgct cgtggaacgt gtacgtgggc cgctcgctga     180
aggcgatcaa cgcccagatg tcgatgtcgc accgcacgat gaagatcgtg aactcgtacg     240
tgaacgacgt gatggagcgc atctgcactg aggccgcgtc gattgttcgc gcgaacaaga     300

-continued

| | |
|---|---|
| agcgcacgtt gggtgcgcgc gaggtgcaga cggcggtgcg cattgtgctg ccggcggagc | 360 |
| tcgcgaagca tgccatggct gagggcacga aggccgtgtc gagcgcgtcc cgctaaagcg | 420 |
| gcttgccgga tgccgtgtga gtaggagggt ggcttgccgc aaacgctgac ctcggcgatt | 480 |
| gcggcgtggc gctccccttc tcctccttgt ccggcggtgt gtgtcatgca tttgcgtgac | 540 |
| tcctccctct tatagatgca agcttttttt ttctcttgac gttttatttt ctcctccccc | 600 |
| tcccttaacg tgaagtgtat atganagcgt actggacatg ananaaaaa aaanaaact | 660 |
| cgag | 664 |

<210> SEQ ID NO 73
<211> LENGTH: 1432
<212> TYPE: DNA
<213> ORGANISM: Leishmania major
<220> FEATURE:
<221> NAME/KEY: misc_feature
<222> LOCATION: (1)...(1432)
<223> OTHER INFORMATION: n = A,T,C or G

<400> SEQUENCE: 73

| | |
|---|---|
| gatgaagaag aggaggacac caccatcaac aactccgacg tggtggtgcg ctacaagaag | 60 |
| gccgcaacgt ggtgcaatga aacgttgcgc gtgcttatcg atgccacaaa acctggcgcc | 120 |
| aaggtgtgcg acctgtgccg cctcggtgat gacaccatca ccgccnaggt caagacaatg | 180 |
| ttcaaaggca cggaaaaagg catcgctttc ccgacctgca tctcggtcaa caactgcgta | 240 |
| tgccacaaca gccctggcgt gtcggacgag acgacgcagc aagagatcgc gatgggtgac | 300 |
| gtcgtgcact acgacctggg catccacgtg gacggctact cgccgtcgt cgcgcacacc | 360 |
| attcaggtga cagaggacaa tgagcttggc aaggacgaga aggcggcgcg cgtcattaca | 420 |
| gcggcgtaca acatcctgaa cacggcgctg cgccagatgc gtcccggtac gaccatctac | 480 |
| caggtgacag acgtagttga aaggctgcg gagcactaca aggtgactcc ggtagacggc | 540 |
| gtcctctcgc atatgatgaa gcgctacatc atagacngat accgctgtat cccgcagcgc | 600 |
| agggtcgcgg agcacatggt gcacgactac gatctcgaga agcgcaggt gtggacgcta | 660 |
| gacattgtca tgacctccgg caagggcaag ctgaaggagc gcgatgcgcg gccgtgcgtg | 720 |
| ttcaaggtgg ctctggactc caactactct gtgaaaatgg aaagcgcgaa ggaggttcag | 780 |
| aaggaaatcg actccnagta tgccaccttc ccctttgcca tccgcaacct ggaggccaag | 840 |
| aaggcccgcc tcggtctcaa cgagatggcg aagcacggtg ctgtcatccc gtaccctatt | 900 |
| ctcttcgaaa aggaaggcga ggtcgtcgcc catttcaaga ttacggtgct catcagcaac | 960 |
| aagaagattg agccgattac cggcctgaag ccgcagaagg ccccgcgct cgagccatac | 1020 |
| acggacgaga tgctgcttgc gacgaacaag ctcttcgctg tcgctagaga agaaggcggc | 1080 |
| gaagtagacg gccgtggcat ccgtgacgct gtactgcgag ctttcgtagg cgtacgcctc | 1140 |
| ttgtgaggcg tacacgtgtg ctgtttgcgg acgaggaggc acccattctg ttccccttct | 1200 |
| tcgctaatct tcgcgtttcc tctgacgctg gcttctytgc cggagtgtgg tgaggcgcgt | 1260 |
| gggggagaaa cggcccacty gcatgcctgt gcatacgcga gcacgtagg gagcgcggtg | 1320 |
| tgtgtgtgtg tggggggcg tgttacgagt acaaaagagg ctcgatcttt gcgatctttt | 1380 |
| ctttctgtaa acaggaacat aagtaaccaa aaaaaaaaa aaaaactcg ag | 1432 |

<210> SEQ ID NO 74
<211> LENGTH: 873
<212> TYPE: DNA
<213> ORGANISM: Leishmania major

```
<220> FEATURE:
<221> NAME/KEY: misc_feature
<222> LOCATION: (1)...(873)
<223> OTHER INFORMATION: n = A,T,C or G

<400> SEQUENCE: 74
ctttattgtc atcactgtaa agcactgttt tttctttcac tttttcttga gtgttttctt      60
tattcacca tgagcattat caaggaggac gacgccgtgg gctgctacat gacggtgacc     120
ctcgtggacg acaccaagt ggagggtacc atcttcacct acaattccaa ggagggcatc     180
atagtactcc tgtccctccg cgacgatcag acgaacatga agctaatccg cactccgtac    240
atcaaagact tcagccttc acacgctgag gagggagcgc acctgccccc ggcactggac      300
tccttcaaca gcttccgtc catgcacgcc ggccgcgaca gtccatctt caagcacgcc       360
agcacgcagc tcaagaacgc cgaggcgaac cgcgaaaagc acttcaactc tgtcacgacc    420
gacacaccga ttgccacact tgatgcgtac ctcaagctcc tgcggctata ccccttaatt    480
gagtggaaca gcgacgaggg tgtcatccag gtctcggaca ccgtcattgt cgtaggagac    540
cccgactggc ggacgcccaa ggcaatgctg gtggacggcg cccctgagaa ggacagaccg    600
cttgtagatc gcctgcaggt tgcgctcggm aacggcaaga agtgattcag tgtgtagcgg    660
acagaacatc gtgtgcttgt gtgtctgttt gangtttgtt tgttttctct ttgtggtact    720
gcgtacgacg gcgccttctc ccggtggtgg gtgagtccat aagcagttga gttctyggtt    780
gtagnaavgc ctyacygccg accatatggg agagggcgaa caaatntttg atagaagttg   840
aaaatcccaa agtyaaaaga aaaaaaaaan aaa                                  873

<210> SEQ ID NO 75
<211> LENGTH: 1238
<212> TYPE: DNA
<213> ORGANISM: Leishmania major
<220> FEATURE:
<221> NAME/KEY: misc_feature
<222> LOCATION: (1)...(1238)
<223> OTHER INFORMATION: n = A,T,C or G

<400> SEQUENCE: 75
tttctgtact ttattgaaca tcagtagaac acgttcttcc cgcaaagatg gccaagaagc     60
acctcaagcg cttgtatgcg cccaaggact ggatgctgag caagctgacc ggcgtgttcg    120
cgccgcgtcc gcgtccgggt ccgcacaagc tgcgcgagtg cctgccgctn ctggtgatca    180
tccgcaaccg gctgaagtac gcgctgaacg cgcgcgaggg tgagatgatc ctgcgccagg    240
gtctggtgca cgtggacaac cacccgcgcc gcgacggcaa gtatcccgcc ggtttcatgg    300
acgtggtcga gatcccgaag acgggcgacc gcttccgcct gatgtacgac gtcaagggcc    360
gcttcgcgtt ggtgaacctg tccgaggcgg aggcgcagat caagctgatg aaggttgtga    420
acctgtacac ggccaccggc cgcgtgccgg tcgctgtgac gcacgacggc caccgcatcc    480
gctacccgga cccgcacacc tccattggtg acaccatcgt gtacaacgtc aaggagaaga    540
agtgcgtgga cctgatcaag aaccgccagg gcaaggccgt gatcgtgacc ggtggcgcca    600
accgcggccg catcggcgag atcgtgaagg tggagtgcca ccccggtgcg ttcaacattg    660
cgcacctgaa ggacgcgtcc ggcgccgagt tcgccacccg cgccgcgaac atcttcgtga    720
tcggcaagga cctgaacaac ctgcaggtaa cggtgccgaa gcagcagggc ctgcgcatga    780
acgtgatcca ggagcgcgag gagcgcctga tcgcggcgga ggcccgcaag aacgcgccgg    840
ctcgtggtgc ccgcagggcc cgcaagtgag gaggcgatta cacgcatgcg tgtttgtggc    900
```

```
tctgaagcga cttggcgggt cggctgtgag ggtttgagag gaggtgtgtg atgcgtgtga    960
agtccttctc cgttctcagc tctctctgtg ctgtagctgt gcctttcccc agatcgcttt   1020
accgcatttg catacatctg tgtagtcgca tgtgcgtgtt tctgtctctc ggtgggtctc   1080
cctctccctc cctttctgcc tctctctttg agtgggtgtg catgcgtcgc gcgcgacggg   1140
ctccgcttna gtgattctct cgtgttttan ggctgtttty tttctyagtt nagcgttttty  1200 gttcatgatt tcctcagacc caaaaaaaaa aaaaaaaa                           1238
```

```
210> SEQ ID NO 76
<211> LENGTH: 712
<212> TYPE: DNA
<213> ORGANISM: Leishmania major
<220> FEATURE:
<221> NAME/KEY: misc_feature
<222> LOCATION: (1)...(712)
<223> OTHER INFORMATION: n = A,T,C or G

<400> SEQUENCE: 76
ctgacggagt tccagacgaa ccttgtgccg tacccgcgca tccacttcgt gctgacaagc     60
tacgctccgg tggtgtctgc cgagaaggcg taccacgagc agctntccgt cgcggacatc    120
acgaactcgg tntttgagcc tgctggcatg ctnacaaagt gcgatcctcg ccacggcaag    180
tacatgtcgt gctgcctcat gtaccgcggt gatgtcgtgc cgaaggatgt caacgccgcg    240
attgcgacga tcaagacgaa gcgcacaatt cagttcgtgg actggtgccc gaccggcttc    300
aagtgcggca tcaactacca gccgccgacc gttgtgcccg gcggtgacct cgcgaaggtg    360
cagcgcgccg tgtgcatgat tgccaactcg accgcgatcg ctgaggtgtt tgcccgcatc    420
gaccacaagt tcgacctgat gtacagcaag cgcgcgtttg tgcactggta cgtgggtgag    480
ggcatggagg agggcgagtt ctccgaggcg cgcgaggatc tcgctgcgct ggagaaggac    540
tacgaggagg ttggcgccga gtccgccgac gacatgggcg aggaggacgt cgaggagtac    600
taaggtagac tcgtgccgcg cgctgatgat gtaggtgcac gcgtgcgtgt gctgcagcgg    660
agccgccgcc accgcgactg tgtgtgtgtg cgcgcgtgac gaccggctcg ag           712
```

```
<210> SEQ ID NO 77
<211> LENGTH: 1086
<212> TYPE: DNA
<213> ORGANISM: Leishmania major
<220> FEATURE:
<221> NAME/KEY: misc_feature
<222> LOCATION: (1)...(1086)
<223> OTHER INFORMATION: n = A,T,C or G

<400> SEQUENCE: 77
caagaagtgg atcaagcagg agacgaacgc cgatggcgag cgcgtgcgcc gcgcgttctg     60
ccagttctgc ctagaccccca tctaccagat cttcgacgct gtgatgaacg agaagaagga    120
caaggtggac aagatgctca agtcgctgca cgtgacgctn acggctgagg agcgcgagca    180
ggtgccgaan aagcttctga agacggtgat gatgaattc ctgccggctg ctgagacgct     240
gctacagatg atcgtggcgc acctgccgtc gcccaagaag gcgcaggcgt accgtgcgga    300
gatgctgtac tctggcgagg cgtcgccgga ggacaagtac ttcatgggta tcaagaactg    360
cgaccccgct gcgccgctca tgctgtacat cagcaagatg gtgccgacgg ccgaccgcgg    420
ccgcttcttc gcctttggcc gcatcttctc cggtaaggtg cgcagcggcc agaaggtgcg    480
catcatgggt aacaactacg tctacggcaa gaagcaggac ctgtacgagg acaagcctgt    540
gcagcgctcc gtgctgatga tgggccgcta ccaggaggcc gtggaggaca tgccgtgcgg    600
```

```
taacgtggtg ggccttgtgg gcgtggacaa gtacatcgtg aagtccgcga cgatcacgga      660
cgatggcgag agcccgcacc cgctgcgcga catgaagtac tctgtgtcgc ccgtcgtgcg      720
tgtggccgtg gaggcgaaga acccgtccga cctgccgaag cttgtggagg gcctgaagcg      780
ccttgccaag tccgacccgc tggtggtgtg cagcattgag gagtctggcg agcacattgt      840
tgccggcgct ggcgagcttc accttgagat ttgcctgaag gatctccagg aggacttcat      900
gaacggcgcg ccgctnaaga tctccgagcc ggtggtgtcg ttccgcgaga cggtgacgga      960
tgtgtcgtcg cagcagtgcc tgtcgaagtc tgcgaacaag cacaaccgtc tcttctgccg     1020
cggtgcgccg ctnacagagg anctggcgct ggcgatngan gaaggcaccg ctggtcccga     1080 ngcgga                                                                1086

<210> SEQ ID NO 78
<211> LENGTH: 447
<212> TYPE: DNA
<213> ORGANISM: Leishmania major
<220> FEATURE:
<221> NAME/KEY: misc_feature
<222> LOCATION: (1)...(447)
<223> OTHER INFORMATION: n = A,T,C or G

<400> SEQUENCE: 78
cgcatcaacg tctacttcga tnagtcgacg ggaggccgct acgtgccgcg cgccgtgctg       60
atggacctcg agcccggcac tatggactcc gttcgcgccg gcccgtacgg ccagctgttc      120
cgcccggaca acttcatctt tggtcagtcc ggcgctggca caactgggc caagggccac      180 tacactgagg gcgcggagct gatcgactcc gtgcttgatg tgtgccgcaa ggaggcggag      240
agctgcgact gcctgcaggg cttccagctg tctcactccc tcggcggcgg cacgggctcc      300
ggcatgggca cgctgctcat ttccaanctg cgcgangagt accggaccg gatcatgatg      360 accttctccg tcatcccgtc cccccgcgtg tcggataccg ttgtggancc gtacaacacg      420
accctctctg tgcaccagct cgtggaa                                         447

<210> SEQ ID NO 79
<211> LENGTH: 375
<212> TYPE: DNA
<213> ORGANISM: Leishmania major
<220> FEATURE:
<221> NAME/KEY: misc_feature
<222> LOCATION: (1)...(375)
<223> OTHER INFORMATION: n = A,T,C or G

<400> SEQUENCE: 79
gtaacccgct ggtgtacgca tatgtagaca cagacgggca gcacgagacg acgttcctcg       60
cgatccctgt ggtgcttggc atgaatggaa tcgagaagcg cctgccgatt ggtccgctgc      120
actcgacgga ggaaacgctg ctgaaggcgg cactgccggt gatcaagaag aatatcgtga      180
agggcagcga gttcgcgcgc tcacacctgt agcacctcag ctttttttt ttgcgttaaa      240 cgggcgtggg aagcacctcg atacttcgct tcgcgctgac ggaccgcac gacatcgttc      300 gtcatccccc tccccctctt cggccctata cgcatgaagg agtggaatta tgcaacagca      360
tgttnatatc aagtg                                                     375

<210> SEQ ID NO 80
<211> LENGTH: 107
<212> TYPE: PRT
<213> ORGANISM: Leishmania major
```

```
<400> SEQUENCE: 80

Met Ala Ser Ser Arg Lys Ala Ser Asn Pro His Lys Ser His Arg Lys
 1               5                  10                  15

Pro Lys Arg Ser Trp Asn Val Tyr Val Gly Arg Ser Leu Lys Ala Ile
            20                  25                  30

Asn Ala Gln Met Ser Met Ser His Arg Thr Met Lys Ile Val Asn Ser
        35                  40                  45

Tyr Val Asn Asp Val Met Glu Arg Ile Cys Thr Glu Ala Ala Ser Ile
 50                  55                  60

Val Arg Ala Asn Lys Lys Arg Thr Leu Gly Ala Arg Glu Val Gln Thr
 65                  70                  75                  80

Ala Val Arg Ile Val Leu Pro Ala Glu Leu Ala Lys His Ala Met Ala
                85                  90                  95

Glu Gly Thr Lys Ala Val Ser Ser Ala Ser Arg
            100                 105

<210> SEQ ID NO 81
<211> LENGTH: 381
<212> TYPE: PRT
<213> ORGANISM: Leishmania major
<220> FEATURE:
<221> NAME/KEY: VARIANT
<222> LOCATION: (1)...(381)
<223> OTHER INFORMATION: Xaa = Any Amino Acid

<400> SEQUENCE: 81

Asp Glu Glu Glu Asp Thr Thr Ile Asn Asn Ser Asp Val Val Val
 1               5                  10                  15

Arg Tyr Lys Lys Ala Ala Thr Trp Cys Asn Glu Thr Leu Arg Val Leu
            20                  25                  30

Ile Asp Ala Thr Lys Pro Gly Ala Lys Val Cys Asp Leu Cys Arg Leu
        35                  40                  45

Gly Asp Asp Thr Ile Thr Ala Xaa Val Lys Thr Met Phe Lys Gly Thr
 50                  55                  60

Glu Lys Gly Ile Ala Phe Pro Thr Cys Ile Ser Val Asn Asn Cys Val
 65                  70                  75                  80

Cys His Asn Ser Pro Gly Val Ser Asp Glu Thr Thr Gln Gln Glu Ile
                85                  90                  95

Ala Met Gly Asp Val Val His Tyr Asp Leu Gly Ile His Val Asp Gly
            100                 105                 110

Tyr Cys Ala Val Val Ala His Thr Ile Gln Val Thr Glu Asp Asn Glu
        115                 120                 125

Leu Gly Lys Asp Glu Lys Ala Ala Arg Val Ile Thr Ala Ala Tyr Asn
130                 135                 140

Ile Leu Asn Thr Ala Leu Arg Gln Met Arg Pro Gly Thr Thr Ile Tyr
145                 150                 155                 160

Gln Val Thr Asp Val Val Glu Lys Ala Ala Glu His Tyr Lys Val Thr
                165                 170                 175

Pro Val Asp Gly Val Leu Ser His Met Met Lys Arg Tyr Ile Ile Asp
            180                 185                 190

Xaa Tyr Arg Cys Ile Pro Gln Arg Arg Val Ala Glu His Met Val His
        195                 200                 205

Asp Tyr Asp Leu Glu Lys Ala Gln Val Trp Thr Leu Asp Ile Val Met
        210                 215                 220

Thr Ser Gly Lys Gly Lys Leu Lys Glu Arg Asp Ala Arg Pro Cys Val
225                 230                 235                 240
```

-continued

```
Phe Lys Val Ala Leu Asp Ser Asn Tyr Ser Val Lys Met Glu Ser Ala
                245                 250                 255

Lys Glu Val Gln Lys Glu Ile Asp Ser Xaa Tyr Ala Thr Phe Pro Phe
            260                 265                 270

Ala Ile Arg Asn Leu Glu Ala Lys Lys Ala Arg Leu Gly Leu Asn Glu
        275                 280                 285

Met Ala Lys His Gly Ala Val Ile Pro Tyr Pro Ile Leu Phe Glu Lys
    290                 295                 300

Glu Gly Glu Val Val Ala His Phe Lys Ile Thr Val Leu Ile Ser Asn
305                 310                 315                 320

Lys Lys Ile Glu Pro Ile Thr Gly Leu Lys Pro Gln Lys Ala Pro Ala
                325                 330                 335

Leu Glu Pro Tyr Thr Asp Glu Met Leu Leu Ala Thr Asn Lys Leu Phe
            340                 345                 350

Ala Val Ala Arg Glu Gly Gly Glu Val Asp Gly Arg Gly Ile Arg
        355                 360                 365

Asp Ala Val Leu Arg Ala Phe Val Gly Val Arg Leu Leu
    370                 375                 380

<210> SEQ ID NO 82
<211> LENGTH: 191
<212> TYPE: PRT
<213> ORGANISM: Leishmania major

<400> SEQUENCE: 82

Met Ser Ile Ile Lys Glu Asp Asp Ala Val Gly Cys Tyr Met Thr Val
1               5                   10                  15

Thr Leu Val Asp Asp Thr Lys Val Glu Gly Thr Ile Phe Thr Tyr Asn
            20                  25                  30

Ser Lys Glu Gly Ile Ile Val Leu Leu Ser Leu Arg Asp Asp Gln Thr
        35                  40                  45

Asn Met Lys Leu Ile Arg Thr Pro Tyr Ile Lys Asp Phe Ser Leu Ser
    50                  55                  60

His Ala Glu Glu Gly Ala His Leu Pro Pro Ala Leu Asp Ser Phe Asn
65                  70                  75                  80

Glu Leu Pro Ser Met His Ala Gly Arg Asp Lys Ser Ile Phe Lys His
                85                  90                  95

Ala Ser Thr Gln Leu Lys Asn Ala Glu Ala Asn Arg Glu Lys His Phe
            100                 105                 110

Asn Ser Val Thr Thr Asp Thr Pro Ile Ala Thr Leu Asp Ala Tyr Leu
        115                 120                 125

Lys Leu Leu Arg Leu Tyr Pro Leu Ile Glu Trp Asn Ser Asp Glu Gly
    130                 135                 140

Val Ile Gln Val Ser Asp Thr Val Ile Val Gly Asp Pro Asp Trp
145                 150                 155                 160

Arg Thr Pro Lys Ala Met Leu Val Asp Gly Ala Pro Glu Lys Asp Arg
                165                 170                 175

Pro Leu Val Asp Arg Leu Gln Val Ala Leu Gly Asn Gly Lys Lys
            180                 185                 190

<210> SEQ ID NO 83
<211> LENGTH: 273
<212> TYPE: PRT
<213> ORGANISM: Leishmania major

<400> SEQUENCE: 83
```

-continued

```
Met Ala Lys Lys His Leu Lys Arg Leu Tyr Ala Pro Lys Asp Trp Met
 1               5                   10                  15

Leu Ser Lys Leu Thr Gly Val Phe Ala Pro Arg Pro Arg Pro Gly Pro
             20                  25                  30

His Lys Leu Arg Glu Cys Leu Pro Leu Leu Val Ile Ile Arg Asn Arg
             35                  40                  45

Leu Lys Tyr Ala Leu Asn Ala Arg Glu Gly Glu Met Ile Leu Arg Gln
         50                  55                  60

Gly Leu Val His Val Asp Asn His Pro Arg Arg Asp Gly Lys Tyr Pro
 65                  70                  75                  80

Ala Gly Phe Met Asp Val Val Glu Ile Pro Lys Thr Gly Asp Arg Phe
                 85                  90                  95

Arg Leu Met Tyr Asp Val Lys Gly Arg Phe Ala Leu Val Asn Leu Ser
                100                 105                 110

Glu Ala Glu Ala Gln Ile Lys Leu Met Lys Val Val Asn Leu Tyr Thr
            115                 120                 125

Ala Thr Gly Arg Val Pro Val Ala Val Thr His Asp Gly His Arg Ile
        130                 135                 140

Arg Tyr Pro Asp Pro His Thr Ser Ile Gly Asp Thr Ile Val Tyr Asn
145                 150                 155                 160

Val Lys Glu Lys Lys Cys Val Asp Leu Ile Lys Asn Arg Gln Gly Lys
                165                 170                 175

Ala Val Ile Val Thr Gly Gly Ala Asn Arg Gly Arg Ile Gly Glu Ile
                180                 185                 190

Val Lys Val Glu Cys His Pro Gly Ala Phe Asn Ile Ala His Leu Lys
                195                 200                 205

Asp Ala Ser Gly Ala Glu Phe Ala Thr Arg Ala Ala Asn Ile Phe Val
            210                 215                 220

Ile Gly Lys Asp Leu Asn Leu Gln Val Thr Val Pro Lys Gln Gln
225                 230                 235                 240

Gly Leu Arg Met Asn Val Ile Gln Glu Arg Glu Arg Leu Ile Ala
                245                 250                 255

Ala Glu Ala Arg Lys Asn Ala Pro Ala Arg Gly Ala Arg Arg Ala Arg
            260                 265                 270

Lys
```

<210> SEQ ID NO 84
<211> LENGTH: 200
<212> TYPE: PRT
<213> ORGANISM: Leishmania major

<400> SEQUENCE: 84

```
Leu Thr Glu Phe Gln Thr Asn Leu Val Pro Tyr Pro Arg Ile His Phe
 1               5                  10                  15

Val Leu Thr Ser Tyr Ala Pro Val Val Ser Ala Glu Lys Ala Tyr His
             20                  25                  30

Glu Gln Leu Ser Val Ala Asp Ile Thr Asn Ser Val Phe Glu Pro Ala
             35                  40                  45

Gly Met Leu Thr Lys Cys Asp Pro Arg His Gly Lys Tyr Met Ser Cys
         50                  55                  60

Cys Leu Met Tyr Arg Gly Asp Val Val Pro Lys Asp Val Asn Ala Ala
 65                  70                  75                  80

Ile Ala Thr Ile Lys Thr Lys Arg Thr Ile Gln Phe Val Asp Trp Cys
                 85                  90                  95
```

-continued

```
Pro Thr Gly Phe Lys Cys Gly Ile Asn Tyr Gln Pro Thr Val Val
            100                 105                 110

Pro Gly Gly Asp Leu Ala Lys Val Gln Arg Ala Val Cys Met Ile Ala
            115                 120                 125

Asn Ser Thr Ala Ile Ala Glu Val Phe Ala Arg Ile Asp His Lys Phe
        130                 135                 140

Asp Leu Met Tyr Ser Lys Arg Ala Phe Val His Trp Tyr Val Gly Glu
145                 150                 155                 160

Gly Met Glu Glu Gly Glu Phe Ser Glu Ala Arg Glu Asp Leu Ala Ala
                165                 170                 175

Leu Glu Lys Asp Tyr Glu Glu Val Gly Ala Glu Ser Ala Asp Asp Met
            180                 185                 190

Gly Glu Glu Asp Val Glu Glu Tyr
            195                 200
```

<210> SEQ ID NO 85
<211> LENGTH: 361
<212> TYPE: PRT
<213> ORGANISM: Leishmania major
<220> FEATURE:
<221> NAME/KEY: VARIANT
<222> LOCATION: (1)...(361)
<223> OTHER INFORMATION: Xaa = Any Amino Acid

<400> SEQUENCE: 85

```
Lys Lys Trp Ile Lys Gln Glu Thr Asn Ala Asp Gly Glu Arg Val Arg
1               5                   10                  15

Arg Ala Phe Cys Gln Phe Cys Leu Asp Pro Ile Tyr Gln Ile Phe Asp
            20                  25                  30

Ala Val Met Asn Glu Lys Lys Asp Lys Val Asp Lys Met Leu Lys Ser
        35                  40                  45

Leu His Val Thr Leu Thr Ala Glu Glu Arg Glu Gln Val Pro Xaa Lys
    50                  55                  60

Leu Leu Lys Thr Val Met Met Xaa Phe Leu Pro Ala Ala Glu Thr Leu
65                  70                  75                  80

Leu Gln Met Ile Val Ala His Leu Pro Ser Pro Lys Lys Ala Gln Ala
                85                  90                  95

Tyr Arg Ala Glu Met Leu Tyr Ser Gly Glu Ala Ser Pro Glu Asp Lys
            100                 105                 110

Tyr Phe Met Gly Ile Lys Asn Cys Asp Pro Ala Ala Pro Leu Met Leu
        115                 120                 125

Tyr Ile Ser Lys Met Val Pro Thr Ala Asp Arg Gly Arg Phe Phe Ala
    130                 135                 140

Phe Gly Arg Ile Phe Ser Gly Lys Val Arg Ser Gly Gln Lys Val Arg
145                 150                 155                 160

Ile Met Gly Asn Asn Tyr Val Tyr Gly Lys Lys Gln Asp Leu Tyr Glu
                165                 170                 175

Asp Lys Pro Val Gln Arg Ser Val Leu Met Met Gly Arg Tyr Gln Glu
            180                 185                 190

Ala Val Glu Asp Met Pro Cys Gly Asn Val Val Gly Leu Val Gly Val
        195                 200                 205

Asp Lys Tyr Ile Val Lys Ser Ala Thr Ile Thr Asp Asp Gly Glu Ser
    210                 215                 220

Pro His Pro Leu Arg Asp Met Lys Tyr Ser Val Ser Pro Val Val Arg
225                 230                 235                 240
```

-continued

```
Val Ala Val Glu Ala Lys Asn Pro Ser Asp Leu Pro Lys Leu Val Glu
                245                 250                 255

Gly Leu Lys Arg Leu Ala Lys Ser Asp Pro Leu Val Val Cys Ser Ile
            260                 265                 270

Glu Glu Ser Gly Glu His Ile Val Ala Gly Gly Glu Leu His Leu
        275                 280                 285

Glu Ile Cys Leu Lys Asp Leu Gln Glu Asp Phe Met Asn Gly Ala Pro
    290                 295                 300

Leu Lys Ile Ser Glu Pro Val Val Ser Phe Arg Glu Thr Val Thr Asp
305                 310                 315                 320

Val Ser Ser Gln Gln Cys Leu Ser Lys Ser Ala Asn Lys His Asn Arg
                325                 330                 335

Leu Phe Cys Arg Gly Ala Pro Leu Thr Glu Xaa Leu Ala Leu Ala Xaa
                340                 345                 350

Xaa Glu Gly Thr Ala Gly Pro Xaa Ala
            355                 360
```

<210> SEQ ID NO 86
<211> LENGTH: 149
<212> TYPE: PRT
<213> ORGANISM: Leishmania major
<220> FEATURE:
<221> NAME/KEY: VARIANT
<222> LOCATION: (1)...(149)
<223> OTHER INFORMATION: Xaa = Any Amino Acid

<400> SEQUENCE: 86

```
Arg Ile Asn Val Tyr Phe Asp Xaa Ser Thr Gly Gly Arg Tyr Val Pro
1               5                   10                  15

Arg Ala Val Leu Met Asp Leu Glu Pro Gly Thr Met Asp Ser Val Arg
            20                  25                  30

Ala Gly Pro Tyr Gly Gln Leu Phe Arg Pro Asp Asn Phe Ile Phe Gly
        35                  40                  45

Gln Ser Gly Ala Gly Asn Asn Trp Ala Lys Gly His Tyr Thr Glu Gly
    50                  55                  60

Ala Glu Leu Ile Asp Ser Val Leu Asp Val Cys Arg Lys Glu Ala Glu
65                  70                  75                  80

Ser Cys Asp Cys Leu Gln Gly Phe Gln Leu Ser His Ser Leu Gly Gly
                85                  90                  95

Gly Thr Gly Ser Gly Met Gly Thr Leu Leu Ile Ser Xaa Leu Arg Xaa
            100                 105                 110

Glu Tyr Pro Asp Arg Ile Met Met Thr Phe Ser Val Ile Pro Ser Pro
        115                 120                 125

Arg Val Ser Asp Thr Val Val Xaa Pro Tyr Asn Thr Thr Leu Ser Val
    130                 135                 140

His Gln Leu Val Glu
145
```

<210> SEQ ID NO 87
<211> LENGTH: 69
<212> TYPE: PRT
<213> ORGANISM: Leishmania major

<400> SEQUENCE: 87

```
Asn Pro Leu Val Tyr Ala Tyr Val Asp Thr Asp Gly Gln His Glu Thr
1               5                   10                  15

Thr Phe Leu Ala Ile Pro Val Val Leu Gly Met Asn Gly Ile Glu Lys
            20                  25                  30
```

Arg Leu Pro Ile Gly Pro Leu His Ser Thr Glu Thr Leu Leu Lys
        35                  40                  45

Ala Ala Leu Pro Val Ile Lys Lys Asn Ile Val Lys Gly Ser Glu Phe
    50                  55                  60

Ala Arg Ser His Leu
65

<210> SEQ ID NO 88
<211> LENGTH: 54
<212> TYPE: DNA
<213> ORGANISM: Artificial Sequence
<220> FEATURE:
<223> OTHER INFORMATION: PCR primer

<400> SEQUENCE: 88
agtattcata tgcaccacca ccaccaccac atgtcctgcg gtaacgccaa gatc          54

<210> SEQ ID NO 89
<211> LENGTH: 33
<212> TYPE: DNA
<213> ORGANISM: Artificial Sequence
<220> FEATURE:
<223> OTHER INFORMATION: PCR primer

<400> SEQUENCE: 89
ctcacaggat ccctgcttgc tgaagtatcc ttc                                 33

<210> SEQ ID NO 90
<211> LENGTH: 36
<212> TYPE: DNA
<213> ORGANISM: Artificial Sequence
<220> FEATURE:
<223> OTHER INFORMATION: PCR primer

<400> SEQUENCE: 90
catttcggat ccatggacgc aactgagctg aagaac                              36

<210> SEQ ID NO 91
<211> LENGTH: 33
<212> TYPE: DNA
<213> ORGANISM: Artificial Sequence
<220> FEATURE:
<223> OTHER INFORMATION: PCR primer

<400> SEQUENCE: 91
cgtagagaat tcctgaccaa aacgaatgat gcc                                 33

<210> SEQ ID NO 92
<211> LENGTH: 33
<212> TYPE: DNA
<213> ORGANISM: Artificial Sequence
<220> FEATURE:
<223> OTHER INFORMATION: PCR primer

<400> SEQUENCE: 92
caccacgaat tcatggcgca gaatgataag atc                                 33

<210> SEQ ID NO 93
<211> LENGTH: 34
<212> TYPE: DNA
<213> ORGANISM: Artificial Sequence
<220> FEATURE:
<223> OTHER INFORMATION: PCR primer

<400> SEQUENCE: 93

```
actgacctcg aggaattctt agtcgcgcat gaac                                34
```

<210> SEQ ID NO 94
<211> LENGTH: 3012
<212> TYPE: DNA
<213> ORGANISM: Artificial Sequence
<220> FEATURE:
<223> OTHER INFORMATION: DNA sequence encoding fusion (poly-protein)
      constructs comprising multiple Leishmania antigens

<400> SEQUENCE: 94

```
catatgcacc accaccaca ccacatgtcc tgcggtaacg ccaagatcaa ctctcccgcg      60
ccgtccttcg aggaggtggc gctcatgccc aacggcagct tcaagaagat cagcctctcc   120
tcctacaagg gcaagtgggt cgtgctcttc ttctacccgc tcgacttcac cttcgtgtgc   180
ccgacagagg tcatcgcgtt ctccgacagc gtgagtcgct tcaacgagct caactgcgag   240
gtcctcgcgt gctcgataga cagcgagtac gcgcacctgc agtggacgct gcaggaccgc   300
aagaagggcg gcctcgggac catggcgatc ccaatgctag ccgacaagac caagagcatc   360
gctcgttcct acgcgtgct ggaggagagc cagggcgtgg cctaccgcgg tctcttcatc   420
atcgaccccc atggcatgct gcgtcagatc accgtcaatg acatgccggt gggccgcagc   480
gtggaggagg ttctacgcct gctggaggct tttcagttcg tggagaagca cggcgaggtg   540
tgccccgcga actggaagaa gggcgccccc acgatgaagc cggaaccgaa tgcgtctgtc   600
gagggatact tcagcaagca gggatccatg acgcaactg agctgaagaa caaggggaac   660
gaagagttct ccgccggccg ctatgtggag gcggtgaact acttctcaaa ggcgatccag   720
ttggatgagc agaacagtgt cctctacagc aaccgctccg cctgttttgc agccatgcag   780
aaatacaagg acgcgctgga cgacgccgac aagtgcatct cgatcaagcc gaattgggcc   840
aagggctacg tgcgccgagg agcagctctc catggcatgc gccgctacga cgatgccatt   900
gccgcgtatg aaaagggct caaggtggac ccttccaaca cggctgcgc gcagggcgtg   960
aaggacgtgc aggtagccaa ggcccgcgaa gcacgtgacc ccatcgctcg cgtcttcacc  1020
ccggaggcgt tccgcaagat ccaagagaat cccaagctgt ctctacttat gctgcagccg  1080
gactacgtga agatggtaga caccgtcatc cgcgaccctt cgcagggccg gctgtacatg  1140
gaagaccagc gctttgccct gacgctcatg tacctgagcg gaatgaagat tcccaacgat  1200
ggtgatggcg aggaggagga acgtccgtct gcgaaggcgg cagagacagc gaagccaaaa  1260
gaggagaagc ctctcaccga caacgagaag gaggccctgg cgctcaagga ggagggcaac  1320
aagctgtacc tctcgaagaa gtttgaggag gcgctgacca gtaccaaaga ggcgcaggtg  1380
aaagacccca caacactttt atacattctg aacgtgtcgg ccgtgtactt cgagcagggt  1440
gactacgaca gtgcatcgc cgagtgcgag cacggtatcg agcacggtcg cgagaaccac  1500
tgcgactaca caatcattgc gaagctcatg acccggaacg ccttgtgcct ccagaggcag  1560
aggaagtacg aggctgctat cgacctttac aagcgcgccc ttgtcgagtg gcgtaaccct  1620
gacaccctca agaagctgac ggagtgcgag aaggagcacc aaaaggcggt ggaggaagcc  1680
tacatcgatc ctgagatcgc gaagcagaag aaagacgaag gtaaccagta cttcaaggag  1740
gataagttcc ccgaggccgt ggcagcgtac acggaggcca tcaagcgcaa ccctgccgag  1800
cacacctcct acagcaatcg cgcggccgcg tacatcaagc ttggagcctt caacgacgcc  1860
ctcaaggacg cggagaagtg cattgagctg aagcccgact ttgttaaggg ctacgcgcgc  1920
aagggtcatg cttacttttg gaccaagcag tacaaccgcg cgctgcaggc gtacaatgag  1980
```

-continued

```
ggcctcaagg tggacccgag caatgcggac tgcaaggatg ggcggtatcg cacaatcatg    2040
aagattcagg agatggcatc tggccaatcc gcggatggcg acgaggcggc gcgccgggcc    2100
atggacgatc ctgaaatcgc ggcaatcatg caagatagca catgcaact agtgttgaag    2160 gagatgcaga acgatcccac gcgcattcag gagtacatga aggactccgg gatctcatcg    2220
aagatcaaca agctgatttc agctggcatc attcgttttg gtcaggaatt catggcgcag    2280
aatgataaga tcgcccccca ggaccaggac tccttcctcg atgaccagcc cggcgttcgc    2340
ccgatcccgt ccttcgacga catgccgctg caccagaacc tgctgcgtgg catctactcg    2400
tacgggttcg agaagccgtc cagcatccag cagcgcgcga tagccccctt cacgcgcggc    2460
ggcgacatca tcgcgcaggc ccagtccggt accggcaaga cgggtgcctt ctccatcggt    2520
ctgctgcagc gcctggactt ccgccacaac ctgatccagg gcctcgtgct ctcccccact    2580
cgcgagctgg ccctgcagac ggcggaggtg atcagccgca tcggtgagtt cctgtcgaac    2640
agctccaagt tctgcgagac ctttgtcggc ggcacgcgcg tgcaggatga cctgcgcaag    2700
ctgcaggccg cgtcatcgt tgccgtgggc acgccgggcc gcgtgtccga cgtgatcaag    2760
cgtggcgcgc tgcgcacaga gtcgctgcgc gtgctggtgc tcgacgaggc tgatgagatg    2820
ctgtctcagg gcttcgcgga ccagatttac gagatcttcc gcttcctgcc gaaggacatc    2880
caggtcgcgc tcttctccgc cacgatgccg gaggaggtac tggagctgac gaagaagttc    2940
atgcgcgact aagaattcct cgagcagatc cggctgctaa caaagcccga aggaagctg    3000 aatggctgct gc                                                         3012
```

<210> SEQ ID NO 95
<211> LENGTH: 982
<212> TYPE: PRT
<213> ORGANISM: Artificial Sequence
<220> FEATURE:
<223> OTHER INFORMATION: Fusion (poly-protein) constructs comprising multiple Leishmania antigens

<400> SEQUENCE: 95

```
Met His His His His His Met Ser Cys Gly Asn Ala Lys Ile Asn
              5                  10                  15

Ser Pro Ala Pro Ser Phe Glu Glu Val Ala Leu Met Pro Asn Gly Ser
             20                  25                  30

Phe Lys Lys Ile Ser Leu Ser Ser Tyr Lys Gly Lys Trp Val Val Leu
             35                  40                  45

Phe Phe Tyr Pro Leu Asp Phe Thr Phe Val Cys Pro Thr Glu Val Ile
         50                  55                  60

Ala Phe Ser Asp Ser Val Ser Arg Phe Asn Glu Leu Asn Cys Glu Val
 65                  70                  75                  80

Leu Ala Cys Ser Ile Asp Ser Glu Tyr Ala His Leu Gln Trp Thr Leu
                 85                  90                  95

Gln Asp Arg Lys Lys Gly Gly Leu Gly Thr Met Ala Ile Pro Met Leu
            100                 105                 110

Ala Asp Lys Thr Lys Ser Ile Ala Arg Ser Tyr Gly Val Leu Glu Glu
            115                 120                 125

Ser Gln Gly Val Ala Tyr Arg Gly Leu Phe Ile Ile Asp Pro His Gly
        130                 135                 140

Met Leu Arg Gln Ile Thr Val Asn Asp Met Pro Val Gly Arg Ser Val
145                 150                 155                 160

Glu Glu Val Leu Arg Leu Leu Glu Ala Phe Gln Phe Val Glu Lys His
                165                 170                 175
```

```
Gly Glu Val Cys Pro Ala Asn Trp Lys Lys Gly Ala Pro Thr Met Lys
                180                 185                 190

Pro Glu Pro Asn Ala Ser Val Glu Gly Tyr Phe Ser Lys Gln Gly Ser
            195                 200                 205

Met Asp Ala Thr Glu Leu Lys Asn Lys Gly Asn Glu Glu Phe Ser Ala
        210                 215                 220

Gly Arg Tyr Val Glu Ala Val Asn Tyr Phe Ser Lys Ala Ile Gln Leu
225                 230                 235                 240

Asp Glu Gln Asn Ser Val Leu Tyr Ser Asn Arg Ser Ala Cys Phe Ala
                245                 250                 255

Ala Met Gln Lys Tyr Lys Asp Ala Leu Asp Asp Ala Asp Lys Cys Ile
        260                 265                 270

Ser Ile Lys Pro Asn Trp Ala Lys Gly Tyr Val Arg Arg Gly Ala Ala
        275                 280                 285

Leu His Gly Met Arg Arg Tyr Asp Asp Ala Ile Ala Ala Tyr Glu Lys
        290                 295                 300

Gly Leu Lys Val Asp Pro Ser Asn Ser Gly Cys Ala Gln Gly Val Lys
305                 310                 315                 320

Asp Val Gln Val Ala Lys Ala Arg Glu Ala Arg Asp Pro Ile Ala Arg
                325                 330                 335

Val Phe Thr Pro Glu Ala Phe Arg Lys Ile Gln Glu Asn Pro Lys Leu
            340                 345                 350

Ser Leu Leu Met Leu Gln Pro Asp Tyr Val Lys Met Val Asp Thr Val
            355                 360                 365

Ile Arg Asp Pro Ser Gln Gly Arg Leu Tyr Met Glu Asp Gln Arg Phe
370                 375                 380

Ala Leu Thr Leu Met Tyr Leu Ser Gly Met Lys Ile Pro Asn Asp Gly
385                 390                 395                 400

Asp Gly Glu Glu Glu Arg Pro Ser Ala Lys Ala Ala Glu Thr Ala
                405                 410                 415

Lys Pro Lys Glu Glu Lys Pro Leu Thr Asp Asn Glu Lys Glu Ala Leu
            420                 425                 430

Ala Leu Lys Glu Glu Gly Asn Lys Leu Tyr Leu Ser Lys Lys Phe Glu
        435                 440                 445

Glu Ala Leu Thr Lys Tyr Gln Glu Ala Gln Val Lys Asp Pro Asn Asn
450                 455                 460

Thr Leu Tyr Ile Leu Asn Val Ser Ala Val Tyr Phe Glu Gln Gly Asp
465                 470                 475                 480

Tyr Asp Lys Cys Ile Ala Glu Cys Glu His Gly Ile Glu His Gly Arg
            485                 490                 495

Glu Asn His Cys Asp Tyr Thr Ile Ile Ala Lys Leu Met Thr Arg Asn
                500                 505                 510

Ala Leu Cys Leu Gln Arg Gln Lys Tyr Glu Ala Ile Asp Leu
        515                 520                 525

Tyr Lys Arg Ala Leu Val Glu Trp Arg Asn Pro Asp Thr Leu Lys Lys
530                 535                 540

Leu Thr Glu Cys Glu Lys Glu His Gln Lys Ala Val Glu Ala Tyr
545                 550                 555                 560

Ile Asp Pro Glu Ile Ala Lys Gln Lys Asp Glu Gly Asn Gln Tyr
            565                 570                 575

Phe Lys Glu Asp Lys Phe Pro Glu Ala Val Ala Ala Tyr Thr Glu Ala
            580                 585                 590
```

-continued

```
Ile Lys Arg Asn Pro Ala Glu His Thr Ser Tyr Ser Asn Arg Ala Ala
            595                 600                 605

Ala Tyr Ile Lys Leu Gly Ala Phe Asn Asp Ala Leu Lys Asp Ala Glu
610                 615                 620

Lys Cys Ile Glu Leu Lys Pro Asp Phe Val Lys Gly Tyr Ala Arg Lys
625                 630                 635                 640

Gly His Ala Tyr Phe Trp Thr Lys Gln Tyr Asn Arg Ala Leu Gln Ala
            645                 650                 655

Tyr Asn Glu Gly Leu Lys Val Asp Pro Ser Asn Ala Asp Cys Lys Asp
                660                 665                 670

Gly Arg Tyr Arg Thr Ile Met Lys Ile Gln Glu Met Ala Ser Gly Gln
            675                 680                 685

Ser Ala Asp Gly Asp Glu Ala Arg Arg Ala Met Asp Pro Glu
            690                 695                 700

Ile Ala Ala Ile Met Gln Asp Ser Tyr Met Gln Leu Val Leu Lys Glu
705                 710                 715                 720

Met Gln Asn Asp Pro Thr Arg Ile Gln Glu Tyr Met Lys Asp Ser Gly
                725                 730                 735

Ile Ser Ser Lys Ile Asn Lys Leu Ile Ser Ala Gly Ile Ile Arg Phe
            740                 745                 750

Gly Gln Glu Phe Met Ala Gln Asn Asp Lys Ile Ala Pro Gln Asp Gln
            755                 760                 765

Asp Ser Phe Leu Asp Asp Gln Pro Gly Val Arg Pro Ile Pro Ser Phe
770                 775                 780

Asp Asp Met Pro Leu His Gln Asn Leu Leu Arg Gly Ile Tyr Ser Tyr
785                 790                 795                 800

Gly Phe Glu Lys Pro Ser Ser Ile Gln Gln Arg Ala Ile Ala Pro Phe
                805                 810                 815

Thr Arg Gly Gly Asp Ile Ile Ala Gln Ala Gln Ser Gly Thr Gly Lys
            820                 825                 830

Thr Gly Ala Phe Ser Ile Gly Leu Leu Gln Arg Leu Asp Phe Arg His
            835                 840                 845

Asn Leu Ile Gln Gly Leu Val Leu Ser Pro Thr Arg Glu Leu Ala Leu
850                 855                 860

Gln Thr Ala Glu Val Ile Ser Arg Ile Gly Phe Leu Ser Asn Ser
865                 870                 875                 880

Ser Lys Phe Cys Glu Thr Phe Val Gly Gly Thr Arg Val Gln Asp Asp
                885                 890                 895

Leu Arg Lys Leu Gln Ala Gly Val Ile Val Ala Val Gly Thr Pro Gly
            900                 905                 910

Arg Val Ser Asp Val Ile Lys Arg Gly Ala Leu Arg Thr Glu Ser Leu
            915                 920                 925

Arg Val Leu Val Leu Asp Glu Ala Asp Glu Met Leu Ser Gln Gly Phe
930                 935                 940

Ala Asp Gln Ile Tyr Glu Ile Phe Arg Phe Leu Pro Lys Asp Ile Gln
945                 950                 955                 960

Val Ala Leu Phe Ser Ala Thr Met Pro Glu Glu Val Leu Glu Leu Thr
                965                 970                 975

Lys Lys Phe Met Arg Asp
            980
```

<210> SEQ ID NO 96
<211> LENGTH: 1641
<212> TYPE: PRT

<213> ORGANISM: Artificial Sequence
<220> FEATURE:
<223> OTHER INFORMATION: Fusion (poly-protein) constructs comprising multiple Leishmania antigens

<400> SEQUENCE: 96

Met His His His His His Met Ser Cys Gly Asn Ala Lys Ile Asn
            5                   10                  15

Ser Pro Ala Pro Ser Phe Glu Glu Val Ala Leu Met Pro Asn Gly Ser
            20                  25                  30

Phe Lys Lys Ile Ser Leu Ser Ser Tyr Lys Gly Lys Trp Val Val Leu
            35                  40                  45

Phe Phe Tyr Pro Leu Asp Phe Thr Phe Val Cys Pro Thr Glu Val Ile
        50                  55                  60

Ala Phe Ser Asp Ser Val Ser Arg Phe Asn Glu Leu Asn Cys Glu Val
65                  70                  75                  80

Leu Ala Cys Ser Ile Asp Ser Glu Tyr Ala His Leu Gln Trp Thr Leu
                85                  90                  95

Gln Asp Arg Lys Lys Gly Gly Leu Gly Thr Met Ala Ile Pro Met Leu
            100                 105                 110

Ala Asp Lys Thr Lys Ser Ile Ala Arg Ser Tyr Gly Val Leu Glu Glu
            115                 120                 125

Ser Gln Gly Val Ala Tyr Arg Gly Leu Phe Ile Ile Asp Pro His Gly
        130                 135                 140

Met Leu Arg Gln Ile Thr Val Asn Asp Met Pro Val Gly Arg Ser Val
145                 150                 155                 160

Glu Glu Val Leu Arg Leu Leu Glu Ala Phe Gln Phe Val Glu Lys His
                165                 170                 175

Gly Glu Val Cys Pro Ala Asn Trp Lys Lys Gly Ala Pro Thr Met Lys
            180                 185                 190

Pro Glu Pro Asn Ala Ser Val Glu Gly Tyr Phe Ser Lys Gln Gly Ser
        195                 200                 205

Met Asp Ala Thr Glu Leu Lys Asn Lys Gly Asn Glu Glu Phe Ser Ala
    210                 215                 220

Gly Arg Tyr Val Glu Ala Val Asn Tyr Phe Ser Lys Ala Ile Gln Leu
225                 230                 235                 240

Asp Glu Gln Asn Ser Val Leu Tyr Ser Asn Arg Ser Ala Cys Phe Ala
                245                 250                 255

Ala Met Gln Lys Tyr Lys Asp Ala Leu Asp Asp Ala Lys Cys Ile
            260                 265                 270

Ser Ile Lys Pro Asn Trp Ala Lys Gly Tyr Val Arg Arg Gly Ala Ala
        275                 280                 285

Leu His Gly Met Arg Arg Tyr Asp Asp Ala Ile Ala Ala Tyr Glu Lys
    290                 295                 300

Gly Leu Lys Val Asp Pro Ser Asn Ser Gly Cys Ala Gln Gly Val Lys
305                 310                 315                 320

Asp Val Gln Val Ala Lys Ala Arg Glu Ala Arg Asp Pro Ile Ala Arg
                325                 330                 335

Val Phe Thr Pro Glu Ala Phe Arg Lys Ile Gln Glu Asn Pro Lys Leu
            340                 345                 350

Ser Leu Leu Met Leu Gln Pro Asp Tyr Val Lys Met Val Asp Thr Val
        355                 360                 365

Ile Arg Asp Pro Ser Gln Gly Arg Leu Tyr Met Glu Asp Gln Arg Phe
    370                 375                 380

-continued

```
Ala Leu Thr Leu Met Tyr Leu Ser Gly Met Lys Ile Pro Asn Asp Gly
385                 390                 395                 400

Asp Gly Glu Glu Glu Arg Pro Ser Ala Lys Ala Glu Thr Ala
            405                 410                 415

Lys Pro Lys Glu Glu Lys Pro Leu Thr Asp Asn Glu Lys Glu Ala Leu
                420                 425                 430

Ala Leu Lys Glu Glu Gly Asn Lys Leu Tyr Leu Ser Lys Lys Phe Glu
            435                 440                 445

Glu Ala Leu Thr Lys Tyr Gln Glu Ala Gln Val Lys Asp Pro Asn Asn
450                 455                 460

Thr Leu Tyr Ile Leu Asn Val Ser Ala Val Tyr Phe Glu Gln Gly Asp
465                 470                 475                 480

Tyr Asp Lys Cys Ile Ala Glu Cys Glu His Gly Ile Glu His Gly Arg
            485                 490                 495

Glu Asn His Cys Asp Tyr Thr Ile Ile Ala Lys Leu Met Thr Arg Asn
            500                 505                 510

Ala Leu Cys Leu Gln Arg Gln Arg Lys Tyr Glu Ala Ala Ile Asp Leu
            515                 520                 525

Tyr Lys Arg Ala Leu Val Glu Trp Arg Asn Pro Asp Thr Leu Lys Lys
530                 535                 540

Leu Thr Glu Cys Glu Lys Glu His Gln Lys Ala Val Glu Glu Ala Tyr
545                 550                 555                 560

Ile Asp Pro Glu Ile Ala Lys Gln Lys Asp Glu Gly Asn Gln Tyr
            565                 570                 575

Phe Lys Glu Asp Lys Phe Pro Glu Ala Val Ala Ala Tyr Thr Glu Ala
            580                 585                 590

Ile Lys Arg Asn Pro Ala Glu His Thr Ser Tyr Ser Asn Arg Ala Ala
            595                 600                 605

Ala Tyr Ile Lys Leu Gly Ala Phe Asn Asp Ala Leu Lys Asp Ala Glu
610                 615                 620

Lys Cys Ile Glu Leu Lys Pro Asp Phe Val Lys Gly Tyr Ala Arg Lys
625                 630                 635                 640

Gly His Ala Tyr Phe Trp Thr Lys Gln Tyr Asn Arg Ala Leu Gln Ala
            645                 650                 655

Tyr Asn Glu Gly Leu Lys Val Asp Pro Ser Asn Ala Asp Cys Lys Asp
            660                 665                 670

Gly Arg Tyr Arg Thr Ile Met Lys Ile Gln Glu Met Ala Ser Gly Gln
            675                 680                 685

Ser Ala Asp Gly Asp Glu Ala Arg Arg Ala Met Asp Asp Pro Glu
690                 695                 700

Ile Ala Ala Ile Met Gln Asp Ser Tyr Met Gln Leu Val Leu Lys Glu
705                 710                 715                 720

Met Gln Asn Asp Pro Thr Arg Ile Gln Glu Tyr Met Lys Asp Ser Gly
            725                 730                 735

Ile Ser Ser Lys Ile Asn Lys Leu Ile Ser Ala Gly Ile Ile Arg Phe
            740                 745                 750

Gly Gln Glu Phe Ser Leu Thr Asp Pro Ala Val Leu Gly Glu Glu Thr
            755                 760                 765

His Leu Arg Val Arg Val Pro Asp Lys Ala Asn Lys Thr Leu Thr
            770                 775                 780

Val Glu Asp Asn Gly Ile Gly Met Thr Lys Ala Asp Leu Val Asn Asn
785                 790                 795                 800

Leu Gly Thr Ile Ala Arg Ser Gly Thr Lys Ala Phe Met Glu Ala Leu
```

-continued

```
                    805                 810                 815
Glu Ala Gly Gly Asp Met Ser Met Ile Gly Gln Phe Gly Val Gly Phe
                820                 825                 830
Tyr Ser Ala Tyr Leu Val Ala Asp Arg Val Thr Val Val Ser Lys Asn
                835                 840                 845
Asn Ser Asp Glu Ala Tyr Val Trp Glu Ser Ser Ala Gly Gly Thr Phe
850                 855                 860
Thr Ile Thr Ser Val Pro Glu Ser Asp Met Lys Arg Gly Thr Arg Ile
865                 870                 875                 880
Thr Leu His Leu Lys Glu Asp Gln Gln Glu Tyr Leu Glu Glu Arg Arg
                885                 890                 895
Val Lys Glu Leu Ile Lys Lys His Ser Glu Phe Ile Gly Tyr Asp Ile
                900                 905                 910
Glu Leu Met Val Glu Lys Thr Ala Glu Lys Glu Val Thr Asp Glu Asp
                915                 920                 925
Glu Glu Glu Asp Glu Ser Lys Lys Ser Cys Gly Asp Glu Gly Glu
930                 935                 940
Pro Lys Val Glu Glu Val Thr Glu Gly Gly Glu Asp Lys Lys Lys Lys
945                 950                 955                 960
Thr Lys Lys Val Lys Glu Val Thr Lys Thr Tyr Glu Val Gln Asn Lys
                965                 970                 975
His Lys Pro Leu Trp Thr Arg Asp Pro Lys Asp Val Thr Lys Glu Glu
                980                 985                 990
Tyr Ala Ala Phe Tyr Lys Ala Ile Ser Asn Asp Trp Glu Asp Pro Ala
                995                 1000                1005
Ala Thr Lys His Phe Ser Val Glu Gly Gln Leu Glu Phe Arg Ala Ile
                1010                1015                1020
Ala Phe Val Pro Lys Arg Ala Pro Phe Asp Met Phe Glu Pro Asn Lys
1025                1030                1035                1040
Lys Arg Asn Asn Ile Lys Leu Tyr Val Arg Arg Val Phe Ile Met Asp
                1045                1050                1055
Asn Cys Glu Asp Leu Cys Pro Asp Trp Leu Gly Phe Val Lys Gly Val
                1060                1065                1070
Val Asp Ser Glu Asp Leu Pro Leu Asn Ile Ser Arg Glu Asn Leu Gln
                1075                1080                1085
Gln Asn Lys Ile Leu Lys Val Ile Arg Lys Asn Ile Val Lys Lys Cys
                1090                1095                1100
Leu Glu Leu Phe Glu Glu Ile Ala Glu Asn Lys Glu Asp Tyr Lys Gln
1105                1110                1115                1120
Phe Tyr Glu Gln Phe Gly Lys Asn Ile Lys Leu Gly Ile His Glu Asp
                1125                1130                1135
Thr Ala Asn Arg Lys Lys Leu Met Glu Leu Leu Arg Phe Tyr Ser Thr
                1140                1145                1150
Glu Ser Gly Glu Glu Met Thr Thr Leu Lys Asp Tyr Val Thr Arg Met
                1155                1160                1165
Lys Pro Glu Gln Lys Ser Ile Tyr Tyr Ile Thr Gly Asp Ser Lys Lys
                1170                1175                1180
Lys Leu Glu Ser Ser Pro Phe Ile Glu Lys Ala Arg Arg Cys Gly Leu
1185                1190                1195                1200
Glu Val Leu Phe Met Thr Glu Pro Ile Asp Glu Tyr Val Met Gln Gln
                1205                1210                1215
Val Lys Asp Phe Glu Asp Lys Lys Phe Ala Cys Leu Thr Lys Glu Gly
                1220                1225                1230
```

-continued

```
Val His Phe Glu Glu Ser Glu Glu Lys Lys Gln Arg Glu Glu Lys
        1235                1240                1245
Lys Ala Ala Cys Glu Lys Leu Cys Lys Thr Met Lys Glu Val Leu Gly
        1250                1255                1260
Asp Lys Val Glu Lys Val Thr Val Ser Glu Arg Leu Ser Thr Ser Pro
1265                1270                1275                1280
Cys Ile Leu Val Thr Ser Glu Phe Gly Trp Ser Ala His Met Glu Gln
            1285                1290                1295
Ile Met Arg Asn Gln Ala Leu Arg Asp Ser Ser Met Ala Gln Tyr Met
        1300                1305                1310
Val Ser Lys Lys Thr Met Glu Val Asn Pro Asp His Pro Ile Ile Lys
        1315                1320                1325
Glu Leu Arg Arg Arg Val Glu Ala Asp Glu Asn Asp Lys Ala Val Lys
        1330                1335                1340
Asp Leu Val Phe Leu Leu Phe Asp Thr Ser Leu Leu Thr Ser Gly Phe
1345                1350                1355                1360
Gln Leu Asp Asp Pro Thr Gly Tyr Ala Glu Arg Ile Asn Arg Met Ile
            1365                1370                1375
Lys Leu Gly Leu Ser Leu Asp Glu Glu Glu Glu Val Ala Glu Ala
        1380                1385                1390
Pro Pro Ala Glu Ala Ala Pro Ala Glu Val Thr Ala Gly Thr Ser Ser
        1395                1400                1405
Met Glu Gln Val Asp Asp Ile Met Ala Gln Asn Asp Lys Ile Ala Pro
        1410                1415                1420
Gln Asp Gln Asp Ser Phe Leu Asp Asp Gln Pro Gly Val Arg Pro Ile
1425                1430                1435                1440
Pro Ser Phe Asp Asp Met Pro Leu His Gln Asn Leu Leu Arg Gly Ile
            1445                1450                1455
Tyr Ser Tyr Gly Phe Glu Lys Pro Ser Ser Ile Gln Gln Arg Ala Ile
        1460                1465                1470
Ala Pro Phe Thr Arg Gly Gly Asp Ile Ile Ala Gln Ala Gln Ser Gly
        1475                1480                1485
Thr Gly Lys Thr Gly Ala Phe Ser Ile Gly Leu Leu Gln Arg Leu Asp
        1490                1495                1500
Phe Arg His Asn Leu Ile Gln Gly Leu Val Leu Ser Pro Thr Arg Glu
1505                1510                1515                1520
Leu Ala Leu Gln Thr Ala Glu Val Ile Ser Arg Ile Gly Glu Phe Leu
            1525                1530                1535
Ser Asn Ser Ser Lys Phe Cys Glu Thr Phe Val Gly Gly Thr Arg Val
        1540                1545                1550
Gln Asp Asp Leu Arg Lys Leu Gln Ala Gly Val Ile Val Ala Val Gly
        1555                1560                1565
Thr Pro Gly Arg Val Ser Asp Val Ile Lys Arg Gly Ala Leu Arg Thr
        1570                1575                1580
Glu Ser Leu Arg Val Leu Val Leu Asp Glu Ala Asp Glu Met Leu Ser
1585                1590                1595                1600
Gln Gly Phe Ala Asp Gln Ile Tyr Glu Ile Phe Arg Phe Leu Pro Lys
            1605                1610                1615
Asp Ile Gln Val Ala Leu Phe Ser Ala Thr Met Pro Glu Glu Val Leu
        1620                1625                1630
Glu Leu Thr Lys Lys Phe Met Arg Asp
        1635                1640
```

```
<210> SEQ ID NO 97
<211> LENGTH: 1427
<212> TYPE: PRT
<213> ORGANISM: Artificial Sequence
<220> FEATURE:
<223> OTHER INFORMATION: Fusion (poly-protein) constructs comprising
      multiple Leishmania antigens

<400> SEQUENCE: 97

Met His His His His His Met Ser Cys Gly Asn Ala Lys Ile Asn
                  5                  10                  15

Ser Pro Ala Pro Ser Phe Glu Glu Val Ala Leu Met Pro Asn Gly Ser
                 20                  25                  30

Phe Lys Lys Ile Ser Leu Ser Ser Tyr Lys Gly Lys Trp Val Val Leu
                 35                  40                  45

Phe Phe Tyr Pro Leu Asp Phe Thr Phe Val Cys Pro Thr Glu Val Ile
 50                  55                  60

Ala Phe Ser Asp Ser Val Ser Arg Phe Asn Glu Leu Asn Cys Glu Val
 65                  70                  75                  80

Leu Ala Cys Ser Ile Asp Ser Glu Tyr Ala His Leu Gln Trp Thr Leu
                 85                  90                  95

Gln Asp Arg Lys Lys Gly Gly Leu Gly Thr Met Ala Ile Pro Met Leu
                100                 105                 110

Ala Asp Lys Thr Lys Ser Ile Ala Arg Ser Tyr Gly Val Leu Glu Glu
                115                 120                 125

Ser Gln Gly Val Ala Tyr Arg Gly Leu Phe Ile Ile Asp Pro His Gly
130                 135                 140

Met Leu Arg Gln Ile Thr Val Asn Asp Met Pro Val Gly Arg Ser Val
145                 150                 155                 160

Glu Glu Val Leu Arg Leu Leu Glu Ala Phe Gln Phe Val Glu Lys His
                165                 170                 175

Gly Glu Val Cys Pro Ala Asn Trp Lys Lys Gly Ala Pro Thr Met Lys
                180                 185                 190

Pro Glu Pro Asn Ala Ser Val Glu Gly Tyr Phe Ser Lys Gln Gly Ser
                195                 200                 205

Met Asp Ala Thr Glu Leu Lys Asn Lys Gly Asn Glu Glu Phe Ser Ala
                210                 215                 220

Gly Arg Tyr Val Glu Ala Val Asn Tyr Phe Ser Lys Ala Ile Gln Leu
225                 230                 235                 240

Asp Glu Gln Asn Ser Val Leu Tyr Ser Asn Arg Ser Ala Cys Phe Ala
                245                 250                 255

Ala Met Gln Lys Tyr Lys Asp Ala Leu Asp Asp Ala Asp Lys Cys Ile
                260                 265                 270

Ser Ile Lys Pro Asn Trp Ala Lys Gly Tyr Val Arg Arg Gly Ala Ala
                275                 280                 285

Leu His Gly Met Arg Arg Tyr Asp Asp Ala Ile Ala Ala Tyr Glu Lys
                290                 295                 300

Gly Leu Lys Val Asp Pro Ser Asn Ser Gly Cys Ala Gln Gly Val Lys
305                 310                 315                 320

Asp Val Gln Val Ala Lys Ala Arg Glu Ala Arg Asp Pro Ile Ala Arg
                325                 330                 335

Val Phe Thr Pro Glu Ala Phe Arg Lys Ile Gln Glu Asn Pro Lys Leu
                340                 345                 350

Ser Leu Leu Met Leu Gln Pro Asp Tyr Val Lys Met Val Asp Thr Val
                355                 360                 365
```

-continued

```
Ile Arg Asp Pro Ser Gln Gly Arg Leu Tyr Met Glu Asp Gln Arg Phe
    370                 375                 380
Ala Leu Thr Leu Met Tyr Leu Ser Gly Met Lys Ile Pro Asn Asp Gly
385                 390                 395                 400
Asp Gly Glu Glu Glu Arg Pro Ser Ala Lys Ala Glu Thr Ala
                405                 410                 415
Lys Pro Lys Glu Glu Lys Pro Leu Thr Asp Asn Glu Lys Glu Ala Leu
                420                 425                 430
Ala Leu Lys Glu Glu Gly Asn Lys Leu Tyr Leu Ser Lys Lys Phe Glu
            435                 440                 445
Glu Ala Leu Thr Lys Tyr Gln Glu Ala Gln Val Lys Asp Pro Asn Asn
450                 455                 460
Thr Leu Tyr Ile Leu Asn Val Ser Ala Val Tyr Phe Glu Gln Gly Asp
465                 470                 475                 480
Tyr Asp Lys Cys Ile Ala Glu Cys Glu His Gly Ile Glu His Gly Arg
                485                 490                 495
Glu Asn His Cys Asp Tyr Thr Ile Ile Ala Lys Leu Met Thr Arg Asn
            500                 505                 510
Ala Leu Cys Leu Gln Arg Gln Arg Lys Tyr Glu Ala Ala Ile Asp Leu
        515                 520                 525
Tyr Lys Arg Ala Leu Val Glu Trp Arg Asn Pro Asp Thr Leu Lys Lys
530                 535                 540
Leu Thr Glu Cys Glu Lys Glu His Gln Lys Ala Val Glu Glu Ala Tyr
545                 550                 555                 560
Ile Asp Pro Glu Ile Ala Lys Gln Lys Lys Asp Glu Gly Asn Gln Tyr
                565                 570                 575
Phe Lys Glu Asp Lys Phe Pro Glu Ala Val Ala Ala Tyr Thr Glu Ala
            580                 585                 590
Ile Lys Arg Asn Pro Ala Glu His Thr Ser Tyr Ser Asn Arg Ala Ala
        595                 600                 605
Ala Tyr Ile Lys Leu Gly Ala Phe Asn Asp Ala Leu Lys Asp Ala Glu
610                 615                 620
Lys Cys Ile Glu Leu Lys Pro Asp Phe Val Lys Gly Tyr Ala Arg Lys
625                 630                 635                 640
Gly His Ala Tyr Phe Trp Thr Lys Gln Tyr Asn Arg Ala Leu Gln Ala
                645                 650                 655
Tyr Asn Glu Gly Leu Lys Val Asp Pro Ser Asn Ala Asp Cys Lys Asp
            660                 665                 670
Gly Arg Tyr Arg Thr Ile Met Lys Ile Gln Glu Met Ala Ser Gly Gln
        675                 680                 685
Ser Ala Asp Gly Asp Glu Ala Ala Arg Arg Ala Met Asp Asp Pro Glu
690                 695                 700
Ile Ala Ala Ile Met Gln Asp Ser Tyr Met Gln Leu Val Leu Lys Glu
705                 710                 715                 720
Met Gln Asn Asp Pro Thr Arg Ile Gln Glu Tyr Met Lys Asp Ser Gly
                725                 730                 735
Ile Ser Ser Lys Ile Asn Lys Leu Ile Ser Ala Gly Ile Ile Arg Phe
            740                 745                 750
Gly Gln Glu Phe Ser Leu Thr Asp Pro Ala Val Leu Gly Glu Glu Thr
        755                 760                 765
His Leu Arg Val Arg Val Pro Asp Lys Ala Asn Lys Thr Leu Thr
770                 775                 780
```

-continued

```
Val Glu Asp Asn Gly Ile Gly Met Thr Lys Ala Asp Leu Val Asn Asn
785                 790                 795                 800

Leu Gly Thr Ile Ala Arg Ser Gly Thr Lys Ala Phe Met Glu Ala Leu
                805                 810                 815

Glu Ala Gly Gly Asp Met Ser Met Ile Gly Gln Phe Gly Val Gly Phe
            820                 825                 830

Tyr Ser Ala Tyr Leu Val Ala Asp Arg Val Thr Val Val Ser Lys Asn
        835                 840                 845

Asn Ser Asp Glu Ala Tyr Val Trp Glu Ser Ser Ala Gly Gly Thr Phe
850                 855                 860

Thr Ile Thr Ser Val Pro Glu Ser Asp Met Lys Arg Gly Thr Arg Ile
865                 870                 875                 880

Thr Leu His Leu Lys Glu Asp Gln Gln Glu Tyr Leu Glu Glu Arg Arg
                885                 890                 895

Val Lys Glu Leu Ile Lys Lys His Ser Glu Phe Ile Gly Tyr Asp Ile
            900                 905                 910

Glu Leu Met Val Glu Lys Thr Ala Glu Lys Glu Val Thr Asp Glu Asp
        915                 920                 925

Glu Glu Glu Asp Glu Ser Lys Lys Ser Cys Gly Asp Glu Gly Glu
930                 935                 940

Pro Lys Val Glu Val Thr Glu Gly Glu Asp Lys Lys Lys
945                 950                 955                 960

Thr Lys Lys Val Lys Glu Val Thr Lys Thr Tyr Glu Val Gln Asn Lys
                965                 970                 975

His Lys Pro Leu Trp Thr Arg Asp Pro Lys Asp Val Thr Lys Glu Glu
            980                 985                 990

Tyr Ala Ala Phe Tyr Lys Ala Ile Ser Asn Asp Trp Glu Asp Pro Ala
        995                 1000                1005

Ala Thr Lys His Phe Ser Val Glu Gly Gln Leu Glu Phe Arg Ala Ile
        1010                1015                1020

Ala Phe Val Pro Lys Arg Ala Pro Phe Asp Met Phe Glu Pro Asn Lys
1025                1030                1035                1040

Lys Arg Asn Asn Ile Lys Leu Tyr Val Arg Arg Val Phe Ile Met Asp
                1045                1050                1055

Asn Cys Glu Asp Leu Cys Pro Asp Trp Leu Gly Phe Val Lys Gly Val
            1060                1065                1070

Val Asp Ser Glu Asp Leu Pro Leu Asn Ile Ser Arg Glu Asn Leu Gln
        1075                1080                1085

Gln Asn Lys Ile Leu Lys Val Ile Arg Lys Asn Ile Val Lys Lys Cys
        1090                1095                1100

Leu Glu Leu Phe Glu Glu Ile Ala Glu Asn Lys Glu Asp Tyr Lys Gln
1105                1110                1115                1120

Phe Tyr Glu Gln Phe Gly Lys Asn Ile Lys Leu Gly Ile His Glu Asp
                1125                1130                1135

Thr Ala Asn Arg Lys Lys Leu Met Glu Leu Leu Arg Phe Tyr Ser Thr
            1140                1145                1150

Glu Ser Gly Glu Glu Met Thr Thr Leu Lys Asp Tyr Val Thr Arg Met
        1155                1160                1165

Lys Pro Glu Gln Lys Ser Ile Tyr Tyr Ile Thr Gly Asp Ser Lys Lys
        1170                1175                1180

Lys Leu Glu Ser Ser Pro Phe Ile Glu Lys Ala Arg Arg Cys Gly Leu
1185                1190                1195                1200

Glu Val Leu Phe Met Thr Glu Pro Ile Asp Glu Tyr Val Met Gln Gln
```

```
                     1205                1210                1215
Val Lys Asp Phe Glu Asp Lys Lys Phe Ala Cys Leu Thr Lys Glu Gly
            1220                1225                1230

Val His Phe Glu Glu Ser Glu Glu Lys Lys Gln Arg Glu Lys
            1235                1240                1245

Lys Ala Ala Cys Glu Lys Leu Cys Lys Thr Met Lys Glu Val Leu Gly
            1250                1255                1260

Asp Lys Val Glu Lys Val Thr Val Ser Glu Arg Leu Ser Thr Ser Pro
1265                1270                1275                1280

Cys Ile Leu Val Thr Ser Glu Phe Gly Trp Ser Ala His Met Glu Gln
                1285                1290                1295

Ile Met Arg Asn Gln Ala Leu Arg Asp Ser Ser Met Ala Gln Tyr Met
            1300                1305                1310

Val Ser Lys Lys Thr Met Glu Val Asn Pro Asp His Pro Ile Ile Lys
            1315                1320                1325

Glu Leu Arg Arg Arg Val Glu Ala Asp Glu Asn Asp Lys Ala Val Lys
            1330                1335                1340

Asp Leu Val Phe Leu Leu Phe Asp Thr Ser Leu Leu Thr Ser Gly Phe
1345                1350                1355                1360

Gln Leu Asp Asp Pro Thr Gly Tyr Ala Glu Arg Ile Asn Arg Met Ile
                1365                1370                1375

Lys Leu Gly Leu Ser Leu Asp Glu Glu Glu Glu Val Ala Glu Ala
            1380                1385                1390

Pro Pro Ala Glu Ala Ala Pro Ala Glu Val Thr Ala Gly Thr Ser Ser
                1395                1400                1405

Met Glu Gln Val Asp Asp Ile His His Thr Gly Gly Arg Ser Ser Arg
            1410                1415                1420

Ser Gly Cys
1425

<210> SEQ ID NO 98
<211> LENGTH: 4929
<212> TYPE: DNA
<213> ORGANISM: Artificial Sequence
<220> FEATURE:
<223> OTHER INFORMATION: DNA sequence encoding fusion (poly-protein)
      constructs comprising multiple Leishmania antigens

<400> SEQUENCE: 98
catatgcacc accaccacca ccacatgtcc tgcggtaacg ccaagatcaa ctctcccgcg    60
ccgtccttcg aggaggtggc gctcatgccc aacggcagct tcaagaagat cagcctctcc   120
tcctacaagg gcaagtgggt cgtgctcttc ttctacccgc tcgacttcac cttcgtgtgc   180
ccgacagagg tcatcgcgtt ctccgacagc gtgagtcgct caacgagct caactgcgag    240 gtcctcgcgt gctcgataga cagcgagtac gcgcacctgc agtggacgct gcaggaccgc   300
aagaagggcg gcctcgggac catggcgatc ccaatgctag ccgacaagac caagagcatc   360
gctcgttcct acgcgtgct ggaggagagc cagggcgtgg cctaccgcgg tctcttcatc    420 atcgacccc atggcatgct gcgtcagatc accgtcaatg acatgccggt gggccgcagc   480
gtggaggagg ttctacgcct gctggaggct tttcagttcg tggagaagca cggcgaggtg   540
tgccccgcga actggaagaa gggcgccccc acgatgaagc cggaaccgaa tgcgtctgtc   600
gagggatact tcagcaagca gggatccatg acgcaactg agctgaagaa caaggggaac   660
gaagagttct ccgccggccg ctatgtggag gcggtgaact acttctcaaa ggcgatccag   720
```

-continued

| | |
|---|---|
| ttggatgagc agaacagtgt cctctacagc aaccgctccg cctgttttgc agccatgcag | 780 |
| aaatacaagg acgcgctgga cgacgccgac aagtgcatct cgatcaagcc gaattgggcc | 840 |
| aagggctacg tgcgccgagg agcagctctc catggcatgc gccgctacga cgatgccatt | 900 |
| gccgcgtatg aaaaggggct caaggtggac ccttccaaca gcggctgcgc gcagggcgtg | 960 |
| aaggacgtgc aggtagccaa ggcccgcgaa gcacgtgacc ccatcgctcg cgtcttcacc | 1020 |
| ccggaggcgt tccgcaagat ccaagagaat cccaagctgt ctctacttat gctgcagccg | 1080 |
| gactacgtga agatggtaga caccgtcatc cgcgacccct tcgcagggcc gctgtacatg | 1140 |
| gaagaccagc gctttgccct gacgctcatg tacctgagcg gaatgaagat tcccaacgat | 1200 |
| ggtgatggcg aggaggagga acgtccgtct gcgaaggcgg cagagacagc gaagccaaaa | 1260 |
| gaggagaagc ctctcaccga caacgagaag gaggccctgg cgctcaagga ggagggcaac | 1320 |
| aagctgtacc tctcgaagaa gtttgaggag gcgctgacca agtaccaaga ggcgcaggtg | 1380 |
| aaagacccca acaacacttt atacattctg aacgtgtcgg ccgtgtactt cgagcagggt | 1440 |
| gactacgaca agtgcatcgc cgagtgcgag cacggtatcg agcacggtcg cgagaaccac | 1500 |
| tgcgactaca caatcattgc gaagctcatg acccggaacg ccttgtgcct ccagaggcag | 1560 |
| aggaagtacg aggctgctat cgacctttac aagcgcgccc ttgtcgagtg gcgtaaccct | 1620 |
| gacaccctca agaagctgac ggagtgcgag aaggagcacc aaaaggcggt ggaggaagcc | 1680 |
| tacatcgatc ctgagatcgc gaagcagaag aaagacgaag gtaaccagta cttcaaggag | 1740 |
| gataagttcc ccgaggccgt ggcagcgtac acggaggcca tcaagcgcaa ccctgccgag | 1800 |
| cacacctcct acagcaatcg cgcggccgcg tacatcaagc ttggagcctt caacgacgcc | 1860 |
| ctcaaggacg cggagaagtg cattgagctg aagcccgact tgttaaggg ctacgcgcgc | 1920 |
| aagggtcatg cttacttttg gaccaagcag tacaaccgcg cgctgcaggc gtacaatgag | 1980 |
| ggcctcaagg tggacccgag caatgcggac tgcaaggatg gcggtatcg cacaatcatg | 2040 |
| aagattcagg agatggcatc tggccaatcc gcggatggcg acgaggcggc gcgccgggcc | 2100 |
| atggacgatc ctgaaatcgc ggcaatcatg caagatagct acatgcaact agtgttgaag | 2160 |
| gagatgcaga acgatcccac gcgcattcag gagtacatga aggactccgg gatctcatcg | 2220 |
| aagatcaaca agctgatttc agctggcatc attcgttttg gtcaggaatt cagcctgacg | 2280 |
| gacccggcgg tgctgggcga ggagactcac ctgcgcgtcc gcgtggtgcc ggacaaggcg | 2340 |
| aacaagacgc tgacggtgga ggataacggc atcggcatga ccaaggcgga cctcgtgaac | 2400 |
| aatctgggca cgatcgcgcg ctccggcacg aaggcgttca tggaggcact ggaggccggc | 2460 |
| ggcgacatga gcatgatcgg ccagttcggt gtcggcttct actccgcgta ccttgtggcg | 2520 |
| gaccgcgtga cggtggtgtc gaagaacaac tcggacgagg cgtacgtatg ggagtcgtcc | 2580 |
| gcgggcggca cgttcaccat cacgagcgtg ccggagtcgg acatgaagcg cggcacgcgc | 2640 |
| atcacgctgc acctaaagga ggaccagcag gagtacctgg aggagcgccg ggtgaaggag | 2700 |
| ctgatcaaga agcactccga gttcatcggc tacgacatcg agctgatggt ggagaagacg | 2760 |
| gcggagaagg aggtgacgga cgaggacgag gaggaggacg agtcgaagaa gaagtcctgc | 2820 |
| ggggacgagg cgagccgaa ggtggaggag gtgacggagg cggcgaggag caagaagaag | 2880 |
| aagacgaaga aggtgaagga ggtgacgaag acgtacgagg tccagaacaa gcacaagccg | 2940 |
| ctctggacgc gcgacccgaa ggacgtgacg aaggaggagt acgcggcctt ctacaaggcc | 3000 |
| atctccaacg actgggagga cccggcggcg acgaagcact tctcggtgga gggccagctg | 3060 |
| gagttccgcg cgatcgcgtt cgtgccgaag cgcgcgccgt tcgacatgtt cgagccgaac | 3120 |

```
aagaagcgca acaacatcaa gctgtacgtg cgccgcgtgt tcatcatgga caactgcgag   3180
gacctgtgcc cggactggct cggcttcgtg aagggcgtcg tggacagcga ggacctgccg   3240
ctgaacatct cgcgcgagaa cctgcagcag aacaagatcc tgaaggtgat ccgcaagaac   3300
atcgtgaaga agtgcctgga gctgttcgaa gagatagcgg agaacaagga ggactacaag   3360
cagttctacg agcagttcgg caagaacatc aagctgggca tccacgagga cacggcgaac   3420
cgcaagaagc tgatggagtt gctgcgcttc tacagcaccg agtcgggggga ggagatgacg   3480 acactgaagg actacgtgac gcgcatgaag ccggagcaga agtcgatcta ctacatcact   3540
ggcgacagca agaagaagct ggagtcgtcg ccgttcatcg agaaggcgag acgctgcggg   3600
ctcgaggtgc tgttcatgac ggagccgatc gacgagtacg tgatgcagca ggtgaaggac   3660
ttcgaggaca agaagttcgc gtgcctgacg aaggaaggcg tgcacttcga ggagtccgag   3720
gaggagaaga agcagcgcga ggagaagaag gcggcgtgcg agaagctgtg caagacgatg   3780
aaggaggtgc tgggcgacaa ggtggagaag gtgaccgtgt cggagcgcct gtcgacgtcg   3840
ccgtgcatcc tggtgacgtc ggagtttggg tggtcggcgc acatggaaca gatcatgcgc   3900
aaccaggcgc tgcgcgactc cagcatggcg cagtacatgg tgtccaagaa gacgatggag   3960
gtgaaccccg accaccccat catcaaggag ctgcgccgcc gcgtggaggc ggacgagaac   4020
gacaaggccg tgaaggacct cgtcttcctg ctcttcgaca cgtcgctgct cacgtccggc   4080
ttccagctgg atgaccccac cggctacgcc gagcgcatca accgcatgat caagctcggc   4140
ctgtcgctcg acgaggagga ggaggaggtc gccgaggcgc cgccggccga ggcagccccc   4200
gcggaggtca ccgccggcac ctccagcatg gagcaggtgg acgatatcat ggcgcagaat   4260
gataagatcg ccccccagga ccaggactcc ttcctcgatg accagcccgg cgttcgcccg   4320
atcccgtcct tcgacgacat gccgctgcac cagaacctgc tgcgtggcat ctactcgtac   4380
gggttcgaga agccgtccag catccagcag cgcgcgatag ccccccttcac gcgcggcggc   4440 gacatcatcg cgcaggccca gtccggtacc ggcaagacgg gtgccttctc catcggtctg   4500
ctgcagcgcc tggacttccg ccacaacctg atccagggcc tcgtgctctc ccccactcgc   4560
gagctggccc tgcagacggc ggaggtgatc agccgcatcg gtgagttcct gtcgaacagc   4620
tccaagttct gcgagacctt tgtcggcggc acgcgcgtgc aggatgacct gcgcaagctg   4680
caggccggcg tcatcgttgc cgtgggcacg ccgggccgcg tgtccgacgt gatcaagcgt   4740
ggcgcgctgc gcacagagtc gctgcgcgtg ctggtgctcg acgaggctga tgagatgctg   4800
tctcagggct tcgcggacca gatttacgag atcttccgct tcctgccgaa ggacatccag   4860
gtcgcgctct tctccgccac gatgccggag gaggtactgg agctgacgaa gaagttcatg   4920
cgcgactaa                                                           4929
```

```
<210> SEQ ID NO 99
<211> LENGTH: 4233
<212> TYPE: DNA
<213> ORGANISM: Artificial Sequence
<220> FEATURE:
<223> OTHER INFORMATION: DNA sequence encoding fusion (poly-protein)
      constructs comprising multiple Leishmania antigens

<400> SEQUENCE: 99
ccagtgtggt ggatgtcctg cggtaacgcc aagatcaact ctcccgcgcc gtccttcgag     60
gaggtggcgc tcatgcccaa cggcagcttc aagaagatca gcctctcctc ctacaagggc    120
aagtgggtcg tgctcttctt ctacccgctc gacttcacct tcgtgtgccc gacagaggtc    180
```

```
atcgcgttct ccgacagcgt gagtcgcttc aacgagctca actgcgaggt cctcgcgtgc      240
tcgatagaca gcgagtacgc gcacctgcag tggacgctgc aggaccgcaa gaagggcggc      300
ctcgggacca tggcgatccc aatgctagcc gacaagacca agagcatcgc tcgttcctac      360
ggcgtgctgg aggagagcca gggcgtggcc taccgcggtc tcttcatcat cgaccccat      420 ggcatgctgc gtcagatcac cgtcaatgac atgccggtgg ccgcagcgt ggaggaggtt      480 ctacgcctgc tggaggcttt tcagttcgtg gagaagcacg gcgaggtgtg ccccgcgaac      540
tggaagaagg gcgccccac gatgaagccg aaccgaatg cgtctgtcga gggatacttc      600
agcaagcagg gatccatgga cgcaactgag ctgaagaaca aggggaacga agagttctcc      660
gccggccgct atgtggaggc ggtgaactac ttctcaaagg cgatccagtt ggatgagcag      720
aacagtgtcc tctacagcaa ccgctccgcc tgttttgcag ccatgcagaa atacaaggac      780
gcgctggacg acgccgacaa gtgcatctcg atcaagccga attgggccaa gggctacgtg      840
cgccgaggag cagctctcca tggcatgcgc cgctacgacg atgccattgc cgcgtatgaa      900 aagggggctca aggtggaccc ttccaacagc ggctgcgcgc agggcgtgaa ggacgtgcag      960
gtagccaagg cccgcgaagc acgtgacccc atcgctcgcg tcttcacccc ggaggcgttc     1020
cgcaagatcc aagagaatcc caagctgtct ctacttatgc tgcagccgga ctacgtgaag     1080
atggtagaca ccgtcatccg cgaccttcg cagggccggc tgtacatgga agaccagcgc     1140
tttgccctga cgctcatgta cctgagcgga atgaagattc ccaacgatgg tgatggcgag     1200
gaggaggaac gtccgtctgc gaaggcggca gagacagcga agccaaaaga ggagaagcct     1260
ctcaccgaca acgagaagga ggccctggcg ctcaaggagg agggcaacaa gctgtacctc     1320
tcgaagaagt ttgaggaggc gctgaccaag taccaagagc gcaggtgaa agaccccaac     1380 aacactttat acattctgaa cgtgtcggcc gtgtacttcg agcagggtga ctacgacaag     1440
tgcatcgccg agtgcgagca cggtatcgag cacggtcgcg agaaccactg cgactacaca     1500
atcattgcga agctcatgac ccggaacgcc ttgtgcctcc agaggcagag gaagtacgag     1560
gctgctatcg acctttacaa gcgcgccctt gtcgagtggc gtaaccctga caccctcaag     1620
aagctgacgg agtgcgagaa ggagcaccaa aaggcggtgg aggaagccta catcgatcct     1680
gagatcgcga agcagaagaa agacgaaggt aaccagtact tcaaggagga taagttcccc     1740
gaggccgtgg cagcgtacac ggaggccatc aagcgcaacc ctgccgagca cacctcctac     1800
agcaatcgcg cggccgcgta catcaagctt ggagccttca acgacgccct caaggacgcg     1860
gagaagtgca ttgagctgaa gcccgacttt gttaagggct acgcgcgcaa gggtcatgct     1920
tactttggga ccaagcagta caccgcgcg ctgcaggcgt acaatgaggg cctcaaggtg     1980
gacccgagca atgcggactg caaggatggg cggtatcgca caatcatgaa gattcaggag     2040
atggcatctg gccaatccgc ggatggcgac gaggcggcgc gccgggccat ggacgatcct     2100
gaaatcgcgg caatcatgca agatagctac atgcaactag tgttgaagga gatgcagaac     2160
gatcccacgc gcattcagga gtacatgaag gactccggga tctcatcgaa gatcaacaag     2220
ctgatttcag ctggcatcat tcgttttggt caggaattca gcctgacgga cccggcggtg     2280
ctgggcgagg agactcacct gcgcgtccgc gtggtgccgg acaaggcgaa caagacgctg     2340
acggtggagg ataacggcat cggcatgacc aaggcggacc tcgtgaacaa tctgggcacg     2400
atcgcgcgct ccggcacgaa ggcgttcatg gaggcactgg aggccggcgg cgacatgagc     2460
atgatcggcc agttcggtgt cggcttctac tccgcgtacc ttgtggcgga ccgcgtgacg     2520
gtggtgtcga agaacaactc ggacgaggcg tacgtatggg agtcgtccgc gggcggcacg     2580
```

| | |
|---|---|
| ttcaccatca cgagcgtgcc ggagtcggac atgaagcgcg gcacgcgcat cacgctgcac | 2640 |
| ctaaaggagg accagcagga gtacctggag gagcgccggg tgaaggagct gatcaagaag | 2700 |
| cactccgagt tcatcggcta cgacatcgag ctgatggtgg agaagacggc ggagaaggag | 2760 |
| gtgacggacg aggacgagga ggaggacgag tcgaagaaga agtcctgcgg ggacgagggc | 2820 |
| gagccgaagg tggaggaggt gacggagggc ggcgaggaca agaagaagaa gacgaagaag | 2880 |
| gtgaaggagg tgacgaagac gtacgaggtc cagaacaagc acaagccgct ctggacgcgc | 2940 |
| gacccgaagg acgtgacgaa ggaggagtac gcggccttct acaaggccat ctccaacgac | 3000 |
| tgggaggacc cggcggcgac gaagcacttc tcggtggagg gccagctgga gttccgcgcg | 3060 |
| atcgcgttcg tgccgaagcg cgcgccgttc gacatgttcg agccgaacaa gaagcgcaac | 3120 |
| aacatcaagc tgtacgtgcg ccgcgtgttc atcatggaca actgcgagga cctgtgcccg | 3180 |
| gactggctcg gcttcgtgaa gggcgtcgtg gacagcgagg acctgccgct gaacatctcg | 3240 |
| cgcgagaacc tgcagcagaa caagatcctg aaggtgatcc gcaagaacat cgtgaagaag | 3300 |
| tgcctggagc tgttcgaaga gatagcggag aacaaggagg actacaagca gttctacgag | 3360 |
| cagttcggca agaacatcaa gctgggcatc cacgaggaca cggcgaaccg caagaagctg | 3420 |
| atggagttgc tgcgcttcta cagcaccgag tcggggggagg agatgacgac actgaaggac | 3480 |
| tacgtgacgc gcatgaagcc ggagcagaag tcgatctact acatcactgg cgacagcaag | 3540 |
| aagaagctgg agtcgtcgcc gttcatcgag aaggcgagac gctgcgggct cgaggtgctg | 3600 |
| ttcatgacgg agccgatcga cgagtacgtg atgcagcagg tgaaggactt cgaggacaag | 3660 |
| aagttcgcgt gcctgacgaa ggaaggcgtg cacttcgagg agtccgagga ggagaagaag | 3720 |
| cagcgcgagg agaagaaggc ggcgtgcgag aagctgtgca agacgatgaa ggaggtgctg | 3780 |
| ggcgacaagg tggagaaggt gaccgtgtcg gagcgcctgt cgacgtcgcc gtgcatcctg | 3840 |
| gtgacgtcgg agtttgggtg gtcggcgcac atggaacaga tcatgcgcaa ccaggcgctg | 3900 |
| cgcgactcca gcatggcgca gtacatggtg tccaagaaga cgatggaggt gaaccccgac | 3960 |
| caccccatca tcaaggagct cgccgccgc gtggaggcgg acgagaacga caaggccgtg | 4020 |
| aaggacctcg tcttcctgct cttcgacacg tcgctgctca cgtccggctt ccagctggat | 4080 |
| gaccccaccg gctacgccga cgcatcaac cgcatgatca agctcggcct gtcgctcgac | 4140 |
| gaggaggagg aggaggtcgc cgaggcgccg ccggccgagg cagcccccgc ggaggtcacc | 4200 |
| gccggcacct ccagcatgga gcaggtggac taa | 4233 |

<210> SEQ ID NO 100
<211> LENGTH: 4917
<212> TYPE: DNA
<213> ORGANISM: Artificial Sequence
<220> FEATURE:
<223> OTHER INFORMATION: DNA sequence encoding fusion (poly-protein)
      constructs comprising multiple Leishmania antigens

<400> SEQUENCE: 100

| | |
|---|---|
| ccagtgtggt ggatgtcctg cggtaacgcc aagatcaact ctcccgcgcc gtccttcgag | 60 |
| gaggtggcgc tcatgcccaa cggcagcttc aagaagatca gcctctcctc ctacaagggc | 120 |
| aagtgggtcg tgctcttctt ctaccgcgtc gacttcacct tcgtgtgccc gacagaggtc | 180 |
| atcgcgttct ccgacagcgt gagtcgcttc aacgagctca actgcgaggt cctcgcgtgc | 240 |
| tcgatagaca gcgagtacgc gcacctgcag tggacgctgc aggaccgcaa gaagggcggc | 300 |
| ctcgggacca tggcgatccc aatgctagcc gacaagacca agagcatcgc tcgttcctac | 360 |

-continued

```
ggcgtgctgg aggagagcca gggcgtggcc taccgcggtc tcttcatcat cgaccccat      420 ggcatgctgc gtcagatcac cgtcaatgac atgccggtgg gccgcagcgt ggaggaggtt      480
ctacgcctgc tggaggcttt tcagttcgtg gagaagcacg cgcgaggtgtg ccccgcgaac    540 tggaagaagg gcgcccccac gatgaagccg aaccgaatg cgtctgtcga gggatacttc      600
agcaagcagg gatccatgga cgcaactgag ctgaagaaca aggggaacga agagttctcc     660
gccggccgct atgtggaggc ggtgaactac ttctcaaagg cgatccagtt ggatgagcag     720
aacagtgtcc tctacagcaa ccgctccgcc tgttttgcag ccatgcagaa atacaaggac    780
gcgctggacg acgccgacaa gtgcatctcg atcaagccga attgggccaa gggctacgtg    840
cgccgaggag cagctctcca tggcatgcgc cgctacgacg atgccattgc cgcgtatgaa    900 aagggctca aggtggaccc ttccaacagc ggctgcgcgc agggcgtgaa ggacgtgcag     960
gtagccaagg cccgcgaagc acgtgacccc atcgctcgcg tcttcacccc ggaggcgttc   1020
cgcaagatcc aagagaatcc caagctgtct ctacttatgc tgcagccgga ctacgtgaag    1080
atggtagaca ccgtcatccg cgaccctctcg cagggccggc tgtacatgga agaccagcgc  1140
tttgccctga cgctcatgta cctgagcgga atgaagattc ccaacgatgg tgatggcgag    1200
gaggaggaac gtccgtctgc gaaggcggca gagacagcga agccaaaaga ggagaagcct    1260
ctcaccgaca acgagaagga ggccctggcg ctcaaggagg agggcaacaa gctgtacctc   1320
tcgaagaagt ttgaggaggc gctgaccaag taccaagagg cgcaggtgaa agaccccaac    1380
aacactttat acattctgaa cgtgtcggcc gtgtacttcg agcagggtga ctacgacaag    1440
tgcatcgccg agtgcgagca cggtatcgag cacggtcgcg agaaccactg cgactacaca   1500
atcattgcga agctcatgac ccggaacgcc ttgtgcctcc agaggcagag gaagtacgag    1560
gctgctatcg accttttacaa cgcgcccctt gtcgagtggc gtaaccctga caccctcaag   1620
aagctgacgg agtgcgagaa ggagcaccaa aaggcggtgg aggaagccta catcgatcct    1680
gagatcgcga agcagaagaa agacgaaggt aaccagtact tcaaggagga taagttcccc    1740
gaggccgtgg cagcgtacac ggaggccatc aagcgcaacc ctgccgagca cacctcctac    1800
agcaatcgcg cggccgcgta catcaagctt ggagccttca cgacgcccct caaggacgcg    1860
gagaagtgca ttgagctgaa gcccgacttt gttaagggct acgcgcgcaa gggtcatgct    1920
tacttttgga ccaagcagta caaccgcgcg ctgcaggcgt acaatgaggg cctcaaggtg   1980
gacccgagca atgcggactg caaggatggg cggtatcgca caatcatgaa gattcaggag   2040
atggcatctg gccaatccgc ggatggcgac gaggcggcgc gccgggccat ggacgatcct   2100
gaaatcgcgg caatcatgca agatagctac atgcaactag tgttgaagga gatgcagaac   2160
gatcccacgc gcattcagga gtacatgaag gactccggga tctcatcgaa gatcaacaag    2220
ctgatttcag ctggcatcat tcgttttggt caggaattca gcctgacgga cccggcggtg    2280
ctgggcgagg agactcacct cgcgcgtccgc gtggtgccgg acaaggcgaa caagacgctg    2340
acggtggagg ataacggcat cggcatgacc aaggcggacc tcgtgaacaa tctgggcacg   2400
atcgcgcgct ccggcacgaa ggcgttcatg gaggcactgg aggccggcgg cgacatgagc   2460
atgatcggcc agttcggtgt cggcttctac tccgcgtacc ttgtggcgga ccgcgtgacg    2520
gtggtgtcga agaacaactc ggacgaggcg tacgtatggg agtcgtccgc gggcggcacg    2580
ttcaccatca cgagcgtgcc gggagtcgga catgaagcgcg gcacgcgcat cacgctgcac    2640
ctaaaggagg accagcagga gtacctggag gagcgccggg tgaaggagct gatcaagaag    2700
cactccgagt tcatcggcta cgacatcgag ctgatggtgg agaagacggc ggagaaggag    2760
```

```
gtgacggacg aggacgagga ggaggacgag tcgaagaaga agtcctgcgg ggacgagggc    2820
gagccgaagg tggaggaggt gacggagggc ggcgaggaca agaagaagaa gacgaagaag    2880
gtgaaggagg tgacgaagac gtacgaggtc cagaacaagc acaagccgct ctggacgcgc    2940
gaccccaagg acgtgacgaa ggaggagtac gcggccttct acaaggccat ctccaacgac    3000
tgggaggacc cggcggcgac gaagcacttc tcggtggagg ccagctgga  gttccgcgcg    3060 atcgcgttcg tgccgaagcg cgcgccgttc gacatgttcg agccgaacaa gaagcgcaac    3120
aacatcaagc tgtacgtgcg ccgcgtgttc atcatggaca actgcgagga cctgtgcccg    3180
gactggctcg gcttcgtgaa gggcgtcgtg gacagcgagg acctgccgct gaacatctcg    3240
cgcgagaacc tgcagcagaa caagatcctg aaggtgatcc gcaagaacat cgtgaagaag    3300
tgcctggagc tgttcgaaga gatagcggag aacaaggagg actacaagca gttctacgag    3360
cagttcggca agaacatcaa gctgggcatc acgaggaca  cggcgaaccg caagaagctg    3420
atggagttgc tgcgcttcta cagcaccgag tcggggagg  agatgacgac actgaaggac    3480
tacgtgacgc gcatgaagcc ggagcagaag tcgatctact acatcactgg cgacagcaag    3540
aagaagctgg agtcgtcgcc gttcatcgag aaggcgagac gctgcgggct cgaggtgctg    3600
ttcatgacga agccgatcga cgagtacgtg atgcagcagg tgaaggactt cgaggacaag    3660
aagttcgcgt gcctgacgaa ggaaggcgtg cacttcgagg agtccgagga ggagaagaag    3720
cagcgcgagg agaagaaggc ggcgtgcgag aagctgtgca agacgatgaa ggaggtgctg    3780
ggcgacaagg tggagaaggt gaccgtgtcg gagcgcctgt cgacgtcgcc gtgcatcctg    3840
gtgacgtcgg agtttgggtg gtcggcgcac atggaacaga tcatgcgcaa ccaggcgctg    3900
cgcgactcca gcatggcgca gtacatggtg tccaagaaga cgatggaggt gaaccccgac    3960
caccccatca tcaaggagct gcgccgccgc gtggaggcgg acgagaacga caaggccgtg    4020
aaggacctcg tcttcctgct cttcgacacg tcgctgctca cgtccggctt ccagctggat    4080
gaccccaccg gctacgccga gcgcatcaac cgcatgatca agctcggcct gtcgctcgac    4140
gaggaggagg aggaggtcgc cgaggcgccg ccggccgagg cagcccccgc ggaggtcacc    4200
gccggcacct ccagcatgga gcaggtggac gatatcatgg cgcagaatga taagatcgcc    4260
ccccaggacc aggactcctt cctcgatgac cagcccggcg ttcgcccgat ccgtccttc    4320 gacgacatgc cgctgcacca gaacctgctg cgtggcatct actcgtacgg gttcgagaag    4380
ccgtccagca tccagcagcg cgcgatagcc cccttcacgc gcggcggcga catcatcgcg    4440
caggcccagt ccggtaccgg caagacgggt gccttctcca tcggtctgct gcagcgcctg    4500
gacttccgcc acaacctgat ccaggcctc  gtgctctccc ccactcgcga gctggccctg    4560
cagacggcgg aggtgatcag ccgcatcggt gagttcctgt cgaacagctc caagttctgc    4620
gagacctttg tcgcggcac  gcgcgtgcag gatgacctgc gcaagctgca ggccggcgtc    4680
atcgttgccg tgggcacgcc gggccgcgtg tccgacgtga tcaagcgtgg cgcgctgcgc    4740
acagagtcgc tgcgcgtgct ggtgctcgac gaggctgatg agatgctgtc tcagggcttc    4800
gcggaccaga tttacgagat cttccgcttc ctgccgaagg acatccaggt cgcgctcttc    4860
tccgccacga tgccggagga ggtactggag ctgacgaaga agttcatgcg cgactaa      4917
```

<210> SEQ ID NO 101
<211> LENGTH: 2735
<212> TYPE: DNA
<213> ORGANISM: Artificial Sequence
<220> FEATURE:
<223> OTHER INFORMATION: DNA sequence encoding fusion (poly-protein)

constructs comprising multiple Leishmania antigens

<400> SEQUENCE: 101

```
catatgcacc accaccacca ccacatgtcc tgcggtaacg ccaagatcaa ctctcccgcg      60
ccgtccttcg aggaggtggc gctcatgccc aacggcagct tcaagaagat cagcctctcc     120
tcctacaagg gcaagtgggt cgtgctcttc ttctacccgc tcgacttcac cttcgtgtgc     180
ccgacagagg tcatcgcgtt ctccgacagc gtgagtcgct tcaacgagct caactgcgag     240
gtcctcgcgt gctcgataga cagcgagtac gcgcacctgc agtggacgct gcaggaccgc     300
aagaagggcg gcctcgggac catggcgatc ccaatgctag ccgacaagac caagagcatc     360
gctcgttcct acggcgtgct ggaggagagc cagggcgtgg cctaccgcgg tctcttcatc     420
atcgaccccc atggcatgct gcgtcagatc accgtcaatg acatgccggt gggccgcagc     480
gtggaggagg ttctacgcct gctggaggct tttcagttcg tggagaagca cggcgaggtg     540
tgccccgcga actggaagaa gggcgccccc acgatgaagc cggaaccgaa tgcgtctgtc     600
gagggatact tcagcaagca gggatccatg acgcaactg agctgaagaa caaggggaac      660
gaagagttct ccgccggccg ctatgtggag gcggtgaact acttctcaaa ggcgatccag     720
ttggatgagc agaacagtgt cctctacagc aaccgctccg cctgttttgc agccatgcag     780
aaatacaagg acgcgctgga cgacgccgac aagtgcatct cgatcaagcc gaattgggcc     840
aagggctacg tgcgccgagg agcagctctc catggcatgc ccgctacga cgatgccatt     900
gccgcgtatg aaaaggggct caaggtggac ccttccaaca gcggctgcgc gcagggcgtg     960
aaggacgtgc aggtagccaa gcccgcgaa gcacgtgacc ccatcgctcg cgtcttcacc    1020
ccggaggcgt tccgcaagat ccaagagaat cccaagctgt ctctacttat gctgcagccg    1080
gactacgtga agatggtaga caccgtcatc cgcgacccctt cgcagggccg gctgtacatg    1140
gaagaccagc gctttgccct gacgctcatg tacctgagcg gaatgaagat tcccaacgat    1200
ggtgatggcg aggaggagga acgtccgtct gcgaaggcgg cagagacagc gaagccaaaa    1260
gaggagaagc ctctcaccga caacgagaag gaggccctgg cgctcaagga ggagggcaac    1320
aagctgtacc tctcgaagaa gtttgaggag gcgctgacca agtaccaaga ggcgcaggtg    1380
aaagacccca caacactttt atacattctg aacgtgtcgg ccgtgtactt cgagcagggt    1440
gactacgaca agtgcatcgc cgagtgcgag cacggtatcg agcacggtcg cgagaaccac    1500
tgcgactaca caatcattgc gaagctcatg acccggaacg ccttgtgcct ccagaggcag    1560
aggaagtacg aggctgctat cgacctttac aagcgcgccc ttgtcgagtg cgtaaccct     1620
gacaccctca gaagctgac ggagtgcgag aaggagcacc aaaaggcggt ggaggaagcc     1680
tacatcgatc ctgagatcgc gaagcagaag aaagacgaag gtaaccagta cttcaaggag    1740
gataagttcc ccgaggccgt ggcagcgtac acggaggcca tcaagcgcaa ccctgccgag    1800
cacacctcct acagcaatcg cgcggccgcg tacatcaagc ttggagcctt caacgacgcc    1860
ctcaaggacg cggagaagtg cattgagctg aagcccgact tgttaaggg ctacgcgcgc     1920
aagggtcatg cttacttttg gaccaagcag tacaaccgcg cgctgcaggc gtacaatgag    1980
ggcctcaagg tggacccgag caatgcggac tgcaaggatg gcggtatcg cacaatcatg     2040
aagattcagg agatggcatc tggccaatcc gcggatggcg acgaggcggc gcgccgggcc    2100
atggacgatc ctgaaatcgc ggcaatcatg caagatagct acatgcaact agtgttgaag    2160
gagatgcaga acgatcccac gcgcattcag gagtacatga aggactccgg gatctcatcg    2220
aagatcaaca agctgatttc agctggcatc attcgttttg gtcaggaatt ctgcagatat    2280
```

```
ccatcacact ggcggccgct cgagcagatc cggctgctaa caaagcccga aaggaagctg    2340
agttggctgc tgccaccgct gagcaataac tagcataacc ccttgggcc tctaaacggg     2400 tcttgagggg ttttttgctg aaaggaggaa ctatatccgg ataattcttg aagacgaaag    2460
ggcctcgtga tacgcctatt tttataggtt aatgtcatga taataatggt ttcttagacg    2520
tcaggtggca cttttcgggg aaatgtgcgc ggaaccccta tttggttatt tttctaaata    2580
cattcaaata tgtatccgct catgagacaa taacccytga taaatgcttc aataatattg    2640
aaaaaaggaa gaatatgaag tatttcaaca tttcccgggt cccccttatt ccctttttt     2700 gccgccattt tgcctttctg tttttggttc accca                               2735
```

<210> SEQ ID NO 102
<211> LENGTH: 1713
<212> TYPE: DNA
<213> ORGANISM: Leishmania major

<400> SEQUENCE: 102

```
atggcgcagt gcgtgcgtcg gctggtgctg gcggcgacgc tcgccgctgc ggtggcgctg     60
ctgctgtgca cgagcagtgc gccggtggcg cgtgctgctg ggacgaacga cttcactgcg    120
gcgcagcgga cgaacacgct ggcggtgctg caggcgtttg ggcgtgcgat ccctgagctt    180
ggggagaagt gggcgggcaa cgacttctgc tcatgggagt ttatcgtgtg taatgttata    240
ggtgtgaacg tacggggaat cagtccgacg tatgccggca cgctgccgga gatacctgtg    300
aacgtcgact acaggcacgt cgtgatcaag cagctcgact tttccgaaat ggggccgggg    360
ctgagcggga cgctgccgga cagctggagc aagctggaag gactgacttc ccttacgttg    420
tcgggcaaca aagtgagcgg tacgctgccc gcctcatggc acttgatgaa gcggttgaca    480
tctttggtaa ttgcagactt tgacagtatc accggcagcc tgccgcctga gtggagctcg    540
atgcctaatt taaacgctgt ggagctgaag cgactaaaac tgagcggtac gttgcctgcg    600
gactggagct cttttgaaatc actgtcgaac gtcgttcttg aggacacgcc gatcacaggc    660
ttgttgcccc cggagtgggc ctcgctggag agaatacagc agctggttct acggaaattg    720
aagctgaccg gccctctccc tcctcagtgg agctcaatga agatattgca gtatcttact    780
ctggatggca ctcaggtctc cggcacgctg ccgccccagt ggagcgcgat ggcatcggtg    840
cgaattctta acctggaggg tactgaggtc tctggtacgc tgccgcctga gtggatatcg    900
atgagcaggc tgcaaactct gaatctgcgg cgcacgaaag tatccggcac tctgccgccc    960
gaatggagtt ctatgagcag cctggagtac tttcaccttt atcttactca ggtctccggc   1020
acgctgccgc cgagtggag tgggatgtcg aaggccgcat acttctggct ggaatactgc    1080
gacctgtccg gcagtctgcc gcccgagtgg tcgtcgatgc aaagctgcg cggtatctca    1140 ctgagcggca acaagttctg cggtgtgtgt ccggactcgt gggatcagaa ggctggtctt   1200
gttgtgggca tcgaggacaa gcacaagggc agcgactgct ggctgctaa ggactgcaca    1260 acgaccacca caaaccccc caccacgaca cgaccccca ctaagccgcc tgccacaacc    1320
accactgagg caccggctga acccacgacc accactgagg caccggctga acccacgacc    1380
accactgagg caccggctga acccacgacc accactgagg caccggctga acccacaacc    1440
accactgagg caccggctga acccacgacc actgctaccc caacaaacac gccgactcct    1500
gcaccagaga cggagtgcga ggtggatggg tgtgaggtgt gcgagggga ctccgctgcg    1560 aggtgcgcga ggtgccgtga ggactactc ctgacgacg agaggacgtg cctggtgtac    1620
tgcgatggcg gtgttgctgc tgtgtcgagc ggagtggcag cagcagctgt tgtgtgcgtg    1680
```

```
gctgtgctgt tcagcgtggg gctggcggcg tga                           1713

<210> SEQ ID NO 103
<211> LENGTH: 2421
<212> TYPE: DNA
<213> ORGANISM: Leishmania major
<220> FEATURE:
<221> NAME/KEY: misc_feature
<222> LOCATION: (1)...(2421)
<223> OTHER INFORMATION: n=A,T,C or G

<400> SEQUENCE: 103
tcgaattcgg cacgagggca cgcacaagac gaagagttcc aaacagcaac gagtatacgc    60
cactgtcgaa aaacagacac gcagtagaga aaggaggag gaggaggagg aggggggaga   120
gcaagaggcg ggtggggggtt ggagggacag cgctgcgtgc cgccgtctga catgtccgtt   180
ttgatgcgtc ttcgcagagt ggaggagga caccactggc gctgttggcg tgtangcaga   240
gcatcgctcg gctcgtgccg aattcggcac gagcggcacg agccctcgct ctgcctggta   300
agctcagcag acaccgacgc ccgagcaatc ccgcccacgg acctgctgcc gccccgctct   360
gctcgtgacc ctggctgcga atggcgcagt gcgtgcgtcg gctggtgctg gcggcgacgc   420
tcgccgctgc ggtggcgctg ctgctgtgca cgagcagtgc gccggtggcg cgtgctgctg   480
ggacgaacga cttcactgcg gcgcagcgga cgaacacgct ggcggtgctg caggcgtttg   540
ggcgtgcgat ccctgagctt ggggagaagt gggcgggcaa cgacttctgc tcatgggagt   600
ttatcgtgtg taatgttata ggtgtgaacg tacgggaat cagtccgacg tatgccggca   660
cgctgccgga gatacctgtg aacgtcgact acaggcacgt cgtgatcaag cagctcgact   720
tttccgaaat ggggccgggg ctgagcggga cgctgccgga cagctggagc aagctggaag   780
gactgacttc ccttacgttg tcgggcaaca agtgagcgg tacgctgccc gcctcatggc   840
acttgatgaa gcggttgaca tctttggtaa ttgcagactt tgacagtatc accggcagcc   900
tgccgcctga gtggagctcg atgcctaatt taaacgctgt ggagctgaag cgactaaaac   960
tgagcggtac gttgcctgcg gactggagct cttttgaaatc actgtcgaac gtcgttcttg  1020
aggacacgcc gatcacaggc ttgttgcccc cggagtgggc ctcgctggag agaatacagc  1080
agctggttct acggaaattg aagctgaccg gccctctccc tcctcagtgg agctcaatga  1140
agatattgca gtatcttact ctggatggca ctcaggtctc cggcacgctg ccgcccagt   1200
ggagcgcgat ggcatcggtg cgaattctta acctggaggg tactgaggtc tctggtacgc  1260
tgccgcctga gtggatatcg atgagcaggc tgcaaactct gaatctgcgg cgcacgaaag  1320
tatccggcac tctgccgccc gaatggagtt ctatgagcag cctggagtac tttcaccttt  1380
atcttactca ggtctccggc acgctgccgc ccgagtggag tgggatgtcg aaggccgcat  1440
acttctggct ggaatactgc gacctgtccg gcagtctgcc gcccgagtgg tcgtcgatgc  1500
caaagctgcg cggtatctca ctgagcggca acaagttctg cgggtgtgtg ccggactcgt  1560
gggatcagaa ggctggtctt gttgtgggca tcgaggacaa gcacaagggc agcgactgct  1620
tggctgctaa ggactgcaca acgaccacca caaaaccccc caccacgaca acgaccccca  1680
ctaagccgcc tgccacaacc accactgagg caccggctga accacgacc accactgagg  1740
caccggctga acccacgacc accactgagg caccggctga acccacgacc accactgagg  1800
caccggctga acccacaacc accactgagg caccggctga acccacgacc actgctaccc  1860
caacaaacac gccgactcct gcaccagaga cggagtgcga ggtggatggg tgtgaggtgt  1920
```

-continued

```
gcgaggggga ctccgctgcg aggtgcgcga ggtgccgtga ggactacttc ctgacggacg    1980
agaggacgtg cctggtgtac tgcgatggcg gtgttgctgc tgtgtcgagc ggagtggcag    2040
cagcagctgt tgtgtgcgtg gctgtgctgt tcagcgtggg gctggcggcg tgaggacgct    2100
gctgctgttg cgcgcaggca gcggcccccg ctgcgtggca cacgactgtc tgcgtgcttg    2160
cgtgcagcgc cgcccctgc gttggcgtgc gcgtgcgtgt ctctgtgagc atggctgcca    2220
gtggtgccct cgctcctgcc tctcggtgcc tctgcctctc tcggcgtgtt gatgctgtgg    2280
gctgtgtgtg gggctctcat gcggcgctgc tgctcccgcg tgtcgctcn tctgccccga    2340 ctctctctgc tgccctcctc tctcgcatgc gggagaggga ggggtggcac gtgcgcgcgc    2400
gcmgttgcgc ttgcgattgt g    2421
```

<210> SEQ ID NO 104
<211> LENGTH: 570
<212> TYPE: PRT
<213> ORGANISM: Leishmania major

<400> SEQUENCE: 104

```
Met Ala Gln Cys Val Arg Arg Leu Val Leu Ala Ala Thr Leu Ala Ala
                 5                  10                  15

Ala Val Ala Leu Leu Leu Cys Thr Ser Ser Ala Pro Val Ala Arg Ala
             20                  25                  30

Ala Gly Thr Asn Asp Phe Thr Ala Ala Gln Arg Thr Asn Thr Leu Ala
         35                  40                  45

Val Leu Gln Ala Phe Gly Arg Ala Ile Pro Glu Leu Gly Glu Lys Trp
     50                  55                  60

Ala Gly Asn Asp Phe Cys Ser Trp Glu Phe Ile Val Cys Asn Val Ile
 65                  70                  75                  80

Gly Val Asn Val Arg Gly Ile Ser Pro Thr Tyr Ala Gly Thr Leu Pro
                 85                  90                  95

Glu Ile Pro Val Asn Val Asp Tyr Arg His Val Ile Lys Gln Leu
            100                 105                 110

Asp Phe Ser Glu Met Gly Pro Gly Leu Ser Gly Thr Leu Pro Asp Ser
        115                 120                 125

Trp Ser Lys Leu Glu Gly Leu Thr Ser Leu Thr Leu Ser Gly Asn Lys
    130                 135                 140

Val Ser Gly Thr Leu Pro Ala Ser Trp His Leu Met Lys Arg Leu Thr
145                 150                 155                 160

Ser Leu Val Ile Ala Asp Phe Asp Ser Ile Thr Gly Ser Leu Pro Pro
                165                 170                 175

Glu Trp Ser Ser Met Pro Asn Leu Asn Ala Val Glu Leu Lys Arg Leu
            180                 185                 190

Lys Leu Ser Gly Thr Leu Pro Ala Asp Trp Ser Ser Leu Lys Ser Leu
        195                 200                 205

Ser Asn Val Val Leu Glu Asp Thr Pro Ile Thr Gly Leu Leu Pro Pro
    210                 215                 220

Glu Trp Ala Ser Leu Glu Arg Ile Gln Gln Leu Val Leu Arg Lys Leu
225                 230                 235                 240

Lys Leu Thr Gly Pro Leu Pro Pro Gln Trp Ser Ser Met Lys Ile Leu
                245                 250                 255

Gln Tyr Leu Thr Leu Asp Gly Thr Gln Val Ser Gly Thr Leu Pro Pro
            260                 265                 270

Gln Trp Ser Ala Met Ala Ser Val Arg Ile Leu Asn Leu Glu Gly Thr
        275                 280                 285
```

```
Glu Val Ser Gly Thr Leu Pro Pro Glu Trp Ile Ser Met Ser Arg Leu
    290                 295                 300
Gln Thr Leu Asn Leu Arg Arg Thr Lys Val Ser Gly Thr Leu Pro Pro
305                 310                 315                 320
Glu Trp Ser Ser Met Ser Ser Leu Glu Tyr Phe His Leu Tyr Leu Thr
                325                 330                 335
Gln Val Ser Gly Thr Leu Pro Pro Glu Trp Ser Gly Met Ser Lys Ala
                340                 345                 350
Ala Tyr Phe Trp Leu Glu Tyr Cys Asp Leu Ser Gly Ser Leu Pro Pro
            355                 360                 365
Glu Trp Ser Ser Met Pro Lys Leu Arg Gly Ile Ser Leu Ser Gly Asn
    370                 375                 380
Lys Phe Cys Gly Cys Val Pro Asp Ser Trp Asp Gln Lys Ala Gly Leu
385                 390                 395                 400
Val Val Gly Ile Glu Asp Lys His Lys Gly Ser Asp Cys Leu Ala Ala
                405                 410                 415
Lys Asp Cys Thr Thr Thr Thr Lys Pro Pro Thr Thr Thr Thr Thr Thr
                420                 425                 430
Pro Thr Lys Pro Pro Ala Thr Thr Thr Glu Ala Pro Ala Glu Pro
            435                 440                 445
Thr Thr Thr Thr Glu Ala Pro Ala Glu Pro Thr Thr Thr Glu Ala
    450                 455                 460
Pro Ala Glu Pro Thr Thr Thr Glu Ala Pro Ala Glu Pro Thr Thr
465                 470                 475                 480
Thr Thr Glu Ala Pro Ala Glu Pro Thr Thr Thr Ala Thr Pro Thr Asn
                485                 490                 495
Thr Pro Thr Pro Ala Pro Glu Thr Glu Cys Glu Val Asp Gly Cys Glu
                500                 505                 510
Val Cys Glu Gly Asp Ser Ala Ala Arg Cys Ala Arg Cys Arg Glu Asp
            515                 520                 525
Tyr Phe Leu Thr Asp Glu Arg Thr Cys Leu Val Tyr Cys Asp Gly Gly
            530                 535                 540
Val Ala Ala Val Ser Ser Gly Val Ala Ala Ala Val Val Cys Val
545                 550                 555                 560
Ala Val Leu Phe Ser Val Gly Leu Ala Ala
                565                 570
```

<210> SEQ ID NO 105
<211> LENGTH: 1688
<212> TYPE: DNA
<213> ORGANISM: Leishmania major

<400> SEQUENCE: 105

| | | | | | |
|---|---|---|---|---|---|
| taacgctata | taagtatcag | tttctgtact | ttattgctca | tcactgccgt | ttgactgccg | 60 |
| cgggcattgg | cgctaccact | ttcctcactc | tttatcccctt | cagcattgtt | tcgtacacac | 120 |
| gcacgcgcac | gtgaaagagc | cgcacgccga | cagagcagcc | gttccggact | ctccgataac | 180 |
| tgaacgccac | ccacccaaaa | aaaatgtcaa | agaacgctga | ccaggaggag | tgggaggatt | 240 |
| acggcgacga | ggaggtgcag | gatgaagaag | aggaggacac | caccatcaac | aactccgacg | 300 |
| tggtggtgcg | ctacaagaag | gccgcaacgt | ggtgcaatga | aacgttgcgc | gtgcttatcg | 360 |
| atgccacaaa | acctggcgcc | aaggtgtgcg | acctgtgccg | cctcggtgat | gacaccatca | 420 |
| ccgccaaggt | caagacaatg | ttcaaaggca | cggaaaaagg | catcgctttc | ccgacctgca | 480 |
| tctcggtcaa | caactgcgta | tgccacaaca | gccctggcgt | gtcggacgag | acgacgcagc | 540 |

```
aagagatcgc gatgggtgac gtcgtgcact acgacctggg catccacgtg gacggctact    600
gcgccgtcgt cgcgcacacc attcaggtga cagaggacaa tgagcttggc aaggacgaga    660
aggcggcgcg cgtcattaca gcggcgtaca acatcctgaa cacggcgctg cgccagatgc    720
gtcccggtac gaccatctac caggtgacag acgtagttga aaggctgcg gagcactaca    780 aggtgactcc ggtagacggc gtcctctcgc atatgatgaa gcgctacatc atagacggat    840
accgctgtat cccgcagcgc agggtcgcgg agcacatggt gcacgactac gatctcgaga    900
aagcgcaggt gtggacgcta gacattgtca tgacctccgg caagggcaag ctgaaggagc    960
gcgatgcgcg gccgtgcgtg ttcaaggtgg ctctggactc caactactct gtgaaaatgg   1020
aaagcgcgaa ggaggttcag aaggaaatcg actccaagta tgccaccttc ccctttgcca   1080
tccgcaacct ggaggccaag aaggcccgcc tcggtctcaa cgagatggcg aagcacggtg   1140
ctgtcatccc gtaccctatt ctcttcgaaa aggaaggcga ggtcgtcgcc catttcaaga   1200
ttacggtgct catcagcaac aagaagattg agccgattac cggcctgaag ccgcagaagg   1260
ccccggcgct cgagccatac acggacgaga tgctgcttgc gacgaacaag ctctcgctgt   1320
cgctagagaa gaaggcggcg aagtagacgg ccgtggcatc cgtgacgctg tactgcgagc   1380
tttcgtaggc gtacgcctct tgtgaggcgt acacgtgtgc tgtttgcgga cgaggaggca   1440
cccattctgt tccccttctt cgctaatctc cgcgtttcct ctgacgctgg cttctctgcc   1500
ggagtgtggt gaggcgcgtg ggggagaaac ggcccactcg catgcctgtg catacgcgag   1560
cacggtaggg agcgcggtgt gtgtgtgtgt gggggggcgt gttacgagta caaaagaggc   1620
tcgatctctg cgactctttt ctttctgtaa acagggaaca taagtaacca aaaaaaaaaa   1680
aaaaaaaa                                                           1688
```

```
210> SEQ ID NO 106
<211> LENGTH: 380
<212> TYPE: PRT
<213> ORGANISM: Leishmania major

<400> SEQUENCE: 106
```

```
Met Ser Lys Asn Ala Asp Gln Glu Glu Trp Glu Asp Tyr Gly Asp Glu
 1               5                  10                  15

Glu Val Gln Asp Glu Glu Glu Asp Thr Thr Ile Asn Asn Ser Asp
             20                  25                  30

Val Val Val Arg Tyr Lys Ala Ala Thr Trp Cys Asn Glu Thr Leu
         35                  40                  45

Arg Val Leu Ile Asp Ala Thr Lys Pro Gly Ala Lys Val Cys Asp Leu
 50                  55                  60

Cys Arg Leu Gly Asp Asp Thr Ile Thr Ala Lys Val Lys Thr Met Phe
65                  70                  75                  80

Lys Gly Thr Glu Lys Gly Ile Ala Phe Pro Thr Cys Ile Ser Val Asn
                 85                  90                  95

Asn Cys Val Cys His Asn Ser Pro Gly Val Ser Asp Glu Thr Thr Gln
                100                 105                 110

Gln Glu Ile Ala Met Gly Asp Val Val His Tyr Asp Leu Gly Ile His
            115                 120                 125

Val Asp Gly Tyr Cys Ala Val Val Ala His Thr Ile Gln Val Thr Glu
        130                 135                 140

Asp Asn Glu Leu Gly Lys Asp Glu Lys Ala Ala Arg Val Ile Thr Ala
145                 150                 155                 160
```

```
Ala Tyr Asn Ile Leu Asn Thr Ala Leu Arg Gln Met Arg Pro Gly Thr
            165                 170                 175

Thr Ile Tyr Gln Val Thr Asp Val Val Glu Lys Ala Ala Glu His Tyr
        180                 185                 190

Lys Val Thr Pro Val Asp Gly Val Leu Ser His Met Met Lys Arg Tyr
    195                 200                 205

Ile Ile Asp Gly Tyr Arg Cys Ile Pro Gln Arg Arg Val Ala Glu His
    210                 215                 220

Met Val His Asp Tyr Asp Leu Glu Lys Ala Gln Val Trp Thr Leu Asp
225                 230                 235                 240

Ile Val Met Thr Ser Gly Lys Gly Lys Leu Lys Glu Arg Asp Ala Arg
            245                 250                 255

Pro Cys Val Phe Lys Val Ala Leu Asp Ser Asn Tyr Ser Val Lys Met
            260                 265                 270

Glu Ser Ala Lys Glu Val Gln Lys Glu Ile Asp Ser Lys Tyr Ala Thr
        275                 280                 285

Phe Pro Phe Ala Ile Arg Asn Leu Glu Ala Lys Lys Ala Arg Leu Gly
    290                 295                 300

Leu Asn Glu Met Ala Lys His Gly Ala Val Ile Pro Tyr Pro Ile Leu
305                 310                 315                 320

Phe Glu Lys Glu Gly Val Val Ala His Phe Lys Ile Thr Val Leu
            325                 330                 335

Ile Ser Asn Lys Lys Ile Glu Pro Ile Thr Gly Leu Lys Pro Gln Lys
            340                 345                 350

Ala Pro Ala Leu Glu Pro Tyr Thr Asp Glu Met Leu Leu Ala Thr Asn
        355                 360                 365

Lys Leu Ser Leu Ser Leu Glu Lys Lys Ala Ala Lys
    370                 375                 380

<210> SEQ ID NO 107
<211> LENGTH: 1565
<212> TYPE: DNA
<213> ORGANISM: Leishmania major

<400> SEQUENCE: 107
taacgctata taagtatcag tttctgtact ttattgctct tcgctctcgt tcttcgaaca      60
aacaccttta aaccgccttc caacccctct ttcttctttt tcagccatgc gtgaggctat     120
ctgcatccac atcggccagg ccggctgcca ggtcggtaac gcgtgctggg agctgttctg     180
ccttgagcac ggcatccagc ctgatggctc catgccctct gacaagtgca tcggtgttga     240
ggatgacgcg ttcaacacgt tcttctcgga gaccggtgct ggcaagcacg ttccgcgctg     300
catcttcctg gacctcgagc ctacggtcgt ggatgaggtg cgcaccggca cgtaccgcca     360
gctgttcaac cccgagcagc tggtgtctgg caaggaggat gcggcgaaca actacgctcg     420
tggccactac acgatcggca aggagatcgt cgaccttgcg ctggaccgca ttcgcaagct     480
ggcggacaac tgcactggtc tccagggctt tatggtgttc cacgctgtgg gtggcggcac     540
cggctctggc ctcggtgcgc tgctgctgga gcgcctgtct gtggactacg caagaagtc     600
caagctcggc tacaccgtgt acccgagccc gcaggtgtcg actgccgtcg tggagccgta     660
caactgcgtg ctgtcgacgc actcgctgct cgagcacacc gatgttgcga cgatgctcga     720
caatgaggcc atctacgacc tcactcgtcg ttctctcgac attgagcgcc cgtcgtacac     780
gaacgtgaac cgcctgatcg gccaggtggt gtcgtctctg acggcgtcgc tgcgcttcga     840
tggtgcgctg aacgtggacc tgacggagtt ccagacgaac cttgtgccgt acccgcgcat     900
```

```
ccacttcgtg ctgacgagct acgctccggt ggtgtctgcc gagaaggcgt accacgagca      960
gctgtccgtc gcggacatca cgaactcggt gtttgagcct gctggcatgc tgacgaagtg     1020
cgatcctcgc cacggcaagt acatgtcgtg ctgcctcatg taccgcggtg atgtcgtgcc     1080
gaaggatgtc aacgccgcga ttgcgacgat caagacgaag cgcacaattc agttcgtgga     1140
ctggtgcccg accggcttca agtgcggcat caactaccag ccgccgaccg ttgtgcccgg     1200
cggtgacctc gcgaaggtgc agcgcgccgt gtgcatgatt gccaactcga ccgcgatcgc     1260
tgaggtgttt gcccgcatcg accacaagtt cgacctgatg tacagcaagc gcgcgtttgt     1320
gcactggtac gtgggtgagg gcatggagga gggcgagttc tccgaggcgc gcgaggatct     1380
cgctgcgctg gagaaggact acgaggaggt tggcgccgag tccgccgacg acatgggcga     1440
ggaggacgtc gaggagtact aaggtagact cgtgccgcgc gctgatgatg taggtgcacg     1500
cgtgcgtgtg ctgcagcgga gccgccgcca ccgcgactgt gtgtgtgtgc gcgcgtgacg     1560
accgg                                                                 1565
```

<210> SEQ ID NO 108
<211> LENGTH: 451
<212> TYPE: PRT
<213> ORGANISM: Leishmania major

<400> SEQUENCE: 108

```
Met Arg Glu Ala Ile Cys Ile His Ile Gly Gln Ala Gly Cys Gln Val
  1               5                  10                  15

Gly Asn Ala Cys Trp Glu Leu Phe Cys Leu Glu His Gly Ile Gln Pro
             20                  25                  30

Asp Gly Ser Met Pro Ser Asp Lys Cys Ile Gly Val Glu Asp Asp Ala
         35                  40                  45

Phe Asn Thr Phe Phe Ser Glu Thr Gly Ala Gly Lys His Val Pro Arg
     50                  55                  60

Cys Ile Phe Leu Asp Leu Glu Pro Thr Val Val Asp Glu Val Arg Thr
 65                  70                  75                  80

Gly Thr Tyr Arg Gln Leu Phe Asn Pro Glu Gln Leu Val Ser Gly Lys
                 85                  90                  95

Glu Asp Ala Ala Asn Asn Tyr Ala Arg Gly His Tyr Thr Ile Gly Lys
            100                 105                 110

Glu Ile Val Asp Leu Ala Leu Asp Arg Ile Arg Lys Leu Ala Asp Asn
        115                 120                 125

Cys Thr Gly Leu Gln Gly Phe Met Val Phe His Ala Val Gly Gly Gly
    130                 135                 140

Thr Gly Ser Gly Leu Gly Ala Leu Leu Leu Glu Arg Leu Ser Val Asp
145                 150                 155                 160

Tyr Gly Lys Lys Ser Lys Leu Gly Tyr Thr Val Tyr Pro Ser Pro Gln
                165                 170                 175

Val Ser Thr Ala Val Val Glu Pro Tyr Asn Cys Val Leu Ser Thr His
            180                 185                 190

Ser Leu Leu Glu His Thr Asp Val Ala Thr Met Leu Asp Asn Glu Ala
        195                 200                 205

Ile Tyr Asp Leu Thr Arg Arg Ser Leu Asp Ile Glu Arg Pro Ser Tyr
    210                 215                 220

Thr Asn Val Asn Arg Leu Ile Gly Gln Val Val Ser Ser Leu Thr Ala
225                 230                 235                 240

Ser Leu Arg Phe Asp Gly Ala Leu Asn Val Asp Leu Thr Glu Phe Gln
```

```
                 245                 250                 255
Thr Asn Leu Val Pro Tyr Pro Arg Ile His Phe Val Leu Thr Ser Tyr
                260                 265                 270

Ala Pro Val Val Ser Ala Glu Lys Ala Tyr His Glu Gln Leu Ser Val
                275                 280                 285

Ala Asp Ile Thr Asn Ser Val Phe Glu Pro Ala Gly Met Leu Thr Lys
                290                 295                 300

Cys Asp Pro Arg His Gly Lys Tyr Met Ser Cys Cys Leu Met Tyr Arg
305                 310                 315                 320

Gly Asp Val Val Pro Lys Asp Val Asn Ala Ala Ile Ala Thr Ile Lys
                325                 330                 335

Thr Lys Arg Thr Ile Gln Phe Val Asp Trp Cys Pro Thr Gly Phe Lys
                340                 345                 350

Cys Gly Ile Asn Tyr Gln Pro Pro Thr Val Val Pro Gly Gly Asp Leu
                355                 360                 365

Ala Lys Val Gln Arg Ala Val Cys Met Ile Ala Asn Ser Thr Ala Ile
                370                 375                 380

Ala Glu Val Phe Ala Arg Ile Asp His Lys Phe Asp Leu Met Tyr Ser
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
                420                 425                 430

Glu Glu Val Gly Ala Glu Ser Ala Asp Asp Met Gly Glu Glu Asp Val
                435                 440                 445

Glu Glu Tyr
    450

<210> SEQ ID NO 109
<211> LENGTH: 1908
<212> TYPE: DNA
<213> ORGANISM: Leishmania major
<220> FEATURE:
<221> NAME/KEY: misc_feature
<222> LOCATION: (1)...(1908)
<223> OTHER INFORMATION: n = A,T,C or G

<400> SEQUENCE: 109
taacgctata taagtatcag tttctgtact ttattgtaag cgcaatcgag tttcaacagc      60
taacaaaatg gtgaacttta ccgtcgatca ggtccgcgag ctgatggact atccggacca    120
gatccggaac atgtccgtga ttgctcacgt cgaccacggc aagtcgacgc tgtccgactc    180
tctcgttggt gctgccggca tcatcaagat ggaggaggct ggcgataagc ggatcatgga    240
tacacgcgcg gatgagatcg cgcgtggtat cacgatcaag tccaccgcca tctccatgca    300
ctaccacgtg ccgaaggaga tgatcggcga tctggatgac gacaagcgcg acttcctgat    360
caacctgatc gactccccg  gacacgtcga cttcagctcc gaggtgactg ccgctcttcg    420
tgtgacggac ggcgcgctgg tcgtggtgga ctgcgtggag ggcgtgtgcg tgcagacgga    480
gacggtgctg cgccaggcgc tgacggagcg catccgccct gttgtgttca tcaacaaggt    540
ggaccgcgcc atccttgagc tccaactgga ccccgaggag gcgtaccagg gcttcgtgaa    600
gacgctgcag aacgtgaacg tggtggttgc cacgtacaat gaccccagca tgggcgacgt    660
gcaggtgtcc cccgagaagg gcactgtggc gatcggctct ggcctgcagg cgtgggcgtt    720
ctcgctgacc cgctttgcga acatgtatgc ggcgaagttc ggcgtggacg agctgaagat    780
```

-continued

```
gcgcgagcgc ctgtggggcg acaacttctt tgacgcgaag aacaagaagt ggatcaagca    840
ggagacgaac gccgatggcg agcgcgtgcg ccgcgcgttc tgccagttct gcctagaccc    900
catctaccag atcttcgacg ctgtgatgaa cgagaagaag acaaggtgg acaagatgct     960 caagtcgctg cacgtgacgc tgacggctga ggagcgcgag caggtgccga agaagcttct   1020
gaagacggtg atgatgaagt tcctgccggc tgctgagacg ctgctacaga tgatcgtggc   1080
gcacctgccg tcgcccaaga aggcgcaggc gtaccgtgcg gagatgctgt actctggcga   1140
ggcgtcgccg gaggacaagt acttcatggg tatcaagaac tgcgaccccg ctgcgccgct   1200
catgctgtac atcagcaaga tggtgccgac ggccgaccgc ggccgcttct cgcctttgg    1260 ccgcatcttc tccggtaagg tgcgcagcgg ccagaaggtg cgcatcatgg gtaacaacta   1320
cgtctacggc aagaagcagg acctgtacga ggacaagcct gtgcagcgct ccgtgctgat   1380
gatgggccgc taccaggagg ccgtggagga catgccgtgc ggtaacgtgg tgggccttgt   1440
gggcgtggac aagtacatcg tgaagtccgc gacgatcacg gacgatggcg agagcccgca   1500
cccgctgcgc gacatgaagt actctgtgtc gcccgtcgtg cgtgtggccg tggaggcgaa   1560
gaacccgtcc gacctgccga agcttgtgga gggcctgaag cgccttgcca agtccgaccc   1620
gctggtggtg tgcagcattg aggagtctgg cgagcacatt gttgccggcg ctggcgagct   1680
tcaccttgag atttgcctga aggatctcca ggaggacttc atgaacggcg cgccgctnaa   1740
gatctccgag ccggtggtgt cgttccgcga cggtgacg gatgtgtcgt cgcagcagtg    1800
cctgtcgaag tctgcgaaca agcacaaccg tctcttctgc cgcggtgcgc cgctnacaga   1860
gganctggcg ctggcgatng angaaggcac cgctggtccc gangcgga              1908
```

<210> SEQ ID NO 110
<211> LENGTH: 845
<212> TYPE: PRT
<213> ORGANISM: Leishmania major
<220> FEATURE:
<221> NAME/KEY: VARIANT
<222> LOCATION: (1)...(845)
<223> OTHER INFORMATION: Xaa = Any Amino Acid

<400> SEQUENCE: 110

```
Met Val Asn Phe Thr Val Asp Gln Val Arg Glu Leu Met Asp Tyr Pro
 1               5                  10                  15

Asp Gln Ile Arg Asn Met Ser Val Ile Ala His Val Asp His Gly Lys
            20                  25                  30

Ser Thr Leu Ser Asp Ser Leu Val Gly Ala Ala Gly Ile Ile Lys Met
        35                  40                  45

Glu Glu Ala Gly Asp Lys Arg Ile Met Asp Thr Arg Ala Asp Glu Ile
    50                  55                  60

Ala Arg Gly Ile Thr Ile Lys Ser Thr Ala Ile Ser Met His Tyr His
65                  70                  75                  80

Val Pro Lys Glu Met Ile Gly Asp Leu Asp Asp Lys Arg Asp Phe
                85                  90                  95

Leu Ile Asn Leu Ile Asp Ser Pro Gly His Val Asp Phe Ser Ser Glu
            100                 105                 110

Val Thr Ala Ala Leu Arg Val Thr Asp Gly Ala Leu Val Val Asp
        115                 120                 125

Cys Val Glu Gly Val Cys Val Gln Thr Glu Thr Val Leu Arg Gln Ala
    130                 135                 140

Leu Thr Glu Arg Ile Arg Pro Val Val Phe Ile Asn Lys Val Asp Arg
145                 150                 155                 160
```

```
Ala Ile Leu Glu Leu Gln Leu Asp Pro Glu Ala Tyr Gln Gly Phe
            165                 170                 175

Val Lys Thr Leu Gln Asn Val Asn Val Val Ala Thr Tyr Asn Asp
            180                 185                 190

Pro Ser Met Gly Asp Val Gln Val Ser Pro Glu Lys Gly Thr Val Ala
            195                 200                 205

Ile Gly Ser Gly Leu Gln Ala Trp Ala Phe Ser Leu Thr Arg Phe Ala
            210                 215                 220

Asn Met Tyr Ala Ala Lys Phe Gly Val Asp Glu Leu Lys Met Arg Glu
225                 230                 235                 240

Arg Leu Trp Gly Asp Asn Phe Phe Asp Ala Lys Asn Lys Lys Trp Ile
            245                 250                 255

Lys Gln Glu Thr Asn Ala Asp Gly Glu Arg Val Arg Arg Ala Phe Cys
            260                 265                 270

Gln Phe Cys Leu Asp Pro Ile Tyr Gln Ile Phe Asp Ala Val Met Asn
            275                 280                 285

Glu Lys Lys Asp Lys Val Asp Lys Met Leu Lys Ser Leu His Val Thr
290                 295                 300

Leu Thr Ala Glu Glu Arg Glu Gln Val Pro Xaa Lys Leu Leu Lys Thr
305                 310                 315                 320

Val Met Met Xaa Phe Leu Pro Ala Ala Glu Thr Leu Leu Gln Met Ile
            325                 330                 335

Val Ala His Leu Pro Ser Pro Lys Lys Ala Gln Ala Tyr Arg Ala Glu
            340                 345                 350

Met Leu Tyr Ser Gly Glu Ala Ser Pro Glu Asp Lys Tyr Phe Met Gly
            355                 360                 365

Ile Lys Asn Cys Asp Pro Ala Ala Pro Leu Met Leu Tyr Ile Ser Lys
            370                 375                 380

Met Val Pro Thr Ala Asp Arg Gly Arg Phe Phe Ala Phe Gly Arg Ile
385                 390                 395                 400

Phe Ser Gly Lys Val Arg Ser Gly Gln Lys Val Arg Ile Met Gly Asn
            405                 410                 415

Asn Tyr Val Tyr Gly Lys Lys Gln Asp Leu Tyr Glu Asp Lys Pro Val
            420                 425                 430

Gln Arg Ser Val Leu Met Met Gly Arg Tyr Gln Glu Ala Val Glu Asp
            435                 440                 445

Met Pro Cys Gly Asn Val Val Gly Leu Val Gly Val Asp Lys Tyr Ile
            450                 455                 460

Val Lys Ser Ala Thr Ile Thr Asp Asp Gly Glu Ser Pro His Pro Leu
465                 470                 475                 480

Arg Asp Met Lys Tyr Ser Val Ser Pro Val Val Arg Val Ala Val Glu
            485                 490                 495

Ala Lys Asn Pro Ser Asp Leu Pro Lys Leu Val Glu Gly Leu Lys Arg
            500                 505                 510

Leu Ala Lys Ser Asp Pro Leu Val Val Cys Ser Ile Glu Glu Ser Gly
            515                 520                 525

Glu His Ile Val Ala Gly Ala Gly Glu Leu His Leu Glu Ile Cys Leu
            530                 535                 540

Lys Asp Leu Gln Glu Asp Phe Met Asn Gly Ala Pro Leu Lys Ile Ser
545                 550                 555                 560

Glu Pro Val Val Ser Phe Arg Glu Thr Val Thr Asp Val Ser Ser Gln
            565                 570                 575
```

```
Gln Cys Leu Ser Lys Ser Ala Asn Lys His Asn Arg Leu Phe Cys Arg
            580                 585                 590

Gly Ala Pro Leu Thr Glu Glu Leu Ala Leu Ala Met Glu Glu Gly Thr
        595                 600                 605

Ala Gly Pro Glu Ala Asp Pro Lys Val Arg Ala Arg Phe Leu Ala Asp
    610                 615                 620

Asn Tyr Glu Trp Asp Val Gln Glu Ala Arg Lys Ile Trp Cys Tyr Gly
625                 630                 635                 640

Pro Asp Asn Arg Gly Pro Asn Val Val Asp Val Thr Lys Gly Val
                645                 650                 655

Gln Asn Met Ala Glu Met Lys Asp Ser Phe Val Ala Ala Trp Gln Trp
            660                 665                 670

Ala Thr Arg Glu Gly Val Leu Cys Asp Glu Asn Met Arg Gly Val Arg
        675                 680                 685

Val Asn Val Glu Asp Val Thr Met His Ala Asp Ala Ile His Arg Gly
    690                 695                 700

Gly Val Gln Ile Ile Pro Thr Ala Arg Arg Val Phe Tyr Ala Cys Cys
705                 710                 715                 720

Leu Thr Ala Ser Pro Arg Leu Met Glu Pro Met Phe Val Val Asp Ile
                725                 730                 735

Gln Thr Val Glu His Ala Met Gly Gly Ile Tyr Gly Val Leu Thr Arg
            740                 745                 750

Arg Arg Gly Val Ile Ile Gly Glu Glu Asn Arg Pro Gly Thr Pro Ile
        755                 760                 765

Tyr Asn Val Arg Ala Tyr Leu Pro Val Ala Glu Ser Phe Gly Phe Thr
    770                 775                 780

Ala Asp Leu Arg Ala Gly Thr Gly Gln Ala Phe Pro Gln Cys Val
785                 790                 795                 800

Phe Asp His Trp Gln Glu Tyr Pro Gly Asp Pro Leu Glu Pro Lys Ser
                805                 810                 815

Leu Ala Asn Thr Thr Thr Leu Gly Ile Arg Thr Arg Lys Gly Leu Lys
            820                 825                 830

Pro Asp Ile Pro Gly Leu Asp Gln Phe Met Asp Lys Leu
        835                 840                 845

<210> SEQ ID NO 111
<211> LENGTH: 997
<212> TYPE: DNA
<213> ORGANISM: Leishmania major

<400> SEQUENCE: 111
ggatccgccg ccaccatggt gaacgtgtgc gttgttggtg ctgccggcgg cattggccag    60
tcgctgtcgc tgctgttggt gcgccagctg ccgtacggga gcacgttgtc gctgttcgac   120
gttgtgggcg ctgcaggcgt cgcagcagac ctgtcgcatg tggacaacgc cggtgtgcag   180
gtgaagtttg cggagggcaa gatcggccat aagcgcgacc ctgcgctggc agagcttgcg   240
aagggcgtgg atgtgtttgt aatggtggct ggcgttccac gcaagccggg catgacgcgc   300
gacgaccttt tcaaaatcaa cgccggaatc atcctggacc ttgtgctgac gtgcgcgtcg   360
tcgagtccaa aggcggtgtt ctgcattgtg acgaaccctg tgaacagcac ggtcgcgatc   420
gcggcagagg cgctgaagag ccttggcgta tacgaccgaa accggctgct ggcgtgtcg   480 ctgctggacg ggctgcgcgc gacgtgcttc atcaacgagg cgcgcaagcc cttagtcgtg   540
tcgcaggtac cagttgttgg cgggcacagc gacacaacga ttgtgccgtt gttctaccag   600
```

-continued

```
ctaccggggc cgttgccgga gcaggcgacg ctggacaaga tcgtgaagcg cgtgcaggtc    660
gcaggcacag aagtggtgaa ggcgaaggcc gggcgcgggt ctgcgacgct gtcgatggcg    720
gaggctggcg cgcggttcgc gttgaaggtt gtggagggtc tgaccggcac gggtaacccg    780
ctggtgtacg catatgtaga cacagacggg cagcacgaga cgacgttcct cgcgatccct    840
gtggtgcttg gcatgaatgg aatcgagaag cgcctgccga ttggtccgct gcactcgacg    900
gaggaaacgc tgctgaaggc ggcactgccg gtgatcaaga gaatatcgt gaagggcagc    960 gagttcgcgc gctcacacct gtagcacctc agaattc                            997
```

<210> SEQ ID NO 112
<211> LENGTH: 322
<212> TYPE: PRT
<213> ORGANISM: Leishmania major

<400> SEQUENCE: 112

```
Met Val Asn Val Cys Val Val Gly Ala Ala Gly Gly Ile Gly Gln Ser
  1               5                  10                  15

Leu Ser Leu Leu Leu Val Arg Gln Leu Pro Tyr Gly Ser Thr Leu Ser
                 20                  25                  30

Leu Phe Asp Val Val Gly Ala Ala Gly Val Ala Ala Asp Leu Ser His
             35                  40                  45

Val Asp Asn Ala Gly Val Gln Val Lys Phe Ala Glu Gly Lys Ile Gly
         50                  55                  60

His Lys Arg Asp Pro Ala Leu Ala Glu Leu Ala Lys Gly Val Asp Val
 65                  70                  75                  80

Phe Val Met Val Ala Gly Val Pro Arg Lys Pro Gly Met Thr Arg Asp
                 85                  90                  95

Asp Leu Phe Lys Ile Asn Ala Gly Ile Ile Leu Asp Leu Val Leu Thr
            100                 105                 110

Cys Ala Ser Ser Pro Lys Ala Val Phe Cys Ile Val Thr Asn Pro
            115                 120                 125

Val Asn Ser Thr Val Ala Ile Ala Ala Glu Ala Leu Lys Ser Leu Gly
        130                 135                 140

Val Tyr Asp Arg Asn Arg Leu Leu Gly Val Ser Leu Leu Asp Gly Leu
145                 150                 155                 160

Arg Ala Thr Cys Phe Ile Asn Glu Ala Arg Lys Pro Leu Val Val Ser
                165                 170                 175

Gln Val Pro Val Val Gly Gly His Ser Asp Thr Thr Ile Val Pro Leu
            180                 185                 190

Phe Tyr Gln Leu Pro Gly Pro Leu Pro Glu Gln Ala Thr Leu Asp Lys
        195                 200                 205

Ile Val Lys Arg Val Gln Val Ala Gly Thr Glu Val Val Lys Ala Lys
    210                 215                 220

Ala Gly Arg Gly Ser Ala Thr Leu Ser Met Ala Glu Ala Gly Ala Arg
225                 230                 235                 240

Phe Ala Leu Lys Val Val Glu Gly Leu Thr Gly Thr Gly Asn Pro Leu
                245                 250                 255

Val Tyr Ala Tyr Val Asp Thr Asp Gly Gln His Glu Thr Thr Phe Leu
            260                 265                 270

Ala Ile Pro Val Val Leu Gly Met Asn Gly Ile Glu Lys Arg Leu Pro
        275                 280                 285

Ile Gly Pro Leu His Ser Thr Glu Glu Thr Leu Leu Lys Ala Ala Leu
    290                 295                 300
```

Pro Val Ile Lys Lys Asn Ile Val Lys Gly Ser Glu Phe Ala Arg Ser
305                 310                 315                 320
His Leu

<210> SEQ ID NO 113
<211> LENGTH: 1617
<212> TYPE: DNA
<213> ORGANISM: Leishmania major and chagasi

<400> SEQUENCE: 113

| | | | | | |
|---|---|---|---|---|---|
| cggaatacgt | acctcctccc | ccttcttggt | agaagaacaa | caacaacgtt | caagacgacg | 60 |
| ccgcgccttc | ttgtaccgca | tttgcttctg | agcacgttca | atccgtgcct | tgcaaacatg | 120 |
| gaggcgtaca | agaagctgga | aacgatcttt | acgaaggtct | accgcctgga | ccacttcctc | 180 |
| ggtctgggca | actgggacat | gaacacaaac | atgccccca | agggcgagga | atcacgcggt | 240 |
| gaggcgatgg | cgatgctctc | ggagctccgc | tttggcttca | tcacggcacc | ggaggtgaaa | 300 |
| agcctgattg | agagtgccac | caagggcagc | gaggagctga | atgcggtgca | gcgcgctaac | 360 |
| ttgcgggaga | tgaggcgtgc | gtggaagagc | gccaccgcct | gccggctga | gtttgtgggc | 420 |
| cgcaagatgc | gcctcacgac | acacgcgcac | agcgtgtggc | gcgacagccg | caaagcaaat | 480 |
| gacttcgcca | agttcctacc | ggtgctcagg | acctggtgg | cgctcgcccg | tgaggagggc | 540 |
| tcatacctcg | ccgccggcac | ctccctctcc | ccgtatgagg | cgctcatgaa | cgagtacgag | 600 |
| ccaggaatca | cgacacaaaa | gctggatgag | gtgtacgcaa | atgtaaagtc | gtggctgccg | 660 |
| cagctgctaa | aggacattgt | gcagaagcag | tccggcgagt | cggtgattgc | gttctcgcat | 720 |
| aagttcccgc | aggacaagca | ggaagcactg | tgcaaggaat | tcatgaagat | ctggcacttc | 780 |
| gacaccgatg | ccggtcgcct | cgacgtcagc | ccccacccct | tcacgggaat | gacgaaggag | 840 |
| gactgccgac | tcacaacaaa | ctacatcgaa | gacacgtttg | ttcagagctt | gtatggcgtc | 900 |
| atccacgaga | gtgggcatgg | caagtacgag | cagaactgtg | gcccacgcga | gcacatcacg | 960 |
| cagccggtgt | gcaacgcccg | ctctcttggc | ctgcatgaga | gccagagcct | ctttgcggag | 1020 |
| tttcagatcg | gccacgcgac | gcccttcatc | gactacctca | caactcgcct | tcctgagttc | 1080 |
| ttcgaggcgc | agccagcgtt | ctcgcaggac | aacatgcgca | agtcgctgca | gcaggtgaag | 1140 |
| ccgggctaca | ttcgcgtcga | tgccgatgag | gtgtgctacc | ctctgcacgt | gatcctgcgc | 1200 |
| tacgagatcg | agcgcgactt | gatggagggc | aaaatggagg | tggaagacgt | gccgcgcgcg | 1260 |
| tggaacgcaa | agatgcagga | gtacttgggt | ctctcaacgg | agggccgtga | cgacgttggg | 1320 |
| tgcctgcagg | acgtgcattg | gtccatgggt | gcgctcggct | actttccgac | gtactcgctc | 1380 |
| ggcgccatgt | atgcggcgca | gatcatggcg | agcatccgaa | aggagctggg | agacgacaag | 1440 |
| gtggatgagt | gcctgcgcac | cggtgagctc | ggccccctcc | tggaaaagca | gcaggagaag | 1500 |
| atctgggatc | atgggtgcct | gtacgagacg | gacgacctca | tgacgcgtgc | gacgggcgag | 1560 |
| acgctgaacc | ccgagtacct | gcgccgccac | ctggaggcgc | gctacctaaa | cgcctga | 1617 |

<210> SEQ ID NO 114
<211> LENGTH: 582
<212> TYPE: DNA
<213> ORGANISM: Leishmania major and chagasi

<400> SEQUENCE: 114

| | | | | | |
|---|---|---|---|---|---|
| atgcatcacc | atcaccatca | cgatccccg | ggctgcagga | attcggcacg | agagctgcag | 60 |
| cagcgcctag | acaccgccac | gcagcagcgc | gccgagctgg | aggcacgggt | ggcacggctg | 120 |
| gccgcggacc | gcgacgaggc | gcgccagcag | ctggccgcga | acgccgagga | gctgcagcag | 180 |

```
cgcctagaca ccgccacgca gcagcgcgcc gagctggagg cacgggtggc acggctggcc      240
gcggacggcg acgaggcccg ccagcagctg gccgcgaacg ccgaggagct gcagcagcgc      300
ctagacaccg ccacgcagca gcgcgccgag ctggaggcac aggtggcacg gctggccgcg      360
aacgccgagg agctgcagca gcgcctagac accgccacgc agcagcgcgc cgagctggag      420
gcacgggtgg cacggctggc cgcggaccgc gacgaggcgc gccagcagct ggccgcgaac      480
gccgaggagc tgcagcagcg cctagacacc gccacgcagc agcgcgccga gctggaggca      540
caggtggcac ggctggccgc gaacgccgct cgtgccgaat aa                        582
```

<210> SEQ ID NO 115
<211> LENGTH: 7065
<212> TYPE: DNA
<213> ORGANISM: Leishmania major and chagasi

<400> SEQUENCE: 115

```
atgtccactc ctgtcagtgg agtagtcccg caggaccgct ggcagcctca gcagagggtg       60
aaggtctgtc agtaccagga ctgcggcgcc cccttcggct tcttctccac caaggtcaac      120
tgccaccgct gcggcatcgt cctctgcagc aagtgcgccc caccaagac cgtgattccc       180 cgctactaca gcaatgaaac cgttcccgtc tgccagcgct gctaccaggt ggtggagcgc      240
tacaaggaac gcgggtcagt gacaccggga tatgttgttc actctaccac catcagcgcc      300
acgccggctc gatcctcgcc ggtgccgcca cttcacacga ctccagccct ccggccgcat      360
gcaccctcgc cgcagcccgc ttccgtcgtg tccacggcaa cactcgtcca tcccgtagaa      420
gaagacgcag tgtccacaaa accctccgtc agcgaggccg acctgcacgc cctgcgaagc      480
atcatcgaga ccctccagca agcactcaac gatgaacaac acaacgccgc cctagccgcc      540
acgtccgctg ccgagcagct ccgaacagcc aaagaagaga acacagcact caaaagcacc      600
gcacatctcc tgcagcagcg cctagacacc gccacgcagc agcgcgccga gctggaggca      660
cgggtggcac ggctggccgc ggaccgcgac gaggcgcgcc agcagctggc cgcgaacgcc      720
gaggagctgc agcagcgcct agacaccgcc acgcagcagc gcgccgagct ggaggcacgg      780
gtggcacggc tggccgcgga ccgcgacgag gcgcgccagc agctggccgc gaacgccgag      840
gagctgcagc agcgcctaga caccgccacg cagcagcgcg ccgagctgga ggcacaggtg      900
gcacggctgg ccgcggacgg cgacgaggcg cgccagcagc tggccgcgaa cgccgaggag      960
ctgcagcagc gcctagacac cgccacgcag cagcgcgccg agctggaggc acgggtggca     1020
cggctggccg cggaccgcga cgaggcgcgc cagcagctgg ccgcgaacgc cgaggagctg     1080
cagcagcgct agacaccgc cacgcagcag cgcgccgagc tggaggcaca ggttggcacgg     1140 ctggccgcgg accgcgacga ggcgcgccag cagctggccg cgaacgccga ggagctgcag     1200
cagcgcctag acaccgccac gcagcagcgc gccgagctgg aggcacaggt ggcacggctg     1260
gccgcgaacg ccgaggagct gcagcagcgc ctagacaccg ccacgcagca gcgcgccgag     1320
ctggaggcac gggtggcacg gctggccgcg gaccgcgacg aggcgcgcca gcagctggcc     1380
gcgaacgccg aggagctgca gcagcgccta gacaccgcca cgcagcagcg cgccgagctg     1440
gaggcacggg tggcacggct ggccgcggac ggcgacgagg cccgcagca gctggccgcg     1500 aacgccgagg agctgcagca gcgcctagac accgccacgc agcagcgcgc cgagctggag     1560
gcacaggtgg cacggctggc cgcgaacgcc gaggagctgc agcagcgcct agacaccgcc     1620
acgcagcagc gcgccgagct ggaggcacgg gtggcacggc tggccgcgga ccgcgacgag     1680
gcgcgccagc agctggccgc gaacgccgag gagctgcagc agcgcctaga caccgccacg     1740
```

```
                                                  -continued cagcagcgcg ccgagctgga ggcacaggtg gcacggctgg ccgcgaacgc cgaggagctg    1800
cagcagcgcc tagacaccgc cacgcagcag cgcgccgagc tggaggcacg ggtggcacgg    1860
ctggccgtgg accgcgacga ggcgcgccag cagctggccg cgaacgccga ggagctgcag    1920
cagcgcctag acaccgccac gcagcagcgc gccgagctgg aggcacaggt ggcacggctg    1980
gccgcggacc gcgacgaggc gcgccagcag ctggccgcga acgccgagga gctgcagcag    2040
cgcctagaca ccgccacgca gcagcgcgcc gagctggagg cacagttggc acggctggcc    2100
gcggaccgcg acgaggcgcg ccagcagctg gccgcgaacg ccgaggagct gcagcagcgc    2160
ctagacaccg ccacgcagca gcgcgccgag ctggaggcac aggtggcacg gctggccgcg    2220
gaccgcgacg aggcgcgcca gcagctggcc gcgaacgccg aggagctgca gcagcgccta    2280
gacaccgcca cgcagcagcg cgccgagctg gaggcacagt tggcacggct ggccgcggac    2340
cgcgacgagg cgcgccagca gctggccgcg aacgccgagg agctgcagca gcgcctagac    2400
accgccacgc agcagcgcgc cgagctggag gcacaggtgg cacggctggc cgcggaccgc    2460
gacgaggcgc gccagcagct ggccgcgaac gccgaggagc tgcagcagcg cctagacacc    2520
gccacgcagc agcgcgccga gctggaggca caggtggcac ggctggccgc ggaccgcgac    2580
gaggcccgcc agcagctggc cgcgaacgcc gaggagctgc agcagcgcct agacaccgcc    2640
acgcagcagc gcgccgagct ggaggcacag gtggcacggc tggccgcgaa cgccgaggag    2700
ctgcagcagc gcctagacac cgccacgcag cagcgcgccg agctggaggc acgggtggca    2760
cggctggccg cggaccgcga cgaggcgcgc cagcagctgg ccgcgaacgc cgaggagctg    2820
cagcagcgcc tagacaccgc cacgcagcag cgcgccgagc tggaggcaca gttggcacgg    2880
ctggccgcgg accgcgacga ggcgcgccag cagctggccg cgaacgccga ggagctgcag    2940
cagcgcctag acaccgccac gcagcagcgc gccgagctgg aggcacagtt ggcacggctg    3000
gccgcggacc gcgacgaggc gcgccagcag ctggccgcga acgccgagga gctgcagcag    3060
cgcctagaca ccgccacgca gcagcgcgcc gagctggagg cacaggtggc acggctggcc    3120
gcggaccgcg acgaggcgcg ccagcagctg gccgcgaacg ccgaggagct gcagcagcgc    3180
ctagacaccg ccacgcagca gcgcgccgag ctggaggcac gggtggcacg gctggccgcg    3240
gaccgcgacg aggcgcgcca gcagctggcc gcgaacgccg aggagctgca gcagcgccta    3300
gacaccgcca cgcagcagcg cgccgagctg gaggcacagg tggcacggct ggccgcggac    3360
ggcgacgagg cgcgccagca gctggccgcg aacgccgagg agctgcagca gcgcctagac    3420
accgccacgc agcagcgcgc cgagctggag gcacgggtgg cacggctggc cgcggaccgc    3480
gacgaggcgc gccagcagct ggccgcgaac gccgaggagc tgcagcagcg cctagacacc    3540
gccacgcagc agcgcgccga gctggaggca cagttggcac ggctggccgc ggaccgcgac    3600
gaggcgcgcc agcagctggc cgcgaacgcc gaggagctgc agcagcgcct agacaccgcc    3660
acgcagcagc gcgccgagct ggaggcacag gtggcacggc tggccgcgga cggcgacgag    3720
gcgcgccagc agctggccgc gaacgccgag gagctgcagc agcgcctaga caccgccacg    3780
cagcagcgcg ccgagctgga ggcacagttg gcacggctgg ccgcggaccg cgacgaggcg    3840
cgccagcagc tggccgcgaa cgccgaggag ctgcagcagc gcctagacac cgccacgcag    3900
cagcgcgccg agctggaggc acaggtggca cggctggccg cgaacgccga ggagctgcag    3960
cagcgcctag acaccgccac gcagcagcgc gccgagctgg aggcacgggt ggcacggctg    4020
gccgcggacc gcgacgaggc gcgccagcag ctggccgcga acgccgagga gctgcagcag    4080
```

```
cgcctagaca ccgccacgca gcagcgcgcc gagctggagg cacgggtggc acggctggcc    4140
gcggaccgcg acgaggcgcg ccagcagctg gccgcgaacg ccgaggagct gcagcagcgc    4200
ctagacaccg ccacgcagca gcgcgccgag ctggaggcac aggtggcacg gctggccgcg    4260
aacgccgagg agctgcagca gcgcctagac accgccacgc agcagcgcgc cgagctggag    4320
gcacgggtgg cacggctggc cgcggaccgc gacgaggcgc gccagcagct ggccgcgaac    4380
gccgaggagc tgcagcagcg cctagacacc gccacgcagc agcgcgccga gctggaggca    4440
caggtggcac ggctggccgc ggaccgcgac gaggcgcgcc agcagctggc cgcgaacgcc    4500
gaggagctgc agcagcgcct agacaccgcc acgcagcagc gcgccgagct ggaggcacgg    4560
gtggcacggc tggccgcgga cggcgacgag ccccgccagc agctggccgc gaacgccgag    4620
gagctgcagc agcgcctaga caccgccacg cagcagcgcg ccgagctgga ggcacagttg    4680
gcacggctgg ccgcggaccg cgacgaggcg cgccagcagc tggccgcgaa cgccgaggag    4740
ctgcagcagc gcctagacac cgccacgcag cagcgcgccg agctggaggc acgggtggca    4800
cggctggccg cggacggcga cgaggcgcgc agcagctgg ccgcgaacgc cgaggagctg    4860
cagcagcgcc tagacaccgc cacgcagcag cgcgccgagc tggaggcacg ggtggcacgg    4920
ctggccgcgg accgcgacga ggcgcgccag cagctggccg cgaacgccga ggagctgcag    4980
cagcgcctag acaccgccac gcagcagcgc gccgagctgg aggcacagtt ggcacggctg    5040
gccgcggacc gcgacgaggc gcgccagcag ctggccgcga acgccgagga gctgcagcag    5100
cgcctagaca ccgccacgca gcagcgcgcc gagctggagg cacagttggc acggctggcc    5160
gcggacggcg acgaggcgcg ccagcagctg gccgcgaacg ccgaggagct gcagcagcgc    5220
ctagacaccg ccacgcagca gcgcgccgag ctggaggtgg agatggcagt tctcctgcgt    5280
gagagggagg aagctcgcgg agagacagca gtggctggag agcaggtgca gctgtaccgg    5340
gaaacggtcg aggaggagga gtgtttaaag gaggaacgat ggtgcctcga gtcacgggtg    5400
gcgcagctga gggaggcgtc cgcggccgcg aagcagcagc ggcaagaagt ggcggcgaag    5460
gcgaatgagg tgcaggagcg ccttgattcg atggcgcgtc ggtgcattgc gcatgaggga    5520
gatgcgccgc agcgggctga cgggagagac gacgccttgc ggcaacttgc taatctgcgt    5580
gaagaggtga agctcagtga gaagcagaag gcgatggagc gtgttattcc gggtgttaga    5640
gagcggcaga tgcgcctcga agcagctgag gagcagcggg cggacttgga agcacgcctc    5700
gtcgacgagg ccggtgacct gcgctctcgt cctgctgcga gcacaaacga agtgaatctg    5760
taccgcgacc tcgctctgca ggaacacgaa gcagcccaga atcggtgcac aacactggaa    5820
gcgcaggtgg caagcctcac gagcgaccgc gacaacgggc gccagcaaga gtcggctgac    5880
ctcagcgagg cgcagcgtca cctcgacaac gtgcaggagc gcgacatggc ccatcatcgg    5940
tgtgccgcgt tggaggagca gaatgctgct atggcctcgg agttgcaagc ggtcaaggct    6000
aaactgcggc aggcctcagt gaaggcctcc tcgttgatga cgcgactctc tgcatcatcc    6060
tcgggagctg tggtgtctc tgcccgtgtg agagtgggag gcagctctgc cgtgccacaa    6120
gcggcgccac accgggatgc ggagctcatc gccgaggtgg gcgaacgcct tcgcgaaagg    6180
ggggaggcca tgcgactgtt ggccgaaggc gtcgaactgc gcgagcgcgc gcggccgctg    6240
gaacgggtgc tcgccgagaa gctgatcggc gaccgtcgca cgagcgacgc ggaagaggtc    6300
gccacggagc ccacgcaggt gcggcggaac gctgcgcact cgcggcacct ggactcgcgt    6360
gaggcgcagc tggacgagcg cgcggcacgg ctgagggaaa aggagcagca gctgctgcgc    6420
gtcgctcgtg aactgcagac taagtcgcgc gcccttcaag tattatacgc acgggcgctg    6480
```

```
aataggccac aggtgacgtc gttgctgctg acggccgacg gcgacgatac ctcctacccc    6540
gacacaccac agcaacagca gcaaggcaca cgcacgccgc tcagagaacc tgtatattcg    6600
ctggacagcg aggtggcgca ctacggccga actgcagggg ccgcagtgag cagtggtctc    6660
gcatcacctc tgccgaggga gccgccacgg gctcggatgg tgcaccgcgc tgtggaggca    6720
acgggcacag aggaagacac gcaggtgcgc ctcacggctg caacggaggc ttaccgcgac    6780
gtactgtacg agcacattct tgagtcgaat gggctccaag gggtggatgt gttggctcag    6840
tacctgcccc accacacctc cggcgtgggg ctgaagacac cgcgactgcc ggggagcggc    6900
attatatcga agacccgggc aatgctacga gcgctggagg agcgcctggg tgcttcccgt    6960
ggcgtcgggc gtggagtcga cccggcggtg caggagcgaa gcctggaagc gttccggcgg    7020
ctcgaggccg ccttgtctgc tctctgtgga ggcagccatg cgtag                   7065
```

<210> SEQ ID NO 116
<211> LENGTH: 2589
<212> TYPE: DNA
<213> ORGANISM: Leishmania major and chagasi
<220> FEATURE:
<221> NAME/KEY: misc_feature
<222> LOCATION: (1)...(2589)
<223> OTHER INFORMATION: n = A,T,C or G

<400> SEQUENCE: 116

```
gtmccttcca agcttgcaat ccgtctcatg cgcagctctc gcggcggctc tctcgcggtg      60
gtcgccttgg cggttttgcct ggcagtgctc ccgcgatcg gcacgtgtgt tttcgactcg    120
caagagatcg gcggcagctc cttcaccttc gtaggctggt cgtctgccag caaggaggaa    180
tcctaccagg gctgcaccct gaccgggaag gcattcagaa ttcaaggcgc tgcaagctct    240
ctgtcggacg acgccacgct gcccggtggg atcctgcggt tctccagcct gcttgtatcg    300
aacggctaca tcgtcgtgga taagtacttt ccccggaaca ccaacatcac catcaaagat    360
gccagcggca ccgtcgctgc ggggatgcct ttcatcgacg ccaacacggc gatatactct    420
gatcagctca gcatcgtggt caccgactcc actctcagtt gggctgccgc acggtcgggt    480
cagagcatgg tgcgtgcacc cttcactatt cagctctcca gctctctctt cgtgctcggc    540
agcaccgtga cgcaggcctc gtcagtggta gaggtggtgg gcccgagcag catctcccag    600
aagtctgcat tggctgtgga ctacgccaag tgcaccggct gtgctcaggg tctggtgcac    660
ttcaccgact ttgtcagagt gtgggaccgc agcttgcttc gcgtctccca ctccagcgtc    720
aagggcgcca ccggcaagcc gctgatcggc atagcacaga gcgcagggc gagcctggcg     780 gtggaaaaca gtctgttcgt tgtcgagaac gtgtcatcgc ccaccagtaa cctcatcgac    840
gcggccgtca gaatgggcac cgatgcgcag atccccctac gcgctgtgac ggtgaagagc    900
attggtgcaa cgatggccgg cagcgtcact gcgcagctct tgacggcaga cgacatcgcc    960
caacaaattc cctccatttc cgtggtgcca gacacccgct gcgctgcggc ctgcgtcccc   1020
acggccacgg tcgactccag ctgcaagtgt gcctgcaatg ccgacatgcc gaacatgaac   1080
ttctgcacgg ccatgaagga cccctacaca aactatgcct acctcggctg ctcggcgggc   1140
tgcacaacgt gcttcaacga gaccgcctgc ctcgagtgca ggccgagcta cgagatgctg   1200
cccgacatga catgctcgct gaccggactt cagtgcacag acccgaactg caagacctgc   1260
acaacttacg gtcagtgcac agactgcaac gacggctacg gtctcacctc ctccagcgtt   1320
tgcgtgcgct gcagtgtagc gggctgcaag agctgccccg tcgacgctaa cgtctgcaaa   1380
gtgtgtctcg gcggcagcga gccgatcaac aatatgtgcc cctgcaccga ccccaactgc   1440
```

```
gccagctgcc ccagcgacgc tggcacgtgc actcagtgcg cgaacggcta cggtctcgtg      1500
gacggcgcct gtgtgagatg ccaggagccc aactgcttca gctgcgacag cgacgcgaat      1560
aagtgcacac aatgtgcgcc gaactactac ctcaccccgc tcttgacctg ctccccggtg      1620
gcctgcaaca tcgagcactg catgcagtgc gacccacaga cgccgtcgcg ctgccaggag      1680
tgcgtgtccc cctacgtggt tgacagctac gacggcctct gcaggctctc cgatgcctgc      1740
tccgtgccca actgcaagaa gtgcgagacc ggtacctcca ggctctgcgc cgagtgcgac      1800
accggctaca gtctctccgc cgacgcgacg agctgcagca gtccaaccac gcagccgtgc      1860
gaggtggagc actgcaacac atgtgtgaac ggcgatagca cccgctgtgc ctactgcaac      1920
accggctact acgtctccga tggcaagtgc aaggccatgc agggctgcta cgtgtcgaac      1980
tgcgcgcagt gcatgctgct tgacagcacc aagtgctcca cgtgcgtgaa agggtacctg      2040
ctcacgtcgt cctacagttg cgtctcgcag aaagtcatca acagtgcggc cgcgccctac      2100
tctctgtggg tggccgccgc cgtgctcctc acctcttttg ccatgcacct agcataggct      2160
agcccgggac gcgtggatcc tcgcaatccc taggaggatt aggcaagggc ttgagctcac      2220
gctcttgtga gggacagaaa tacaatcagg ggcagtatat gaatactcca tggagaaacc      2280
cagatctacg tatgatcagc ctcgactgtg ccttctagtt gccagccatc tgttgtttgc      2340
ccctcccccg tgccttcctt gaccctggaa ggtgccactc ccactgtcct ttcctaataa      2400
aatgaggaaa ttgcatcgca ttgtctgagt aggtgtcatt ctattctggg gggtggggtg      2460
gggcangaca gcaaggggga ggattgggaa gacaatagca ggcatgctgg ggatgcggtg      2520
ggctctatgg cttctgaggc ggaaagaacc agctggggct cgacagctcg agctaggacc      2580 gctatcang                                                              2589

<210> SEQ ID NO 117
<211> LENGTH: 909
<212> TYPE: DNA
<213> ORGANISM: Leishmania major and chagasi

<400> SEQUENCE: 117
atgcatcacc atcaccatca cgactcgcaa gagatcggcg gcagctcctt caccttcgta        60
ggctggtcgt ctgccagcaa ggaggaatcc taccagggct gcaccctgac cgggaaggca       120
ttcagaattc aaggcgctgc aagctctctg tcggacgacg ccacgctgcc cggtgggatc       180
ctgcggttct ccagcctgct tgtatcgaac ggctacatcg tcgtggataa gtactttccc       240
cggaacacca acatcaccat caaagatgcc agcggcaccg tcgctgcggg gatgccttc        300 atcgacgcca acacgcgat atactctgat cagctcagca tcgtggtcac cgactccact       360
ctcagttggg ctgccgcacg gtcgggtcag agcatggtgc gtgcaccctt cactattcag       420
ctctccagct ctctcttcgt gctcggcagc accgtgacgc aggcctcgtc agtggtagag       480
gtggtgggcc cgagcagcat ctcccagaag tctgcattgg ctgtggacta cgccaagtgc       540
accggctgtg ctcagggtct ggtgcacttc accgactttg tcagagtgtg ggaccgcagc       600
ttgcttcgcg tctcccactc cagcgtcaag ggcgccaccg gcaagccgct gatcggcata       660
gcacagagcg caggggcgag cctggcggtg gaaaacagtc tgttcgttgt cgagaacgtg       720
tcatcgccca ccagtaacct catcgacgcg gccgtcagaa tgggcaccga tgcgcagatc       780
accctacgcg ctgtgacggt gaagagcatt ggtgcaacga tggccggcag cgtcactgcg       840
cagctcttga cggcagacga catcgcccaa caaattccct ccatttccgt ggtgccagac       900
acccgctaa                                                               909
```

<210> SEQ ID NO 118
<211> LENGTH: 538
<212> TYPE: PRT
<213> ORGANISM: Leishmania major and chagasi

<400> SEQUENCE: 118

```
Arg Asn Thr Tyr Leu Leu Pro Leu Leu Gly Arg Arg Thr Thr Thr
                 5                  10                  15

Phe Lys Thr Thr Pro Arg Leu Leu Val Pro His Leu Leu Ser Thr
                20                  25                  30

Phe Asn Pro Cys Leu Ala Asn Met Glu Ala Tyr Lys Lys Leu Glu Thr
                35                  40                  45

Ile Phe Thr Lys Val Tyr Arg Leu Asp His Phe Leu Gly Leu Gly Asn
 50                  55                  60

Trp Asp Met Asn Thr Asn Met Pro Pro Lys Gly Glu Ser Arg Gly
 65                  70                  75                  80

Glu Ala Met Ala Met Leu Ser Glu Leu Arg Phe Gly Phe Ile Thr Ala
                 85                  90                  95

Pro Glu Val Lys Ser Leu Ile Glu Ser Ala Thr Lys Gly Ser Glu Glu
                100                 105                 110

Leu Asn Ala Val Gln Arg Ala Asn Leu Arg Glu Met Arg Arg Ala Trp
                115                 120                 125

Lys Ser Ala Thr Ala Leu Pro Ala Glu Phe Val Gly Arg Lys Met Arg
130                 135                 140

Leu Thr Thr His Ala His Ser Val Trp Arg Asp Ser Arg Lys Ala Asn
145                 150                 155                 160

Asp Phe Ala Lys Phe Leu Pro Val Leu Arg Asp Leu Val Ala Leu Ala
                165                 170                 175

Arg Glu Glu Gly Ser Tyr Leu Ala Ala Gly Thr Ser Leu Ser Pro Tyr
                180                 185                 190

Glu Ala Leu Met Asn Glu Tyr Glu Pro Gly Ile Thr Thr Gln Lys Leu
                195                 200                 205

Asp Glu Val Tyr Ala Asn Val Lys Ser Trp Leu Pro Gln Leu Leu Lys
                210                 215                 220

Asp Ile Val Gln Lys Gln Ser Gly Glu Ser Val Ile Ala Phe Ser His
225                 230                 235                 240

Lys Phe Pro Gln Asp Lys Gln Glu Ala Leu Cys Lys Glu Phe Met Lys
                245                 250                 255

Ile Trp His Phe Asp Thr Asp Ala Gly Arg Leu Asp Val Ser Pro His
                260                 265                 270

Pro Phe Thr Gly Met Thr Lys Glu Asp Cys Arg Leu Thr Thr Asn Tyr
                275                 280                 285

Ile Glu Asp Thr Phe Val Gln Ser Leu Tyr Gly Val Ile His Glu Ser
                290                 295                 300

Gly His Gly Lys Tyr Glu Gln Asn Cys Gly Pro Arg Glu His Ile Thr
305                 310                 315                 320

Gln Pro Val Cys Asn Ala Arg Ser Leu Gly Leu His Glu Ser Gln Ser
                325                 330                 335

Leu Phe Ala Glu Phe Gln Ile Gly His Ala Thr Pro Phe Ile Asp Tyr
                340                 345                 350

Leu Thr Thr Arg Leu Pro Glu Phe Phe Glu Ala Gln Pro Ala Phe Ser
                355                 360                 365

Gln Asp Asn Met Arg Lys Ser Leu Gln Gln Val Lys Pro Gly Tyr Ile
                370                 375                 380
```

```
Arg Val Asp Ala Asp Glu Val Cys Tyr Pro Leu His Val Ile Leu Arg
385                 390                 395                 400

Tyr Glu Ile Glu Arg Asp Leu Met Glu Gly Lys Met Glu Val Glu Asp
            405                 410                 415

Val Pro Arg Ala Trp Asn Ala Lys Met Gln Glu Tyr Leu Gly Leu Ser
            420                 425                 430

Thr Glu Gly Arg Asp Asp Val Gly Cys Leu Gln Asp Val His Trp Ser
            435                 440                 445

Met Gly Ala Leu Gly Tyr Phe Pro Thr Tyr Ser Leu Gly Ala Met Tyr
        450                 455                 460

Ala Ala Gln Ile Met Ala Ser Ile Arg Lys Glu Leu Gly Asp Asp Lys
465                 470                 475                 480

Val Asp Glu Cys Leu Arg Thr Gly Glu Leu Gly Pro Leu Leu Glu Lys
            485                 490                 495

Gln Gln Glu Lys Ile Trp Asp His Gly Cys Leu Tyr Glu Thr Asp Asp
            500                 505                 510

Leu Met Thr Arg Ala Thr Gly Glu Thr Leu Asn Pro Gly Tyr Leu Arg
        515                 520                 525

Arg His Leu Glu Ala Arg Tyr Leu Asn Ala
    530                 535

<210> SEQ ID NO 119
<211> LENGTH: 193
<212> TYPE: PRT
<213> ORGANISM: Leishmania major and chagasi

<400> SEQUENCE: 119

Met His His His His His Asp Pro Pro Gly Cys Arg Asn Ser Ala
                5                  10                  15

Arg Glu Leu Gln Gln Arg Leu Asp Thr Ala Thr Gln Arg Ala Glu
            20                  25                  30

Leu Glu Ala Arg Val Ala Arg Leu Ala Ala Asp Arg Asp Glu Ala Arg
        35                  40                  45

Gln Gln Leu Ala Ala Asn Ala Glu Glu Leu Gln Gln Arg Leu Asp Thr
50                  55                  60

Ala Thr Gln Gln Arg Ala Glu Leu Glu Ala Arg Val Ala Arg Leu Ala
65                  70                  75                  80

Ala Asp Gly Asp Glu Ala Arg Gln Gln Leu Ala Ala Asn Ala Glu Glu
            85                  90                  95

Leu Gln Gln Arg Leu Asp Thr Ala Thr Gln Gln Arg Ala Glu Leu Glu
        100                 105                 110

Ala Gln Val Ala Arg Leu Ala Ala Asn Ala Glu Glu Leu Gln Gln Arg
        115                 120                 125

Leu Asp Thr Ala Thr Gln Gln Arg Ala Glu Leu Glu Ala Arg Val Ala
    130                 135                 140

Arg Leu Ala Ala Asp Arg Asp Glu Ala Arg Gln Gln Leu Ala Ala Asn
145                 150                 155                 160

Ala Glu Glu Leu Gln Gln Arg Leu Asp Thr Ala Thr Gln Gln Arg Ala
            165                 170                 175

Glu Leu Glu Ala Gln Val Ala Arg Leu Ala Ala Asn Ala Ala Arg Ala
        180                 185                 190

Glu

<210> SEQ ID NO 120
```

-continued

```
<211> LENGTH: 2310
<212> TYPE: PRT
<213> ORGANISM: Leishmania major and chagasi

<400> SEQUENCE: 120

Met Ser Thr Pro Val Ser Gly Val Pro Gln Asp Arg Trp Gln Pro
                  5                  10                  15

Gln Gln Arg Val Lys Val Cys Gln Tyr Gln Asp Cys Gly Ala Pro Phe
             20                  25                  30

Gly Phe Phe Ser Thr Lys Val Asn Cys His Arg Cys Gly Ile Val Leu
             35                  40                  45

Cys Ser Lys Cys Ala Ala Thr Lys Thr Val Ile Pro Arg Tyr Tyr Ser
 50                  55                  60

Asn Glu Thr Val Pro Val Cys Gln Arg Cys Tyr Gln Val Val Glu Arg
 65                  70                  75                  80

Tyr Lys Glu Arg Gly Ser Val Thr Pro Gly Tyr Val Val His Ser Thr
             85                  90                  95

Thr Ile Ser Ala Thr Pro Ala Arg Ser Ser Pro Val Pro Pro Leu His
            100                 105                 110

Thr Thr Pro Ala Leu Arg Pro His Ala Pro Ser Pro Gln Pro Ala Ser
            115                 120                 125

Val Val Ser Thr Ala Thr Leu Val His Pro Val Glu Glu Asp Ala Val
            130                 135                 140

Ser Thr Lys Pro Ser Val Ser Glu Ala Asp Leu His Ala Leu Arg Ser
145                 150                 155                 160

Ile Ile Glu Thr Leu Gln Gln Ala Leu Asn Asp Glu Gln His Asn Ala
                165                 170                 175

Ala Leu Ala Ala Thr Ser Ala Ala Glu Gln Leu Arg Thr Ala Lys Glu
            180                 185                 190

Glu Asn Thr Ala Leu Lys Ser Thr Ala His Leu Leu Gln Gln Arg Leu
            195                 200                 205

Asp Thr Ala Thr Gln Gln Arg Ala Glu Leu Glu Ala Gln Val Ala Arg
            210                 215                 220

Leu Ala Ala Asp Arg Asp Glu Ala Arg Gln Gln Leu Ala Ala Asn Ala
225                 230                 235                 240

Glu Glu Leu Gln Gln Arg Leu Asp Thr Ala Thr Gln Gln Arg Ala Glu
                245                 250                 255

Leu Glu Ala Arg Val Ala Arg Leu Ala Ala Asp Arg Asp Glu Ala Arg
            260                 265                 270

Gln Gln Leu Ala Ala Asn Ala Glu Glu Leu Gln Gln Arg Leu Asp Thr
            275                 280                 285

Ala Thr Gln Gln Arg Ala Glu Leu Glu Ala Gln Val Ala Arg Leu Ala
            290                 295                 300

Ala Asn Ala Glu Glu Leu Gln Gln Arg Leu Asp Thr Ala Thr Gln Gln
305                 310                 315                 320

Arg Ala Glu Leu Glu Ala Gln Leu Ala Arg Leu Ala Ala Asp Arg Asp
                325                 330                 335

Glu Ala Arg Gln Gln Leu Ala Ala Asn Ala Glu Glu Leu Gln Gln Arg
            340                 345                 350

Leu Asp Thr Ala Thr Gln Gln Arg Ala Glu Leu Glu Ala Gln Val Ala
            355                 360                 365

Arg Leu Ala Ala Asn Ala Glu Glu Leu Gln Gln Arg Leu Asp Thr Ala
            370                 375                 380

Thr Gln Gln Arg Ala Glu Leu Glu Ala Arg Val Ala Arg Leu Ala Ala
```

```
385                 390                 395                 400

Asp Arg Asp Glu Ala Arg Gln Gln Leu Ala Ala Asn Ala Glu Glu Leu
                405                 410                 415

Gln Gln Arg Leu Asp Thr Ala Thr Gln Gln Arg Ala Glu Leu Glu Ala
                420                 425                 430

Gln Val Ala Arg Leu Ala Ala Asn Arg Asp Glu Ala Arg Gln Gln Leu
                435                 440                 445

Ala Ala Asn Ala Glu Glu Leu Gln Gln Arg Leu Asp Thr Ala Thr Gln
                450                 455                 460

Gln Arg Ala Glu Leu Glu Ala Gln Val Ala Arg Leu Ala Ala Asp Arg
465                 470                 475                 480

Asp Glu Ala Arg Gln Gln Leu Ala Ala Asn Ala Glu Glu Leu Gln Gln
                485                 490                 495

Arg Leu Asp Thr Ala Thr Gln Gln Arg Ala Glu Leu Glu Ala Arg Val
                500                 505                 510

Ala Arg Leu Ala Ala Asp Arg Asp Glu Ala Arg Gln Gln Leu Ala Ala
                515                 520                 525

Asn Ala Glu Glu Leu Gln Gln Arg Leu Asp Thr Ala Thr Gln Gln Arg
                530                 535                 540

Ala Glu Leu Glu Ala Arg Val Ala Arg Leu Ala Ala Asn Ala Glu Glu
545                 550                 555                 560

Leu Gln Gln Arg Leu Asp Thr Ala Thr Gln Gln Arg Ala Glu Leu Glu
                565                 570                 575

Ala Gln Val Ala Arg Leu Ala Ala Asn Ala Glu Glu Leu Gln Gln Arg
                580                 585                 590

Leu Asp Thr Ala Thr Gln Gln Arg Ala Glu Leu Glu Ala Arg Val Ala
                595                 600                 605

Arg Leu Ala Ala Asp Arg Asp Glu Ala Arg Gln Gln Leu Ala Ala Asn
610                 615                 620

Ala Glu Glu Leu Gln Gln Arg Leu Asp Thr Ala Thr Gln Gln Arg Ala
625                 630                 635                 640

Glu Leu Glu Ala Gln Leu Ala Arg Leu Ala Ala Asp Gly Asp Glu Ala
                645                 650                 655

Arg Gln Gln Leu Ala Ala Asn Ala Glu Glu Leu Gln Gln Arg Leu Asp
                660                 665                 670

Thr Ala Thr Gln Gln Arg Ala Glu Leu Glu Ala Arg Val Ala Arg Leu
                675                 680                 685

Ala Ala Asp Arg Asp Glu Ala Arg Gln Gln Leu Ala Ala Asn Ala Glu
                690                 695                 700

Glu Leu Gln Gln Arg Leu Asp Thr Ala Thr Gln Gln Arg Ala Glu Leu
705                 710                 715                 720

Glu Ala Gln Leu Ala Arg Leu Ala Ala Asp Arg Asp Glu Ala Arg Gln
                725                 730                 735

Gln Leu Ala Ala Asn Ala Glu Glu Leu Gln Gln Arg Leu Asp Thr Ala
                740                 745                 750

Thr Gln Gln Arg Ala Glu Leu Glu Ala Arg Val Ala Arg Leu Ala Ala
                755                 760                 765

Asp Gly Asp Glu Ala Arg Gln Gln Leu Ala Ala Asn Ala Glu Glu Leu
                770                 775                 780

Gln Gln Arg Leu Asp Thr Ala Thr Gln Gln Arg Ala Glu Leu Glu Ala
785                 790                 795                 800

Arg Val Ala Arg Leu Ala Ala Asp Arg Asp Glu Ala Arg Gln Gln Leu
                805                 810                 815
```

-continued

Ala Ala Asn Ala Glu Glu Leu Gln Gln Arg Leu Asp Thr Ala Thr Gln
        820                 825                 830

Gln Arg Ala Glu Leu Glu Ala Gln Leu Ala Arg Leu Ala Ala Asp Gly
        835                 840                 845

Asp Glu Ala Arg Gln Gln Leu Ala Ala Asn Ala Glu Glu Leu Gln Gln
        850                 855                 860

Arg Leu Asp Thr Ala Thr Gln Gln Arg Ala Glu Leu Glu Ala Arg Val
865                 870                 875                 880

Ala Arg Leu Ala Ala Asp Arg Asp Glu Ala Arg Gln Gln Leu Ala Ala
        885                 890                 895

Asn Ala Glu Glu Leu Gln Gln Arg Leu Asp Thr Ala Thr Gln Gln Arg
        900                 905                 910

Ala Glu Leu Glu Ala Gln Leu Ala Arg Leu Ala Ala Asp Arg Asp Glu
        915                 920                 925

Ala Arg Gln Gln Leu Ala Ala Asn Ala Glu Glu Leu Gln Gln Arg Leu
        930                 935                 940

Asp Thr Ala Thr Gln Gln Arg Ala Glu Leu Glu Ala Gln Val Ala Arg
945                 950                 955                 960

Leu Ala Ala Asp Gly Asp Glu Ala Arg Gln Gln Leu Ala Ala Asn Ala
        965                 970                 975

Glu Glu Leu Gln Gln Arg Leu Asp Thr Ala Thr Gln Gln Arg Ala Glu
        980                 985                 990

Leu Glu Ala Gln Leu Ala Arg Leu Ala Ala Asp Arg Asp Glu Ala Arg
        995                 1000                1005

Gln Gln Leu Ala Ala Asn Ala Glu Glu Leu Gln Gln Arg Leu Asp Thr
        1010                1015                1020

Ala Thr Gln Gln Arg Ala Glu Leu Glu Ala Gln Val Ala Arg Leu Ala
1025                1030                1035                1040

Ala Asn Ala Glu Glu Leu Gln Gln Arg Leu Asp Thr Ala Thr Gln Gln
        1045                1050                1055

Arg Ala Glu Leu Glu Ala Arg Val Ala Arg Leu Ala Ala Asp Arg Asp
        1060                1065                1070

Glu Ala Arg Gln Gln Leu Ala Ala Asn Ala Glu Glu Leu Gln Gln Arg
        1075                1080                1085

Leu Asp Thr Ala Thr Gln Gln Arg Ala Glu Leu Glu Ala Arg Val Ala
        1090                1095                1100

Arg Leu Ala Ala Asn Ala Glu Glu Leu Gln Gln Arg Leu Asp Thr Ala
1105                1110                1115                1120

Thr Gln Gln Arg Ala Glu Leu Glu Ala Gln Val Ala Arg Leu Ala Ala
        1125                1130                1135

Asn Ala Glu Glu Leu Gln Gln Arg Leu Asp Thr Ala Thr Gln Gln Arg
        1140                1145                1150

Ala Glu Leu Glu Ala Arg Val Ala Arg Leu Ala Ala Asp Arg Asp Glu
        1155                1160                1165

Ala Arg Gln Gln Leu Ala Ala Asn Ala Glu Glu Leu Gln Gln Arg Leu
        1170                1175                1180

Asp Thr Ala Thr Gln Gln Arg Ala Glu Leu Glu Ala Gln Val Ala Arg
1185                1190                1195                1200

Leu Ala Ala Asn Ala Glu Glu Leu Gln Gln Arg Leu Asp Thr Ala Thr
        1205                1210                1215

Gln Gln Arg Ala Glu Leu Glu Ala Gln Leu Ala Arg Leu Ala Ala Asp
        1220                1225                1230

```
Arg Asp Glu Ala Arg Gln Gln Leu Ala Ala Asn Ala Glu Glu Leu Gln
        1235                1240                1245

Gln Arg Leu Asp Thr Ala Thr Gln Gln Arg Ala Glu Leu Glu Ala Gln
    1250                1255                1260

Val Ala Arg Leu Ala Ala Asn Ala Glu Glu Leu Gln Gln Arg Leu Asp
1265                1270                1275                1280

Thr Ala Thr Gln Gln Arg Ala Glu Leu Glu Ala Arg Val Ala Arg Leu
            1285                1290                1295

Ala Ala Asp Arg Asp Glu Ala Arg Gln Gln Leu Ala Ala Asn Ala Glu
        1300                1305                1310

Glu Leu Gln Gln Arg Leu Asp Thr Ala Thr Gln Gln Arg Ala Glu Leu
        1315                1320                1325

Glu Ala Arg Val Ala Arg Leu Ala Ala Asp Gly Asp Glu Ala Arg Gln
        1330                1335                1340

Gln Leu Ala Ala Asn Ala Glu Glu Leu Gln Gln Arg Leu Asp Thr Ala
1345                1350                1355                1360

Thr Gln Gln Arg Ala Glu Leu Glu Ala Gln Val Ala Arg Leu Ala Ala
            1365                1370                1375

Asn Ala Glu Glu Leu Gln Gln Arg Leu Asp Thr Ala Thr Gln Gln Arg
        1380                1385                1390

Ala Glu Leu Glu Ala Arg Val Ala Arg Leu Ala Ala Asp Arg Asp Glu
        1395                1400                1405

Ala Arg Gln Gln Leu Ala Ala Asn Ala Glu Glu Leu Gln Gln Arg Leu
        1410                1415                1420

Asp Thr Ala Thr Gln Gln Arg Ala Glu Leu Glu Ala Gln Val Ala Arg
1425                1430                1435                1440

Leu Ala Ala Asp Arg Asp Glu Ala Arg Gln Gln Leu Ala Ala Asn Ala
            1445                1450                1455

Glu Glu Leu Gln Gln Arg Leu Asp Thr Ala Thr Gln Gln Arg Ala Glu
        1460                1465                1470

Leu Glu Ala Arg Val Ala Arg Leu Ala Ala Asp Gly Asp Glu Ala Arg
        1475                1480                1485

Gln Gln Leu Ala Ala Asn Ala Glu Glu Leu Gln Gln Arg Leu Asp Thr
    1490                1495                1500

Ala Thr Gln Gln Arg Ala Glu Leu Glu Ala Gln Leu Ala Arg Leu Ala
1505                1510                1515                1520

Ala Asp Arg Asp Glu Ala Arg Gln Gln Leu Ala Ala Asn Ala Glu Glu
            1525                1530                1535

Leu Gln Gln Arg Leu Asp Thr Ala Thr Gln Gln Arg Ala Glu Leu Glu
        1540                1545                1550

Ala Arg Val Ala Arg Leu Ala Ala Asp Gly Asp Glu Ala Arg Gln Gln
        1555                1560                1565

Leu Ala Ala Asn Ala Glu Glu Leu Gln Gln Arg Leu Asp Thr Ala Thr
    1570                1575                1580

Gln Gln Arg Ala Glu Leu Glu Ala Arg Val Ala Arg Leu Ala Ala Asp
1585                1590                1595                1600

Arg Asp Glu Ala Arg Gln Gln Leu Ala Ala Asn Ala Glu Glu Leu Gln
            1605                1610                1615

Gln Arg Leu Asp Thr Ala Thr Gln Gln Arg Ala Glu Leu Glu Ala Gln
        1620                1625                1630

Leu Ala Arg Leu Ala Ala Asp Arg Asp Glu Ala Arg Gln Gln Leu Ala
        1635                1640                1645

Ala Asn Ala Glu Glu Leu Gln Gln Arg Leu Asp Thr Ala Thr Gln Gln
```

-continued

```
            1650                1655                1660
Arg Ala Glu Leu Glu Ala Gln Leu Ala Arg Leu Ala Ala Asp Gly Asp
1665                1670                1675                1680
Glu Ala Arg Gln Gln Leu Ala Ala Asn Ala Glu Glu Leu Gln Gln Arg
                    1685                1690                1695
Leu Asp Thr Ala Thr Gln Gln Arg Ala Glu Leu Glu Val Glu Met Ala
                1700                1705                1710
Val Leu Arg Glu Arg Glu Ala Arg Gly Glu Thr Ala Val Ala
            1715                1720                1725
Gly Glu Gln Val Gln Leu Tyr Arg Glu Thr Val Glu Glu Glu Cys
        1730                1735                1740
Leu Lys Glu Glu Arg Trp Cys Leu Glu Ser Arg Val Ala Gln Leu Arg
1745                1750                1755                1760
Glu Ala Ser Ala Ala Lys Gln Gln Arg Gln Glu Val Ala Ala Lys
                1765                1770                1775
Ala Asn Glu Val Gln Glu Arg Leu Asp Ser Met Ala Arg Arg Cys Ile
            1780                1785                1790
Ala His Glu Gly Asp Ala Pro Gln Arg Ala Asp Gly Arg Asp Asp Ala
        1795                1800                1805
Leu Arg Gln Leu Ala Asn Leu Arg Glu Glu Val Lys Leu Ser Glu Lys
    1810                1815                1820
Gln Lys Ala Met Glu Arg Val Ile Pro Gly Val Arg Glu Arg Gln Met
1825                1830                1835                1840
Arg Leu Glu Ala Ala Glu Gln Arg Ala Asp Leu Glu Ala Arg Leu
                1845                1850                1855
Val Asp Glu Ala Gly Asp Leu Arg Ser Arg Pro Ala Ala Ser Thr Asn
            1860                1865                1870
Glu Val Asn Leu Tyr Arg Asp Leu Ala Leu Gln Glu His Glu Ala Ala
        1875                1880                1885
Gln Asn Arg Cys Thr Thr Leu Glu Ala Gln Val Ala Ser Leu Thr Ser
    1890                1895                1900
Asp Arg Asp Asn Gly Arg Gln Gln Glu Ser Ala Asp Leu Ser Glu Ala
1905                1910                1915                1920
Gln Arg His Leu Asp Asn Val Gln Glu Arg Asp Met Ala His His Arg
                1925                1930                1935
Cys Ala Ala Leu Glu Glu Gln Asn Ala Ala Met Ala Ser Glu Leu Gln
            1940                1945                1950
Ala Val Lys Ala Lys Leu Arg Gln Ala Ser Val Lys Ala Ser Ser Leu
        1955                1960                1965
Met Thr Arg Leu Ser Ala Ser Ser Ser Gly Ala Gly Gly Val Ser Ala
    1970                1975                1980
Arg Val Arg Val Gly Gly Ser Ser Ala Val Pro Gln Ala Ala Pro His
1985                1990                1995                2000
Arg Asp Ala Glu Leu Ile Ala Glu Val Gly Glu Arg Leu Arg Glu Arg
                2005                2010                2015
Gly Glu Ala Met Arg Leu Leu Ala Glu Gly Val Glu Leu Arg Glu Arg
                2020                2025                2030
Ala Arg Pro Leu Glu Arg Val Leu Ala Glu Lys Leu Ile Gly Asp Arg
            2035                2040                2045
Arg Thr Ser Asp Ala Glu Glu Val Ala Thr Glu Pro Thr Gln Val Arg
        2050                2055                2060
Arg Asn Ala Ala His Ser Arg His Leu Asp Ser Arg Glu Ala Gln Leu
2065                2070                2075                2080
```

```
Asp Glu Arg Ala Ala Arg Leu Arg Glu Lys Glu Gln Gln Leu Leu Arg
            2085                2090                2095

Val Ala Arg Glu Leu Gln Thr Lys Ser Arg Ala Leu Gln Val Leu Tyr
        2100                2105                2110

Ala Arg Ala Leu Asn Arg Pro Gln Val Thr Ser Leu Leu Thr Ala
        2115                2120                2125

Asp Gly Asp Thr Ser Tyr Pro Asp Thr Pro Gln Gln Gln Gln Gln
        2130                2135                2140

Gly Thr Arg Thr Pro Leu Arg Glu Pro Val Tyr Ser Leu Asp Ser Glu
2145                2150                2155                2160

Val Ala His Tyr Gly Arg Thr Ala Gly Ala Val Ser Ser Gly Leu
            2165                2170                2175

Ala Ser Pro Leu Pro Arg Glu Pro Pro Arg Ala Arg Met Val His Arg
            2180                2185                2190

Ala Val Glu Ala Thr Gly Thr Glu Asp Thr Gln Val Arg Leu Thr
            2195                2200                2205

Ala Ala Thr Glu Ala Tyr Arg Asp Val Leu Tyr Glu His Ile Leu Glu
            2210                2215                2220

Ser Asn Gly Leu Gln Gly Val Asp Val Leu Ala Gln Tyr Leu Pro His
2225                2230                2235                2240

His Thr Ser Gly Gly Gly Leu Lys Thr Pro Arg Leu Pro Gly Ser Gly
            2245                2250                2255

Ile Ile Ser Lys Thr Arg Ala Met Leu Arg Ala Leu Glu Glu Arg Leu
            2260                2265                2270

Gly Ala Ser Arg Gly Val Gly Arg Gly Val Asp Pro Ala Val Gln Glu
            2275                2280                2285

Arg Ser Leu Glu Ala Phe Arg Arg Leu Glu Ala Ala Leu Ser Ala Leu
            2290                2295                2300

Cys Gly Gly Ser His Ala
2305                2310

<210> SEQ ID NO 121
<211> LENGTH: 709
<212> TYPE: PRT
<213> ORGANISM: Leishmania major and chagasi

<400> SEQUENCE: 121

Met Arg Ser Ser Arg Gly Gly Ser Leu Ala Val Val Ala Leu Ala Val
                5                   10                  15

Cys Leu Ala Val Leu Ala Ala Ile Gly Thr Cys Val Phe Asp Ser Gln
            20                  25                  30

Glu Ile Gly Gly Ser Ser Phe Thr Phe Val Gly Trp Ser Ser Ala Ser
        35                  40                  45

Lys Glu Glu Ser Tyr Gln Gly Cys Thr Leu Thr Gly Lys Ala Phe Arg
    50                  55                  60

Ile Gln Gly Ala Ala Ser Ser Leu Ser Asp Asp Ala Thr Leu Pro Gly
65                  70                  75                  80

Gly Ile Leu Arg Phe Ser Ser Leu Leu Val Ser Asn Gly Tyr Ile Val
                85                  90                  95

Val Asp Lys Tyr Phe Pro Arg Asn Thr Asn Ile Thr Ile Lys Asp Ala
            100                 105                 110

Ser Gly Thr Val Ala Ala Gly Met Pro Phe Ile Asp Ala Asn Thr Ala
        115                 120                 125

Ile Tyr Ser Asp Gln Leu Ser Ile Val Val Thr Asp Ser Thr Leu Ser
```

```
            130                 135                 140
Trp Ala Ala Ala Arg Ser Gly Gln Ser Met Val Arg Ala Pro Phe Thr
145                 150                 155                 160

Ile Gln Leu Ser Ser Ser Leu Phe Val Leu Gly Ser Thr Val Thr Gln
                    165                 170                 175

Ala Ser Ser Val Val Glu Val Val Gly Pro Ser Ser Ile Ser Gln Lys
                180                 185                 190

Ser Ala Leu Ala Val Asp Tyr Ala Lys Cys Thr Gly Cys Ala Gln Gly
            195                 200                 205

Leu Val His Phe Thr Asp Phe Val Arg Val Trp Asp Arg Ser Leu Leu
        210                 215                 220

Arg Val Ser His Ser Ser Val Lys Gly Ala Thr Gly Lys Pro Leu Ile
225                 230                 235                 240

Gly Ile Ala Gln Ser Ala Gly Ala Ser Leu Ala Val Glu Asn Ser Leu
                    245                 250                 255

Phe Val Val Glu Asn Val Ser Ser Pro Thr Ser Asn Leu Ile Asp Ala
                260                 265                 270

Ala Val Arg Met Gly Thr Asp Ala Gln Ile Thr Leu Arg Ala Val Thr
            275                 280                 285

Val Lys Ser Ile Gly Ala Thr Met Ala Gly Ser Val Thr Ala Gln Leu
        290                 295                 300

Leu Thr Ala Asp Asp Ile Ala Gln Gln Ile Pro Ser Ile Ser Val Val
305                 310                 315                 320

Pro Asp Thr Arg Cys Ala Ala Cys Val Pro Thr Ala Thr Val Asp
                    325                 330                 335

Ser Ser Cys Lys Cys Ala Cys Asn Ala Asp Met Pro Asn Met Asn Phe
                340                 345                 350

Cys Thr Ala Met Lys Asp Pro Tyr Thr Asn Tyr Ala Tyr Leu Gly Cys
            355                 360                 365

Ser Ala Gly Cys Thr Thr Cys Phe Asn Glu Thr Ala Cys Leu Glu Cys
        370                 375                 380

Arg Pro Ser Tyr Glu Met Leu Pro Asp Met Thr Cys Ser Leu Thr Gly
385                 390                 395                 400

Leu Gln Cys Thr Asp Pro Asn Cys Lys Thr Cys Thr Thr Tyr Gly Gln
                    405                 410                 415

Cys Thr Asp Cys Asn Asp Gly Tyr Gly Leu Thr Ser Ser Val Cys
                420                 425                 430

Val Arg Cys Ser Val Ala Gly Cys Lys Ser Cys Pro Val Asp Ala Asn
            435                 440                 445

Val Cys Lys Val Cys Leu Gly Gly Ser Glu Pro Ile Asn Asn Met Cys
450                 455                 460

Pro Cys Thr Asp Pro Asn Cys Ala Ser Cys Pro Ser Asp Ala Gly Thr
465                 470                 475                 480

Cys Thr Gln Cys Ala Asn Gly Tyr Gly Leu Val Asp Gly Ala Cys Val
                485                 490                 495

Arg Cys Gln Glu Pro Asn Cys Phe Ser Cys Asp Ser Asp Ala Asn Lys
            500                 505                 510

Cys Thr Gln Cys Ala Pro Asn Tyr Tyr Leu Thr Pro Leu Leu Thr Cys
        515                 520                 525

Ser Pro Val Ala Cys Asn Ile Glu His Cys Met Gln Cys Asp Pro Gln
            530                 535                 540

Thr Pro Ser Arg Cys Gln Glu Cys Val Ser Pro Tyr Val Val Asp Ser
545                 550                 555                 560
```

```
Tyr Asp Gly Leu Cys Arg Leu Ser Asp Ala Cys Ser Val Pro Asn Cys
                565                 570                 575
Lys Lys Cys Glu Thr Gly Thr Ser Arg Leu Cys Ala Glu Cys Asp Thr
            580                 585                 590
Gly Tyr Ser Leu Ser Ala Asp Ala Thr Ser Cys Ser Ser Pro Thr Thr
            595                 600                 605
Gln Pro Cys Glu Val Glu His Cys Asn Thr Cys Val Asn Gly Asp Ser
        610                 615                 620
Thr Arg Cys Ala Tyr Cys Asn Thr Gly Tyr Tyr Val Ser Asp Gly Lys
625                 630                 635                 640
Cys Lys Ala Met Gln Gly Cys Tyr Val Ser Asn Cys Ala Gln Cys Met
                645                 650                 655
Leu Leu Asp Ser Thr Lys Cys Ser Thr Cys Val Lys Gly Tyr Leu Leu
                660                 665                 670
Thr Ser Ser Tyr Ser Cys Val Ser Gln Lys Val Ile Asn Ser Ala Ala
            675                 680                 685
Ala Pro Tyr Ser Leu Trp Val Ala Ala Val Leu Leu Thr Ser Phe
        690                 695                 700
Ala Met His Leu Ala
705

<210> SEQ ID NO 122
<211> LENGTH: 302
<212> TYPE: PRT
<213> ORGANISM: Leishmania major and chagasi

<400> SEQUENCE: 122

Met His His His His His Asp Ser Gln Glu Ile Gly Gly Ser Ser
                5                   10                  15
Phe Thr Phe Val Gly Trp Ser Ser Ala Ser Lys Glu Glu Ser Tyr Gln
            20                  25                  30
Gly Cys Thr Leu Thr Gly Lys Ala Phe Arg Ile Gln Gly Ala Ala Ser
        35                  40                  45
Ser Leu Ser Asp Asp Ala Thr Leu Pro Gly Gly Ile Leu Arg Phe Ser
    50                  55                  60
Ser Leu Leu Val Ser Asn Gly Tyr Ile Val Val Asp Lys Tyr Phe Pro
65                  70                  75                  80
Arg Asn Thr Asn Ile Thr Ile Lys Asp Ala Ser Gly Thr Val Ala Ala
                85                  90                  95
Gly Met Pro Phe Ile Asp Ala Asn Thr Ala Ile Tyr Ser Asp Gln Leu
            100                 105                 110
Ser Ile Val Val Thr Asp Ser Thr Leu Ser Trp Ala Ala Ala Arg Ser
        115                 120                 125
Gly Gln Ser Met Val Arg Ala Pro Phe Thr Ile Gln Leu Ser Ser Ser
    130                 135                 140
Leu Phe Val Leu Gly Ser Thr Val Thr Gln Ala Ser Ser Val Val Glu
145                 150                 155                 160
Val Val Gly Pro Ser Ser Ile Ser Gln Lys Ser Ala Leu Ala Val Asp
                165                 170                 175
Tyr Ala Lys Cys Thr Gly Cys Ala Gln Gly Leu Val His Phe Thr Asp
            180                 185                 190
Phe Val Arg Val Trp Asp Arg Ser Leu Leu Arg Val Ser His Ser Ser
        195                 200                 205
Val Lys Gly Ala Thr Gly Lys Pro Leu Ile Gly Ile Ala Gln Ser Ala
```

-continued

```
            210                 215                 220
Gly Ala Ser Leu Ala Val Glu Asn Ser Leu Phe Val Val Glu Asn Val
225                 230                 235                 240

Ser Ser Pro Thr Ser Asn Leu Ile Asp Ala Ala Val Arg Met Gly Thr
                245                 250                 255

Asp Ala Gln Ile Thr Leu Arg Ala Val Thr Val Lys Ser Ile Gly Ala
            260                 265                 270

Thr Met Ala Gly Ser Val Thr Ala Gln Leu Leu Thr Ala Asp Asp Ile
        275                 280                 285

Ala Gln Gln Ile Pro Ser Ile Ser Val Val Pro Asp Thr Arg
    290                 295                 300
```

LEISHMANIA ANTIGENS FOR USE IN THE THERAPY AND DIAGNOSIS OF LEISHMANIASIS

REFERENCE TO RELATED APPLICATIONS

This application is a continuation-in-part of U.S. patent application Ser. No. 09/639,206 filed Aug. 14, 2000, which is a continuation-in-part of U.S. patent application Ser. No. 09/565,501 filed May 5, 2000, which is a continuation-in-part of U.S. patent application Ser. No. 09/551,974 filed Apr. 14, 2000, which is a continuation-in-part of U.S. patent application Ser. No. 09/183,861, filed Oct. 30, 1998, now U.S. Pat. No. 6,365,165, which is a continuation-in-part of U.S. patent application Ser. No. 09/022,765, filed Feb. 12, 1998, now U.S. Pat. No. 6,375,955, which is a continuation-in-part of U.S. patent application Ser. No. 08/920,609, filed Aug. 27, 1997, which is a continuation-in-part of U.S. patent application Ser. No. 08/798,841, filed Feb. 12, 1997, which is a continuation-in-part of U.S. patent application Ser. No. 08/533,869, filed Sep. 22, 1995, now U.S. Pat. No. 5,834,592.

TECHNICAL FIELD

The present invention relates generally to compositions and methods for preventing, treating and detecting leishmaniasis, and for stimulating immune responses in patients. The invention is more particularly related to polypeptides comprising an immunogenic portion of a Leishmania antigen or a variant thereof, and to vaccines and pharmaceutical compositions comprising one or more such polypeptides. The vaccines and pharmaceutical compositions may be used, for example, for the prevention and therapy of leishmaniasis, as well as for the detection of Leishmania infection.

BACKGROUND OF THE INVENTION

Leishmania organisms are intracellular protozoan parasites of macrophages that cause a wide range of clinical diseases in humans and domestic animals, primarily dogs. In some infections, the parasite may lie dormant for many years. In other cases, the host may develop one of a variety of forms of leishmaniasis. For example, the disease may be asymptomatic or may be manifested as subclinical visceral leishmaniasis, which is characterized by mild symptoms of malaise, diarrhea and intermittent hepatomegaly. Patients with subclinical or asymptomatic disease usually have low antibody titers, making the disease difficult to detect with standard techniques. Alternatively, leishmaniasis may be manifested as a cutaneous disease, which is a severe medical problem but is generally self-limiting, or as a highly destructive mucosal disease, which is not self-limiting. Finally, and most seriously, the disease may be manifested as an acute visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis. There are, however, no vaccines or effective treatments currently available.

Accurate diagnosis of leishmaniasis is frequently difficult to achieve. There are 20 species of Leishmania that infect humans, including L. donovani, L. chagasi, L. infantum, L. major, L. amazonensis, L. braziliensis, L. panamensis, L. mexicana, L. tropica, and L. guyanensis, and there are no distinctive signs or symptoms that unambiguously indicate the presence of Leishmania infection. Parasite detection methods have been used, but such methods are neither sensitive nor clinically practical. Current skin tests typically use whole or lysed parasites. Such tests are generally insensitive, irreproducible and prone to cross-reaction with a variety of other diseases. In addition, the preparations employed in such tests are often unstable. Thus, there is a need for improved methods for the detection of Leishmania infection.

Current experimental vaccines consisting of whole organisms have not proven effective in humans. Accordingly, there remains a need in the art for vaccines to prevent leishmaniasis in humans and dogs, and for improved therapeutic compositions for the treatment of leishmaniasis.

SUMMARY OF THE INVENTION

Briefly stated, the present invention provides compositions and methods for preventing, treating and detecting leishmaniasis, as well as for stimulating immune responses in patients. In one aspect, polypeptides are provided which comprise at least an immunogenic portion of a Leishmania antigen, or a variant of such an antigen that differs only in conservative substitutions and/or modifications. In specific embodiments of the invention, the Leishmania antigen comprises an amino acid sequence selected from the group consisting of SEQ ID NO: 2, 4, 20, 22, 24, 26, 36–38, 41, 50–53, 82, 104, 106, 108, 110, 112 and 118–122,. DNA sequences encoding the above polypeptides, recombinant expression vectors comprising these DNA sequences and host cells transformed or transfected with such expression vectors are also provided.

In further aspects, the present invention provides fusion proteins comprising Leishmania antigens, together with polynucleotides encoding such fusion proteins. In certain specific embodiments, such fusion proteins comprise an amino acid sequence selected from the group consisting of SEQ ID NOs:95, 96, and 97 and encoded by a polynucleotide sequence selected from the group consisting of SEQ ID NOs:94, 98, 99, 100, and 101.

In related aspects, the present invention provides pharmaceutical compositions which comprise one or more of the polypeptides and/or fusion proteins described herein, or a polynucleotide encoding such polypeptides and fusion proteins, and a physiologically acceptable carrier. Vaccines which comprise one or more such polypeptides, fusion proteins or polynucleotides, together with an immunostimulant are also provided. In specific embodiments of these aspects, the Leishmania antigen has an amino acid sequence selected from the group consisting of SEQ ID NO: 2, 4, 20, 22, 24, 26, 36–38, 41, 50–53, 82, 104, 106, 108, 110, 112 and 118–122.

In still further related embodiments, the pharmaceutical compositions and vaccines comprise at least two different polypeptides, each polypeptide comprising an immunogenic portion of a Leishmania antigen having an amino acid sequence selected from the group consisting of sequences recited in SEQ ID NO: 2, 4, 6, 8, 10, 20, 22, 24, 26, 36–38, 41, 50–53, 82, 104, 106, 108, 110, 112 and 118–122, and variants thereof that differ only in conservative substitutions and/or modifications. In other embodiments, the inventive pharmaceutical compositions comprise one or more of the inventive polypeptides in combination with a known Leishmania antigen.

In yet other related embodiments, the pharmaceutical compositions and vaccines comprise soluble Leishmania antigens.

In another aspect, the present invention provides methods for inducing protective immunity against leishmaniasis in a patient, comprising administering to a patient a pharmaceutical composition or vaccine as described above.

In further aspects, methods and diagnostic kits are provided for detecting Leishmania infection in a patient. The methods comprise: (a) contacting dermal cells of a patient with a pharmaceutical composition as described above; and (b) detecting an immune response on the patient's skin, therefrom detecting Leishmania infection in the patient. The diagnostic kits comprise: (a) a pharmaceutical composition as described above; and (b) an apparatus sufficient to contact the pharmaceutical composition with the dermal cells of a patient.

In further aspects, the present invention provides methods for stimulating a cellular and/or humoral immune response in a patient, comprising administering to a patient a pharmaceutical composition or vaccine as described above.

In a related aspect, methods are provided for treating a patient afflicted with a disease responsive to IL-12 stimulation, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 19 presents a comparison of a Lbhsp83 sequence (SEQ ID NO:6) with homologous sequences from L. amazonensis (Lahsp83) (SEQ ID NO:16), T. cruzi (Tchsp83) (SEQ ID NO:17) and humans (Huhsp89) (SEQ ID NO:18).

FIG. 21 shows the cDNA and predicted amino acid sequence for the Leishmania antigen Lmsp1a.

DETAILED DESCRIPTION OF THE INVENTION

Figure 1:
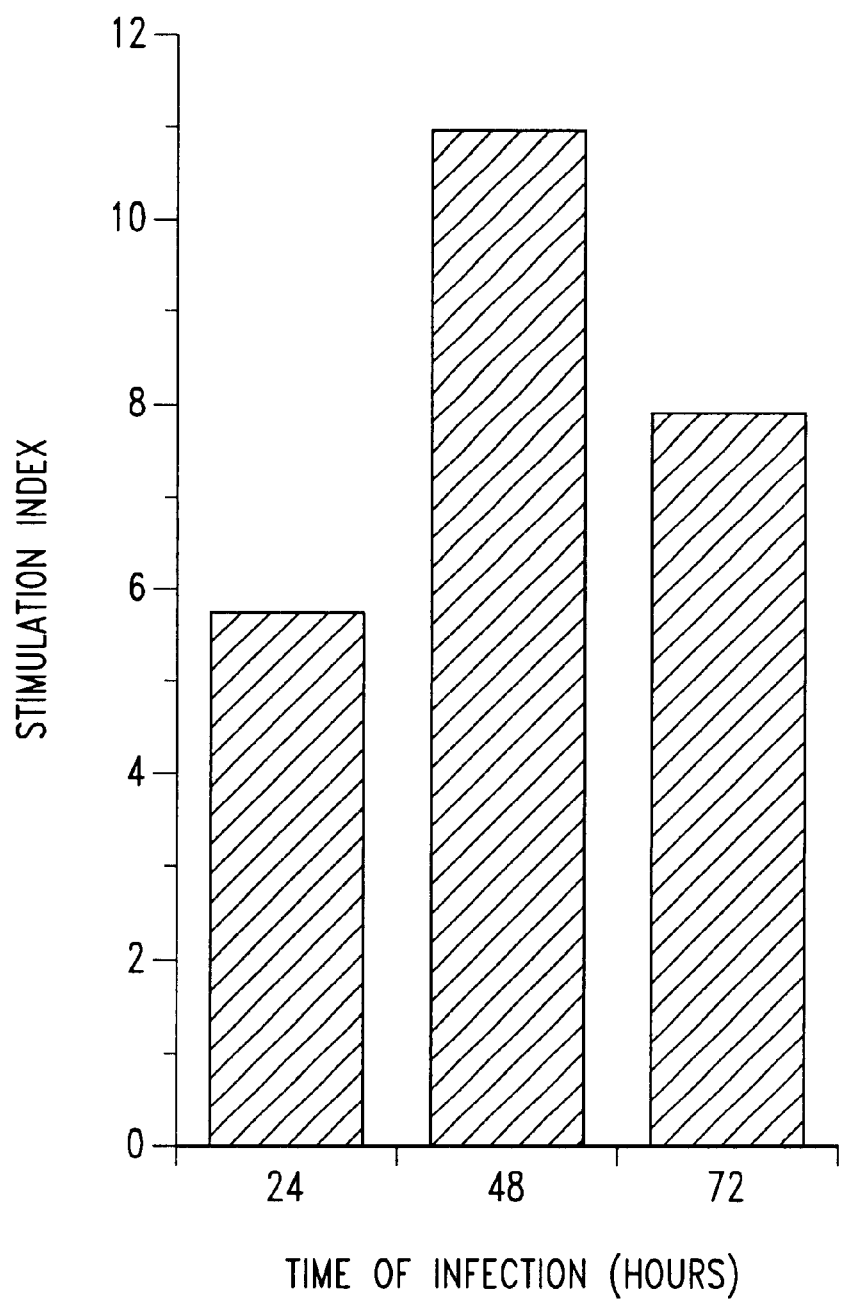
FIG. 1 shows the stimulation of proliferation of T-cells obtained from *L. donovani*-immunized BALB/c mice (represented by stimulation index) by *L. donovani*-infected macrophages after incubation for 24, 48 and 72 hours.

As noted above, the present invention is generally directed to compositions and methods for preventing, treating and detecting leishmaniasis, as well as for stimulating immune responses in patients. The compositions of the subject invention include polypeptides that comprise at least an immunogenic portion of a Leishmania antigen, or a variant of such an antigen. In one preferred embodiment, compositions of the present invention include multiple polypeptides selected so as to provide enhanced protection against a variety of Leishmania species.

Polypeptides within the scope of the present invention include, but are not limited to, polypeptides comprising immunogenic portions of Leishmania antigens comprising the sequences recited in SEQ ID NO:2 (referred to herein as M15), SEQ ID NO:4 (referred to herein as Ldp23), SEQ ID NO:6 (referred to herein as Lbhsp83), SEQ ID NO:8 (referred to herein as Lt-210), SEQ ID NO:10 (referred to herein as LbeIF4A), SEQ ID NO: 20 (referred to herein as Lmspla), SEQ ID NO: 22 (referred to herein as Lmsp9a), SEQ ID NOs: 24 and 26 (referred to herein as MAPS-1A), and SEQ ID NO: 36–38, 41, 50–53, 82, 104, 106, 108, 110, 112 and 118–122. As used herein, the term "polypeptide" encompasses amino acid chains of any length, including full length proteins (i.e., antigens), wherein the amino acid residues are linked by covalent bonds. Thus, a polypeptide comprising an immunogenic portion of one of the above antigens may consist entirely of the immunogenic portion, or may contain additional sequences. The additional sequences may be derived from the native Leishmania antigen or may be heterologous, and such sequences may (but need not) be immunogenic. An antigen "having" a particular sequence is an antigen that contains, within its full length sequence, the recited sequence. The native antigen may, or may not, contain additional amino acid sequence.

An immunogenic portion of a Leishmania antigen is a portion that is capable of eliciting an immune response (i.e., cellular and/or humoral) in a presently or previously Leishmania-infected patient (such as a human or a dog) and/or in cultures of lymph node cells or peripheral blood mononuclear cells (PBMC) isolated from presently or previously Leishmania-infected individuals. The cells in which a response is elicited may comprise a mixture of cell types or may contain isolated component cells (including, but not limited to, T-cells, NK cells, macrophages, monocytes and/or B cells). In particular, immunogenic portions are capable of inducing T-cell proliferation and/or a dominantly Th1-type cytokine response (e.g., IL-2, IFN-γ, and/or TNF-α production by T-cells and/or NK cells; and/or IL-12 production by monocytes, macrophages and/or B cells). Immunogenic portions of the antigens described herein may generally be identified using techniques known to those of ordinary skill in the art, including the representative methods provided herein.

The compositions and methods of the present invention also encompass variants of the above polypeptides. A polypeptide "variant," as used herein, is a polypeptide that differs from a native protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, 99% or more identity (determined as described below) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polynucleotides may comprise a native sequence (i.e., an endogenous sequence that encodes a protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5× SSC, 0.5% SDS, 1.0 mM EDTA (pH 8.0); hybridizing at 50° C–65° C., 5× SSC, overnight; followed by washing twice at 65° C. for 20 minutes with each of 2×, 0.5× and 0.2× SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

"Polypeptides" as described herein also include combination polypeptides, also referred to as fusion proteins. A "combination polypeptide" is a polypeptide comprising at least one of the above immunogenic portions and one or more additional immunogenic Leishmania sequences, which are joined via a peptide linkage into a single amino acid chain. The sequences may be joined directly (i.e., with no intervening amino acids) or may be joined by way of a linker sequence (e.g., Gly-Cys-Gly) that does not significantly diminish the immunogenic properties of the component polypeptides.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in frame. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide. The preparation of fusion proteins of Leishmania antigens is described in detail below in Example 19.

In general, Leishmania antigens having immunogenic properties, and DNA sequences encoding such antigens, may be prepared using any of a variety of procedures from one or more Leishmania species including, but not limited to, *L. donovani, L. chagasi, L. infantum, L. major, L. amazonensis, L. braziliensis, L. panamensis, L. mexicana, L. tropica*, and *L. guyanensis*. Such species are available, for example, from the American Type Culture Collection (ATCC), Rockville, Md. For example, peptides isolated from MHC class II molecules of macrophages infected with a Leishmania species may be used to rescue the corresponding Leishmania donor antigens. MHC class II molecules are expressed mainly by cells of the immune system, including macrophages. These molecules present peptides, which are usually 13–17 amino acids long, derived from foreign antigens that are degraded in cellular vesicles. The bound peptide antigens are then recognized by CD4 T-cells. Accordingly, foreign peptides isolated from MHC class II molecules of, for example, Leishmania-infected murine macrophages may be used to identify immunogenic Leishmania proteins.

Briefly, peptides derived from Leishmania antigens may be isolated by comparing the reverse phase HPLC profile of peptides extracted from infected macrophages with the profile of peptides extracted from uninfected cells. Peptides giving rise to distinct HPLC peaks unique to infected macrophages may then be sequenced using, for example, Edman chemistry as described in Edman and Berg, *Eur J Biochem,* 80:116–132 (1967). A DNA fragment corresponding to a portion of a Leishmania gene encoding the peptide may then be amplified from a Leishmania cDNA library using an oligonucleotide sense primer derived from the peptide sequence and an oligo dT antisense primer. The resulting DNA fragment may then be used as a probe to screen a Leishmania library for a full length cDNA or genomic clone that encodes the Leishmania antigen. Such screens may generally be performed using techniques well known to those of ordinary skill in the art, such as those described in Sambrook et al., *Molecular Cloning: 4 Laboratory Manual*, Cold Spring Harbor Laboratories, Cold Spring Harbor, N.Y. (1989).

This approach may be used to identify a 23 kD *Leishmania donovani* antigen (referred to herein as Ldp23). The sequence of a polynucleotide encoding Ldp23 is provided in SEQ ID NO:3 and the amino acid sequence of Ldp23 is provided in SEQ ID NO: A Using the methods described herein, Ldp23 has been shown to induce a Th1 immune response in T-cells prepared from Leishmania-infected mice.

Alternatively, a Leishmania cDNA or genomic expression library may be screened with serum from a Leishmania-infected individual, using techniques well known to those of ordinary skill in the art. Polynucleotides encoding reactive antigens may then be used to express the recombinant antigen for purification. The immunogenic properties of the purified Leishmania antigens may then be evaluated using, for example the representative methods described herein.

For example, sera from Leishmania-infected mice may be used to screen a cDNA library prepared from Leishmania amastigotes. Reactive clones may then be expressed and recombinant proteins assayed for the ability to stimulate T-cells or NK cells derived from Leishmania-immune individuals (i.e., individuals having evidence of infection, as documented by positive serological reactivity with Leishmania-specific antibodies and/or a Leishmania-specific DTH response, without clinical symptoms of leishmaniasis). This procedure may be used to obtain a recombinant polynucleotide encoding the Leishmania antigen designated M15. The sequence of such a polynucleotide is provided in SEQ ID NO:1, and the amino acid sequence of the encoded protein is provided in SEQ ID NO:2.

A similar approach may be used to isolate a genomic polynucleotide encoding an immunogenic *Leishmania braziliensis* antigen, referred to herein as Lbhsp83. More specifically, a genomic clone encoding Lbhsp83 may be isolated by screening a *L. braziliensis* expression library with sera from a Leishmania-infected individual. The DNA encoding Lbhsp83 is homologous to the gene encoding the eukaryotic 83 kD heat shock protein. The sequence of a polynucleotide encoding nearly all of Lbhsp83 is presented in SEQ ID NO:5, and the encoded amino acid sequence is provided in SEQ ID NO:6. Using the methods described below, Lbhsp83 has been found to stimulate proliferation, and a mixed Th1 and Th2 cytokine profile, in PBMC isolated from *L. braziliensis*-infected patients. Accordingly, Lbhsp83 is an immunogenic Leishmania antigen. Regions of Lbhsp83 that are not conserved with the mammalian gene have been found to be particularly potent for T-cell stimulation and antibody binding. Such regions may be identified, for example, by visual inspection of the sequence comparison provided in FIG. 19.

This approach may also be used to isolate a polynucleotide encoding a 210 kD immunogenic L. tropica antigen, referred to herein as Lt-210. The preparation and characterization of Lt-210, and immunogenic portions thereof (such as Lt-1 and immunogenic repeat and non-repeat sequences), is described in detail in U.S. patent application Ser. No. 08/511,872, filed Aug. 4, 1995. The sequence of a polynucleotide encoding Lt-1 is provided in SEQ ID NO:7 and the encoded amino acid sequence is presented in SEQ ID NO:8.

The above approach may further be used to isolate a polynucleotide encoding a *L. braziliensis* antigen referred to herein as LbeIF4A. Briefly, such a clone may be isolated by screening a *L. braziliensis* expression library with sera obtained from a patient afflicted with mucosal leishmaniasis, and analyzing the reactive antigens for the ability to stimulate proliferative responses and preferential Th1 cytokine production in PBMC isolated from Leishmania-infected patients, as described below. The preparation and characterization of LbeIF4A is described in detail in U.S. patent application Ser. Nos. 08/454,036 and 08/488,386, which are continuations-in-part of U.S. patent application Ser. No. 08/232,534, filed Apr. 22, 1994. The sequence of a polynucleotide encoding LbeIF4A is provided in SEQ ID NO:9 and the encoded amino acid sequence is presented in SEQ ID NO:10. Homologs of LbeIF4A, such as that found in *L. major*, may also be isolated using this approach, and are within the scope of the present invention.

Compositions of the present invention may also, or alternatively, contain soluble Leishmania antigens. As used herein, "soluble Leishmania antigens" refers to a mixture of at least 8 different Leishmania antigens that may be isolated from the supernatant of Leishmania promastigotes of any species grown for 8–12 hours in protein-free medium. Briefly, the organisms are grown to late log phase in complex medium with serum until they reach a density of $2-3\times10^7$ viable organisms per mL of medium. The organisms are thoroughly washed to remove medium components and resuspended at $2-3\times10^7$ viable organisms per mL of defined serum-free medium consisting of equal parts RPMI 1640 and medium 199, both from Gibco BRL, Gaithersburg, Md. After 8–12 hours, the supernatant containing soluble Leishmania antigens is removed, concentrated 10 fold and dialyzed against phosphate-buffered saline for 24 hours. The presence of at least eight different antigens within the mixture of Leishmania antigens may be confirmed using SDS-PAGE (i.e., through the observation of at least 8 different bands). The immunogenic properties of the soluble Leishmania antigens may be confirmed by evaluating the ability of the preparation to elicit an immune response in cultures of lymph node cells and/or peripheral blood mononuclear cells (PBMC) isolated from presently or previously Leishmania-infected individuals. Such an evaluation may be performed as described below.

Individual antigens present within the mixture of soluble Leishmania antigens may be isolated by immunizing mice or rabbits with Leishmania culture supernatant, containing soluble antigens, and employing the resultant sera to screen a Leishmania cDNA expression library as described in detail below. This procedure may be used to isolate recombinant polynucleotides encoding the *L. major* antigens referred to herein as Lmsp1a, Lmsp9a and MAPS-1A. DNA sequences encoding Lmsp1a, Lmsp9a and MAPS-1A are provided in SEQ ID NO: 19, 21 and 23, respectively, with the corresponding predicted amino acid sequences being presented in SEQ ID NO: 20, 22 and 24, respectively. Similarly, sera from mice or rabbits immunized with *L. major* culture supernatant may be used to screen an *L. major* genomic DNA library. As detailed below, this procedure may be used to isolate polynucleotides encoding the *L. major* antigens referred to herein as LmgSP1, LmgSP3, LmgSP5, LmgSP8, LmgSP9, LmgSP13, LmgSP19, and polynucleotides encoding the *L. chagasi* antigens LcgSP1, LcgSP3, LcgSP4, LcgSP8, and LcgSP10. The DNA sequences encoding these antigens are provided in SEQ ID NO:29–35 and 44–48, respectively, with the corresponding amino acid sequences being provided in SEQ ID NO: 36–42 and 49–53. The *L. major* antigens referred to herein as 1G6-34, 1E6-44, 4A5-63, 1B11-39, 2A10-37, 4G2-83, 4H6-41 and 8G3-100 may be isolated by means of CD4+ T cell expression cloning as described below. DNA sequences encoding these antigens are provided in SEQ ID NO: 72–79, respectively, with the corresponding predicted amino acid sequences being provided in SEQ ID NO: 80–87. The immunogenic properties of the isolated Leishmania antigens may be evaluated using, for example, the representative methods described herein.

Regardless of the method of preparation, the antigens described herein are immunogenic. In other words, the antigens (and immunogenic portions thereof) are capable of eliciting an immune response in cultures of lymph node cells and/or peripheral blood mononuclear cells (PBMC) isolated from presently or previously Leishmania- infected individuals. More specifically, the antigens, and immunogenic portions thereof, have the ability to induce T-cell proliferation and/or to elicit a dominantly Th1-type cytokine response (e.g., IL-2, IFN-γ, and/or TNF-α production by T-cells and/or NK cells; and/or IL-12 production by monocytes, macrophages and/or B cells) in cells isolated from presently or previously Leishmania-infected individuals. A Leishmania-infected individual may be afflicted with a form of leishmaniasis (such as subclinical, cutaneous, mucosal or active visceral) or may be asymptomatic. Such individuals may be identified using methods known to those of ordinary skill in the art. Individuals with leishmaniasis may be identified based on clinical findings associated with at least one of the following: isolation of parasite from lesions, a positive skin test with Leishmania lysate or a positive serological test. Asymptomatic individuals are infected individuals who have no signs or symptoms of the disease. Such individuals can be identified based on a positive serological test and/or skin test with Leishmania lysate.

The term "PBMC," which refers to a preparation of nucleated cells consisting primarily of lymphocytes and monocytes that are present in peripheral blood, encompasses both mixtures of cells and preparations of one or more purified cell types. PBMC may be isolated by methods known to those in the art. For example, PBMC may be isolated by density centrifugation through, for example, Ficoll™ (Winthrop Laboratories, New York). Lymph node cultures may generally be prepared by immunizing BALB/c mice (e.g., in the rear foot pad) with Leishmania promastigotes emulsified in complete Freund's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a polypeptide (e.g., a Leishmania antigen or a portion or other variant thereof) to induce a response in PBMC or lymph node cell cultures may be evaluated by contacting the cells with the polypeptide and measuring a suitable response. In general, the amount of polypeptide that is sufficient for the evaluation of about $2\times10^5$ cells ranges from about 10 ng to about 100 μg, and preferably is about 1–10 μg. The incubation of polypeptide with cells is typically performed at 37° C. for about 1–3 days. Following incubation with polypeptide, the cells are assayed for an appropriate response. If the response is a proliferative response, any of a variety of techniques well known to those of ordinary skill in the art may be employed. For example, the cells may be exposed to a pulse of radioactive thymidine and the incorporation of label into cellular DNA measured. In general, a polypeptide that results in at least a three fold increase in proliferation above background (i.e., the proliferation observed for cells cultured without polypeptide) is considered to be able to induce proliferation.

Alternatively, the response to be measured may be the secretion of one or more cytokines (such as interferon-γ (IFN-γ), interleukin-4 (IL-4), interleukin-12 (p70 and/or p40), interleukin-2 (IL-2) and/or tumor necrosis factor-α (TNF-α) or the change in the level of mRNA encoding one or more specific cytokines. In particular, the secretion of interferon-γ, interleukin-2, tumor necrosis factor-α and/or interleukin-12 is indicative of a Th1 response, which is responsible for the protective effect against Leishmania. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, Calif. and PharMingen, San Diego, Calif., and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1-3 \times 10^5$ cells, the production of 30 pg/mL of IL-12, IL-4, IFN-γ, TNF-α or IL-12 p40, or 10 pg/mL of IL-12 p70, is considered able to stimulate production of a cytokine.

Immunogenic portions of the antigens described herein may be prepared and identified using well known techniques, such as those summarized in Paul, Fundamental Immunology, 3rd ed., 243–247 (Raven Press, 1993) and references cited therein. Such techniques include screening polypeptides derived from the native antigen for immunogenic properties using, for example, the representative techniques described herein. An immunogenic portion of a polypeptide is a portion that, within such representative assays, generates an immune response (e.g., proliferation and/or cytokine production) that is substantially similar to that generated by the full length antigen. In other words, an immunogenic portion of an antigen may generate at least about 25%, and preferably at least about 50%, of the response generated by the full length antigen in the model assays described herein.

Portions and other variants of immunogenic Leishmania antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystemsDivision, Foster City, Calif., and may be operated according to the manufacturer's instructions.

Recombinant polypeptides containing portions and/or variants of a native antigen may be readily prepared from a DNA sequence encoding the antigen. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

In general, any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof. For example, variants of a native antigen may generally be prepared using standard mutagenesis techniques, such as oligonucleotide-directed site-specific mutagenesis, and sections of the DNA sequence may be removed to permit preparation of truncated polypeptides.

In another aspect, the present invention provides epitope repeat sequences, or antigenic epitopes, of a Leishmania antigen, together with polypeptides comprising at least two such contiguous antigenic epitopes. As used herein an "epitope" is a portion of an antigen that reacts with sera from Leishmania-infected individuals (i.e. an epitope is specifically bound by one or more antibodies present in such sera). As discussed above, epitopes of the antigens described in the present application may be generally identified using techniques well known to those of skill in the art.

In one embodiment, antigenic epitopes of the present invention comprise an amino acid sequence provided in SEQ ID NO:43, 56, 57 or 58. As discussed in more detail below, antigenic epitopes provided herein may be employed in the diagnosis and treatment of Leishmania infection, either alone or in combination with other Leishmania antigens or antigenic epitopes. Antigenic epitopes and polypeptides comprising such epitopes may be prepared by synthetic means, as described generally above and in detail in Example 15.

In certain aspects of the present invention, described in detail below, the polypeptides, antigenic epitopes, fusion proteins and/or soluble Leishmania antigens of the present invention may be incorporated into pharmaceutical compositions or vaccines. For clarity, the term "polypeptide" will be used when describing specific embodiments of the inventive therapeutic compositions and diagnostic methods. However, it will be clear to one of skill in the art that the antigenic epitopes and fusion proteins of the present invention may also be employed in such compositions and methods.

Pharmaceutical compositions comprise one or more polypeptides, each of which may contain one or more of the above sequences (or variants thereof), and a physiologically acceptable carrier. Vaccines, also referred to as immunogenic compositions, comprise one or more of the above polypeptides and an immunostimulant, such as an adjuvant (e.g., LbeIF4A, interleukin-12 or other cytokines) or a liposome (into which the polypeptide is incorporated). Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. By virtue of its ability to induce an exclusive Th1 immune response, the use of LbeIF4A, and variants thereof, as an adjuvant in the vaccines of the present invention is particularly preferred. Certain other preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, WA; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or Gypsophila or Chenopodium quinoa saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Enhanzyn™ (Corixa, Hamilton, Mont.), RC-529 (Corixa, Hamilton, Mont.) and other aminoalkyl glucosaminide 4-phosphates (AGPs), such as those described in U.S. Pat. No. 6,113,918 and pending U.S. patent application Ser. No. 09/074,720, the disclosures of which are incorporated herein by reference in their entireties, and polyoxyethylene ether adjuvants such as those described in WO 99/52549A1.

Other preferred adjuvants include adjuvant molecules of the general formula (i):

$HO(CH_2CH_2O)_n$—A—R, wherein, n is 1–50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549. The polyoxyethylene ether according to the general formula (I) above may, if desired, be combined with another adjuvant. For example, a preferred adjuvant combination is preferably with CpG as described in the pending UK patent application GB 9820956.2.

Vaccines may additionally contain a delivery vehicle, such as a biodegradable microsphere (disclosed, for example, in U.S. Pat. Nos. 4,897,268 and 5,075,109). Pharmaceutical compositions and vaccines within the scope of the present invention may also contain other Leishmania antigens, either incorporated into a combination polypeptide or present within one or more separate polypeptides.

Alternatively, a pharmaceutical or immunogenic composition may contain an immunostimulant, such as an adjuvant (e.g., LbeIF4A, interleukin-12 or other cytokines, or DNA coding for such enhancers), and DNA encoding one or more of the polypeptides or fusion proteins described above, such that the polypeptide is generated in situ. In such compositions, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993) and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In one preferred embodiment, compositions of the present invention include multiple polypeptides selected so as to provide enhanced protection against a variety of Leishmania species. Such polypeptides may be selected based on the species of origin of the native antigen or based on a high degree of conservation of amino acid sequence among different species of Leishmania. A combination of individual polypeptides may be particularly effective as a prophylactic and/or therapeutic vaccine because (1) stimulation of proliferation and/or cytokine production by a combination of individual polypeptides may be additive, (2) stimulation of proliferation and/or cytokine production by a combination of individual polypeptides may be synergistic, (3) a combination of individual polypeptides may stimulate cytokine profiles in such a way as to be complementary to each other and/or (4) individual polypeptides may be complementary to one another when certain of them are expressed more abundantly on the individual species or strain of Leishmania responsible for infection. A preferred combination contains polypeptides that comprise immunogenic portions of M15, Ldp23, Lbhsp83, Lt-1 and LbeIF4A. Alternatively, or in addition, the combination may include one or more polypeptides comprising immunogenic portions of other Leishmania antigens disclosed herein, and/or soluble Leishmania antigens.

In another preferred embodiment, compositions of the present invention include single polypeptides selected so as to provide enhanced protection against a variety of Leishmania species. A single individual polypeptide may be particularly effective as a prophylactic and/or therapeutic vaccine for those reasons stated above for combinations of individual polypeptides.

In another embodiment, compositions of the present invention include individual polypeptides and combinations of the above described polypeptides employed with a variety of adjuvants, such as IL-12 (protein or DNA) to confer a protective response against a variety of Leishmania species.

In yet another embodiment, compositions of the present invention include DNA constructs of the various Leishmania species employed alone or in combination with variety of adjuvants, such as IL-12 (protein or DNA) to confer a protective response against a variety of Leishmania species.

The above pharmaceutical compositions and vaccines may be used, for example, to induce protective immunity against Leishmania in a patient, such as a human or a dog, to prevent leishmaniasis. Appropriate doses and methods of administration for this purposes are described in detail below.

The pharmaceutical and immunogenic compositions described herein may also be used to stimulate an immune response, which may be cellular and/or humoral, in a patient. For Leishmania-infected patients, the immune responses that may be generated include a preferential Th1 immune response (i.e., a response characterized by the production of the cytokines interleukin-1, interleukin-2, interleukin-12 and/or interferon-γ, as well as tumor necrosis factor-α). For uninfected patients, the immune response may be the production of interleukin-12 and/or interleukin-2, or the stimulation of gamma delta T-cells. In either category of patient, the response stimulated may include IL-12 production. Such responses may also be elicited in biological samples of PBMC or components thereof derived from Leishmania-infected or uninfected individuals. As noted above, assays for any of the above cytokines may generally be performed using methods known to those of ordinary skill in the art, such as an enzyme-linked immunosorbent assay (ELISA).

Suitable pharmaceutical compositions and vaccines for use in this aspect of the present invention are those that contain at least one polypeptide comprising an immunogenic portion of a Leishmania antigen disclosed herein (or a variant thereof). Preferably, the polypeptides employed in the pharmaceutical compositions and vaccines are complementary, as described above. Soluble Leishmania antigens, with or without additional polypeptides, may also be employed.

The pharmaceutical compositions and vaccines described herein may also be used to treat a patient afflicted with a disease responsive to IL-12 stimulation. The patient may be any warm-blooded animal, such as a human or a dog. Such diseases include infections (which may be, for example, bacterial, viral or protozoan) or diseases such as cancer. In one embodiment, the disease is leishmaniasis, and the patient may display clinical symptoms or may be asymptomatic. In general, the responsiveness of a particular disease to IL-12 stimulation may be determined by evaluating the effect of treatment with a pharmaceutical composition or vaccine of the present invention on clinical correlates of immunity. For example, if treatment results in a heightened Th1 response or the conversion of a Th2 to a Th1 profile, with accompanying clinical improvement in the treated patient, the disease is responsive to IL-12 stimulation. Polypeptide administration may be as described below, or may extend for a longer period of time, depending on the indication. Preferably, the polypeptides employed in the pharmaceutical compositions and vaccines are complementary, as described above. A particularly preferred combination contains polypeptides that comprise immunogenic portions of M15, Ldp23, Lbhsp83, Lt-1and LbeIF4A, Lmspla, Lmsp9a, and MAPS-1A. Soluble Leishmania antigens, with or without additional polypeptides, may also be employed.

Routes and frequency of administration, as well as dosage, for the above aspects of the present invention will vary from individual to individual and may parallel those currently being used in immunization against other infections, including protozoan, viral and bacterial infections. In general, the pharmaceutical compositions and vaccines may be administered by injection (e.g., intracutaneous, intramuscular, intravenous or subcutaneous), intranasally (e.g., by aspiration) or orally. Between 1 and 12 doses may be administered over a 1 year period. For therapeutic vaccination (i.e., treatment of an infected individual), 12 doses are preferably administered, at one month intervals. For prophylactic use, 3 doses are preferably administered, at 3 month intervals. In either case, booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from leishmaniasis for at least 1–2 years. In general, the amount of polypeptide present in a dose (or produced in situ by the DNA in a dose) ranges from about 100 ng to about 1 mg per kg of host, typically from about 10 μg to about 100 μg. Suitable dose sizes will vary with the size of the patient, but will typically range from about 0.1 mL to about 5 mL.

In another aspect, this invention provides methods for using one or more of the polypeptides described above to diagnose Leishmania infection in a patient using a skin test. As used herein, a "skin test" is any assay performed directly on a patient in which a delayed-type hypersensitivity (DTH) reaction (such as induration and accompanying redness) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 72 hours after injection.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, induration that is greater than about 0.5 cm in diameter, preferably greater than about 1.0 cm in diameter, is a positive response, indicative of Leishmania infection, which may or may not be manifested as an active disease.

The polypeptides of this invention are preferably formulated, for use in a skin test, as pharmaceutical compositions containing at least one polypeptide and a physiologically acceptable carrier, as described above. Such compositions typically contain one or more of the above polypeptides in an amount ranging from about 1 µg to 100 µg, preferably from about 10 µg to 50 µg in a volume of 0.1 mL. Preferably, the carrier employed in such pharmaceutical compositions is a saline solution with appropriate preservatives, such as phenol and/or Tween 80™.

The inventive polypeptides may also be employed in combination with one or more known Leishmania antigens in the diagnosis of leishmaniasis, using, for example, the skin test described above. Preferably, individual polypeptides are chosen in such a way as to be complementary to each other. Examples of known Leishmania antigens which may be usefully employed in conjunction with the inventive polypeptides include K39 (Burns et al., *Proc. Natl. Acad. Sci. USA*, 1993 90:775–779).

The following Examples are offered by way of illustration and not by way of limitation.

EXAMPLES

Example 1

Preparation of M15

This Example illustrates the preparation of a Leishmania antigen M15, having the sequence provided in SEQ ID NO:2.

An *L. major* (Friedlan strain) amastigote cDNA expression library prepared in the λZAP II vector (Stratagene, La Jolla, Calif.) was screened according to manufacturer's instructions using sera obtained from *L. major* infected BALB/c mice (8 weeks post inoculation). Approximately 40,000 plaques were screened and four clones expressing reactive antigens were purified to homogeneity by two subsequent rounds of low density screening. Bluescript phagemid inserts were excised from positive clones for further analysis. An EcoRI/SstII restriction fragment from the 5' end of one partial cDNA insert isolated during first round screening (pLmaI-1) was subsequently used as a probe to rescreen for clones containing full length cDNA inserts. The probe was labeled to high specific activity (~$10^9$ cpm/µg) with [α-$^{32}$P]dCTP using the random primer method and was used to screen ~10,000 plaques of the *L. major* expression library described above. Positive clones were compared by restriction enzyme digestion and the clone with the largest insert (pfl1-1) was chosen for subsequent analysis.

DNA sequence analyses were performed on an Applied Biosystems automated sequencer using Taq polymerase and dye coupled ddNTP terminators or dye-labeled sequencing primers. The complete sequence of the 2685 bp insert was determined using a combination of primer-directed sequencing and by sequencing a series of overlapping Exonuclease III deletion subclones generated using the Erase-a-base system (Promega, Madison, Wis.). The sequence of this insert is provided in SEQ ID NO: 1, and the deduced amino acid sequence is provided in SEQ ID NO:2.

The complete insert of clone pfl1–1 was excised by digestion with BamHI/KpnI and was subcloned in frame into BamHI/KpnI digested pQE31 (QUIAGEN) to generate the construct pM151A. *E. coli* containing this construct inducibly expressed high levels of the *L. major* antigen encoded by pfl1-1 (designated as M15) with the addition of a 6-histidine tag at the amino terminus. Large volume cultures (500 ml) of *E. coli* host cells containing the pM151 A construct were induced to express recombinant protein by the addition of 2 mM IPTG at mid-log phase of growth. Growth was continued for 4 to 5 hours and bacteria were then pelleted and washed once with cold PBS. Bacteria were resuspended in 20 ml of lysis buffer (50 mM $Na_2HPO_4$, pH 8.0, 300 mM NaCl, 10 mM β-mercaptoethanol) containing 20 mg of lysozyme and were lysed by a 1 hour incubation at 4° C. followed by brief sonication. Insoluble material was removed by centrifugation at 10,000× g for 10 minutes and although the recombinant protein was found to be evenly distributed between the soluble and insoluble fractions the insoluble material was discarded at this point. Recombinant protein containing the amino terminal histidine tag was affinity purified using Ni-NTA resin (QIAGEN) according to the manufacturer's recommendations. Briefly, 8 ml of Ni-NTA resin resuspended in lysis buffer was added to the soluble lysate fraction and binding was conducted with constant mixing for 1 hour at 4° C. The mixture was then loaded into a gravity flow column and the non-binding material was allowed to flow through. The Ni-NTA matrix was washed 3 times with 25 ml of wash buffer (50 mM $Na_2HPO_4$, pH 6.0, 300 mM NaCl, 10 mM β-mercaptoethanol) and bound material was eluted in 25 ml of elution buffer (50 mM $Na_2HPO_4$, pH 5.0, 300 mM NaCl, 10 mM β-mercaptoethanol). The eluted material was then dialyzed against 3 changes of PBS, sterile filtered and stored at −20° C. The purified recombinant protein was shown by SDS-PAGE analysis to be free of any significant amount of *E. coli* protein. A small number of bands of lower molecular weight were assumed to be proteolytic products of the *L. major* antigen based on their reactivity by western blot analysis. A high titre polyclonal antisera against M15 was generated in rabbits by repeated subcutaneous injection of recombinant protein. Western blot analysis of lysates from *L. major* promastigotes and amastigotes using this antisera indicated that the protein is constitutively expressed throughout the parasite lifecycle.

Example 2

Preparation of LDP23

This Example illustrates the preparation of a Leishmania antigen Ldp23, having the sequence provided in SEQ ID NO:4.

A. Purification of MHC Class II-associated Peptides from P388D1 Macrophages Infected with *L. donovani*

To ascertain that in vitro infection of macrophages would load their MHC class II molecules with parasite peptides, initial experiments were carried out to test the ability of *L. donovani*-infected macrophage cell line P388D1 to present parasite antigens to *L. donovani* specific T-cells. This macrophage cell line was chosen because it has the same H-2 haplotype as the BALB/c mouse, which is a strain of mouse moderately susceptible to *L. donovani* infection and selected to conduct the in vivo experiments. Using a proportion of 3–5 parasites per cell and an initial incubation at room temperature for 4–6 hours follows by 37° C. for 24–48 hours, close to 90% of the macrophages were infected. The level of MHC class II molecule expression, as determined by FACS analysis, indicated that infection did not cause an effect on the levels of MHC class II expression when compared to non-infected control cells.

To test the ability of the *L. donovani*-infected P388D1 cells to present parasite antigens, macrophages were infected as indicated above and incubated at 26° C. for 6 hours, and then as 37° C. for either 24, 48 or 72 hours. At each of these time points the non-adherent cells and free parasites were washed out and the adherent cells were mechanically dislodged, washed and fixed with paraformaldehyde. These cells were then used as antigen presenting cells (APCs) for purified lymph node T-cells from BALB/c mice immunized with *L. donovani* promastigotes. To generate these anti-*L. donovani* specific T-cells, BALB/c mice (H-2$^d$) of both sexes (The Jackson Laboratory, Bar Harbor, Me.) were immunized at 8 to 14 weeks of age in the rear foot pad with 5–10×10$^6$ *L. donovani* promastigotes emulsified in complete Freund's adjuvant (CFA) (Difco Laboratories, Madison, Mich.) as described in Rodrigues et al., *Parasite Immunol.* 14:49 (1992). The draining lymph nodes were excised 8 days after the immunization and T-cells were purified in an anti-mouse Ig column to remove the B cells, as described in Bunn-Moreno and Campos-Neto, *J. Immunol.* 127:427 (1981), followed by a passage through a Sephadex G10 column to remove the macrophages.

Stimulation index was calculated by dividing the cpm obtained for the cells cultured in the presence of infected P388D1 macrophages by the cpm obtained for the cells cultured in the presence of non-infected macrophages, but subjected to the same conditions as the infected macrophages. The results shown FIG. 1 indicate that *L. donovani*-infected P388D1 macrophage process parasite antigens and that optimal presentation occurs after 48 hours of infection. No stimulation of the T-cells by the non-infected macrophages was observed.

To isolate the MHC class II associated *L. donovani* peptides, P388D1 macrophages were infected with *L. donovani* promastigotes for an initial incubation of 6 hours at room temperature. The cultures were then transferred to 37° C. for the remainder of the 48 hour incubation period. At a ratio of 3–5 parasites per macrophage nearly 90% of the macrophages were infected after 24 hours of incubation at 37° C.

The MHC class II molecules were then affinity-purified. Approximately 1.5×10$^{10}$ *L. donovani*-infected or an equal number of non-infected P388D1 macrophages were used for each purification. The cells were harvested, washed with PBS and incubated for 30 minutes in cold lysis buffer (PBS, 1% Nonidet P40, 25 mM iodoacetamide, 0.04% sodium azide, 1 mM aprotinin and 1 mM PMSF). The insoluble material was removed by centrifugation at 40,000 g for 1 hour and the supernatant was recycled overnight at 4° C. over a 5 ml anti-MHC class II molecules (H-2d) Sepharose column (Protein G Sepharose column to which the monoclonal antibody MK-D6 has been bound). Culture supernatants of MK-D6 hybridoma cells (American Type Culture Collection, Rockville, Md.) were employed as the source for anti-MHC class II (H-2 d) monoclonal antibody. The column was washed with 50 ml of lysis buffer and then with 50 ml of PBS containing 0.5% octyl glucopyranoside detergent. Bound molecules were eluted from the column with 1M acetic acid in 0.2% NaCl. The MHC/peptide molecules were separated from the IgG (MK-D6 monoclonal antibody) using a Centricon 100 filter unit (Amicon Division, W.R. Grace & Co., Beverly, Mass.). The peptides were then dissociated from the class II molecules by the addition of acetic acid to 2.5M, followed by separation using a Centricon 10 filter unit. The resulting peptide preparation, present in the low molecular weight sample, was then dried using a speed vac concentrator (Savant Instrument Inc., Farmingdale, N.Y.).

Figure 2A:
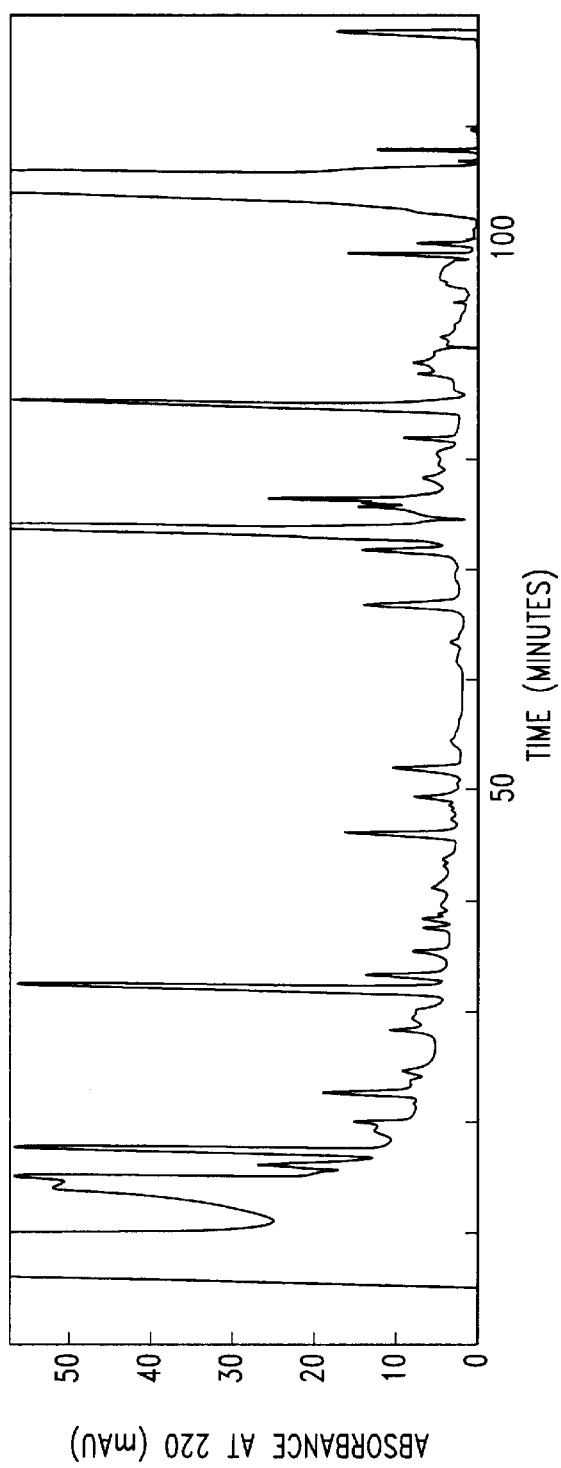
FIG. 2 illustrates representative HPLC profiles of peptides isolated from MHC class II molecules of P388D1 macrophages. Panel A shows peptides isolated from uninfected macrophages and panel B shows peptides isolated from *L. donovani* infected macrophages. The arrows in panel B indicate peptide peaks present only in the infected macrophage preparation.
Figure 2B:
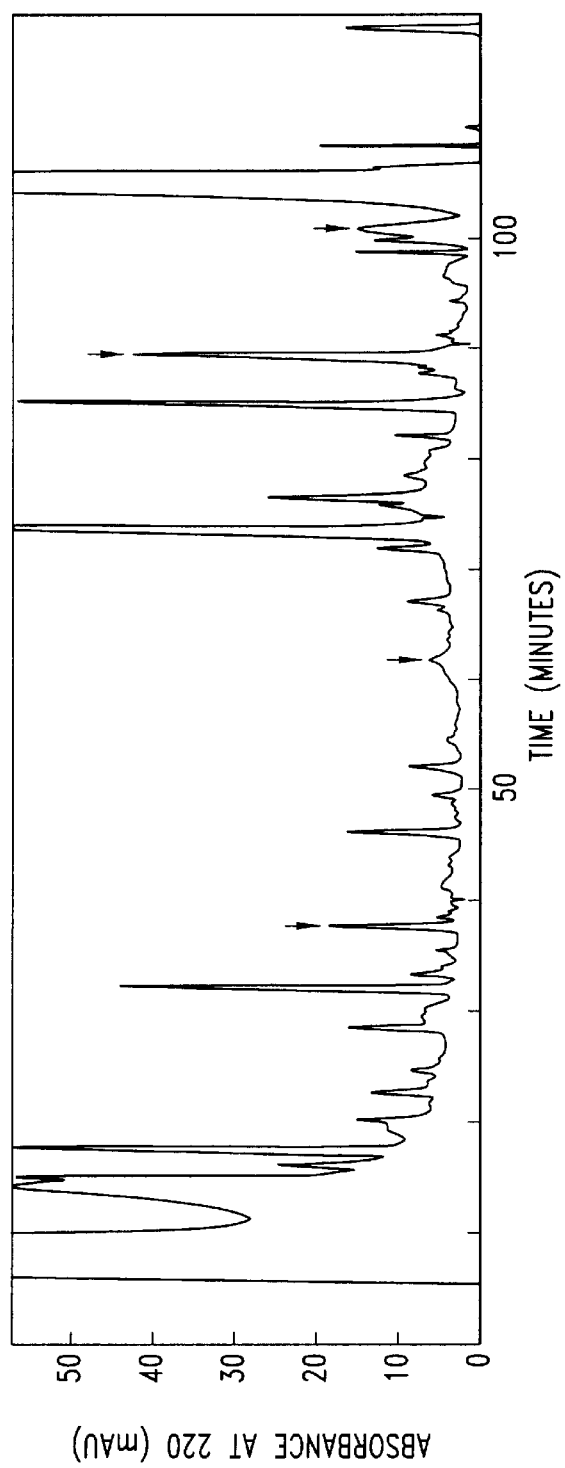

The peptides were redissolved in 200 μl of 0.05% TFA and separated by reverse-phase high performance liquid chromatography (RP-HPLC) using a 2.1 mm×25 cm Vydac C-18 column at a flow rate of 0.15 ml/min employing a 1 to 30% acetonitrile gradient (60 min) followed by a 30 to 60% gradient (30 min) and then a 60 to 80% gradient (90–110 min). Non-infected P388D1 cells were similarly processed to serve as background control for endogenous MHC class II associated peptides. FIG. 2 shows a representative experiment; four distinct peaks which are present only in the material isolated from infected macrophages (panel B), and not in the material isolated from uninfected macrophages (panel A) are indicated.

Out of three independent peptide extractions, twenty five distinct HPLC peptide peaks were isolated from *L. donovani*-infected macrophages and were subjected to protein sequence analysis using automated Edman degradation on an Applied Biosystems 477 gas-phase protein sequencer. Protein sequence and amino acid analysis were performed by the W.M. Keck Foundation, Biotechnology Resource Laboratory, Yale University, New Haven, Conn. In practically all determinations, no assignment could be made for the first position. Also, in most cases the definition of the amino acid residues of the 10–15 positions was based on the quantitative dominance of one residue over others. Using this approach, the sequences obtained for several peptides showed the presence of 3–6 different residues in many of the 10–15 sequence cycles analyzed for each determination, reflecting a mixture of peptides. In addition, sequences could not be obtained for some peaks because the peptides were blocked. Notwithstanding, three peptides sequences were determined. Amino-acid sequences were searched for identity with proteins in the GenBank database using the GENPETP, PIR and SWISSPROT programs. The sequence data base analysis revealed that one of the peptides was highly homologous to glyceraldehyde-3-phosphate dehydrogenase of various species. Another peptide had homology with elongation factor of several species, including Leishmania. The third sequence was not clearly related to any known proteins, and is shown below:

XQXPQ(L/K)VFDEXX (SEQ ID NO:11).

B. Cloning and Sequencing of the Ldp23 Gene

In order to retrieve the *L. donovani* protein that was processed into a peptide associated with the MHC class II molecules of infected macrophages, the peptide sequence of uncertain origin was chosen to guide the strategy for cloning the corresponding parasite gene. A DNA fragment was initially amplified from *L. donovani* promastigote cDNA by PCR. The sense primer was a peptide derived oligonucleotide (5'>GGAATTCCCCInCAGCTInGTInTTCGAC<3')

(SEQ ID NO:12) containing an EcoRI restriction endonuclease site (underlined). The bases were selected following the preferential codon usage of *L. donovani*, as described in Langford et al., *Exp. Parasitol.* 74:360 (1992). Inosine was used for the residues of positions 4, 6 and 7 because of the low codon usage assurance for the corresponding amino acids. In addition, the carboxyl-terminal L-glutamic acid was not included for the design of the primer. The antisense primer was a poly-thymidine oligonucleotide (oligo dT, downstream primer) containing a XhoI restriction endonuclease site.

The gene fragment was amplified from a *L. donovani* promastigote cDNA preparation using the following reaction conditions: one cycle of 3 min at 94° C. immediately followed by 35 cycles of 1 min at 94° C., 1 min at 45° C. and 1 min at 72° C. The *L. donovani* cDNA was prepared from $5 \times 10^7$ washed promastigote forms harvested at the log growth phase (3 days culture). The cDNA was obtained using an Invitrogen cDNA cycle™ kit (Invitrogen Co., San Diego, Calif.). Oligonucleotide primers were synthesized by the DNA Synthesis Laboratory, Department of Pathology, Yale University School of Medicine.

The PCR products were analyzed by gel electrophoresis. Only one band of approximately 300 bp was obtained. This fragment was cloned and its sequence confirmed the sequence of the peptide-based primer including the glutamic acid codon, deliberately not included in the primer sequence.

The PCR amplified gene fragment was ligated into the pCR™ vector using the TA cloning system (Invitrogen Co., San Diego, Calif.). Transformants were selected in LB medium containing 100µg/ml ampicillin and the plasmid DNA was isolated using the Wizard™ Minipreps DNA purification kit (Promega Co., Madison, Wis.). Insert DNA was released with the restriction enzymes EcoRI and XhoI (New England Biolabs, Beverly, Mass.), purified from an agarose gel electrophoresis and labeled with $^{32}$P using a random priming method (Megaprime Labeling Kit, Amersham Life Science, Buckinghamshire, England).

This DNA fragment was used as probe to screen a *L. donovani* promastigote cDNA library as described in Skeiky et al., *Infect. Immun.* 62:1643 (1994). An approximately 650 bp cDNA (Ldp23) was excised from the phagemid by in vivo excision using the Stratagene protocol. DNA sequencing was performed using the Sequenase version 2 system (DNA sequencing kit) in the presence or absence of 7-deaza-GTP (United States Biochemical, Cleveland, Ohio). The sequence is provided as SEQ ID NO:3, and shows complete homology with the original 300 bp PCR fragment. A 525 bp open reading frame containing an ATG codon that follows the last 4 bases of the spliced leader sequence and 3 stop codons adjacent to the poly A tail was identified. This frame also codes the carboxyl terminal sequence (KVFDE) (SEQ ID NO:13) of the purified MHC class II associated peptide. The sequence analysis of the deduced protein sequence revealed one potential glycosylation site (Asn-Cys-Ser) at positions 68–70.

Sequence analysis was performed using the University of Wisconsin Genetics Computer Group Programs and the GenBank and EMBL data bases of protein and DNA sequences. The search for homology of the Ldp23 gene with known sequences revealed no significant homology.

C. Bacterial Expression and Purification of Recombinant Protein

The recombinant *L. donovani* peptide donor protein was produced in *E. coli* transformed with the pGEX 2T expression vector in which the Ldp23 gene was subcloned in frame. PCR was used to subclone the cloned gene in frame into the expression vector pGEX 2T. Primers containing the appropriate restriction site enzymes, initiation and termination codons were: 5'>GGATCCATGGTCAAGTCCCACTACATCTGC<3' (SEQ ID NO:14) for the upstream primer and 5'>GAATTCAGACCGGATAGAAATAAGCCAATGAAA<3' (SEQ ID NO:15) for the downstream primer (restriction sites of BamHI and EcoRI are underlined respectively). PCR conditions were as indicated above for the amplification of the original peptide related DNA fragment. The template used was pBluescript plasmid containing the cloned gene from the cDNA library.

Overexpression of the recombinant fusion protein was accomplished by growing the transformed *E. coli* (DH5α) and inducing the tac promoter with 1 mM isopropyl-β-thiogalactopyranoside (IPTG) (Stratagene, La Jolla, Calif.). Cells were collected, centrifuged, and analyzed for the presence of the fusion protein by SDS-PAGE. A glutathione-S-transferase fusion protein of 43–44 kD was produced, indicating a leishmanial protein of approximately 18 kD, as glutathione-S-transferase (GST) has a MW of 26 kD. However, the fusion protein was very insoluble and therefore could not be purified by affinity chromatography using a glutathione column. The use of low concentrations of detergents like SDS, sarcosyl, deoxycolate, and octyl-glucopyranoside during the extraction steps was efficient to solubilize the protein but unfortunately prevented its binding to the glutathione column. Other maneuvers, such as the growth of the *E. coli* and incubation and induction of the tac promoter with IPTG at 33° C., did not improve the protein solubility. However, the purification was achieved by preparative SDS-PAGE. The band was visualized with 0.1M KCl, cut and electroeluted from the gel followed by extensive dialysis against PBS and concentration on Centricon 10 filters.

Figure 3A:
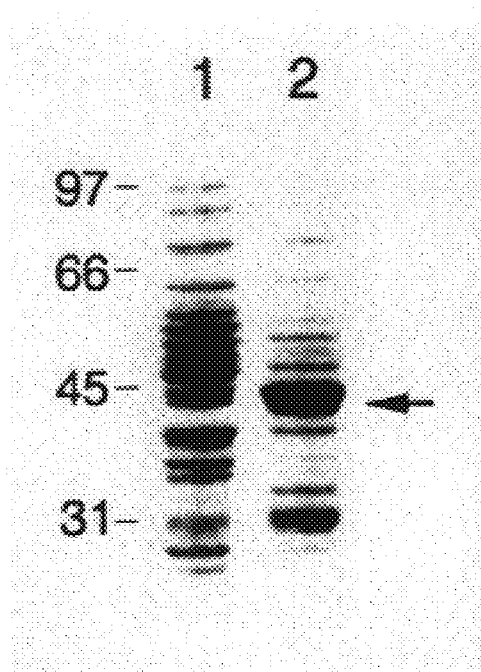
FIG. 3 illustrates the expression and purification of the Leishmania antigen Ldp23 as a recombinant fusion protein. Panel A shows a Coomassie blue-stained SDS-PAGE gel of lysed *E. coli* without (lane 1) and with (lane 2) IPTG induction of Ldp23 expression. Arrow indicates the recombinant fusion protein. Panel B shows the fusion protein following excision from a preparative SDS-PAGE gel, electroelution, dialysis against PBS and analytical SDS-PAGE.
Figure 3B:
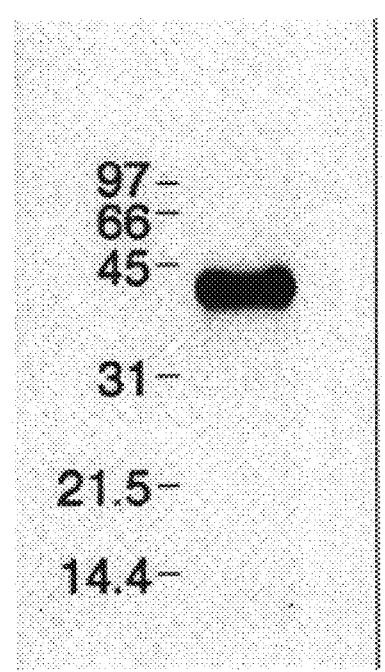

Approximately 500 µg of purified protein was obtained. The purified protein is shown in FIG. 3. In panel A, *E. coli* (DH5α) transformed with the expression vector pGEX 2T containing the Ldp23 gene was grown in LB medium and the tac promoter was induced with IPTG for 3 hours. The cells were pelleted, resuspended in loading buffer and submitted to SDS-PAGE (10%) under reducing condition. The gel was stained with Coomassie blue. Lane 1 shows the uninduced E. coli and land 2 shows the induced *E. coli*. The arrow indicates the recombinant protein. Panel B shows the protein prepared as in panel A and submitted to a preparative SDS-PAGE. The band corresponding to the overexpressed recombinant fusion protein was identified by KCl, cut out, electroeluted from the gel strip, dialyzed against PBS and submitted to analytical SDS-PAGE (12%). Numbers on the left side indicate the molecular weights of the markers. Attempts to further purify the leishmanial protein by cleaving it out from the fusion protein GST with thrombin were unsuccessful.

D. Expression of Ldp23

To ascertain that the Ldp23 peptide is expressed in Leishmania organisms, a Northern blot analysis was performed using RNA prepared from different promastigote growth phases (logarithmic and stationary) and from the amastigote form of these parasites.

The RNA was prepared from $2 \times 10^7$ parasite cells using the Micro RNA isolation kit (Stratagene, La Jolla, Calif.) according to the company's recommended instructions. RNA was prepared from L. donovani promastigotes (logarithmic growth phase); from *L. major* promastigotes (logarithmic and stationary growth phases); from *L. amazonensis*, both promastigotes (logarithmic and stationary growth phases) and amastigotes purified from CBA/J infected mice; and from *L. pifanoi*, both promastigotes (logarithmic and stationary growth phases) and amastigotes (from axenic culture medium). L. donovani (1S strain), *L. amazonensis* (MHOM/BR/77/LTB0016), *L. major* (MHOM/IR/79/LRC-L251) and *L. pifanoi* (MHOM/VE/60/Ltrod) promastigotes were grown and maintained at 26° C. in Schneider's medium containing 20% FCS and 50 μg/ml gentamicin. The amastigote forms of *L. amazonensis* were obtained by differential centrifugation of a "pus-like" foot pad lesion of a CBA/J mouse infected for 6 months with this parasite. *L. pifanoi* amastigotes were obtained from axenic culture as previously reported by Pan et al., *J. Euk. Microbiol.* 40:213 (1993).

The hybridization was carried out at 45° C. in the presence of 50% formamide, 5× Denhardt's solution, 0.1% SDS, 100 μg/ml single stranded salmon sperm DNA and 5× SSPE using 0.45 μm Nytran membrane filters (Schleicher & Schuell, Keene, NH). The probe was the $^{32}$P labeled Ldp23 gene.

Figure 4:
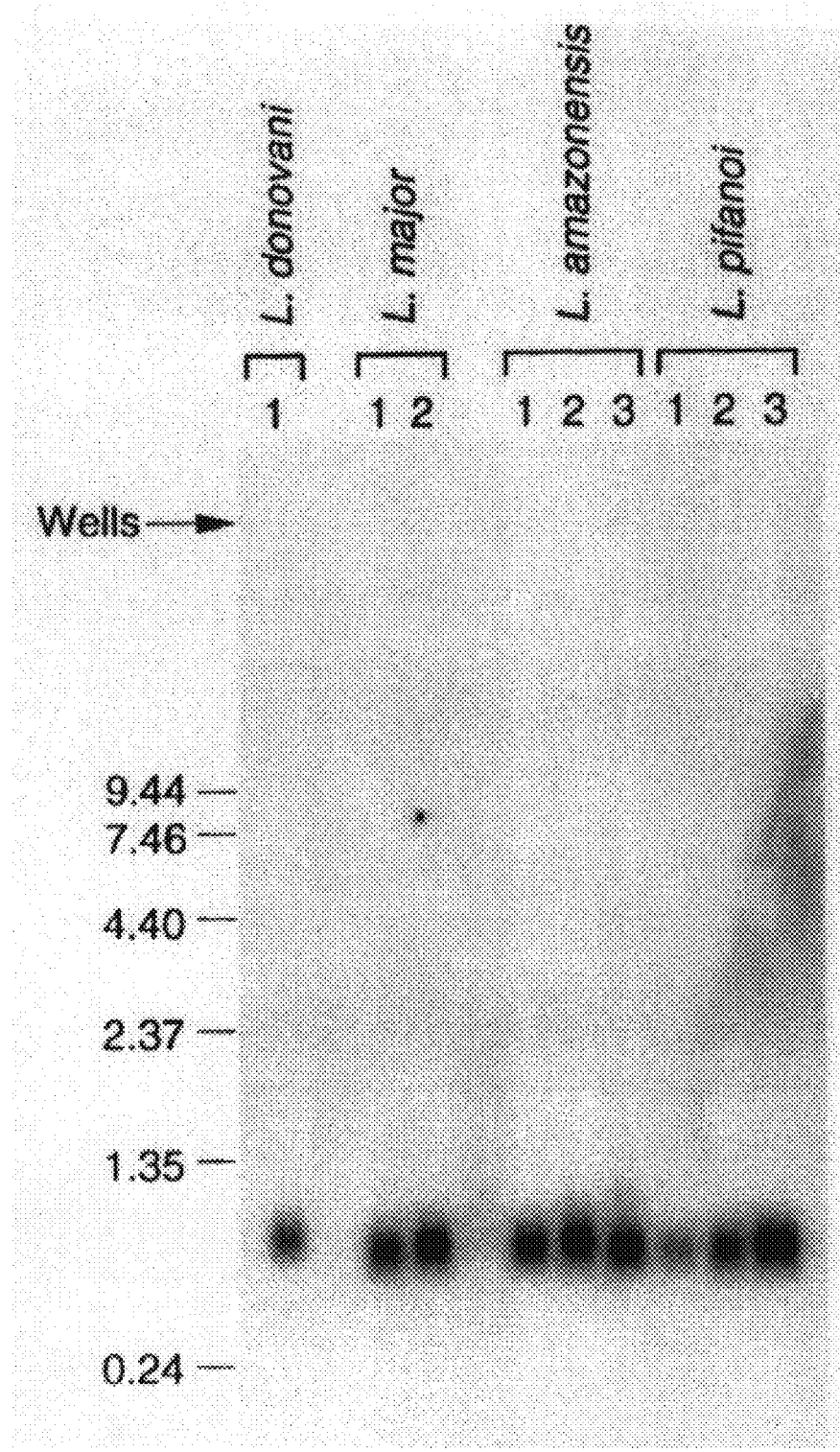
FIG. 4 presents a Northern blot analysis of total RNA prepared from *L. donovani*, *L. major*, *L. amazonensis* and *L. pifanoi* with a $^{32}$P labeled Ldp23 gene. 1, 2 and 3 refer to RNA obtained from promastigotes at the logarithmic growth phase, promastigotes at the stationary growth phase and amastigote forms, respectively.

FIG. 4 shows that one single RNA band of 680 bp was observed for all growth phases and forms of all tested Leishmania. Within FIG. 4, the numbers 1, 2 and 3 refer to RNA obtained from promastigotes at the logarithmic growth phase, promastigotes at the stationary growth phase and amastigote forms, respectively, and the numbers on the left side indicate the molecular weights of the markers in base pairs. This result is consistent with the corresponding gene size (525 bp) and with the molecular weight of the expressed protein and points to the ubiquitous distribution and expression of this gene within the genus Leishmania.

E. Induction of Anti-*L. donovani* Antibody Response in Mice and Rabbits by Purified Recombinant Protein In order to evaluate the immunogenicity of the recombinant leishmanial protein, and to investigate its expression in the parasites, mice and rabbits were immunized with the GST-fusion protein in CFA. BALB/c mice were immunized in the rear foot pad with 5–10 μg of protein emulsified in CFA. Protein concentration was determined using the Bio-Rad Protein Assay reagent (Bio-Rad Laboratories, Richmond, Calif.). The mice were boosted 7 days later with 5–10 μg of protein emulsified in incomplete Freund's adjuvant (IFA) inoculated into the peritoneal cavity. The mice were bled 7 days after the second immunization. New Zealand white rabbits (Millbrook Farm, Amherst, Mass.) were immunized according to the following protocol: one intramuscular (IM) injection of 25–30 μg of purified recombinant protein emulsified in CFA into each thigh on day one; one 1M injection of 25–30 μg of purified protein emulsified in IFA into each shoulder on day 7; on day 15, 25–30 μg of the purified protein in PBS was injected into the subcutaneous tissue. The rabbit was bled 7 days after the last immunization.

Sera were prepared and the anti-Leishmania antibody response was measured by Western blot analysis and by FACScan. In both cases *L. donovani* promastigotes were used as antigen. Approximately 2×10$^6$ *L. donovani* promastigotes were grown in Schneider's medium for 3 days (log phase), were washed with PBS, lysed with SDS-PAGE loading buffer and submitted to electrophoresis under reducing conditions using a 15% polyacrylamide gel. The proteins were transferred onto 0.45μ Immobilon-P transfer membrane (Millipore Co., Bedford, Mass.) using a wet-type electroblotter (Mini Trans-Blot Electrophoretic Transfer Cell, Bio Rad Life Science Division, Richmond, Calif.) for 2 hours at 50 V. The membranes were blocked overnight at room temperature with PBS containing 3% normal goat serum (NGS), 0.2% Tween-20 and 0.05% sodium azide, followed by 3 washes with PBS. The blots were then incubated for 3–4 hours at 4° C. with a ½00 dilution of pre-immune rabbit serum (lane A, FIG. 5) or with the same dilution of anti-fusion protein rabbit antiserum (lane B, FIG. 5). The sera was previously absorbed 2× with non-viable desiccated *Mycobacterium tuberculosis* H-37 RA (Difco Laboratories, Detroit, Mich.) and were diluted in PBS containing 1% NGS and 5% powdered non-fat bovine milk (Carnation, Nestlé Food Company, Glendale, Calif.). The membranes were then washed with PBS, incubated for 1 hour at room temperature with goat anti-rabbit IgG antibody conjugated with alkaline phosphatase (Promega, Madison, Wis.), washed once with PBS and 2× with veronal buffer pH 9.4. The reaction was visualized using the substrate mixture 5-bromo-4-chloro-3-indoyl-phosphate and nitroblue tetrazolium (Kirkegaard & Perry Laboratories Inc., Gaithersburg, Md.) according to the manufacturer's instructions.

Figure 5A:
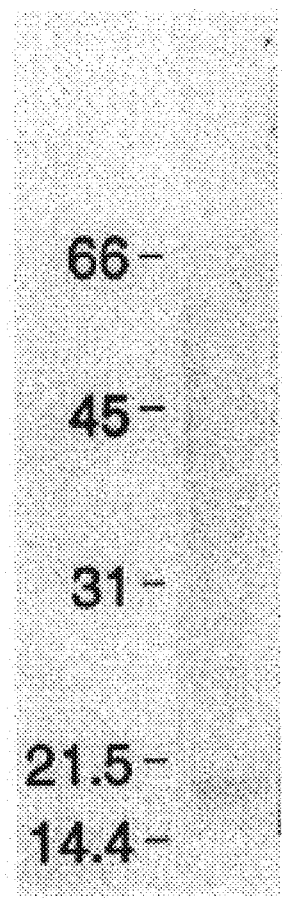
FIG. 5 shows a Western blot analysis of *L. donovani* promastigote antigens incubated with pre-immune rabbit serum (lane A) or with anti-Ldp23 rabbit antiserum (lane B).
Figure 5B:
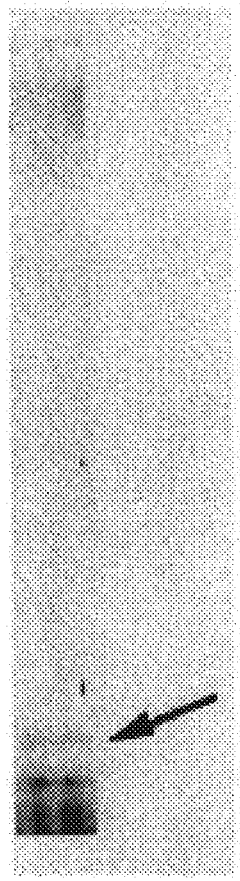
Figure 6:
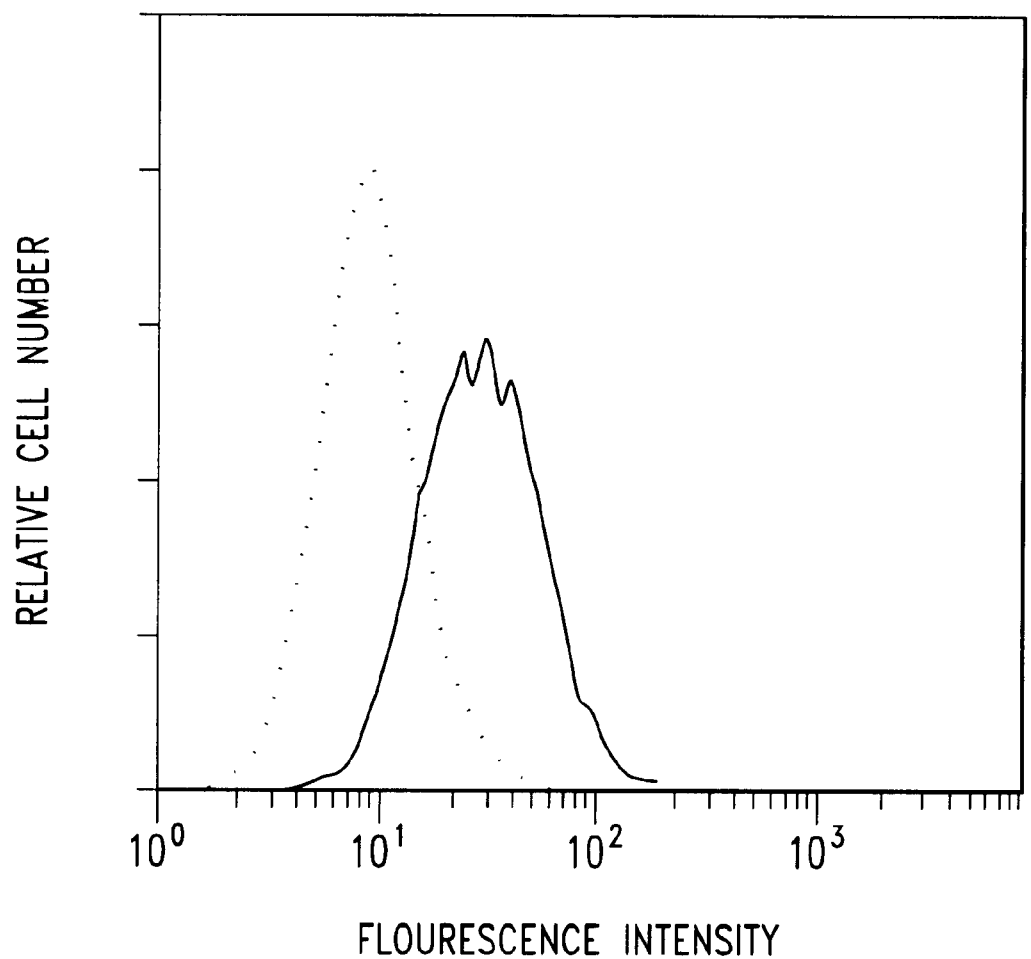
FIG. 6 illustrates the surface expression of Ldp23 on live *L. donovani* promastigotes. The dotted line shows the indirect immunofluorescence performed using pre-immune mouse serum and the solid line shows the result obtained with mouse anti-GST-Ldp23 antiserum. Fluorescence intensity was analyzed by FACScan.

FIG. 5 shows that the rabbit anti-recombinant protein antiserum detects a single protein of 23 kDa (Ldp23) in the Leishmania crude extract antigen preparation. No bands were observed when an anti-GST antiserum was used (not shown). Moreover, the FACScan analysis (FIG. 6) shows that the antibody induced by the recombinant Ldp23 reacts with intact live *L. donovani* promastigotes, thus pointing to a cell surface expression of this molecule on these organisms. The dotted line in FIG. 6 shows the indirect immunofluorescence performed using pre-immune mouse serum and the solid line in FIG. 6 shows the result obtained with mouse anti-GST-Ldp23 antiserum. Both sera were diluted at ¹⁄100. Parasites were washed with staining buffer and incubated with FITC conjugated goat anti-mouse immunoglobulin antibody. Fluorescence intensity was analyzed by FACScan.

F. Recognition of Recombinant Ldp23 by Leishmania-specific Lymph Node T-cells

Figure 7:
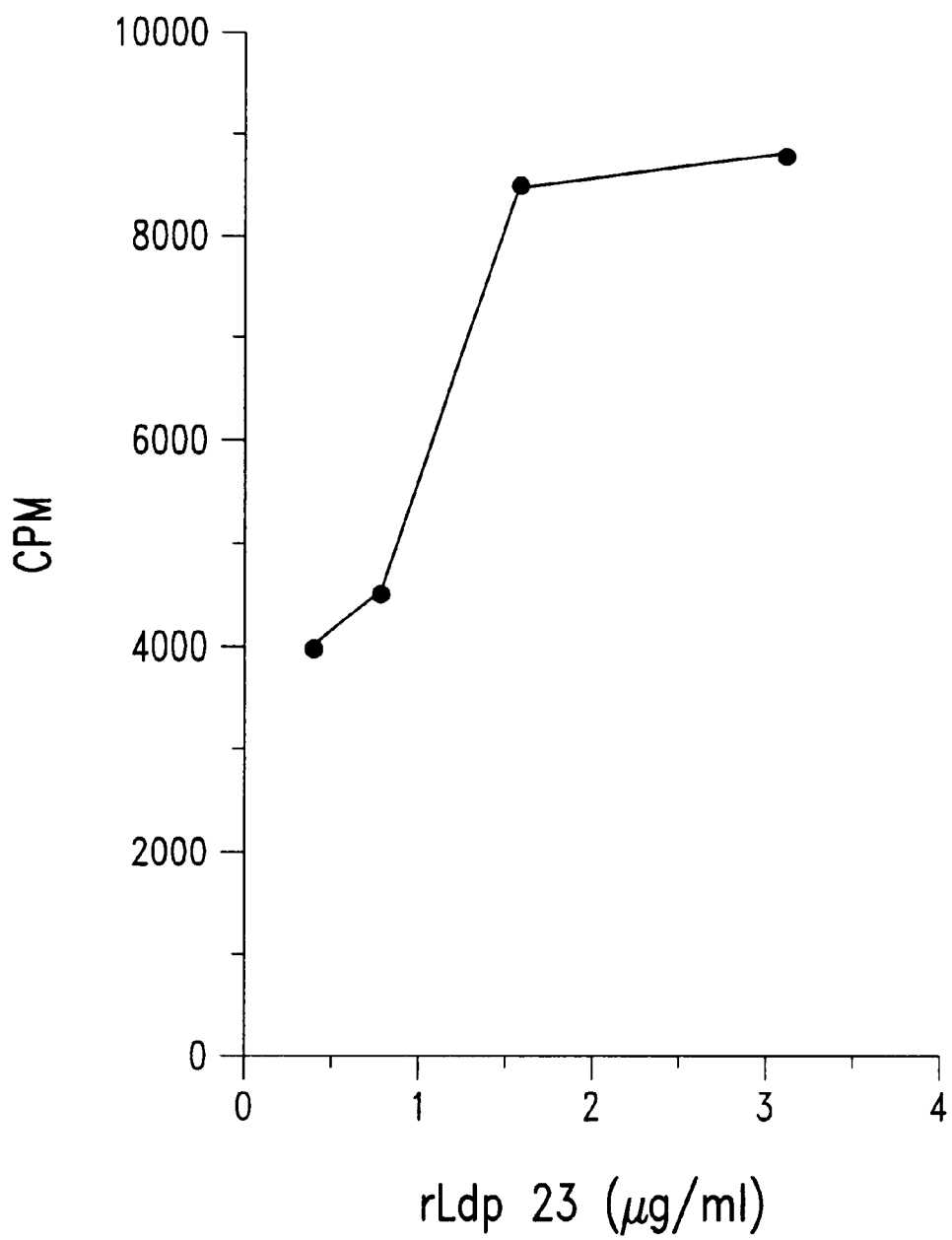
FIG. 7 shows the stimulation of Leishmania-specific T-cell proliferation by Ldp23. The results are presented as relative cell number as a function of fluorescence intensity. T-cells ($10^5$/well) were purified from lymph nodes of BALB/c mice immunized in the foot pad with *L. donovani* promastigotes in CFA and were cultured with various concentrations of the purified recombinant Ldp23 in the presence of $2\times10^5$ Mitomycin C-treated normal BALB/c spleen mononuclear cells. Proliferation of T-cells was measured at 27 hours of culture. Values are expressed as cpm and represent the mean of [$^3$H]TdR incorporation of triplicate cultures.

To test the responsiveness of T-cells to the Ldp23 protein, two sets of experiments were performed. In the first experiment, lymph node T-cells (10$^5$/well) from BALB/c mice immunized with *L. donovani* promastigotes (as described above) were stimulated to proliferate with 2×10$^5$ Mitomycin C-treated normal mononuclear spleen cells (APC) and pulsed with the purified recombinant fusion protein. Proliferation of T-cells was measured at 72 hours of culture. Values are expressed in FIG. 7 as cpm and represent the mean of [$^3$H]TdR incorporation of triplicate cultures. Background cpm of cells (T cells+APC) cultured in the presence of medium alone was 1291. FIG. 7 shows that Leishmania specific T-cells proliferate well and in a dose response manner to recombinant Ldp23. No response was observed when purified GST was added instead of the recombinant fusion protein nor when lymph node T-cells from mice immunized with CFA alone were stimulated to proliferate in the presence of the Leishmanial fusion protein (not shown).

The recognition of the recombinant Ldp23 protein by Leishmania-specific T-cells was also tested using two murine models of leishmaniasis, the *L. major* highly susceptible BALB/c mice and the *L. amazonensis* susceptible CBA/J mice as described in Champsi and McMahon-Pratt, *Infect. Immun.* 56:3272 (1988). These models were selected to investigate the cytokine pattern induced by Ldp23. In the mouse model of leishmaniasis, resistance is associated with Th 1 cytokines while susceptibility is linked to Th 2 responses.

Lymph node cells were obtained 3 weeks after the initiation of infection of BALB/c mice with *L. major* and the ability of these cells to recognize the recombinant Ldp23 was measured by proliferation and by the production of the cytokines IFN-γ and IL-4. 2×10⁶ cells obtained from the draining popliteal lymph node of infected mice were cultured for 72 hours in the presence of recombinant Ldp23 or Leishmania lysate. The levels of IFN-γ and IL-4 in culture supernatants were measured by ELISA as previously described (Chatelain et al., *J. Immunol.* 148:1172 (1992), Curry et al., *J. Immunol. Meth.* 104:137 (1987), and Mossman and Fong, *J. Immunol. Meth.* 116:151 (1989)) using specific anti IFN-γ and IL-4 monoclonal antibodies (PharMingen, San Diego, Calif.).

Figure 8B:
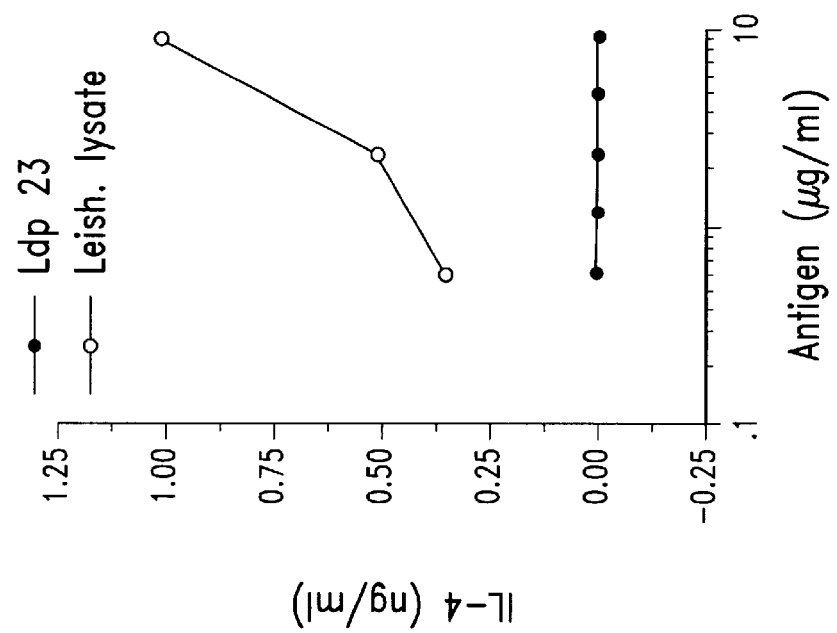
FIG. 8 illustrates Ldp23-induced cytokine production by lymph node cells of BALB/c mice. Cultures were incubated with varying amounts of Ldp23 or Leishmania lysate, presented as µg/mL, and were assayed by ELISA for the production of interferon-γ (panel A) or interleukin-4 (panel B), both of which are shown as ng/mL.
Figure 8A:
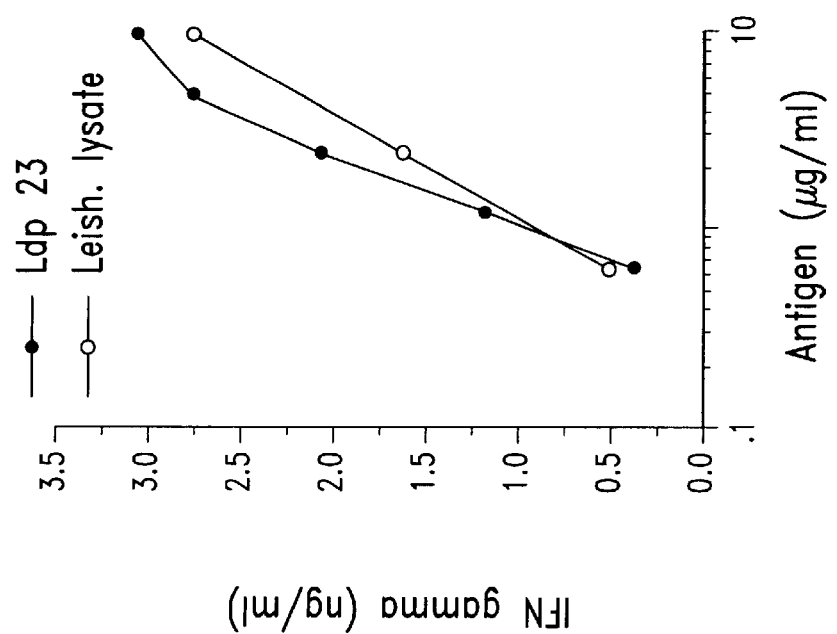

Ldp23 did stimulate these cells to proliferate (not shown) and induced a typical Th 1 type of cytokine response as indicated by the production of high levels of IFN-γ (panel A of FIG. 8) and no IL-4 (panel B of FIG. 8). Stimulation of these cells with a Leishmania crude lysate yielded a mixed Th cytokine profile. Exactly the same pattern of cytokine production was obtained from the CBA/J mice infected with *L. amazonensis* (not shown). These results clearly indicate that Ldp23 is a powerful and selective activator of the Th 1 cytokines by mouse cells.

Example 3

Preparation of HsP83

This Example illustrates the preparation of a Leishmania antigen Hsp83, having the sequence provided in SEQ ID NO:6.

A genomic expression library was constructed with sheared DNA from *L. braziliensis* (MHOM/BR/75/M2903) in bacteriophage λZAP II (Stratagene, La Jolla, Calif.). The expression library was screened with *Escherichia coli* preadsorbed serum from an *L. braziliensis*-infected individual with ML. Immunoreactive plaques were purified, and the pBSK(−) phagemid was excised by protocols suggested by the manufacturer. Nested deletions were performed with exonuclease III to generate overlapping deletions for single-stranded template preparations and sequencing. Single-stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems automated sequencer model 373A.

Recombinant antigens produced by these clones were purified from 500 ml of isopropyl-β-D-thiogalactopyranoside (IPTG)-induced cultures as described in Skeiky et al., *J. Exp. Med.* 176:201–211 (1992). These antigens were then assayed for the ability to stimulate PBMC from Leishmania-infected individuals to proliferate and secrete cytokine. Peripheral blood was obtained from individuals living in an area (Corte de Pedra, Bahia, Brazil) where *L. braziliensis* is endemic and where epidemiological, clinical, and immunological studies have been performed for over a decade, and PBMC were isolated from whole blood by density centrifugation through Ficoll (Winthrop Laboratories, New York, N.Y.). For in vitro proliferation assays, 2×10⁵ to 4×10⁵ cells per well were cultured in complete medium (RPMI 1640 supplemented with gentamicin, 2-mercaptoethanol, L-glutamine, and 10% screened pooled A+ human serum; Trimar, Hollywood, Calif.) in 96-well flat-bottom plates with or without 10 μg of the indicated antigens per ml or 5 μg of phytohemagglutinin per ml (Sigma Immunochemicals, St. Louis, Mo.) for 5 days. The cells were then pulsed with 1 μCi of [³H]thymidine for the final 18 h of culture. For determination of cytokine production 0.5 to 1 ml of PBMC was cultured at 1×10⁶ to 2×10⁶ cells per ml with or without the Leishmania antigens for 48 and 72 h.

The supernatants and cells were harvested and analyzed for secreted cytokine or cytokine mRNAs. Aliquots of the supernatants were assayed for gamma interferon (IFN-γ), tumor necrosis factor alpha (TNF-α), interleukin-4 (IL-4), and IL-10 as described in Skeiky et al., *J. Exp. Med.* 181:1527–1537 (1995). For cytokine mRNA PCR analysis, total RNA was isolated from PBMC and cDNA was synthesized by using poly(dT) (Pharmacia, Piscataway, N.J.) and avian mycloblastosis virus reverse transcriptase. Following normalization to β-actin, diluted cDNA was amplified by PCR using Taq polymerase (Perkin-Elmer Cetus, Foster City, Calif.) with 0.2 μM concentrations of the respective 5' and 3' external primers in a reaction volume of 50 μl. The nucleotide sequences of the primary pairs and the PCR conditions used were as described in Skeiky et al., *J. Exp. Med.* 181:1527–1537 (1995). We verified that our PCR conditions were within the semiquantitative range by initially performing serial dilutions of the cDNAs and varying the number of cycles used for PCR. Plasmids containing the human sequences for IL-2, IFN-γ, IL-4, IL-10, and β-actin were digested, and the DNA inserts were purified after separation on 1% agarose gels. Radiolabeled ³²P probes were prepared by the random priming method. PCR products were analyzed by electrophoresis on 1.5% agarose gels, transferred to nylon membranes, and probed with the appropriate ³²P-labeled DNA insert.

A recombinant clone was identified in the above assays which, following sequence comparison of its predicted amino acid sequence with sequences of other proteins, was identified as a *Leishmania braziliensis* homolog of the eukaryotic 83 kD heat shock protein (Lbhsp83). The sequence of the clone is provided in SEQ ID NO:5 and the deduced protein sequence is provided in SEQ ID NO:6. On the basis of the homology, this clone, designated Lbhsp83a, appears to lack the first 47 residues of the full length 703 amino acid residues. Lbhsp83 has an overall homology of 94% (91% identity and 3% conservative substitution), 91% (84% identity and 7% conservative substitution) and 77% (61% identity and 16% conservative substitution) with *L. amazonensis* hsp83, *T. cruzi* hsp83 and human hsp89, respectively. A second clone (designated Lbhsp83b), which contained the 43 kD C-terminal portion of hsp83 (residues 331 to 703) was also isolated. FIG. 19 presents a comparison of the Lbhsp83 sequence with *L. amazonensis* hsp83 (Lahsp83), *T. cruzi* hsp83 (Tchsp83) and human hsp89 (Huhsp89).

The results of proliferation assays using Lbhsp83a are shown in Table 1. Cells from all mucosal leishmaniasis (ML) patients proliferated strongly in response to Lbhsp83a, with stimulation indices (SIs) ranging from 19 to 558 (as compared to 20 to 1,634 for parasite lysate). Proliferation of PBMC from cutaneous leishmaniasis (CL) patients was variable and except for levels in two patients (IV and VII), levels were significantly lower than those of ML patients. By comparison, the proliferative responses of individuals with self-healing CL to Lbhsp83a were similar to those of individuals with ML. However, the responses of all six self-healing individuals to Lbhsp83 were consistently higher than those to Lbhsp83b. This suggests that PBMC from self-healing CL patients preferentially recognize one or more T-cell epitopes located within the amino portion of Lbhsp83.

TABLE 1

In vitro Proliferation of PMBC from *L. braziliensis*-infected Individuals in Response to Lbhsp83

| Group and Patient | Mean [$^3$H]thymidine incorporation [$10^3$ cpm (SD)], SI with: | | |
|---|---|---|---|
| | Lysate | Lbhsp83a | Lbhsp83b |
| ML | | | |
| I | 41.3, (1.3), 294 | 32.5, (6.6), 221 | 46.7, (1.4), 318 |
| II | 44.2, (0.5), 104 | 20, (3.7), 47 | 36.7, (0.76), 86 |
| III | 27.4, (1.5), 150 | 8.1, (1.7), 44 | 9.9, (0.32), 54 |
| IV | 52.7, (3.3), 138 | 54.1, (6.2), 142 | 32.0, (1.3), 84 |
| V | 140.6, (7.6), 308 | 151.8, (57), 333 | 150.4, (7.9), 331 |
| VI | 15.8, (1.8), 20 | 21.3, (4.4), 28 | 14.4, (1.3), 19 |
| VII | 300.1, (9.4), 1634 | 102.1, (7.6), 558 | 41.7, (4.9), 228 |
| CL | | | |
| I | 0.26, (0.0), 1.5 | 0.57, (0.3), 3.3 | 0.43, (0.17), 3.3 |
| II | 55.63, (8.6), 218 | 0.42, (0.0), 1.6 | 0.8, (0.14), 3.2 |
| III | 0.39, (0.5), 4.0 | 3.4, (0.5), 9 | 2.6, (0.9), 6.6 |
| IV | 19.14, (1.3), 87 | 7.17, (0.6), 32 | 5.9, (0.9), 27 |
| V | 0.32, (0.2), 3.0 | 1.47, (0.5), 14 | 0.3, (0.1), 3.0 |
| VI | 0.77, (0.1), 4.7 | 1.44, (0.2), 9 | 1.3, (0.6), 8.0 |
| VII | 4.01, (1.0), 2.0 | 60.3, (8.5), 15 | 66.7, (3.9), 16.6 |
| Self-healing CL | | | |
| I | 19.7, (4.4), 94 | 61.3, (4.6), 293 | 5.0, (2.0), 24 |
| II | 0.6, (0.1), 6.5 | 7.0, (2.0), 79 | 1.2, (0.8), 13 |
| III | 59.6, (7.1), 519 | 49.4, (3.1), 429 | 21.4, (3.7), 186 |
| IV | 0.2, (0.1), 1.6 | 13.1, (1.7), 108 | 0.6, (0.1), 5 |
| V | 27.1, (2.0), 225 | 6.3, (2.6), 52 | 3.0, (1.5), 25 |
| VI | 130.3, (14), 340 | 28.2, (2.9), 74 | 7.7, (3.8), 20 |
| Control (uninfected) | | | |
| I | 0.19, (0.0), 1.4 | 0.18, (0.0), 1.3 | 0.40, (0.16), 2.8 |
| II | 0.31, (0.1), 1.7 | 0.19, (0.0), 1.0 | 0.27, (0.0), 1.5 |
| III | 0.44, (0.2), 4.1 | 0.48, (0.1), 5.0 | 0.51, (0.2), 5.2 |
| IV | 0.4, (0.1), 3.2 | 0.52, (0.2), 5.1 | 0.50, (0.1), 5.0 |

Figure 9A:
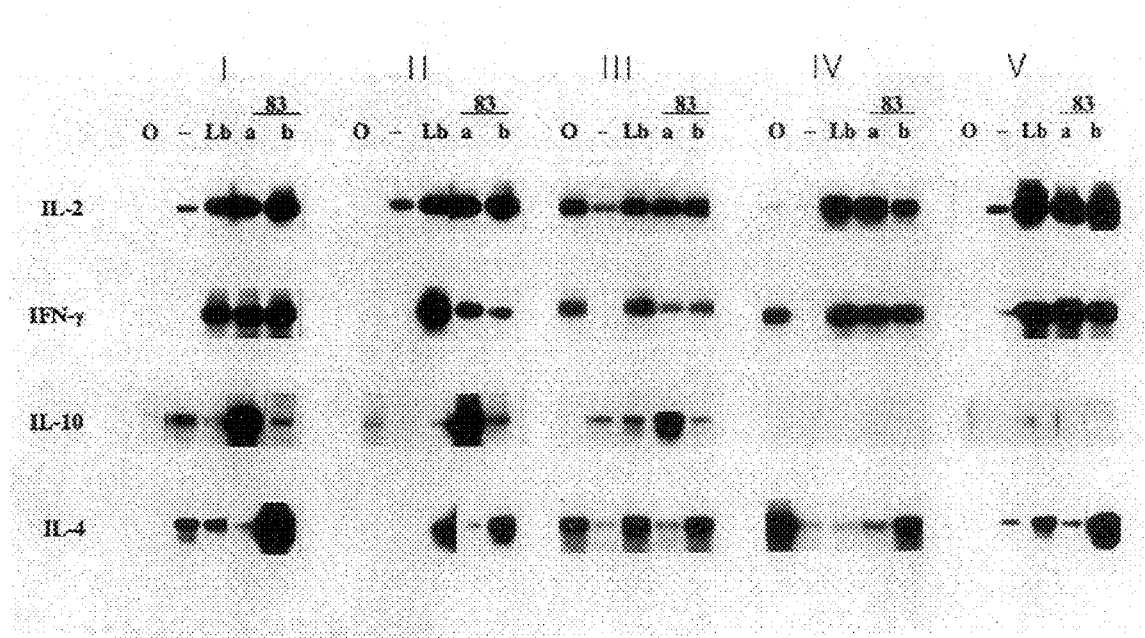
FIG. 9 shows the PCR amplification of cytokine mRNAs isolated from mucosal leishmaniasis (Panel A) and cutaneous leishmaniasis (panel B) patient PBMC before and after stimulation with representative polypeptides of the present invention. Lanes O and - indicate the level of PCR products at the initiation of culture and after 72 hours of culture, respectively, in the absence of added polypeptide; lanes Lb, 83a and 83b indicate the level of PCR products following culturing of PBMC with *L. braziliensis* lysate, and the Leishmania antigens Lbhsp83a and Lbhsp83b, respectively.
Figure 9B:
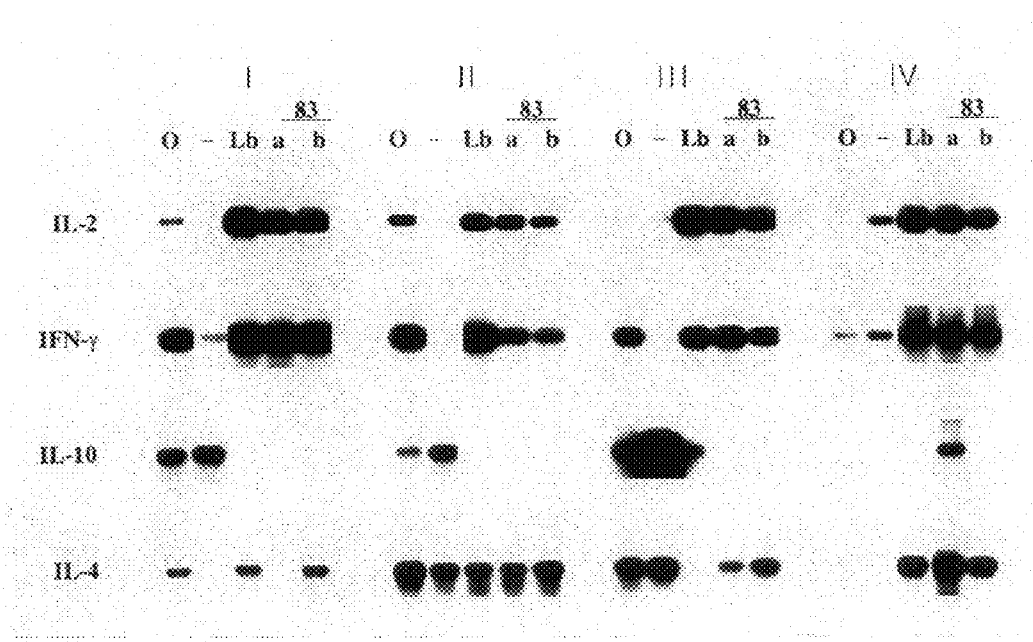

A more detailed analysis of cytokine patterns of PBMC from ML patients was performed by reverse transcriptase PCR. Cytokine mRNAs were evaluated in cells prior to culturing (FIG. 9, lanes O) or following culturing in the absence (lanes –) or presence of the indicated antigen for 48 and 72 h. FIG. 4A shows the results for five of the six ML patients whose PBMC were analyzed. In about half of the ML patients, noncultured (resting) PBMC had detectable levels of mRNA for IFN-γ, IL-2, and IL-4 but not IL-10. CL patient PBMC, however, had IL-10 mRNA in the resting state in addition to mRNAs for the other cytokines tested (FIG. 4B). Following in vitro culture without antigen, the levels of mRNA for IFN-γ, IL-2, and IL-4 in resting cells from ML patients decreased to background levels while IL-10 mRNA levels increased. In contrast, PBMC of most CL patients had stable or increased IL-10 mRNA, while the mRNAs for IL-2, IFN-γ, and IL-4 were reduced to barely detectable levels in the absence of antigen stimulation.

In PBMC of three ML patients, stimulation with lysate resulted in increased expression of mRNA for IFN-Y, IL-2, and IL-4 but not IL-10. By comparison, both Lbhsp83 polypeptides elicited the production of mRNA for IFN-γ and IL-2 from all ML patient PBMC tested. In contrast, profiles of mRNA for IL-10 and IL-4 differed for the two hsp83 polypeptides. Lbhsp83a stimulated the production of IL-10 but not IL-4 mRNA (patients I, II, III, and IV), while Lbhsp83b stimulated the production of IL-4 but not IL-10 mRNA in all six patients.

All CL patients tested responded to both Lbhsp83 polypeptides as well as to the parasite lysate by upregulating the synthesis of mRNAs for IL-2 and IFN-γ, and in two of four patients (I and IV), the level of IL-4 mRNA also increased, indicating stimulation of both Th1 and Th2 cytokines. Interestingly and as in the case of ML patient uncultured PBMC which did not have detectable levels of IL-10 mRNA, Lbhsp83a and not Lbhsp83b stimulated PBMC from one CL patient (IV) to synthesize IL-10 mRNA. However, in the other three patients (I, II, and III) with resting levels of IL-10 mRNA, both rLbhsp83 polypeptides as well as the parasite lysate downregulated the expression of IL-10 mRNA.

Figure 10A:
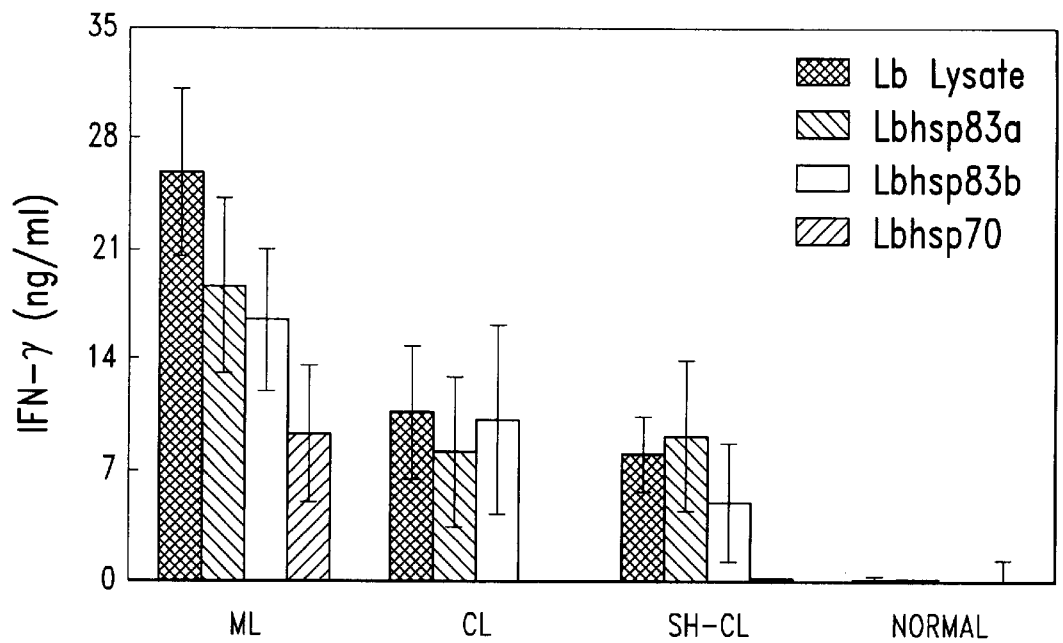
FIG. 10 presents a comparison of the levels of interferon-γ (panel A) and TNF-α (panel B) in the supernatants of 72 hour PBMC cultures from Leishmania-infected and control individuals in response to stimulation with parasite lysate or the indicated polypeptides.

PBMC supernatants were also assayed for the presence of secreted IFN-γ, TNF-α, IL-4, and IL-10. Cells from all ML and self-healing CL patients (seven and six patients, respectively) and from four of seven CL patients were analyzed for secreted IFN-γ following stimulation with both rLbhsp83 polypeptides, parasite lysate and Lbhsp70, an *L. braziliensis* protein homologous to the eukaryotic 70 kD heat shock protein (FIG. 10A). In general, rLbhsp83a stimulated patient PBMC to secrete higher levels of IFN-γ than did rLbhsp83b (0.2 to 36 and 0.13 to 28 ng/ml, respectively). The presence of secreted IFN-γ correlated well with the corresponding mRNA detected by PCR.

Figure 10B:
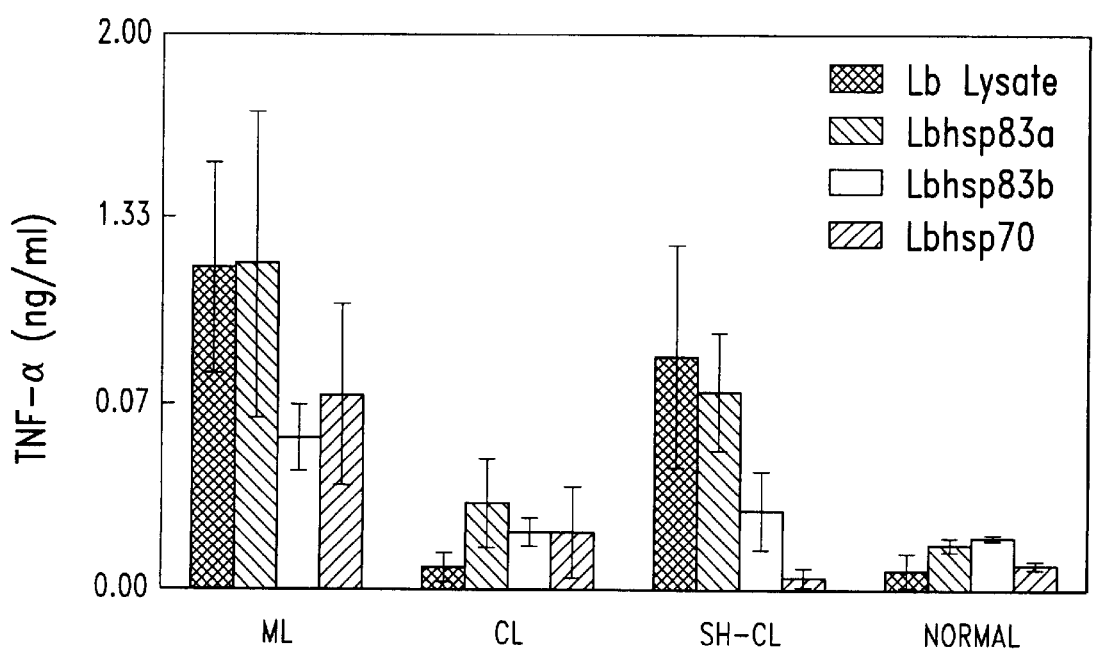

PBMC from four of five ML patients (I, II, V, and VII) had supernatant TNF-α levels (0.8 to 2.2 ng/ml) higher than those detected in cultures of PBMC from uninfected controls following stimulation with parasite lysate (FIG. 10B). Similarly, the same PBMC were stimulated by rLbhsp83 to produce levels of TNF-α in supernatant ranging from 0.61 to 2.9 ng/ml. Compared with those of uninfected controls, PBMC from three (I, V, and VI), five (I, II, IV, V, and VI), and two (II and V) of six individuals analyzed produced higher levels of TNF-α in response to parasite lysate, rLbhsp83a, and rLbhsp83b, respectively. The levels of TNF-α produced by PBMC from CL patients in response to parasite lysate were comparable to those produced by uninfected controls. However, rLbhsp83 stimulated TNF-α production in the PBMC of two of these patients. rLbhsp83a stimulated higher levels of TNF-α, production than did rLbhsp83b. In the absence of antigen stimulation, only PBMC from ML patients (five of six) produced detectable levels of supernatant TNF-α (60 to 190 pg/ml).

Figure 11:
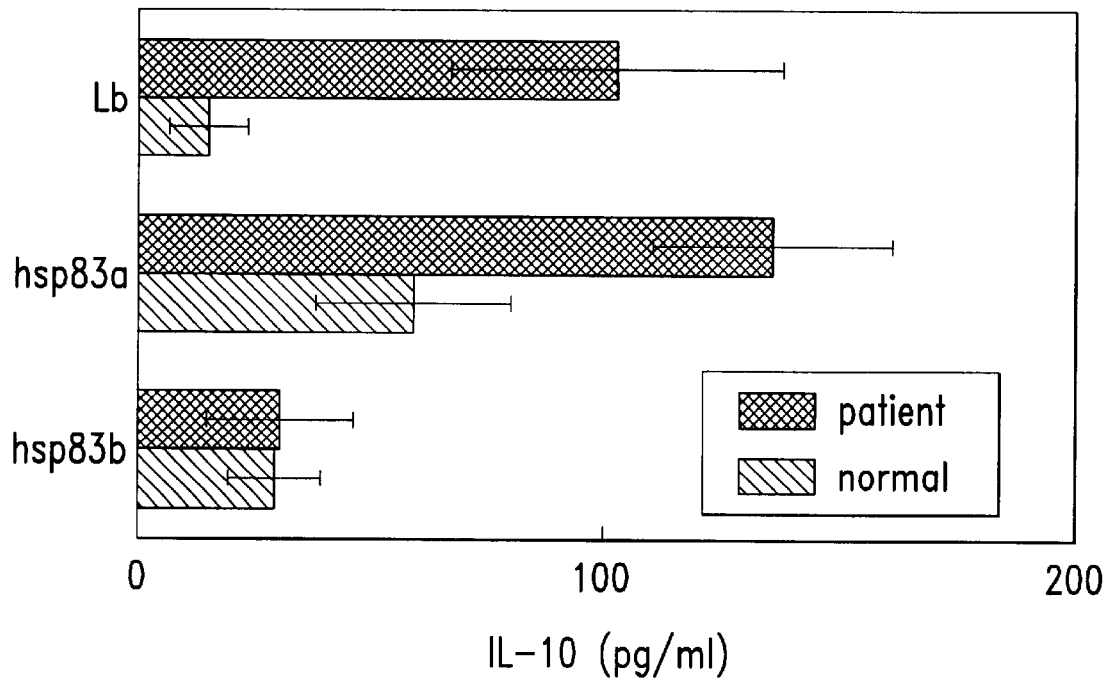
FIG. 11 illustrates the levels of IL-10 p40 (in pg/mL) in the supernatant of PBMC cultures from *L. braziliensis*-infected individuals and uninfected controls 72 hours following stimulation with parasite promastigote lysate (Lb), Lbhsp83a or Lbhsp83b.

In agreement with the IL-10 mRNA, IL-10 was detected by ELISA in the antigen-stimulated PMBC culture supernatants from ML and CL patients. The levels (49 to 190 pg) were significantly higher (up to 10-fold) following stimulation with rLbhsp83a compared with those after parallel stimulation of the same cells with rLbhsp83b (FIG. 11). Parasite lysate also stimulated PMBC from some of the patients to produce IL-10. Although rLbhsp83 stimulated PMBC from uninfected individuals to produce IL-10, with one exception, the levels were lower than those observed with patient PMBC. IL-4 was not detected in any of the supernatants analyzed. Therefore, the level of any secreted IL-4 is below the detection limit of the ELISA employed (50 pg/ml). Taken together, the results demonstrate that a predominant Th1 -type cytokine profile is associated with PMBC from *L. braziliensis*-infected individuals following stimulation with rLbhsp83 polypeptides.

Figure 12:
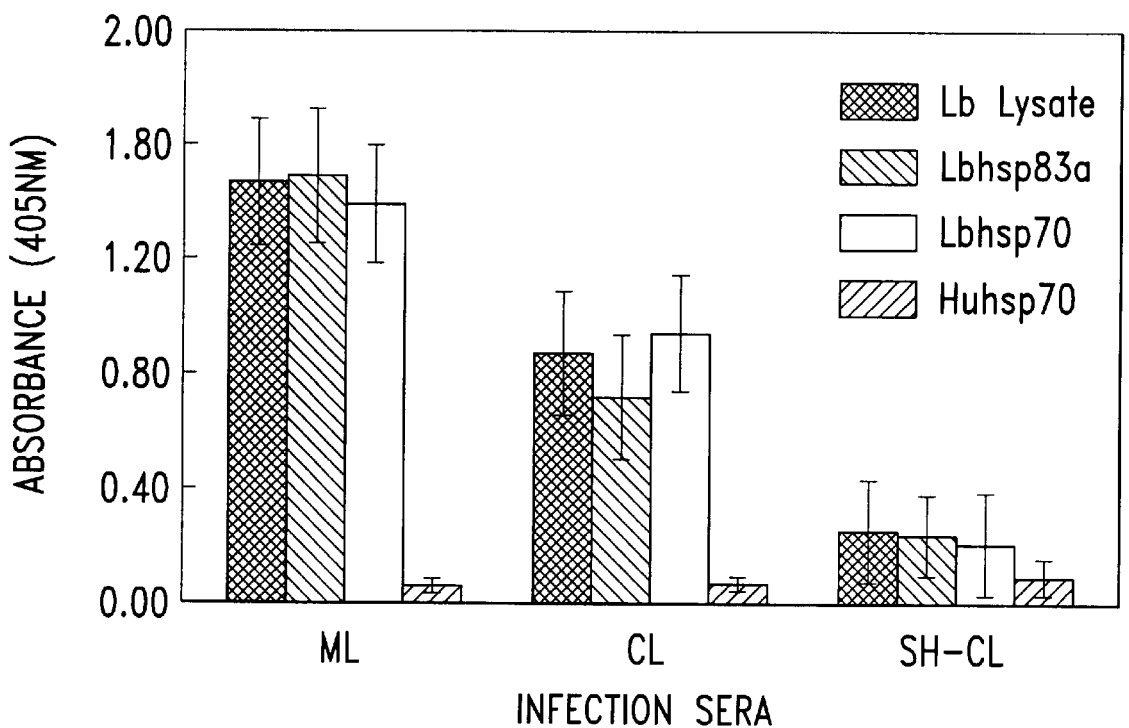
FIG. 12 presents the reactivities of sera from *L. braziliensis* infected-patients with representative polypeptides of the present invention in a standard ELISA. Values are expressed as absorbance at 405 nm.

To determine the correlation between the observed T-cell responses and antibody production to Lbhsp83, we compared the antibody (immunoglobulin G) reactivities to Lbhsp83 in sera from the three patient groups (FIG. 12). The ELISA reactivities of ML patient sera with rLbhsp83a were comparable to those observed with parasite lysate, and in general, there was a direct correlation between ML patient anti-Lbhsp83 antibody titer and T-cell proliferation. Of 23 serum samples from ML patients analyzed, 22 were positive (~96%) with absorbance values of 0.20 to >3.0. Eleven of the ML patient serum samples had optical density values that were >1. In general, CL patients had significantly lower anti-Lbhsp83 antibody titers (x̄=0.74; standard error of the mean [SEM]=0.1) compared to those of ML patients. Therefore, ML and CL patient anti-rhsp83 antibody titers correlated with their respective T-cell proliferative responses. Anti-rLbhsp83 antibody titers were significantly higher in patients with ML (x̄=1.5; SEM=0.2) than in self-healing CL patients (x̄=0.35; SEM=0.056), although their T-cell proliferative responses were similar. In fact, anti-Lbhsp83 antibody titers in serum from self-healing CL patients were comparable to those from uninfected controls (x̄=0.24; SEM=0.028). By using 2 standard deviations greater than the mean absorbance value of uninfected control (0.484) as a criterion for positive reactivity to Lbhsp83, eight of nine of the self-healing patient serum samples tested were negative.

Example 4

Preparation Of Clones Encoding LT-210

This Example illustrates the preparation of clones encoding portions of the Leishmania antigen Lt-210, and which has the sequence provided in SEQ ID NO:8.

An expression library was constructed from *L. tropica* (MHOM/SA/91/WR1063C) genomic DNA. The DNA was isolated by solubilizing *L. tropica* promastigotes in 10 mM Tris-HCl, pH 8.3, 50 mM EDTA, 1% SDS and treating with 100 μg/ml RNaseA and 100 μg/ml proteinase K. The sample was then sequentially extracted with an equal volume of phenol, phenol: chloroform (1:1), and Chloroform. DNA was precipitated by adding 0.1 volume of 3M sodium acetate (pH 5.2) and 2.5 volume 95% ethanol. The precipitate was resuspended in 10 μM Tris, 1 mM EDTA. DNA was sheared by passage through a 30-gauge needle to a size range of 2–6 kilobase, and was repaired by incubation with DNA poli in the presence of 100 μM each DATP, dCTP, dGTP, and dTTP. EcoRI adapters were ligated to the DNA fragments. After removal of unligated adapters by passage over a G-25 Sephadex™ column, the fragments were inserted in EcoRI cut Lambda ZapII (Stratagene, La Jolla, Calif.).

Approximately 43,000 pfu were plated and screened with sera isolated from viscerotropic leishmaniasis (VTL) patients. Sera from VTL patients were received from Drs. M. Grogl and A. Magill. The VTL patient group included eight individuals from whom parasites were isolated and cultured, seven of which had confirmed infection with *L. tropica*. Four other patients were culture negative, but were still considered to be infected based on either PCR analysis or a positive monoclonal antibody smear (Dr. Max Grogl, personal communication). Serum samples from the 11 infected patients were pooled and anti-*E. coli* reactivity removed by affinity chromatography (Sambrook et al., supra, p. 12.27–12.28). Lambda phage expressing reactive proteins were detected after antibody binding by protein A-horseradish peroxidase and ABTS substrate.

Three clones, Lt-1, Lt-2, and Lt-3, containing a portion of the Lt-210 gene were identified and purified. The clones ranged in size from 1.4 to 3.3 kb and encoded polypeptides of 75 kD, 70 kD, and 120 kD, respectively. These three clones contain partial sequences of the Lt-210 gene. Lt-1 and Lt-2 are overlapping clones and were chosen for further study.

The DNA sequences of Lt-1 and Lt-2 were determined. Exonuclease III digestion was used to create overlapping deletions of the clones (Heinikoff, *Gene* 28:351–359, 1984). Single strand template was prepared and the sequence determined with Applied Biosystems Automated Sequencer model 373A or by Sanger dideoxy sequencing. The sequence on both strands of the coding portion of Lt-1 clone was determined. The partial sequence of one strand of Lt-2 clone was determined.

SEQ ID NO:7 presents the DNA sequence of Lt-1, and SEQ ID NO:8 provides the predicted amino acid sequence of the open reading frame. The DNA sequence of the coding portion of the Lt-1 clone includes a repeated nucleotide sequence at the 5' portion of the clone containing eight copies of a 99 bp repeat, three copies of a 60 bp repeat unit, which is part of the larger 99 bp repeat, and 800 bp of non-repeat sequence. The deduced amino acid sequence of the 99 bp repeat contains limited degeneracies. The mass of the predicted recombinant protein is 67,060 Daltons. A database search of PIR with the predicted amino acid sequence of the open reading frame yielded no significant homology to previously submitted sequences. Predicted secondary structure of the repeat portion of the clone is entirely α-helical.

Sequence analysis of Lt-2 revealed that the 3' portion of the clone consisted of a mixture of 60 and 99 bp repeats that were identical, excepting occasional degeneracies, to the 60 and 99 bp repeats observed in Lt-1. Collectively, the sequencing data suggest that Lt-1 and Lt-2 are different portions of the same gene, Lt-2 being upstream of Lt-1, with possibly a small overlap.

Hybridization analysis confirmed that rLt-2 and rLt-1 contain overlapping sequences. Genomic DNAs of various Leishmania species were restricted with a variety of enzymes, separated by agarose gel electrophoresis, and blotted on Nytran membrane filter (Schleicher & Schuell, Keene, N.H.). Inserts from rLt-1 and rLt-2 were labeled with $^{32}P$ CTP by reverse transcriptase from random oligonucleotide primers and used as probes after separation from unincorporated nucleotides on a Sephadex G-50 column. Hybridizations using the rLt-1 or the rLt-2 probe are performed in 0.2M $NaH_2PO_4$/3.6 M NaCl at 65° C., whereas hybridization using the rLt-lr probe is performed in 0.2 M $NaH_2PO_4$/3.6 M NaCl/0.2 M EDTA at 60° C. overnight. Filters are washed in 0.075 M NaCl/0.0075 M sodium citrate pH 7.0 (0.15 M NaCl/0.0150 M sodium citrate for the Lt-lr probe), plus 0.5% SDS at the same temperature as hybridization.

Genomic DNA from a number of Leishmania species including *L. tropica* were analyzed by Southern blots as described above using the Lt-1, Lt-2, and Lt-1r inserts separately as probes. Collectively, various digests of *L. tropica* DNA indicate that this gene has a low copy number. A similar, overlapping pattern was observed using either the Lt-1 or Lt-2 insert as a probe, consistent with the premise that these two clones contain sequences near or overlapping one another. In addition, sequences hybridizing with these clones are present in other Leishmania species.

*L. tropica* isolates have limited heterogeneity. Southern analyses of digested genomic DNA from four *L. tropica* parasite strains isolated from VTL patients and three *L. tropica* parasite strains isolated from CL cases (two human, one canine) were performed. The Lt-1r insert described below was labeled and used as a probe. The seven different *L. tropica* isolates yielded similar intensities and restriction patterns, with only a single restriction fragment length polymorphism among the isolates. These data, along with Southern analyses with additional enzymes, indicate limited heterogeneity in this region among the *L. tropica* isolates.

The recombinant proteins of Lt-1 and Lt-2 were expressed and purified. The nested deletion set of Lt-1 formed for sequencing included a clone referred to as Lt-1r, which contains one and one-third repeats. This polypeptide was also expressed and purified. In vivo excision of the pBluescript $SK^-$ phagemid from Lambda Zap II was performed according to the manufacturer's protocol. Phagemid virus particles were used to infect *E. coli* XL-1 Blue. Production of protein was induced by the addition of IPTG. Protein was recovered by first lysing pellets of induced bacteria in buffer (LB, 50 mM Tris-HCl, pH 8.0, 100 mM NaCl, 10 mM EDTA) using a combination of lysozyme (750 μg/mL) and sonication. rLt-1, rLt-2, and rLt-1r, were recovered from the inclusion bodies after solubilization in 8M urea (rLt-1 and rLt-2) or 4M urea (rLt-1r). Proteins rLt-1 and rLt-2 were enriched and separated by precipitation with 25%–40% ammonium sulfate and rLt-1r was enriched by precipitation with 10%–25% ammonium sulfate. The proteins were further purified by preparative gel electrophoresis in 10% SDS-PAGE. Recombinant proteins were eluted from the gels and dialyzed in phosphate-buffered saline (PBS). Concentration was measured by the Pierce (Rockford, Ill.) BCA assay, and purity assessed by Coomassie blue staining after SDS-PAGE.

Example 5

Preparation of LBEIF4A

This example illustrates the molecular cloning of a DNA sequence encoding the *L. braziliensis* ribosomal antigen LbeIF4A.

A genomic expression library was constructed with sheared DNA from *L. braziliensis* (MHOM/BR/75/M2903) in bacteriophage λZAPII (Stratagene, La Jolla, Calif.). The expression library was screened with *E. coli*-preadsorbed patient sera from an *L. braziliensis*-infected individual with mucosal leishmaniasis. Plaques containing immunoreactive recombinant antigens were purified, and the pBSK(−) phagemid excised using the manufacturer's protocols. Nested deletions were performed with Exonuclease III to generate overlapping deletions for single stranded template preparations and sequencing. Single stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems Automated Sequencer Model 373A.

The immunoreactive recombinant antigens were then analyzed in patient T-cell assays for their ability to stimulate a proliferative and cytokine production, as described in Examples 7 and 8 below.

A recombinant clone was identified in the above assays which, following sequence comparison of its predicted amino acid sequence with sequences of other proteins, was identified as a *Leishmania braziliensis* homolog of the eukaryotic initiation factor 4A (eIF4A). The isolated clone (pLeIF.1) lacked the first 48 amino acid residues (144 nucleotides) of the full length protein sequence. The pLeIF. 1 insert was subsequently used to isolate the full length genomic sequence.

SEQ ID NO:9 shows the entire nucleotide sequence of the full-length LbeIF4A polypeptide. The open reading frame (nucleotides 115 to 1323) encodes a 403 amino acid protein with a predicted molecular weight of 45.3 kD. A comparison of the predicted protein sequence of LbeIF4A with the homologous proteins from tobacco (TeIF4A), mouse (MeIF4A), and yeast (YeIF4A) shows extensive sequence homology, with the first 20–30 amino acids being the most variable. The lengths (403, 413, 407, and 395 amino acids), molecular weights (45.3, 46.8, 46.4, and 44.7 kDa), and isoelectric points (5.9, 5.4, 5.5, and 4.9) of LbeIF4A, TeIF4A, MeIF4A and YeIF4A, respectively, are similar. LbeIF4A shows an overall homology of 75.5% (57% identity, 18.5% conservative substitution) with TeIF4A, 68.6% (50% identity, 18.6% conservative substitution) with MeIF4A and 67.2% (47.6% identity, 19.6% conservative substitution) with YeIF4A.

Example 6

Preparation of Soluble Leishmania Antigens

This Example illustrates the preparation of soluble Leishmania antigens from an *L. major* culture supernatant. *L. major* promastigotes were grown to late log phase in complex medium with serum until they reached a density of 2–3×$10^7$ viable organisms per mL of medium. The organisms were thoroughly washed to remove medium components and resuspended at 2–3×$10^7$ viable organisms per mL of defined serum-free medium consisting of equal parts RPMI 1640 and medium 199, both from Gibco BRL, Gaithersburg, Md. After 8–12 hours, the supernatant was removed, concentrated 10 fold and dialyzed against phosphate-buffered saline for 24 hours. Protein concentration was then determined and the presence of at least eight different antigens confirmed by SDS- PAGE. This mixture is referred to herein as "soluble Leishmania antigens."

Example 7

Comparison of Intepleukin-4 and Interferon-γ Production Stimulated by Leishmani Antigens This Example illustrates the immunogenic properties of the antigens prepared according to Examples 1, 2, 5 and 6, as determined by their ability to stimulate IL-4 and IFN-γ in lymph node cultures from infected mice and in human PBMC preparations. Lymph node cultures for use in these studies were prepared from *L. major*-infected BALB/c mice 10 days after infection, as described in Example 2. PBMC were prepared using peripheral blood obtained from individuals with cured *L. donovani* infections who were immunologically responsive to Leishmania. Diagnosis of the patients was made by clinical findings associated with at least one of the following: isolation of parasite from lesions, a positive skin test with Leishmania lysate or a positive serological test. Uninfected individuals were identified based on a lack of clinical signs or symptoms, a lack of history of exposure or travel to endemic areas, and the absence of a serological or cellular response to Leishmania antigens. Peripheral blood was collected and PBMC isolated by density centrifugation through Ficoll™ (Winthrop Laboratories, New York).

Culture supernatants were assayed for the levels of secreted IL-4 and IFN-γ. IFN-γ was quantitated by a double sandwich ELISA using mouse anti-human IFN-γ mAb (Chemicon, Temucula, Calif.) and polyclonal rabbit anti-human IFN-γ serum. Human rIFN-γ(Genentech Inc., San Francisco, Calif.) was used to generate a standard curve. IL-4 was quantitated in supernatants by a double sandwich ELISA using a mouse anti-human IL-4 mAb (M1) and a polyclonal rabbit anti-human IL-4 sera (P3). Human IL-4 (Immunex Corp., Seattle, Wash.) was used to generate a standard curve ranging from 50 pg/ml to 1 ng/ml.

Figure 13A:
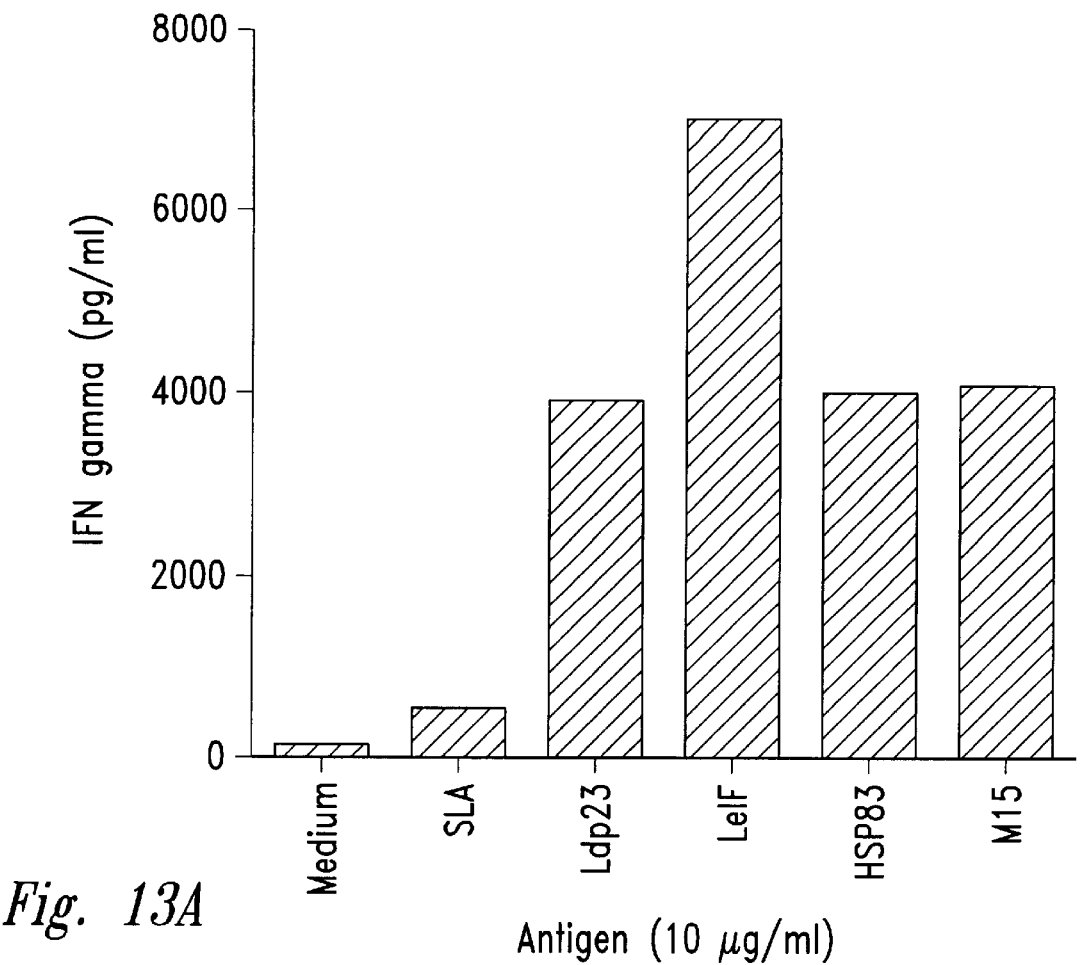
FIGS. 13A and 13B illustrate the level of secreted IL-4 and IFN-γ (in pg/mL) stimulated in mouse lymph node cultures by the addition of representative polypeptides of the present invention.
Figure 13B:
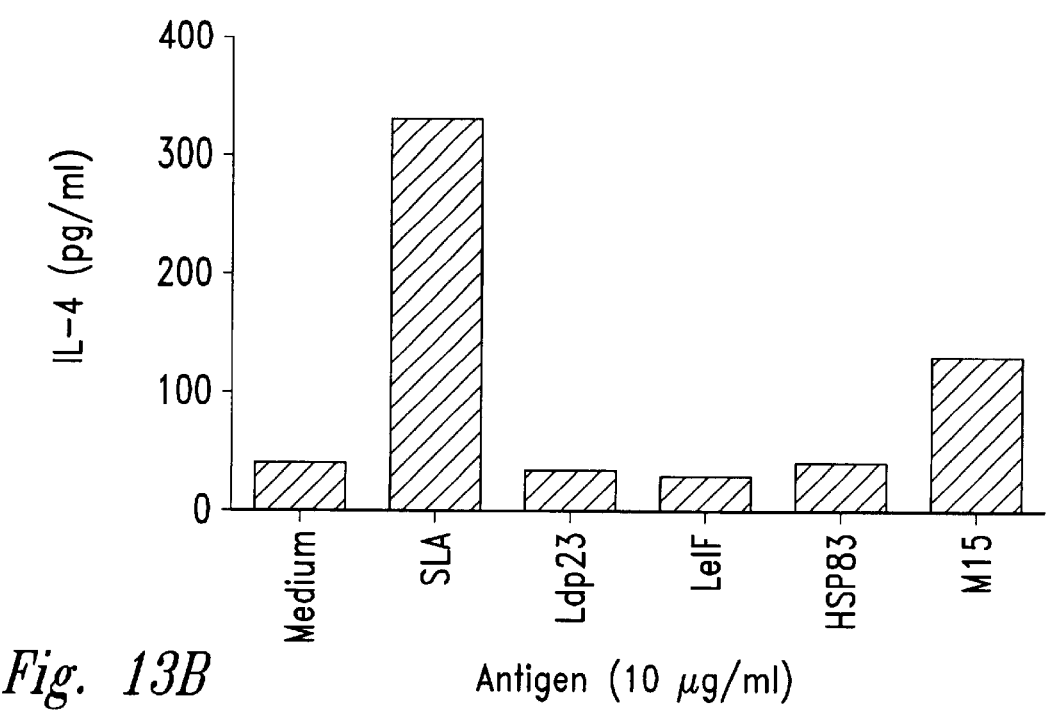

FIGS. 13A and 13B, illustrate the mean level of secreted IL-4 and IFN-γ, respectively, 72 hours after addition of 10 µg/mL of each of the following antigens to a lymph node culture prepared as described above: soluble Leishmania antigen (i.e., an extract prepared from ruptured promastigotes which contains membrane and internal antigens (SLA)), Ldp23, LbeIF4A (LeIF), Lbhsp83, M15 and LmeIF (the L. major homolog of LbeIF4A). The levels of secreted IL-4 and IFN-γ in medium alone (i.e., unstimulated) are also shown. While SLA elicits a predominantly Th2 response from lymph node cells of Leishmania-infected mice, Ldp23, LbeIF4A, Lbhsp83 and M15 elicited relatively little IL-4 and large amounts of IFN-γ, consistent with a Th1 response profile.

Figure 14:
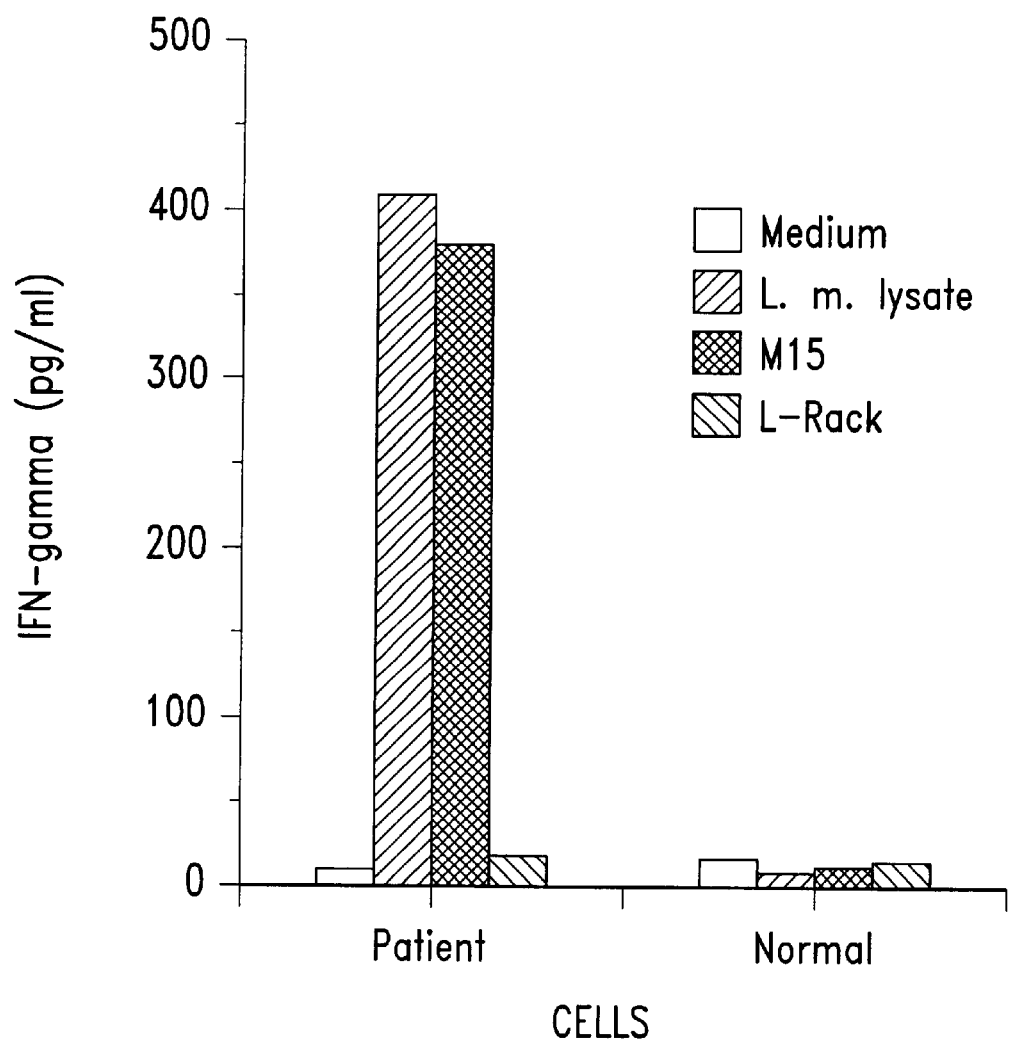
FIG. 14 shows the level of IFN-γ (in pg/mL) secreted by Leishmania-infected and uninfected human PBMC stimulated by the Leishmania antigen M15, as compared to the levels stimulated by *L. major* lysate and L-Rack, an antigen that does not appear to be recognized by Leishmania-infected humans.
Figure 15:
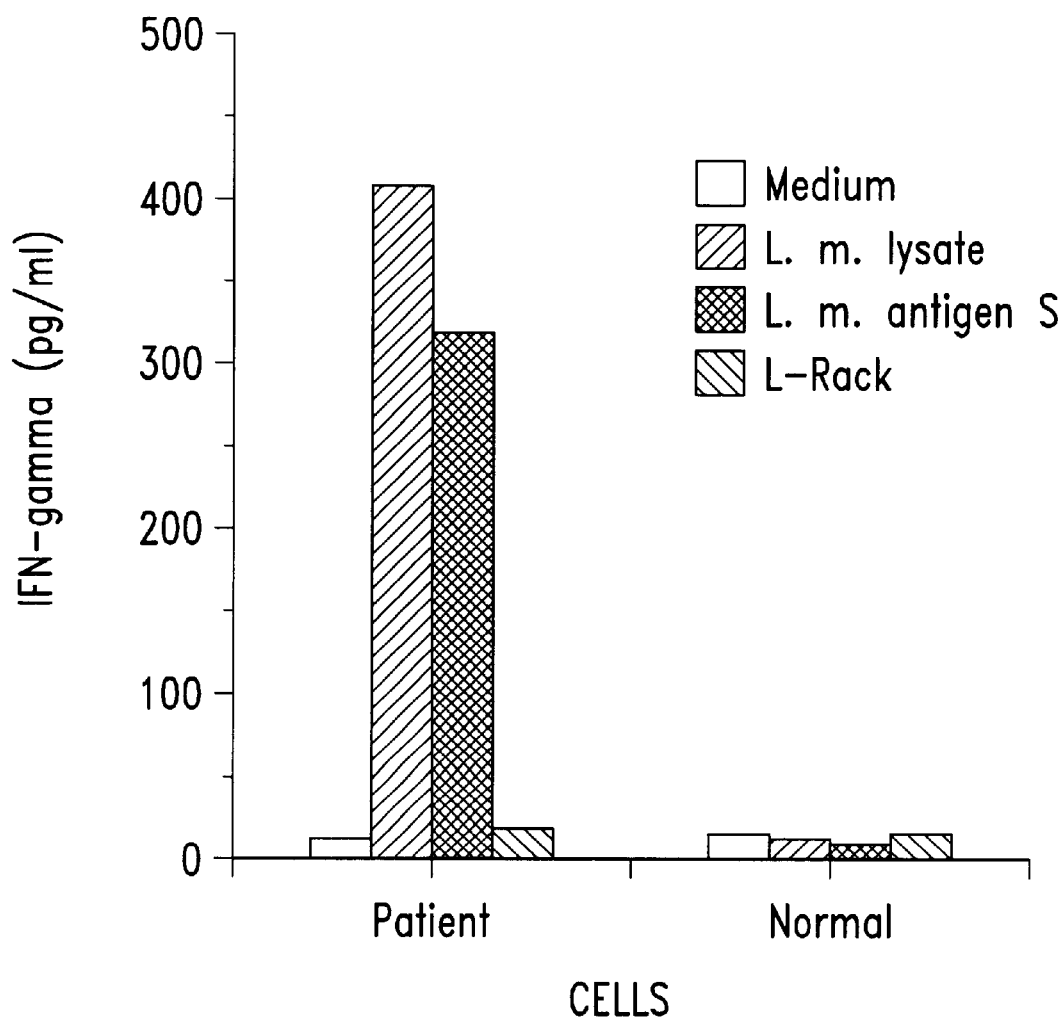
FIG. 15 shows the level of IFN-γ (in pg/mL) secreted by infected and uninfected human PBMC stimulated by soluble Leishmania antigens (S antigens), as compared to the levels stimulated by *L. major* lysate and L-Rack.

FIG. 14 shows the level of secreted IFN-γ in culture filtrate from infected and uninfected human PBMC preparations 72 hours after addition of 10 µg/mL L. major lysate, M15 or L-Rack, an immunodominant leishmanial antigen in murine leishmaniasis. Similarly, FIG. 15 illustrates the level of secreted IFN-γ in culture filtrate from infected and uninfected human PBMC preparations 72 hours after addition of 10 µg/mL L. major lysate, soluble Leishmania antigens (prepared as described in Example 6) or L-Rack. These results indicate that M15 and soluble Leishmania antigens, but not L-Rack, are potent stimulators of IFN-γ production in patient PBMC, but not in PBMC obtained from uninfected individuals. Thus, M15 and soluble Leishmania antigens elicit a dominant Th1 cytokine profile in both mice and humans infected with Leishmania.

Example 8

Comparison of Proliferation Stimulated by Leishmania Antigens

This Example illustrates the immunogenic properties of the antigens prepared according to Examples 1, 2, 5 and 6, as determined by their ability to stimulate proliferation in lymph node cultures from infected mice and in human PBMC preparations.

For in vitro proliferation assays, 2–4×10$^5$ cells/well were cultured in complete medium (RPMI 1640 supplemented with gentamycin, 2-ME, L-glutamine, and 10% screened pooled A+ human serum; Trimar, Hollywood, Calif.) in 96-well flat bottom plates with or without 10 µg/ml of the indicated antigens or 5 µg/ml PHA (Sigma Immunochemicals, St. Louis, Mo.) for five days. The cells were then pulsed with 1 µCi of [$^3$H] thymidine for the final 18 hours of culture.

Figure 16:
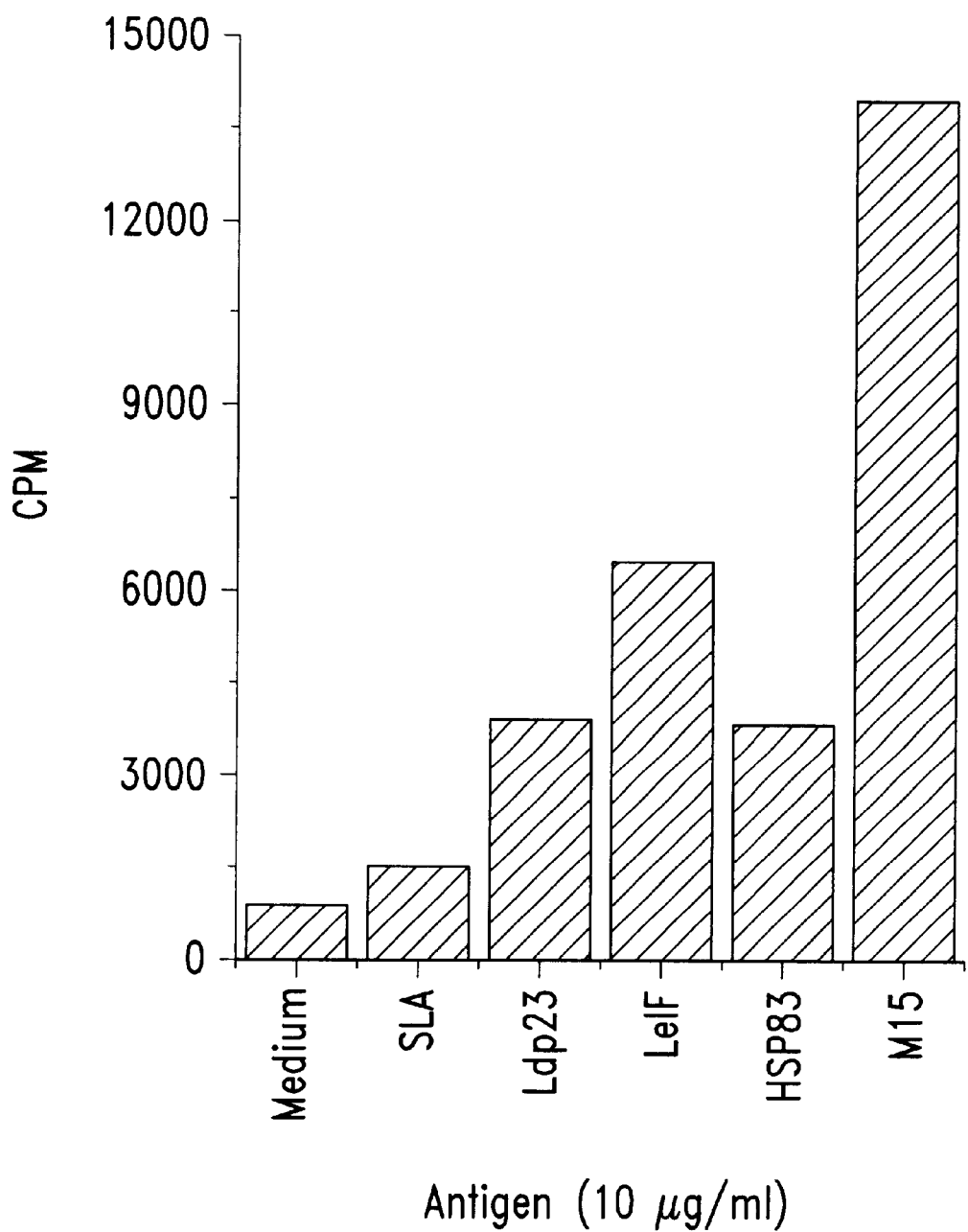
FIG. 16 illustrates the proliferation of murine lymph node cultures stimulated by the addition of representative polypeptides of the present invention. Values are expressed as cpm.

FIG. 16 illustrates the proliferation observed after addition of 10 µg/mL or 20 µg/mL of each of the following antigens to a lymph node culture prepared as described in Example 7: SLA, Ldp23, LbeIF4A, Lbhsp83, and M15. The level of proliferation without the addition of antigen is also shown. Data are represented as mean cpm. These results demonstrate that a variety of leishmanial antigens are capable of stimulatory lymph node cell proliferation from Leishmania-infected mice.

Figure 17:
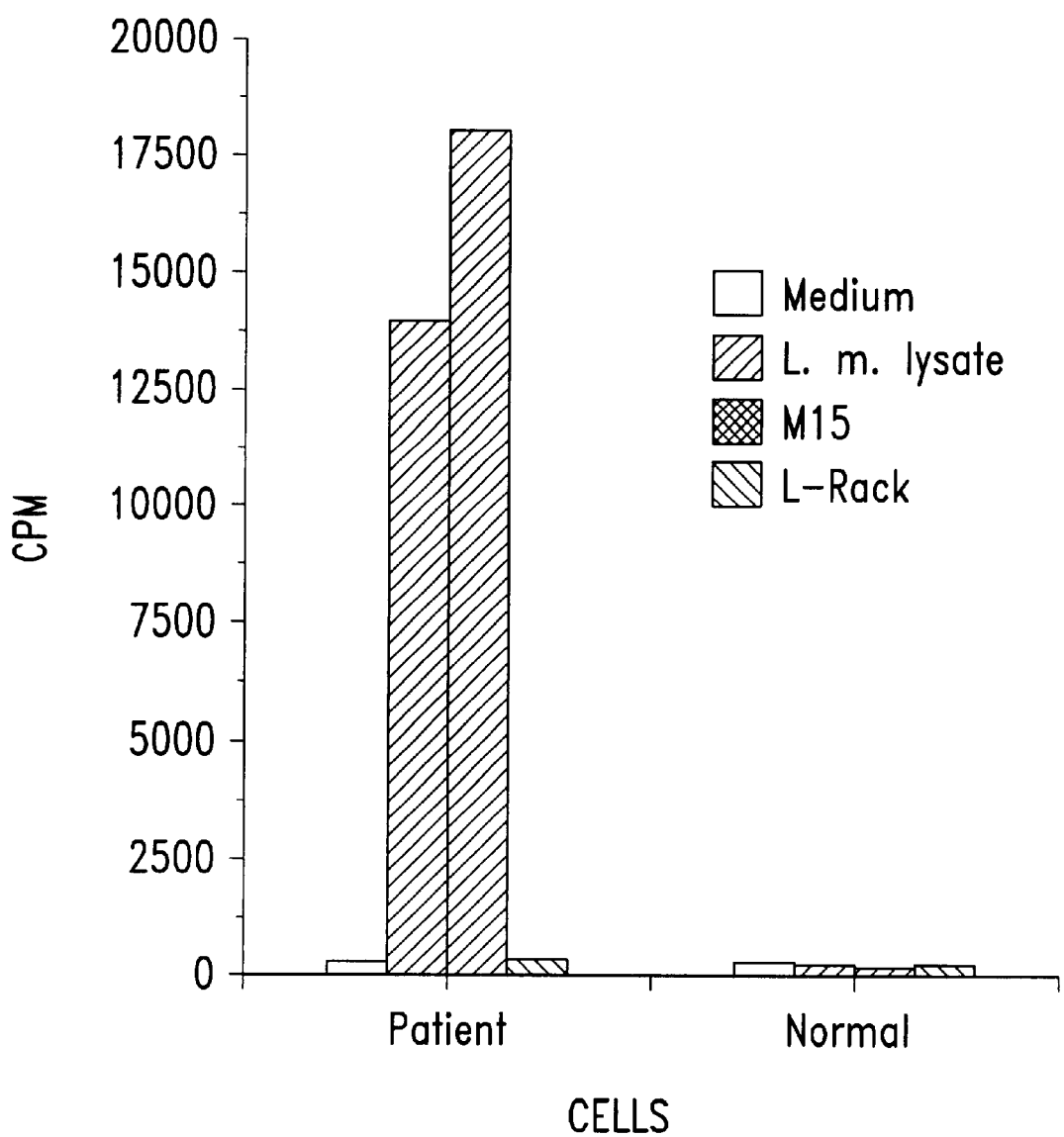
FIG. 17 shows the proliferation of human PBMC, prepared from Leishmania-immune and uninfected individuals, stimulated by M15 as compared to the proliferation stimulated by L. major lysate and L-Rack. Values are expressed as cpm.
Figure 18:
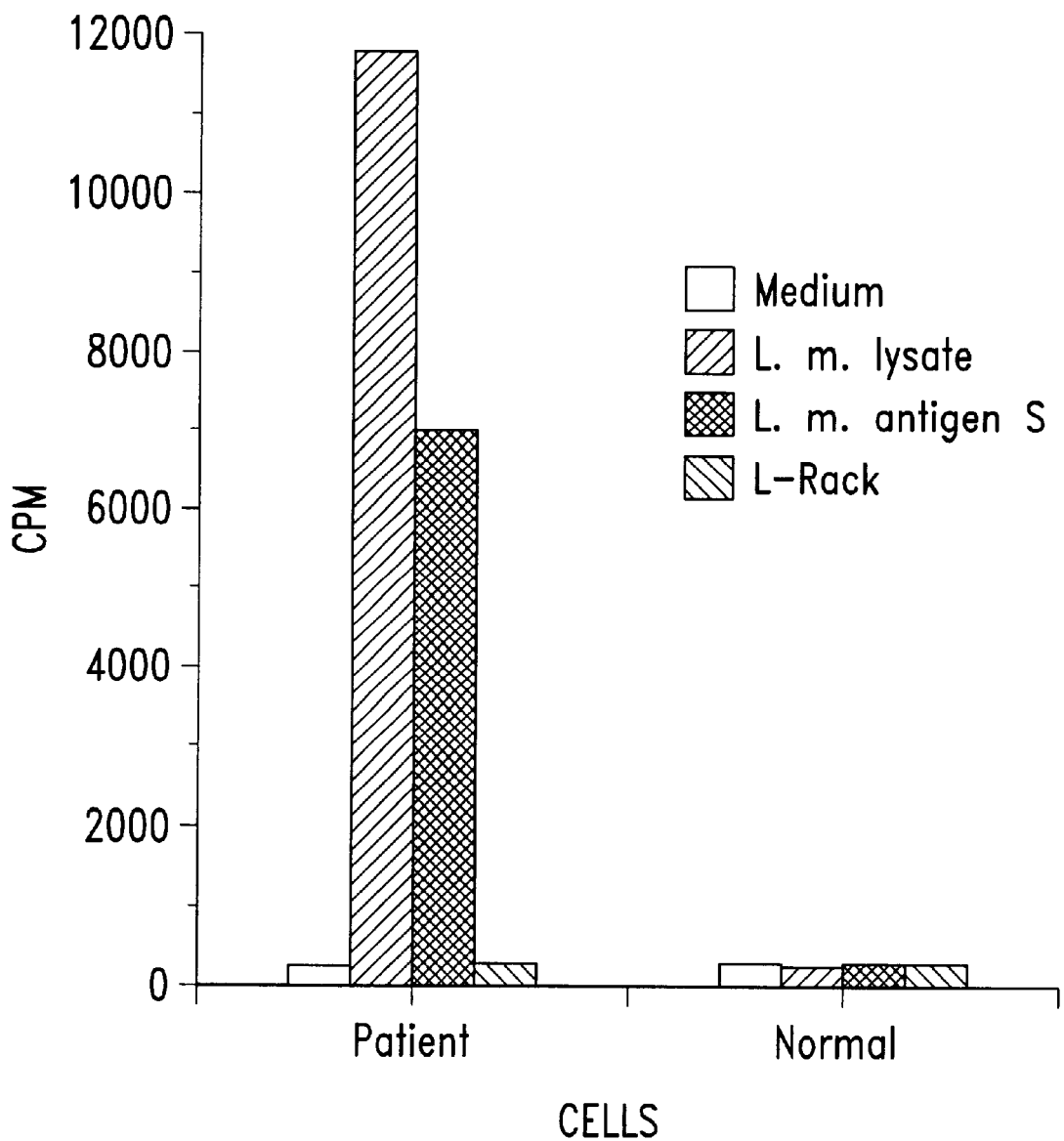
FIG. 18 illustrates the proliferation of human PBMC, prepared from Leishmania-infected and uninfected individuals, stimulated by soluble Leishmania antigens as compared to the proliferation stimulated by culture medium, L. major lysate and L-Rack. Values are expressed as cpm.

FIGS. 17 and 18 illustrate the proliferation observed in human PBMC preparations from Leishmania-immune and uninfected individuals following the addition of 10 µg/mL M15 and soluble Leishmania antigens, respectively. These values are compared to the proliferation observed following the addition of culture medium, L. major lysate or L-Rack. The results show that M15 and soluble Leishmania antigens stimulate proliferation in Leishmania-immune PBMC, but not in PBMC obtained from uninfected individuals, demonstrating that M15 and soluble antigens (but not L-Rack) are recognized by PBMC from individuals immune to Leishmania due to a previous infection.

Example 9

Preparation of Lmsp1A and Lmsp9A

This Example illustrates the preparation of two soluble Leishmania antigens, Lmsp1a and Lmsp9a.
A. Purification of Lmsp1a and Lmsp9a from a Mixture of Soluble L. major Antigens A high titer rabbit sera was raised against L. major soluble antigens, prepared as described above in Example 6. Specifically, a New Zealand white rabbit was immunized subcutaneously at multiple sites with 180 µg of L. major soluble antigens in a suspension containing 100 µg muramyl dipeptide and 50% incomplete Freund's adjuvant. Six weeks later the rabbit was given a subcutaneous boost of 100 µg of the same soluble antigen preparation in incomplete Freund's adjuvant. This was followed by two intravenous boosts spaced two weeks apart, each with 100 µg of the soluble antigen preparation. Sera was collected from the rabbit 11 days after the final boost.

Figure 20:
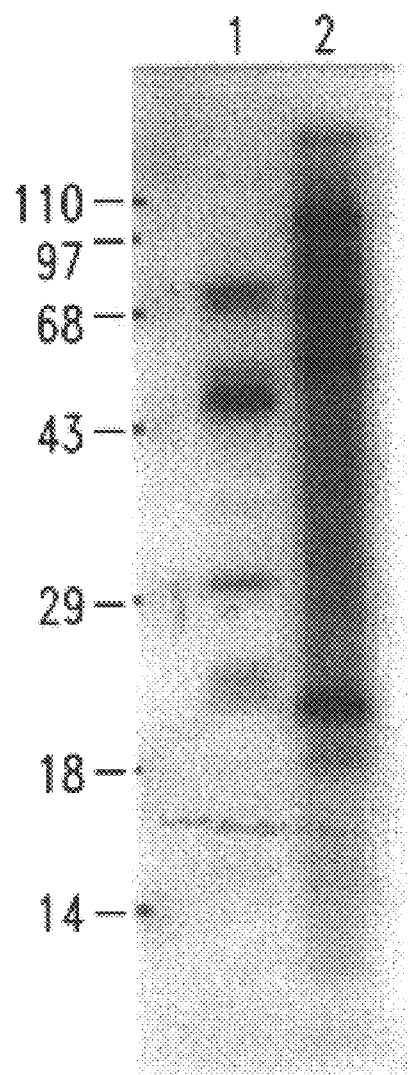
FIG. 20 illustrates the reactivity of rabbit sera raised against soluble Leishmania antigens with Leishmania promastigote lysate (lane 1) and soluble Leishmania antigens (lane 2).

Anti E. coli antibody reactivities were removed from the rabbit sera by pre-adsorbing on nitrocellulose filters containing lysed E. coli. Adsorbed sera were evaluated by Western blot analysis using 10 µg Leishmania promastigote lysate (lane 1) and 1 µg soluble L. major antigen mixture (lane 2). As shown in FIG. 20, the rabbit sera was found to be reactive with seven dominant antigens of the soluble L. major antigen mixture with molecular weights ranging from 18 to >200 kDa. A four times longer exposure of the same blot revealed three additional immunoreactive species with molecular weights less than 18 kDa. The same sera reacted with approximately 10 antigens of the promastigote lysate, but with a pattern significantly different from that observed with the soluble L. major antigens (FIG. 20). This is suggestive of potential post-translational modification of the same antigen before (intracellular localization) and after secretion/shedding. Such modifications may include cleavage of a leader sequence and/or the addition of carbohydrate molecules to the secreted/shed antigens.

The rabbit sera described above was subsequently used to screen an L. major cDNA expression library prepared from L. major promastigote RNA using the unidirectional Lambda ZAP (uni-ZAP) kit (Stratagene) according to the manufacturer's protocol. A total of 70,000 pfu of the amplified cDNA library was screened with the rabbit sera at a 1:250 dilution. Nineteen positive clones were confirmed in the tertiary screening. The phagemid were excised and DNA from each of the 19 clones was sequenced using a Perkin Elmer/Applied Biosystems Division automated sequencer Model 373A. All 19 clones were found to represent two distinct sequences, referred to as Lmsp1a and Lmsp9a. The determined cDNA sequences for Lmsp1a and Lmsp9a are provided in SEQ ID NO: 19 and 21, respectively, with the corresponding amino acid sequences being provided in SEQ ID NO: 20 and 22, respectively.
B. Characterization of Lmsp1a and Lmsp9a FIG. 21 shows the full-length cDNA (SEQ ID NO: 19) and predicted amino acid sequence (SEQ ID NO: 20) for the antigen Lmsp1a. The EcoRI/XhoI insert is 1019 bp long and contains the following features: a) the last 17 nt of the spliced leader sequence characteristic of all trypanosoma nuclearly encoded mRNA; b) 39 nt of 5' untranslated sequence; c) an open reading frame of 453 nt long coding for a 151 deduced amino acid sequence with a predicted molecular mass of 16.641 kDa; and d) 471 nt of 3' untranslated sequence terminating with a poly A tail. The predicted amino acid sequence contains three potential phosphorylation sites at amino acid residues 3, 85 and 102. In addition, Lmsp1a contains an RGD sequence at residue 104, a sequence that may play a role in parasite invasion of the macrophage. RGD sequences have been shown to mediate the binding of various adhesion proteins to their cell surface receptors. There is no obvious leader sequence (secretory signal) at the amino terminal portion suggesting that the protein might be shed or excreted. Lmsp1a appears to be one of the most abundant antigens found in the culture supernatant of live promastigote, since 17 of the 19 clones contain sequences of variable lengths identical to Lmsp1a.

Comparison of the amino acid sequence of Lmps1a with known sequences using the DNA STAR system (Version 87) revealed that Lmsp1a shares between 65% to 70% homology with the eukaryotic nucleoside diphosphate kinase protein, also referred to in the mouse and human as a tumor metastasis inhibitor gene.

Figure 22:
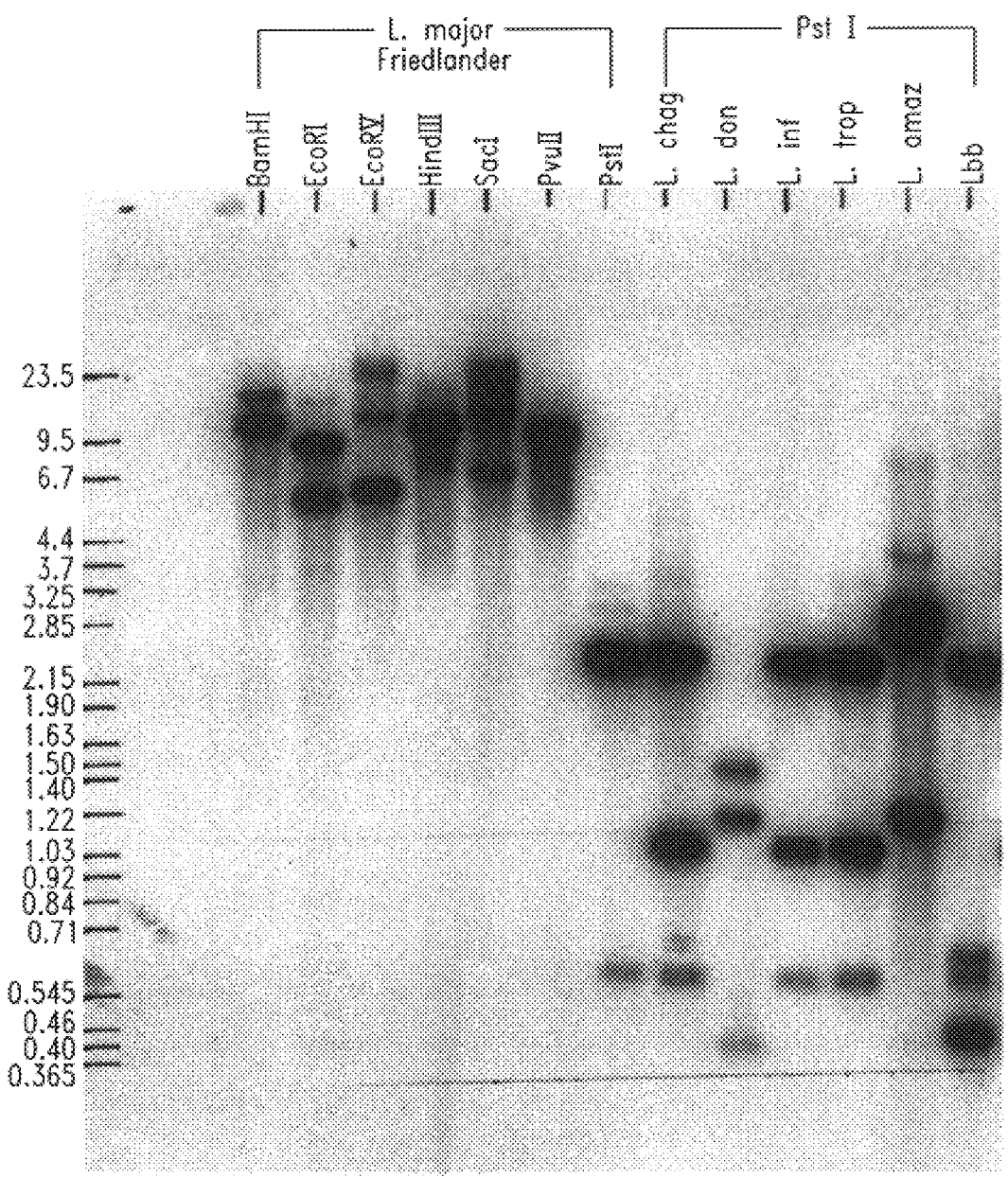
FIG. 22 shows a Southern blot of genomic DNA from L. major digested with a panel of restriction enzymes (lanes 1 to 7) and six other Leishmania species digested with PstI (lanes 8 to 13) probed with the full-length cDNA insert of Lmspla.

Southern blot analysis of genomic DNA from *L. major* (Friedlander strain) digested with a panel of restriction enzymes (lanes 1 to 7) and six other Leishmania species of different geographic locations digested with PstI (lanes 8 to 13) using the full-length cDNA insert of Lmps1a, demonstrated that Lmsp1a is present in all the species characterized with a high degree of conservation (FIG. 22). This suggests evolutionary significance for the maintenance of Lmsp1a and the existence of homologous species among all the Leishmania species.

The remaining two cDNA clones isolated from the soluble *L. major* antigen mixture represent identical sequences (referred to as Lmsp9a; SEQ ID NO: 21), suggesting that the two copies resulted from amplification of the primary library. Sequencing of the Lmsp9a cDNA revealed that the clone does not contain the full length 5' sequence since it is lacking both the spliced leader and 5' untranslated sequences. The 3' end of the cDNA contains a poly A stretch, as would be expected for a Leishmania mRNA. Of the predicted translated sequence (SEQ ID NO: 22), 34 of the 201 amino acids (17%) represent cysteine residues. Comparison of the predicted protein sequence with those of known proteins as described above, revealed some homology with other cysteine rich proteins such as the major surface trophozoite antigen of Giardia lamblia and furin proteases.

Example 10

Preparation and Characterization of MAPS-1A

This Example illustrates the preparation and characterization of the Leishmania antigen MAPS-1A (SEQ ID NO: 24).

A pool of sera was obtained from 5 BALB/c mice that had been given a primary immunization and two boosts with crude *L. major* promastigote culture supernatant as described below in Example 12. These mice were subsequently shown to be protected when challenged with a dose of live *L. major* promastigotes generally found to be lethal. The mouse sera thus obtained were used to screen an *L. major* amastigote cDNA expression library prepared as described in Example 1. Several seroreactive clones were isolated and sequenced using a Perkin Elmer/Applied Biosystems Division automated sequencer Model 373A (Foster City, Calif.).

One of these clones, referred to herein as MAPS-1A, was found to be full-length. Comparison of the cDNA and deduced amino acid sequences for MAPS-1A (SEQ ID Nos: 23 and 24, respectively) with known sequences in the gene bank using the DNA STAR system revealed no significant homologies to known Leishmania sequences, although some sequence similarity was found to a group of proteins, known as thiol-specific antioxidants, found in other organisms.

Figure 23:
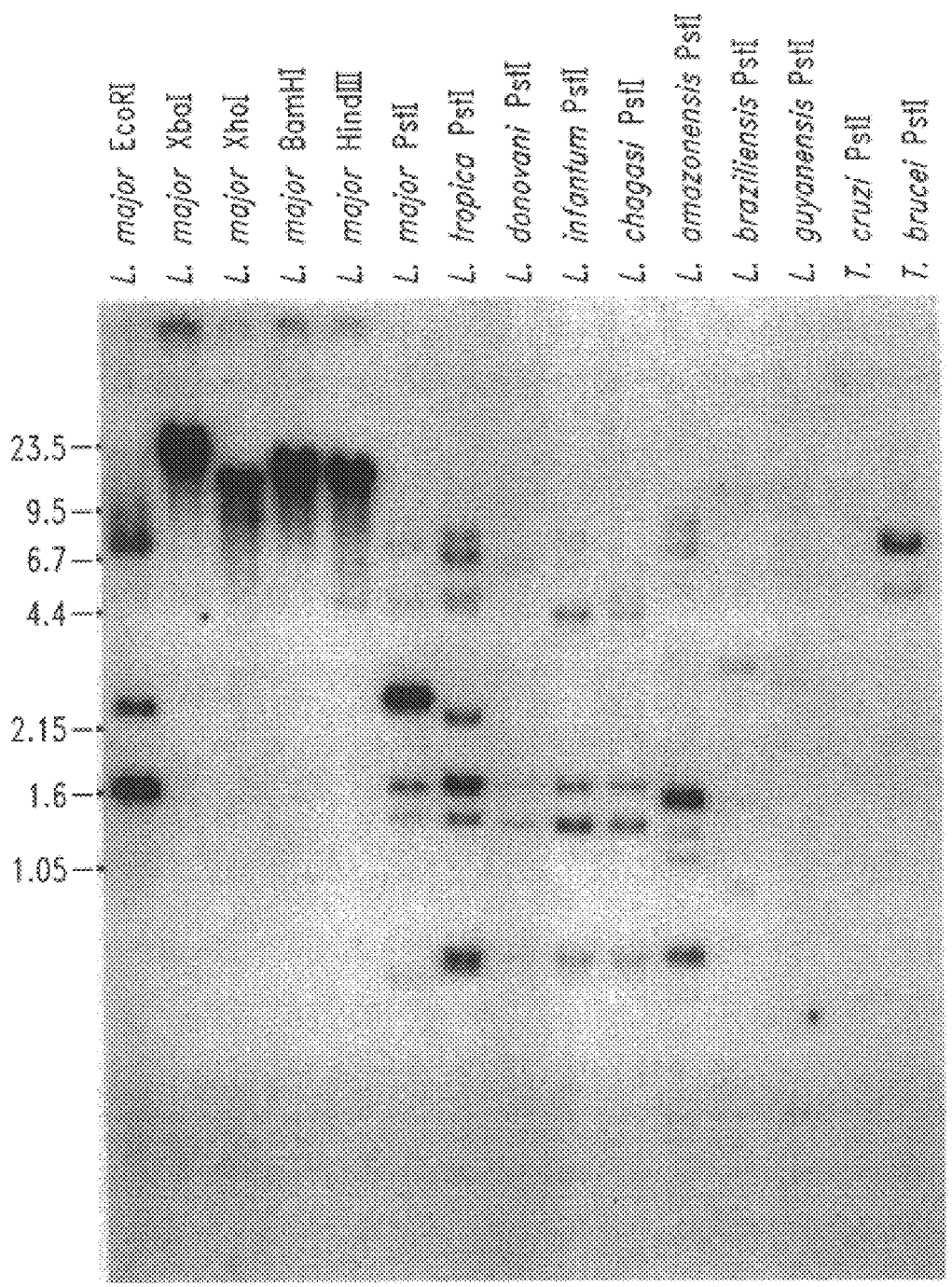
FIG. 23 shows a Southern blot of genomic DNA from L. major digested with a panel of restriction enzymes, six other Leishmania species digested with PstI and the infectious pathogens T. cruzi and T. brucei, probed with the full-length cDNA insert of the Leishmania antigen MAPS-1A.

Recombinant MAPS-1A protein having an amino-terminal HIS-Tag was prepared using a high level *E. coli* expression system and recombinant protein was purified by affinity chromatography as described in Example 1. Southern blot analysis of genomic DNA from *L. major* digested with a panel of restriction enzymes, seven other Leishmania species digested with PstI, and two other infectious-disease pathogens (*T. cruzi* and *T. brucei*), using the full length insert of MAPS-1A, demonstrated that MAPS-1A is present in all eight Leishmania species tested (FIG. 23). Northern blot analysis of *L. major* promastigote and amastigote RNAs indicated that MAPS-1A is constitutively expressed.

Using oligonucleotide primers (SEQ ID NOs:27 and 28) based on the MAPS-1A cDNA sequence provided in SEQ ID NO: 23, the corresponding gene was isolated from *L. tropica* by means of PCR (using 30 cycles of the following temperature step sequence: 94° C., 1 minute; 50° C., 1 minute; 72° C., 1 minute) The determined cDNA sequence for the *L. tropica* MAPS-1A protein is provided in SEQ ID NO: 25, with the corresponding amino acid sequence being provided in SEQ ID NO: 26.

Figure 24:
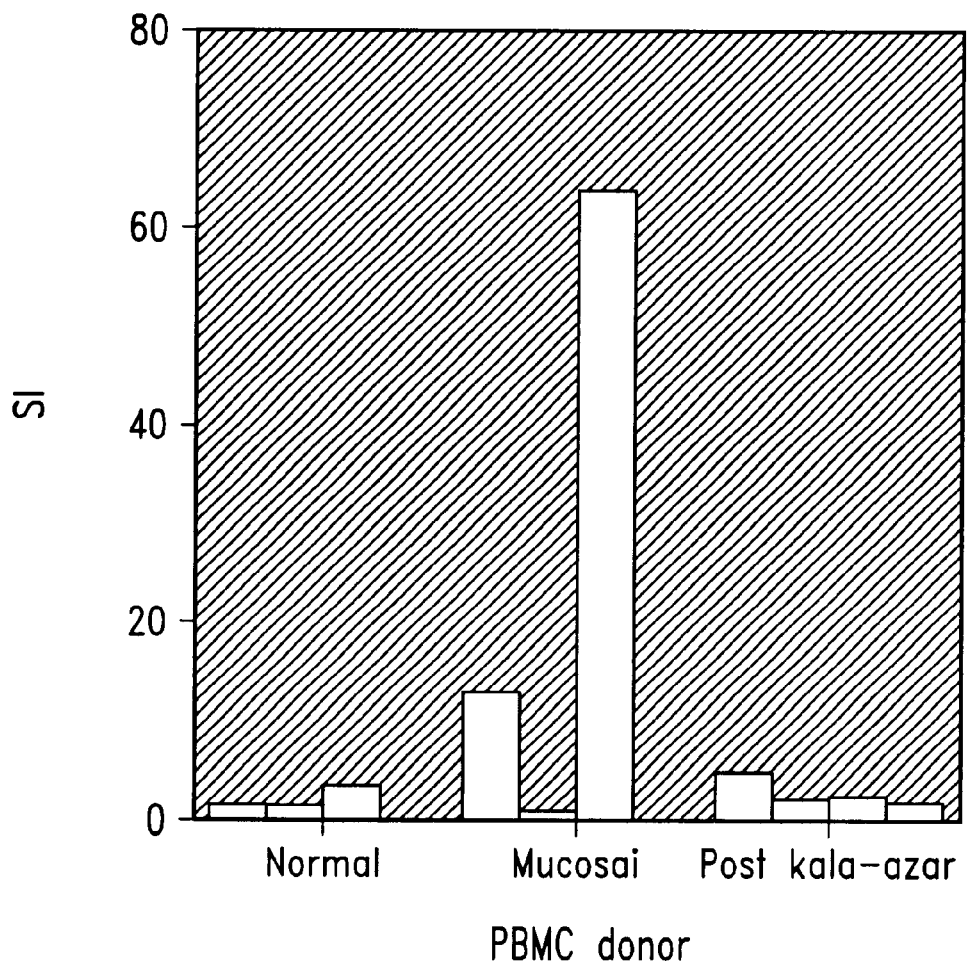
FIG. 24 illustrates the proliferation of PBMC isolated from uninfected-individuals, patients with active mucosal leishmaniasis and patients post kala-azar infection, stimulated by MAPS-1A.

The ability of recombinant MAPS-1A to stimulate cell proliferation was investigated as follows. PBMC from 3 *L. braziliensis*-infected patients having active mucosal leishmaniasis, from 4 patients post kala-azar infection (previously infected with *L. chagasi* and/or *L. donovani*) and from 3 uninfected-individuals were prepared as described above in Example 7. The ability of MAPS-1A to stimulate proliferation of these PBMC was determined as described in Example 8 above. As shown in FIG. 24, significant levels of MAPS-1A specific PBMC proliferation were seen in 2 of the 7 Leishmania patients.

Figure 25:
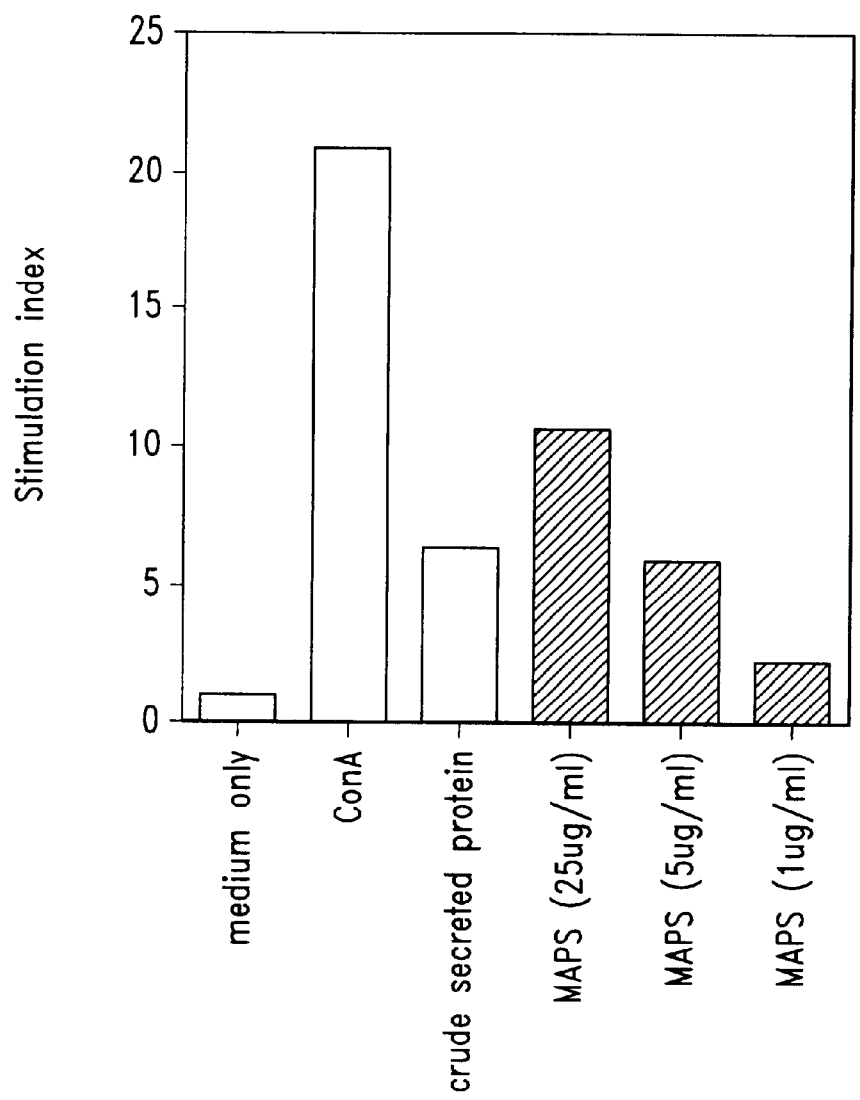
FIG. 25 illustrates the proliferation of murine lymph node cultures stimulated by MAPS-1A.

The ability of MAPS-1A to stimulate proliferation in mice lymph node cultures was determined as described in Example 8. FIG. 25 shows the amount of proliferation stimulated by MAPS-1A (at 25 μg/ml, 5 μg/ml and 1 μg/ml) as compared to that stimulated by the positive control ConA and by crude *L. major* promastigote supernatant proteins, 20 days post-infection with *L. major*. Cells isolated 20 days post-infection were highly responsive to MAPS-1A, whereas cells isolated 10 days post-infection were unresponsive.

Example 11

Immunoreactivity of Soluble Leishmania Antigens with Sera from Leishmania-infected Patients The reactivity of MAPS-1A with sera from uninfected individuals, from human leishmaniasis patients with cutaneous infection, from human patients with acute visceral leishmaniasis, and from *L. major*-infected BALB/c mice was determined as follows.

Assays were performed in 96-well plates coated with 200 ng antigen diluted to 50 μL in carbonate coating buffer, pH 9.6. The wells were coated overnight at 4° C. (or 2 hours at 37° C.). The plate contents were then removed and the wells were blocked for 2 hours with 200 μL of PBS/1% BSA. After the blocking step, the wells were washed five times with PBS/0.1% Tween 20™. 50 μL sera, diluted 1:100 in PBS/0.1% Tween 20™/0.1% BSA, was then added to each well and incubated for 30 minutes at room temperature. The plates were then washed again five times with PBS/0.1% Tween 20™.

The enzyme conjugate (horseradish peroxidase—Protein A, Zymed, San Francisco, Calif.) was then diluted 1:10,000 in PBS/0.1% Tween 20™/0.1% BSA, and 50 μL of the diluted conjugate was added to each well and incubated for 30 minutes at room temperature. Following incubation, the wells were washed five times with PBS/0.1% Tween 20™. 100 μL of tetramethylbenzidine peroxidase (TMB) substrate (Kirkegaard and Perry Laboratories, Gaithersburg, Md.) was added, undiluted, and incubated for about 15 minutes. The reaction was stopped with the addition of 100 μL of 1 N $H_2SO_4$ to each well, and the plates were read at 450 mn.

Figure 26:
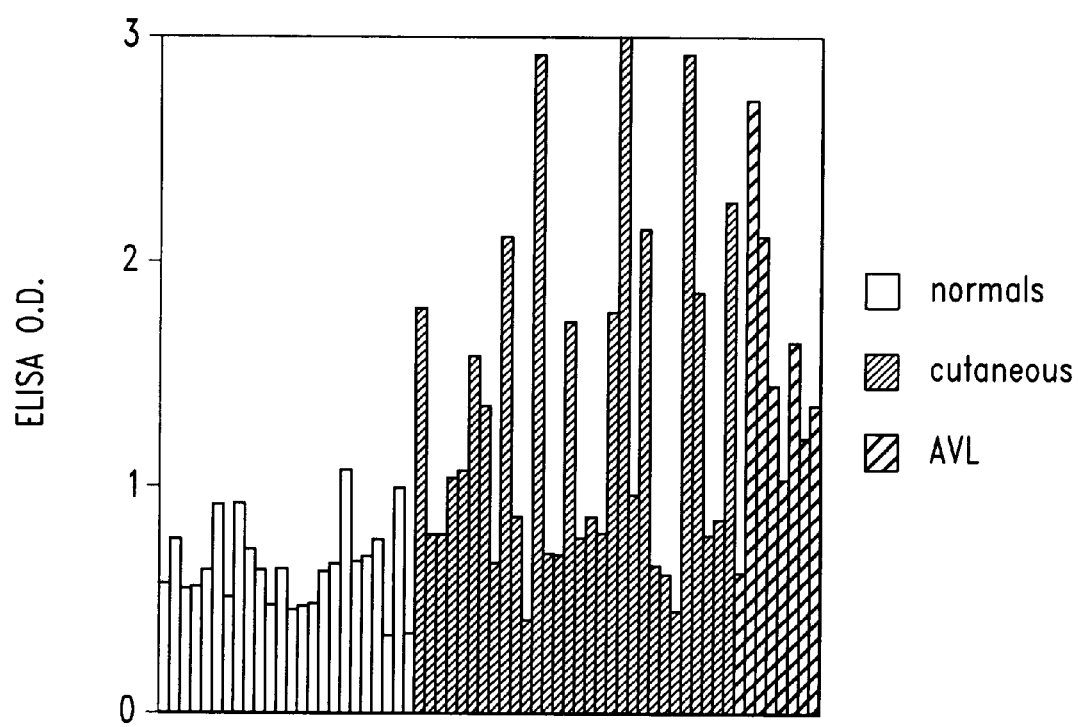
FIG. 26 illustrates the reactivity of MAPS-1A with sera from human leishmaniasis patients.
Figure 27:
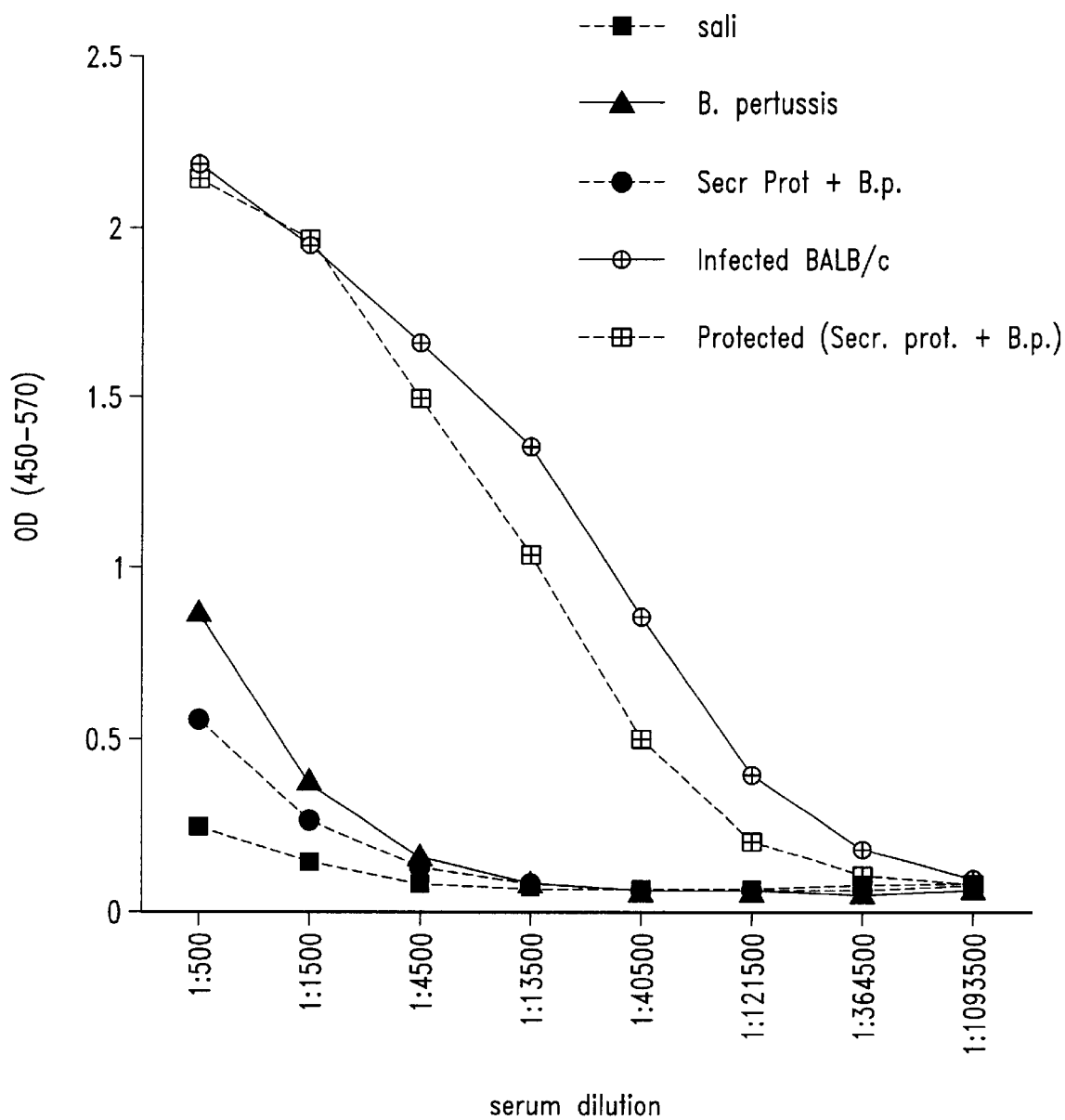
FIG. 27 illustrates the reactivity of MAPS-1A with sera from mice immunized against and/or infected with leishmaniasis.

As shown in FIG. 26, approximately 50% of the samples from human leishmaniasis patients showed reactivities with recombinant MAPS-1A substantially above background. FIG. 27 shows the reactivity of MAPS-1A with increasing dilutions of sera from BALB/c mice previously administered either (i) saline solution; (ii) the adjuvant B. pertussis; (iii) soluble Leishmania antigens plus B. pertussis; (iv) live L. major promastigotes; or (v) soluble Leishmania antigens plus B. pertussis followed by live L. major promastigotes (as described below in Example 12). Considerably higher absorbances were seen with sera from mice infected with live L. major promastigotes and with mice infected with live L. major promastigotes following immunization with soluble Leishmania antigens plus B. pertussis, than with sera from the other three groups of mice, indicating that anti-MAPS-1A antibody titers increase following Leishmania infection.

Example 12

Use of Leishmania Antigens for Vaccination Against Leishmania Infection

This example illustrates the effectiveness of Leishmania antigens in conferring protection against disease in the experimental murine leishmaniasis model system. For a discussion of the murine leishmaniasis model system see, for example, Reiner et al. Annu. Rev. Immunol., 13:151–77, 1995.

Figure 28:
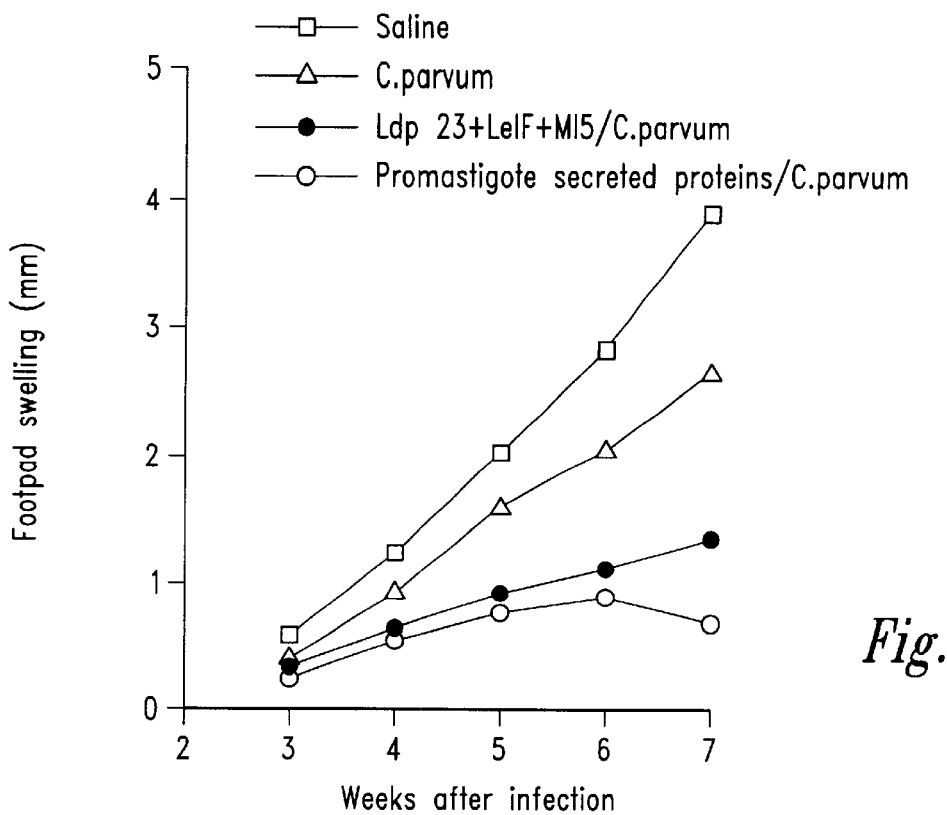
FIG. 28 illustrates the effectiveness of immunization with either soluble Leishmania antigens or a mixture of Ldp23, LbeiF4A and M15 plus adjuvant in conferring protection against infection (as measured by footpad swelling) in a murine leishmaniasis model system, as compared to the administration of adjuvant alone.
Figure 29:
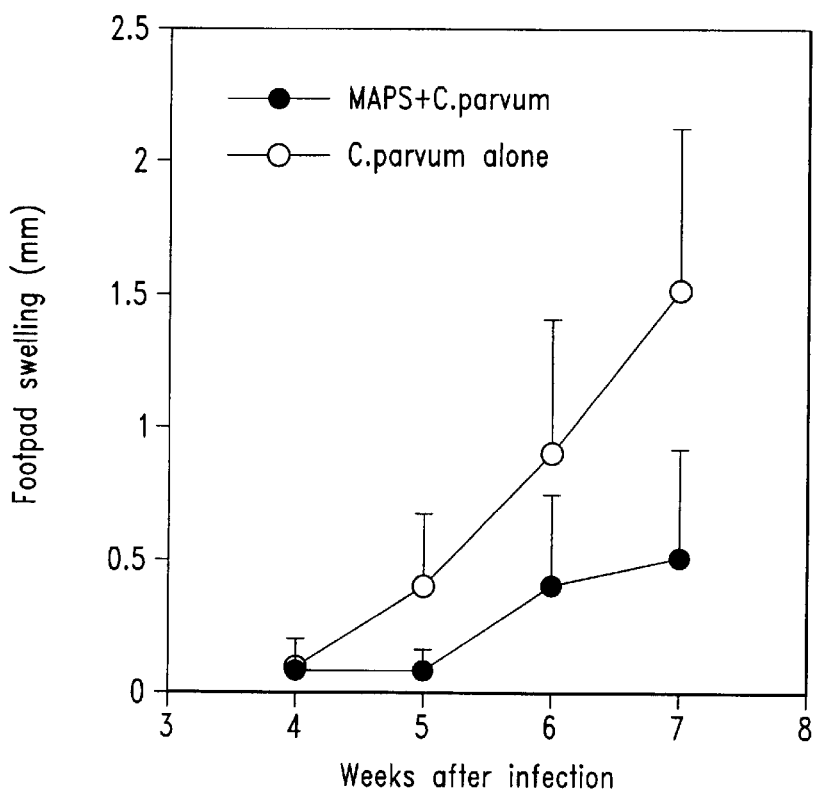
FIG. 29 illustrates the effectiveness of immunization with MAPS-1A plus adjuvant in conferring protection against infection (as measured by footpad swelling) in a murine leishmaniasis model system, as compared to the administration of adjuvant alone.

The effectiveness of (i) crude soluble Leishmania antigens, (ii) MAPS-1A, and (iii) a mixture of Ldp23, LbeIF4A and M15, as vaccines against Leishmania infection was determined as follows. BALB/c mice (5 per group) were immunized intra-peritoneally three times at biweekly intervals with either (i) 30 μg crude soluble Leishmania antigens, (ii) 20 μg MAPS-1A or (iii) a mixture containing 10 μg each of LeIF, Ldp23 and M15, together with 100 μg of the adjuvant C. parvum. Two control groups were immunized with either saline or C. parvum alone. Two weeks after the last immunization, the mice were challenged with $2\times10^5$ late-log phase promastigotes of L. major. Infection was monitored weekly by measurement of footpad swelling. The amount of footpad swelling seen in mice immunized with either crude soluble Leishmania antigens, a mixture of Ldp23, LbeiF4A and M15 (FIG. 28), or MAPS-1A (FIG. 29) was significantly less than that seen in mice immunized with C. parvum alone. These results demonstrate that the Leishmania antigens of the present invention are effective in conferring protection against Leishmania infection.

Example 13

Isolation of DNA Encoding for Soluble Antigens from an L. major Genomic DNA Library This example illustrates the isolation of seven soluble Leishmania antigen genes from an L. major genomic DNA library.

An L. major genomic DNA expression library was prepared from L. major promastigotes using the unidirectional Lambda ZAP (uni-ZAP) kit (Stratagene) according to the manufacturer's protocol. This library was screened with a high titer rabbit sera raised against L. major soluble antigens, as described above in Example 9. Seven positive clones were identified. The phagemid were excised and DNA from each of the seven clones was sequenced using a Perkin Elmer/Applied Biosystems Division automated sequencer Model 373A. The DNA sequences for these antigens, referred to as LmgSP1, LmgSP3, LmgSP5, LmgSP8, LmgSP9, LmgSP13, LmgSP19, are provided in SEQ ID NO:29–35, respectively, with the corresponding amino acid sequences being provided in SEQ ID NO: 36–42, respectively. LmgSP13 was found to contain a 39 amino acid repeat sequence shown in SEQ ID NO:43.

Subsequent studies led to the isolation of an extended cDNA sequence for LmgSP13 which contains an ORF (cDNA sequence provided in SEQ ID NO: 114) encoding a 194 amino acid sequence (SEQ ID NO: 119). Comparison of these sequences with those in the public databases revealed that LmgSP13 encodes a portion of a clone recently identified in the L. major genome sequencing project (genomic DNA sequence provided in SEQ ID NO: 115). The full-length ORF encodes a 2310 amino acid polypeptide sequence (provided in SEQ ID NO: 120) containing unique amino- and carboxy-terminal regions flanking 42 highly related 39 amino acid repeats.

The 5 repeats of the original LmgSP 13 clone were subcloned into a modified pET vector both alone and as a fusion downstream of the M. tuberculosis antigen Ra12. The resulting recombinant protein was expressed, purified and used to generate a highly specific rabbit antiserum. Western blotting indicated that L. chagasi contains a LmgSp13 homologue.

Subsequent studies resulted in the isolation of an extended sequence for LmgSP9. The extended DNA sequence is provided in SEQ ID NO: 54, with the corresponding predicted amino acid sequence being provided in SEQ ID NO: 55. The amino acid sequence was found to contain six 14 amino acid repeat units (SEQ ID NO: 56), with each unit being further divided into two 7 amino acid units, provided in SEQ ID NO: 57 and 58. Comparison of the isolated sequences for LmgSP9 with sequences in the public databases, revealed that LmgSP9 encodes for the carboxy-terminal region of a larger DNA sequence (SEQ ID NO: 116) that encodes a 708 amino acid polypeptide (SEQ ID NO: 121) identified in the L. major genome sequencing project. LmgSP9 was found to share low homology with serine protease, endo-protease furin and the major surface-labeled trophozoite antigen of Giardia lamblia (25–30% identity). Surface localization of LmgSP9 is consistent with motif predictions of an amino-terminal signal sequence, carboxy-terminal transmembrane domain and GPI anchor. Southern hybridization using the original LmgSP9 clone indicated that homologous sequences are present in all tested Leishmania species. The amino-terminal 295 amino acids of LmgSP9 excluding the signal sequence (referred to as LmgSP9N-ht; cDNA sequence provided in SEQ ID NO: 117 and amino acid sequence provided in SEQ ID NO: 122) were subcloned into a modified pET vector and recombinant protein was expressed and purified.

Comparison of the DNA and amino acid sequences for the isolated antigens as described above, revealed no significant homologies to LmgSP1 and LmgSP3. LmgSP5 was found to be related to the known Promastigote surface antigen-2 (PSA2) family. LmgSP8 was found to bear some homology to a sequence previously identified in *E. coli* (2-succinyl-6-hydroxy-2,4-cyclohexadiene-1-carboxylic acid synthase). LmgSP9 and LmgSP 19 were found to be homologous to a *L. major* hydrophilic surface protein referred to as Gene B (Flinn, H. M. et al. *Mol. Biochem. Parasit.* 65:259–270, 1994), and to ubiquitin, respectively. To the best of the inventors' knowledge, none of these antigens have been previously shown to elicit T or B cell responses.

In further studies, a 220 bp DNA fragment was amplified from LmgSP5 and used to screen a *L. major* genomic library in Lambda ZAP. Seventeen positive clones were purified after secondary screening. To select for a clone that had a likelihood of having the 5' sequence of the LmgSP5 insert, a labeled oligonucleotide from the 5' region was used to screen the DNA from the secondary positive clones. DNA from three clones hybridized to the 5' oligonucleotide, with one clone hybridizing stronger than the other two. This clone (cDNA sequence provided in SEQ ID NO: 103) was found to contain an insert of 2421 bp which contained the entire open reading frame for the novel PSA-2 gene. This ORF was amplified and cloned in the expression vector pET-17b for expression of recombinant protein in *E. coli*. The cDNA sequence of the ORF is provided in SEQ ID NO: 102, with the corresponding amino acid sequence being provided in SEQ ID NO: 104.

The reactivity of recombinant LmgSP9 with sera from patients with visceral leishmaniasis, (from both Sudan and Brazil) and from normal donors was evaluated by ELISA as described above. The absorbance values were compared with those obtained using the known Leishmania antigen K39 described above, with *L. chagasi* lysate being employed as a positive control. Representative results of these assays are provided below in Table 2, wherein all the patients from Brazil and those from the Sudan designated as "VL" were inflicted with visceral leishmaniasis. The results demonstrated that LmgSP9 specifically detects antibody in most individuals with visceral leishmaniasis, regardless of geographical location. In several cases, the absorbance values of the antibody reactivity to LmgSP9 were comparable to that observed with K39. In addition, LmgSP9 detected several cases of leishmaniasis that were not detected using K39. These results indicate that LmgSP9 can be used to complement the reactivity of K39.

TABLE 2

REACTIVITY OF LMGSP9 WITH SERA FROM LEISHMANIA PATIENTS

| Patient No. | *L. chagasi* lysate | K39 | LmgSP9 |
|---|---|---|---|
| Sudanese samples: | | | |
| B19 | 1.067 | 0.306 | 0.554 |
| B25 | 1.884 | 3.435 | 0.974 |
| B43 | 1.19 | 3.225 | 0.86 |
| B47 | 2.405 | 2.892 | 0.375 |
| B50 | 0.834 | 0.748 | 0.432 |
| B58 | 0.921 | 0.235 | 0.92 |
| B63 | 1.291 | 0.303 | 0.764 |
| B70 | 0.317 | 0.089 | 3.056 |
| VL4 | 1.384 | 3.035 | 2.965 |
| VL11 | 0.382 | 0.144 | 0.142 |
| VL12 | 0.277 | 0.068 | 0.098 |
| VL13 | 0.284 | 0.12 | 0.194 |
| Brazilian samples: | | | |
| 105 | 3.508 | 3.53 | 0.374 |
| 106 | 2.979 | 3.373 | 2.292 |
| 107 | 2.535 | 3.444 | 0.46 |

TABLE 2-continued

REACTIVITY OF LMGSP9 WITH SERA FROM LEISHMANIA PATIENTS

| Patient No. | *L. chagasi* lysate | K39 | LmgSP9 |
|---|---|---|---|
| 109 | 1.661 | 3.415 | 3.319 |
| 111 | 3.595 | 3.537 | 0.781 |
| 112 | 2.052 | 3.469 | 0.63 |
| 113 | 3.352 | 3.429 | 0.963 |
| 114 | 2.316 | 3.437 | 1.058 |
| 115 | 2.073 | 3.502 | 1.186 |
| 116 | 3.331 | 3.461 | 0.96 |
| Normal Donors: | | | |
| 129 | 0.157 | 0.104 | 0.08 |
| 130 | 0.195 | 0.076 | 0.095 |
| 131 | 0.254 | 0.134 | 0.086 |
| 132 | 0.102 | 0.035 | 0.043 |

In subsequent ELISA analyses performed as described above, LmgSP 13 was demonstrated to react as strongly with sera from patients infected with *L. chagasi* as with sera from *L. major* infected patients. This is consistent with the Western blot studies discussed above wherein *L. chagasi* was found to contain an LmgSp13 homologue.

In order to obtain a higher specificity for the detection of antibodies in sera from visceral leishmaniasis patients, a homologue of LmgSP9 was isolated from *L. chagasi*, one of the causative agents of visceral leishmaniasis. A total of 80,000 pfu of an amplified *L. chagasi* genomic library were screened with the entire coding region of LmgSP9 (amplified from *L. major* genomic DNA). Seven hybridizing clones were purified to homogeneity. The determined DNA sequences for two of these clones, referred to as Lc Gene A and LcGene B, are provided in SEQ ID NO: 59 and 60, respectively, with the corresponding predicted amino acid sequences being provided in SEQ ID NO: 61 and 62, respectively. The open reading frame for Lc Gene A was found to show some homology to Gene A/C, previously isolated from *L. major* (McKlean et al., *Mol. Bio. Parasitol.*, 85:221–231, 1997). The open reading frame for Lc Gene B showed some homology to Gene B of *L. major*, discussed above, and was found to contain eleven repeats of a 14 amino acid repeat unit (SEQ ID NO: 63), with each repeat being further divided into two 7 amino acid units, provided in SEQ ID NO: 64 and 65.

The diagnostic potentials of Lc Gene A and Lc Gene B were evaluated by ELISA as described above using sera from visceral leishmaniasis patients from Sudan and Brazil, and from uninfected controls. Absorbance values were compared to those obtained using LmgSP9. Much higher absorbance values were obtained with Lc Gene A and Lc Gene B than with LmgSP9, with Lc Gene B appearing to be more effective that Lc Gene A in detecting antibodies in certain cases. These results indicate that Lc Gene B is highly effective in the diagnosis of visceral leishmaniasis.

In order to assess the diagnostic potential of the repeats found within Lc Gene B, a series of 6 peptides were synthesized (SEQ ID NO: 66–71; referred to as Pep 1–6), differing in an R or H residue. An ELISA was carried out using the full-length LcGene B protein and the six peptides. The absorbance values obtained with Pep 3 were higher than those obtained with the other 5 peptides, however they were not as high as those obtained with the full length protein.

Example 14

Isolation and Characterization of DNA Encoding for Soluble Antigens from an *L. chagasi* Genomic DNA Library This example illustrates the preparation of five soluble Leishmania antigen genes from an *L. chagasi* genomic DNA library.

An *L. chagasi* genomic DNA expression library was prepared from *L. chagasi* promastigotes using the unidirectional Lambda ZAP (uni-ZAP) kit (Stratagene) according to the manufacturer's protocol. This library was screened with a high titer rabbit sera raised against *L. major* soluble antigens, as described above in Example 9. Five positive clones were identified. The phagemid were excised and DNA from each of the Five clones was sequenced using a Perkin Elmer/Applied Biosystems Division automated sequencer Model 373A. The DNA sequences for these antigens, referred to as LcgSP1, LcgSP3, LcgSP4, LcgSP8, and LcgSP10 are provided in SEQ ID NO:44–48, respectively, with the corresponding amino acid sequences being provided in SEQ ID NO:49–53, respectively.

Comparison of these sequences with known sequences in the gene bank as described above, revealed no known homologies to LcgSP3, LcgSP4, LcgSP8 and LcgSP10. LcgSP1 was found to be homologous to the known antigen HSP70.

Subsequent studies led to the isolation of a longer cDNA sequence for LcgSP3. This clone was found to contain an ORF (cDNA sequence provided in SEQ ID NO: 113) encoding an amino acid sequence of 539 residues (SEQ ID NO: 118). Comparison of the sequence for LcgSP3 with those in the public database, revealed it to be most closely related to the thermostable carboxypeptidase of *Vibrio cholera* (45% identity). Moreover, LcgSP3 was found to contain the active site residues characteristic of this class of carboxypeptidase. Southern hybridization using the LcgSP3 ORF indicated that homologous sequences are present in all tested Leishmania species. The LcgSP3 ORF was subcloned into a modified pET vector and recombinant protein was expressed, purified and used to generate a highly specific rabbit antiserum, using conventional techniques.

Figure 30A:
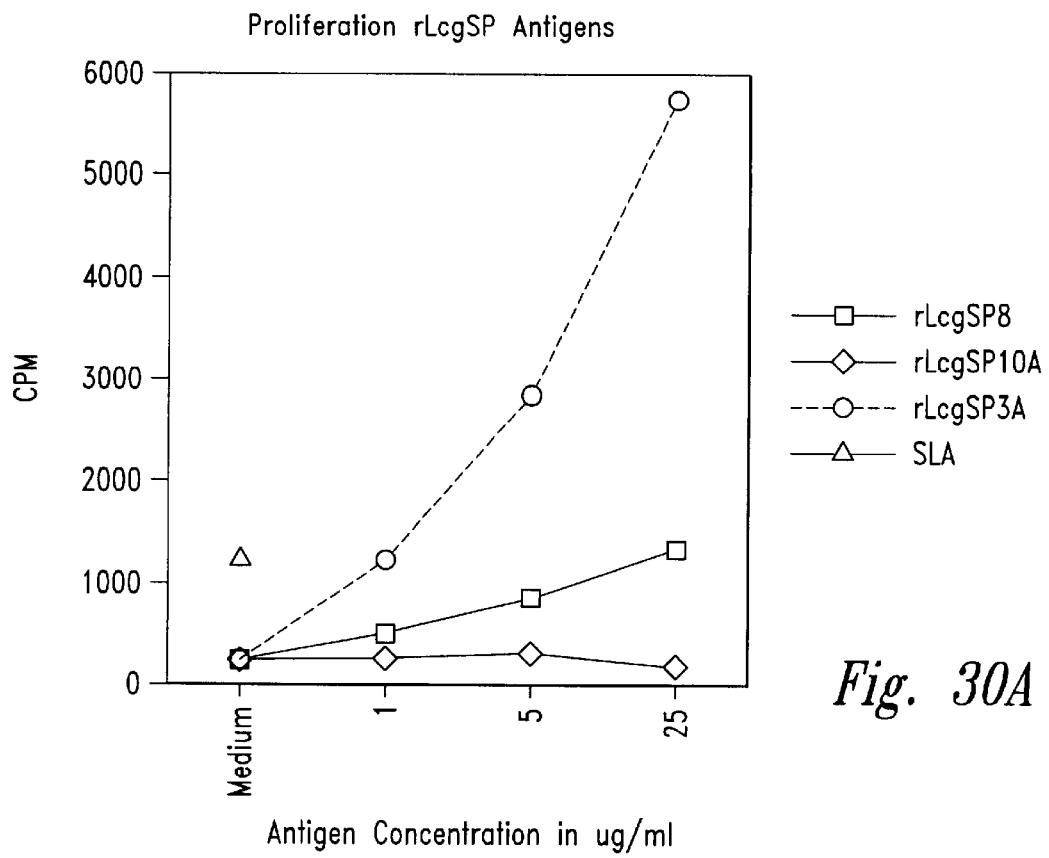
FIGS. 30A and B illustrate the proliferation of murine lymph node cultures stimulated with either LcgSP8, LcgSP10 or LcgSP3.
Figure 30B:
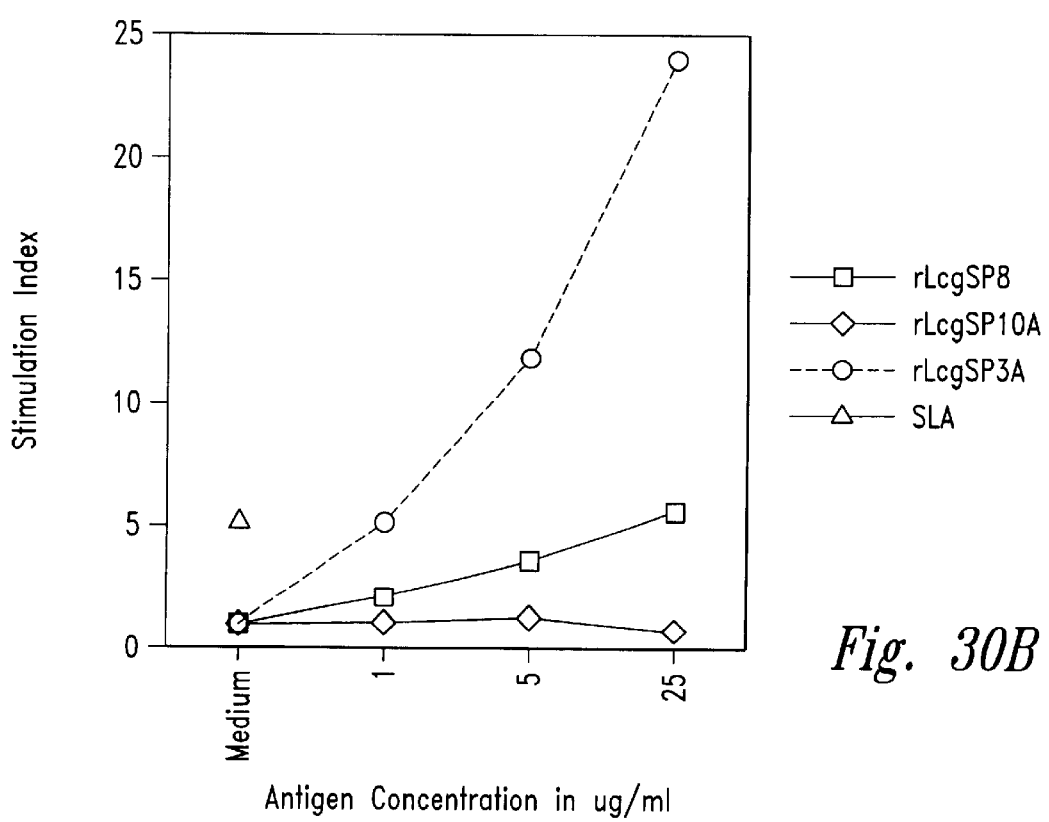

FIGS. 30A and B illustrate the proliferative response of murine lymph nodes to recombinant LcgSP8, LcgSP10 and LcgSP3. Lymph nodes were taken BALB/c mice 17 days after infection with *L. major*. Infection occurred by footpad injection of 2×10⁶ parasites/footpad. The cells were stimulated with recombinant antigen and proliferation was measured at 72 hours using $^3$H-thymidine. FIG. 30A shows the CPM, a direct measurement of mitotic activity in response to the antigens, and FIG. 30B shows the stimulation index, which measures the proliferative response relative to the negative control.

Example 15

Isolation of DNA Encoding for *L. major* Antigens By CD4+ T Cell Expression Cloning This example illustrates the isolation of T cell antigens of *L. major* using a direct T cell screening approach.

Leishmania-specific CD4+ T cell lines were derived from the PBMC of an individual who tested positive in a leishmania skin test but had no clinical history of disease. These T cell lines were used to screen a *L. major* amastigote cDNA expression library prepared as described in Example 1. Immunoreactive clones were isolated and sequenced as described above. The determined cDNA sequences for the 8 isolated clones referred to as 1G6-34, 1E6-44, 4A5-63, 1B11-39, 2A10-37, 4G2-83, 4H6-41, 8G3-100 are provided in SEQ ID NO: 72–79, respectively, with the corresponding predicted amino acid sequences being provided in SEQ ID NO: 80–87, respectively. The cDNA sequences provided for 1E6-44, 2A10-37, 4G2-83, 4H6-41 and 8G3-100 are believe to represent partial clones. All of these clones were shown to stimulate T cell proliferation.

Comparison of these sequences with those in the gene bank as described above revealed no known homologies to the antigen 4A5-63. 1G6-34 was found to have some homology to histone H2B previously identified in *L. enrietti*. Antigens 1E6-44, 1B11-39 and 8G3-100 showed some homology to sequences previously identified in other eukaryotes, in particular *Saccharomyces cerevisae*. 2A10-37 and 4H6-41 were found to be homologous to the two previously identified proteins alpha tubulin from *L. donovani* and beta tubulin from *L. major*, respectively, and 4G2-83 was found to be homologous to elongation initiation factor 2 previously identified in *T. cruzi*.

Subsequent full-length cloning studies, using standard techniques, led to the isolation of an extended cDNA sequence for 1E6-44, provided in SEQ ID NO: 105. The corresponding amino acid sequence is provided in SEQ ID NO: 106. An extended cDNA sequence for 2A10-37 is provided in SEQ ID NO: 107. This sequence was found to contain a complete open reading frame which encodes the amino acid sequence of SEQ ID NO: 108. An extended cDNA sequence for 4G2-83 is provided in SEQ ID NO: 109. This sequence contains a complete open reading frame which encodes the amino acid sequence of SEQ ID NO: 110. An extended cDNA sequence for 8G3-100 is provided in SEQ ID NO: 111, with the corresponding amino acid sequence being provided in SEQ ID NO: 112.

All eight of the antigens described above (1G6-34, 1E6-44, 4A5-63, 1B11-39, 2A10-37, 4G2-83, 4H6-41, 8G3-100) were expressed in *E. coli* as recombinant fusion proteins containing N-terminal histidine tags and were purified to homogeneity using nickel affinity chromatography. All 8 purified recombinant proteins elicited strong proliferative responses from the CD4+ T cell lines employed in the library screening. T cell reactivity to 1G6-34, 4H6-41 and 8G3-100 was also observed in T cells generated against both Leishmania promastigote culture filtrate and amastigote culture filtrate, indicating that these antigens are expressed in both the promastigote and amastigote life stages at levels that are sufficient to evoke strong cellular immunes response.

The ability of the 8 antigens to stimulate proliferation and IFN-γ production in PBMC from patients with active cutaneous leishmaniasis (CL) and from normal donors was examined as described above. In addition to the 8 antigens, leishmanial promastigote lysate (LPr) and purified protein derivative from *M. tuberculosis* (PPD) were also tested. The number of patients and/or donors responding to each antigen is shown in Table 3 below. All CL patients responded to at least one of the 8 antigens. Most notably, the antigens 1G6-34 and 4H6-41 elicited cell proliferation in 6/7 and 7/7 CL patients, respectively, and IFN-γ production in 6/7 and 5/7 CL patients, respectively. In addition 1G6-34 was not recognized by PBMC from uninfected control donors.

TABLE 3

CELL PROLIFERATION AND IFN-γ PRODUCTION IN PBMC FROM PATIENTS WITH CUTANEOUS LEISHMANIASIS

| | CL Patients | | Normal donors | |
|---|---|---|---|---|
| Antigen | IFN-γ production | Cell Proliferation | IFN-γ production | Cell Proliferation |
| LPr | 7/7 | 6/7 | 3/8 | 5/8 |
| 1G6-34 | 6/7 | 5/7 | 0/8 | 0/8 |
| 1E6-44 | 0/7 | 4/7 | 5/8 | 2/8 |
| 4A5-63 | 1/7 | 1/7 | 0/8 | 0/8 |
| 1B11-39 | 5/7 | 3/7 | 1/8 | 0/8 |

TABLE 3-continued CELL PROLIFERATION AND IFN-γ PRODUCTION IN PBMC
FROM PATIENTS WITH CUTANEOUS LEISHMANIASIS

|  | CL Patients | | Normal donors | |
| --- | --- | --- | --- | --- |
| Antigen | IFN-γ production | Cell Proliferation | IFN-γ production | Cell Proliferation |
| 2A10-37 | 1/7 | 3/7 | 1/8 | 0/8 |
| 4H6-41 | 7/7 | 5/7 | 3/8 | 1/8 |
| 8G3-100 | 0/7 | 2/7 | 5/8 | 2/8 |
| PPD | 7/7 | 7/7 | 7/8 | 7/8 |

Example 16

Synthesis of Polypeptides

Polypeptides may be synthesized on a Perkin Elmer/Applied Biosystems Division 430A peptide synthesizer using FMOC chemistry with HPTU (O-Benzotriazole-N,N,N,',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 17

Figure 31:
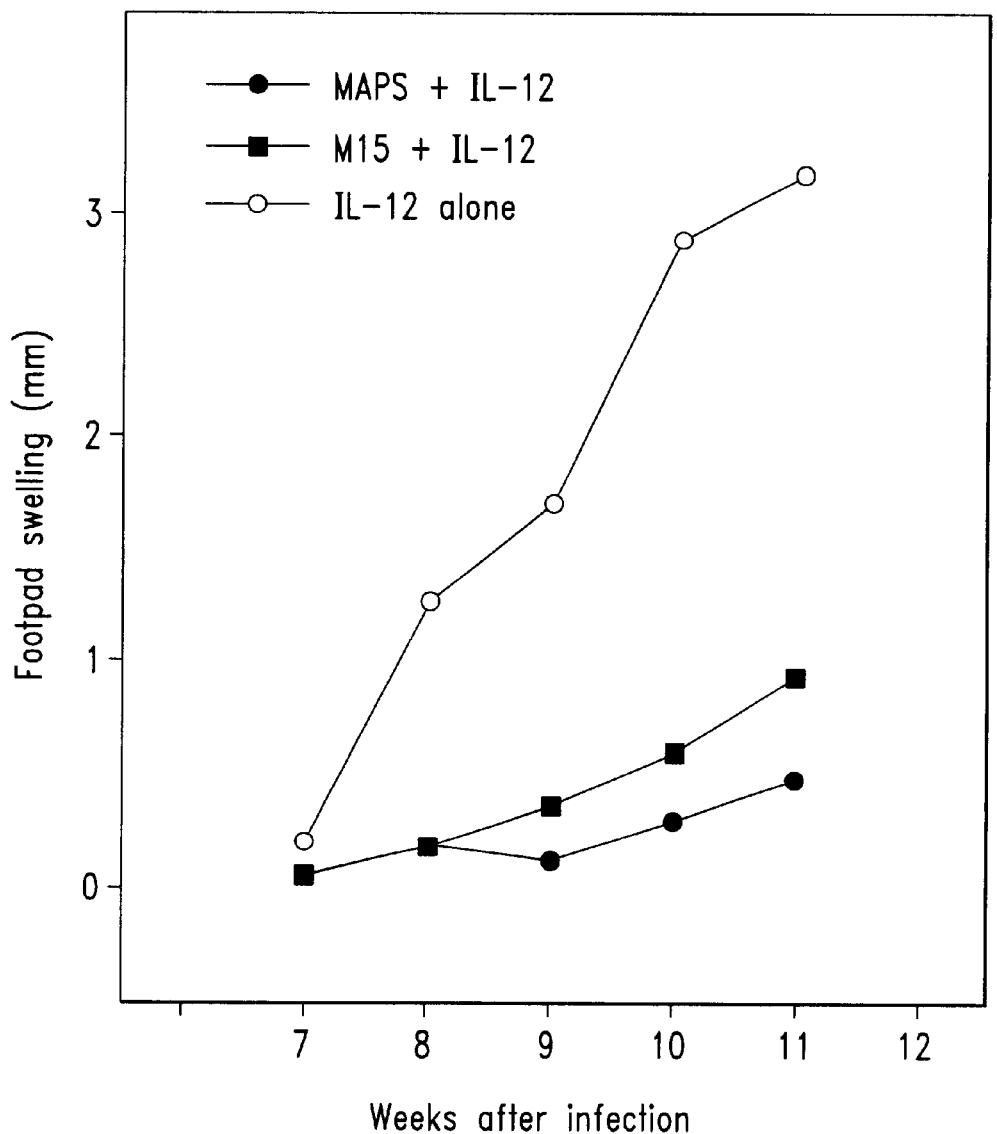
FIG. 31 illustrates the effectiveness of immunization with soluble Leishmania antigens, MAPS-1A and M15 plus adjuvant, IL-12, in conferring protection against infection (as measured by footpad swelling) in a murine leishmaniasis model system, as compared to the administration of adjuvant IL-12 alone.

Use of Leishmania Antigens Plus Adjuvant for Vaccination Against Leishmania Infection This example illustrates the effectiveness of recombinant Leishmania antigens, M15 and MAPS, plus an adjuvant, IL-12, in conferring protection against disease in the experimental murine leishmaniasis model system. For discussion of the murine leishmaniasis model system see, for example, Reiner et al., Annu. Rev. Immunol., 13:151–77, 1995. The effectiveness of M15 and MAPS in combination with IL-12, as vaccine against Leishmania infection was determined as follows: BALB/c mice (5 per group) were immunized subcutaneously in the left footpad, twice (3 weeks apart) with the 10 µg of the individual antigens mixed with 1 µg of IL-12. As controls, three separate groups of mice were immunized with soluble leishmania lysate antigens (SLA) plus IL-12, with IL-12 alone or with PBS. Three weeks after the last immunization the mice were infected in the right footpad with $2 \times 10^5$ promastigote forms of L. major (stationary phase). Footpad swelling was then measured weekly. Results are expressed in FIG. 31 and clearly indicate that the mice immunized with either M15 or MAPS and IL-12 were greatly protected against the infection; whereas mice immunized with IL-12 alone did not show protection from infection. The protection induced by these antigens was as efficient or better than that induced by SLA+IL-12, a regimen known to induce good protection against leishmaniasis in this animal model (Afonso, L. C. C., T. M. Scharton, L. Q. Vieira, M. Wysocka, G. Trinchieri, and P. Scott. 1994. *The adjuvant effect of interleukin-12 in a vaccine against Leishmania major. Science* 263:235–237). The same pattern of protection described above, was obtained i.e., M15, MAPS, and SLA, induced protection against L. major infection when C. parvum instead of IL-12 was used as adjuvant (Example 12). These results demonstrate that both M15 and MAPS recombinant antigens induce excellent protection against L. major infection in the BALB/c model of human leishmaniasis. In addition, both antigens induced protection when tested in two different adjuvant formulations, (e.g., IL-12 and C. parvim.) This finding is of high significance because it demonstrates that immunity to leishmaniasis can be induced by the specific antigens delivered in adjuvants that are suitable for human use.

Example 18

Use of Leishmania DNA for Vaccination Against Leishmania Infection

Figure 32:
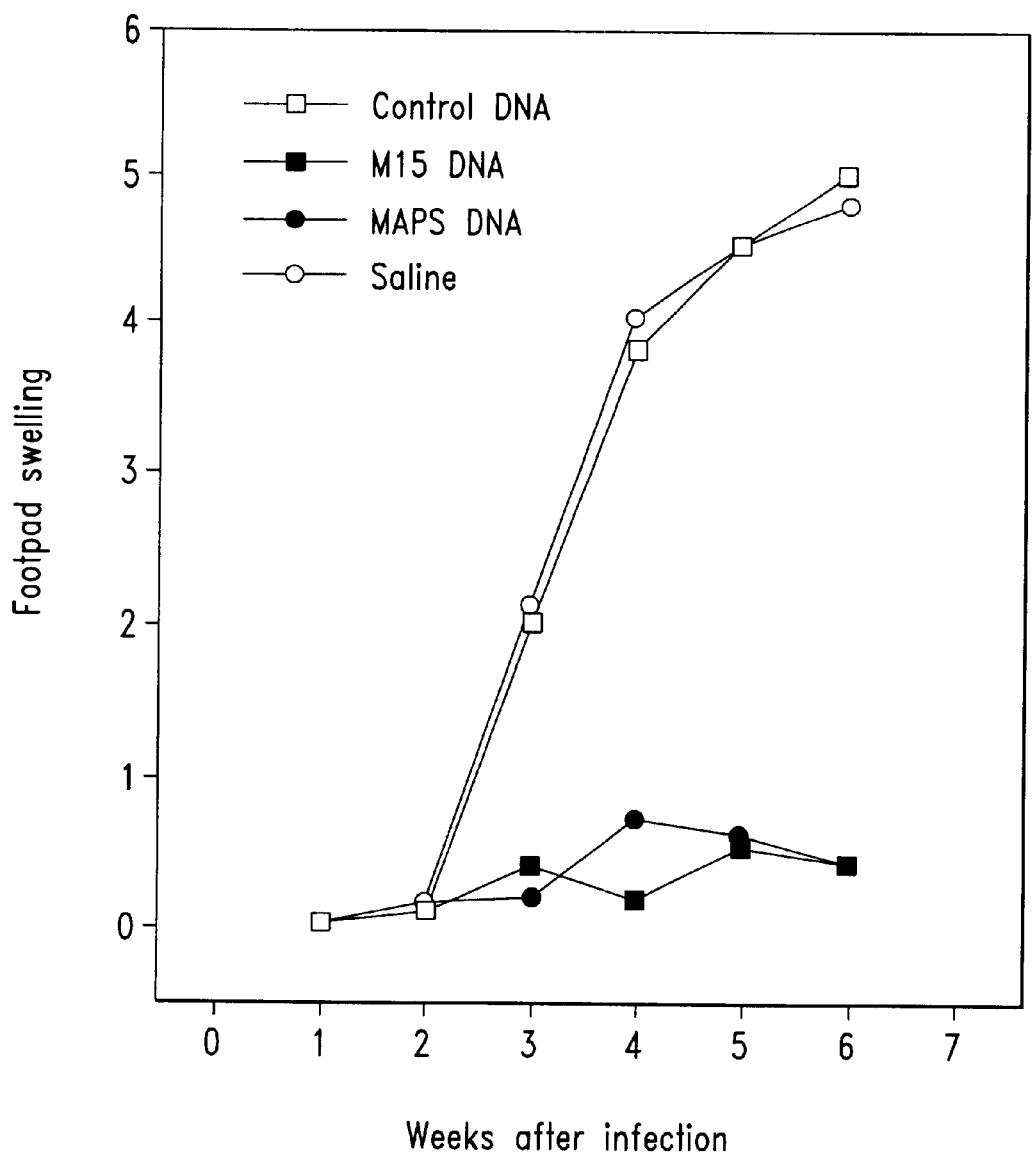
FIG. 32 illustrates the effectiveness of immunization with M15 DNA and MAPS-1A DNA in conferring protection against infection (as measured by footpad swelling) in a murine leishmaniasis model system, as compared to control DNA and saline.

This example illustrates the effectiveness of Leishmania DNA in conferring protection against disease in the experimental murine leishmaniasis model system. For discussion of the murine leishmaniasis model system see, for example, Reiner et al., Annu. Rev. Immunol., 13:151–77, 1995. The protection properties of the recombinant antigens was tested by immunizing mice with naked DNA containing the corresponding M15 and MAPS genes. The DNA construct used was the pcDNA3.1 vector (Invitrogen) containing a CMV promotor. BALB/c mice (5 per group) were injected in the left footpad three times (3 weeks apart) with 100 g of the indicated naked DNA preparations. Mice were bled before and after the immunizations to monitor the development of specific immune response. The antibody response was evaluated by ELISA. Specific anti-M15 and anti-MAPS IgG2a antibodies were detected after the second immunization in the sera of the mice immunized with the respective naked DNA. The presence of specific antibodies indicates that the DNA immunization resulted in the production of specific protein antigen. Three weeks after the last immunization, the mice were then challenged in the right footpad with $2 \times 10^5$ promastigote forms of L. major (stationary phase). Footpad swelling was then measured weekly thereafter. Results are expressed in FIG. 32 and clearly indicated that, again, mice immunized with naked DNA containing either the M15 or MAPS genes were greatly protected against the infection with L. major. These results demonstrate that both M15 and MAPS genes induce excellent protection against L. major infection in the BALB/c model of human leishmaniasis.

Example 19

Preparation and Characterization of Leishmania Fusion Proteins

Fusion proteins comprising the Leishmania antigens MAPS-iA (SEQ ID NO: 24), M15 (SEQ ID NO: 2), Lbhsp83 (SEQ ID NO: 6) and LbeIF4A (SEQ ID NO: 10) were prepared as follows.

A fusion construct of MAPS-1A and M15 was prepared by first PCR amplifying the full-length coding sequence of MAPS-1A using the primers of SEQ ID NO: 88 and 89. The resulting products were digested with NdeI and BamHI follows by sub-cloning into the pET17b expression vector, also digested with NdeI and BamHI. The ligated products were transformed into *E. coli* and transformants containing the correct insert were identified by restriction digest and verified by DNA sequencing. The MAPS-1A-pET plasmid was digested with BamHI and EcoRI. The latter cuts within the poly-linker sequence of the pET vector which is located downstream of the BamHI site.

The primers of SEQ ID NO: 90 and 91 were employed to PCR amplify the full-length coding sequence of M15 and the resulting product was digested with BamHI and EcoRI followed by sub-cloning into the predigested MAPS1A-pET plasmid above. The ligated products were then transformed into *E. coli* and transformants with the correct insert were identified by restriction digest and verified by DNA sequencing. The MAPS1A-M15 pET construct was transformed into the bacterial host (BL21; pLysE). Expression of the protein resulted in a single recombinant molecule with a predicted molecular weight of 85.7 kDa. The recombinant MAPS1A-M15 fusion protein also contained 33 amino acid residues of run-through vector as a result of the removal of the stop codon of M15 and was subsequently digested with EcoRI. The DNA sequence of the MAPS1A-M15 construct is provided in SEQ ID NO: 101.

The primers of SEQ ID NO: 92 and 93 were used to PCR amplify the first 226 amino acid residues of LbeIF4A. The resulting PCR product was digested with EcoRI and sub-cloned into the MAPS1A-M15-pET plasmid. The ligated products were then transformed into *E. coli* and transformants with the correct insert and orientation were identified by restriction digest and verified by DNA sequencing. The expressed recombinant protein was purified by affinity chromatography over a Ni column. The DNA and amino acid sequences of the fusion protein MAPS1A-M15-LbeIF4A are provided in SEQ ID NO: 94 and 95, respectively.

Additional fusion proteins were prepared using the methodology described above. The amino acid sequences for the fusion proteins MAPS1A-M15-Lbhsp83 and MAPS1A-M15-Lbhsp83-LeIF4A are provided in SEQ ID NO: 96 and 97, respectively. The DNA sequence that encodes the amino acid sequence of SEQ ID NO: 97 is provided in SEQ ID NO: 98. The DNA sequences of MAPS1A-M15-Lbhsp83 and MAPS1A-M15-Lbhsp83-LeIF4A vectors employed in DNA vaccines are provided in SEQ ID NO: 99 and 100, respectively.

Example 20

Use of Leishmania Fusion Proteins Plus Adjuvant for Vaccination against Leishmania Infection The ability of the Leishmania fusion proteins MAPS1A-M15 (referred to as the diFusion) and MAPS1A-M15-LbeIF4A (referred to as the triFusion), plus adjuvant, to confer protection against disease in the experimental murine leishmaniasis model system was examined as follows.

The diFusion and triFusion were prepared as described above. In a first series of experiments, groups of BALB/c mice were immunized with either the individual recombinant antigens, (MAPS1A, M15 or LbeIF4A), the diFusion or the triFusion, with IL-12 as an adjuvant, as described above in Example 17. Control mice were immunized with IL-12 alone or saline. Before challenge, some mice (three per group) were sacrificed and the immune responses to the fusion proteins and to the individual antigens were investigated. Both T cell (cytokine production by spleen cells) and B cell responses (antibody response) were evaluated. The results indicated that immunization of mice with the fusion proteins did not interfere with the immunogenicity of the individual antigens. More specifically, Th1 responses (namely induction of IFN-γ production and specific IgG2a production) were observed to both MAPS1A and M15, when mice were immunized with both the diFusion and triFusion recombinant proteins. In addition, immunization with the triFusion resulted in good immune response to LeIF.

Figure 33:
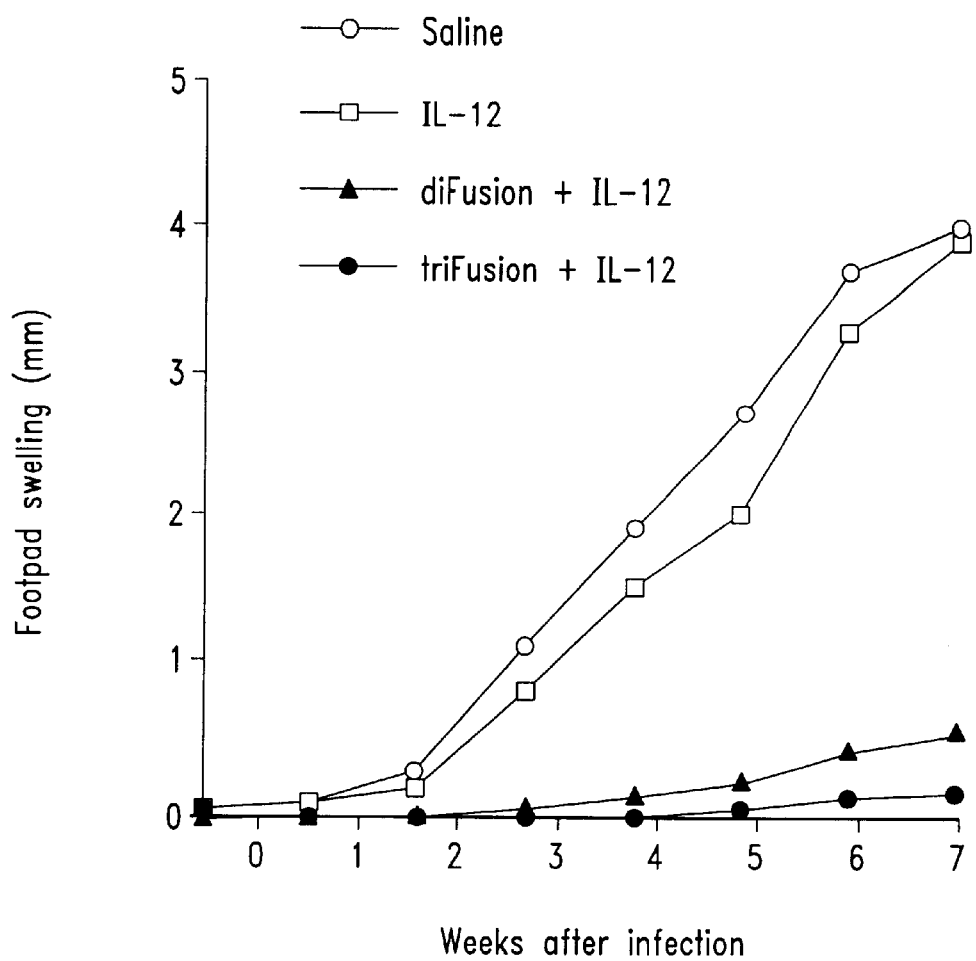
FIG. 33 illustrates the effectiveness of immunization with Leishmania fusion proteins plus IL-12 as adjuvant, in conferring protection against infection in a murine leishmaniasis model system.

To evaluate the protection conferred by these fusion proteins, the immunized and control mice were infected in the right footpad with $2 \times 10^3$ amastigote forms of *L. major* and footpad swelling was measured weekly thereafter. The results, shown in FIG. 33, clearly indicated that both fusion proteins induced protection comparable to MAPS1A and M15.

A second series of experiments was performed in which MPL-SE (Ribi ImmunoChem Research Inc. (Hamilton, Mont.) was employed as the adjuvant. BALB/c mice were immunized three times (three weeks interval) with 2 μg of the individual antigens (MAPS1A, M15 or LbeIF4A), diFusion or triFusion proteins plus MPL-SE, and tested for immunogenicity of the antigens and for protection as described above. As with the experiments performed with IL-12 as adjuvant, the mice immunized with the individual antigens as well as with the fusion proteins showed both specific T and B cell responses to the immunizing antigens. Moreover, no antigen competition between the individual antigens was observed when the fusion proteins were used as immunogens.

Figure 34:
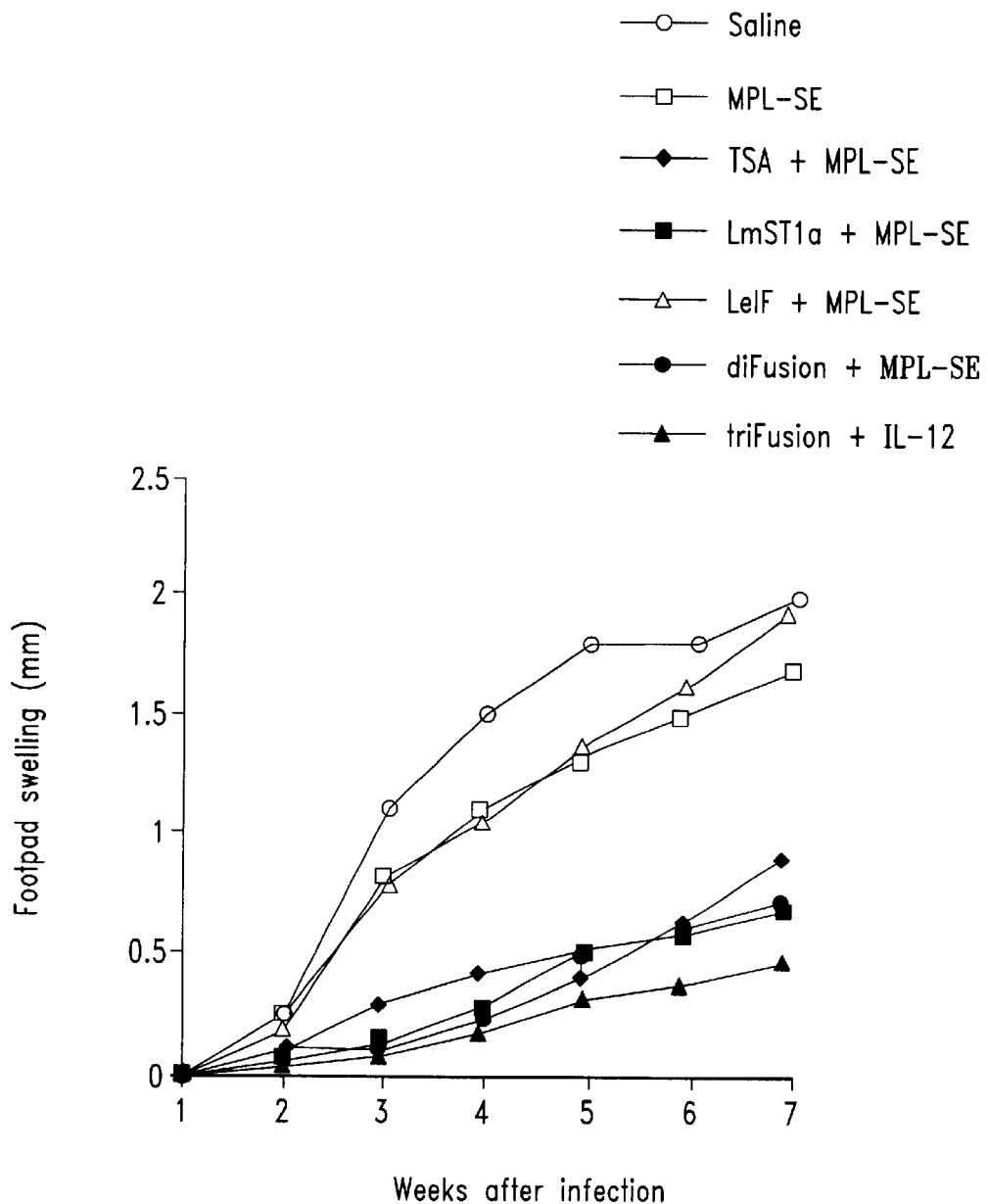
FIG. 34 illustrates the effectiveness of immunization with Leishmania fusion proteins plus the adjuvant MPL-SE, in conferring protection against infection in a murine leishmaniasis model system.

As with the protection studies in which IL-12 was used as adjuvant, protection was achieved with the individual antigens MAS1A and M15, as well as with the two fusion proteins (FIG. 34). Slightly better protection was observed in the group of mice immunized with the triFusion than in mice immunized with the diFusion.

Example 21

Formulation of Compositions Comprising Leishmania Fusion Proteins

A stable preparation of the tri-fusion of MAPS1A, M15 and LbeIF4A described above was prepared as follows. The purified protein was put into ammonium bicarbonate buffer (pH 8.0) by dialysis, and the following were added: 5% (w/v) mannitol, sucrose at 10:1 (w/w) excess sucrose to protein and 0.1% (v/v) polysorbate 80. The protein was lyophilized to dryness to yield a stable powder which can be readily resuspended as needed.

From the foregoing, it will be appreciated that, although specific embodiments of the invention have been described herein for the purpose of illustration, various modifications may be made without deviating from the spirit and scope of the invention.

What is claimed is:

1. A method for inducing protective immunity against leishmaniasis in a patient comprising administering an immunogenic composition comprising a fusion protein and an immunostimulant, wherein the fusion protein comprises the amino acid sequence of SEQ ID NO:24.

2. The method of claim 1, wherein the fusion protein comprises the amino acid sequence of SEQ ID NO:95.

3. The method of any one of claims 1 and 2, wherein the immunostimulant is selected from the group consisting of: aminoalkyl glucosaminide 4-phosphates; monophosphoryl lipid A; and 3-de-O-acylated monophosphoryl lipid A.

* * * * *